(12) United States Patent
Nørremark et al.

(10) Patent No.: US 8,765,676 B2
(45) Date of Patent: Jul. 1, 2014

(54) CALCIUM SENSING RECEPTOR MODULATING COMPOUNDS AND PHARMACEUTICAL USE THEREOF

(75) Inventors: Bjarne Nørremark, Stenløse (DK); Lars Kristian Albert Blæhr, København Ø (DK); Anne Eeg Knapp, Brønshøj (DK); Kristoffer Månsson, Malmø (DK)

(73) Assignee: Leo Pharma A/S, Ballerup (DK)

( * ) Notice: Subject to any disclaimer, the term of this patent is extended or adjusted under 35 U.S.C. 154(b) by 0 days.

(21) Appl. No.: 13/322,514

(22) PCT Filed: May 26, 2010

(86) PCT No.: PCT/DK2010/000070
§ 371 (c)(1),
(2), (4) Date: Feb. 2, 2012

(87) PCT Pub. No.: WO2010/136037
PCT Pub. Date: Dec. 2, 2010

(65) Prior Publication Data
US 2012/0122784 A1     May 17, 2012

Related U.S. Application Data

(60) Provisional application No. 61/181,579, filed on May 27, 2009.

(30) Foreign Application Priority Data

May 27, 2009 (DK) .................................. 2009 00664

(51) Int. Cl.
| | | |
|---|---|---|
| C07D 211/16 | (2006.01) | |
| A61K 31/33 | (2006.01) | |
| A61P 19/00 | (2006.01) | |
| C07D 213/643 | (2006.01) | |
| C07D 257/04 | (2006.01) | |
| C07D 265/30 | (2006.01) | |
| C07D 277/22 | (2006.01) | |
| C07D 317/62 | (2006.01) | |
| A61K 38/23 | (2006.01) | |
| A61K 38/00 | (2006.01) | |
| C07K 14/585 | (2006.01) | |

(52) U.S. Cl.
CPC ............... *C07D 211/16* (2013.01); *A61K 31/33* (2013.01)
USPC ....................................................... 514/11.9

(58) Field of Classification Search
CPC ............. C07D 211/16; C07D 213/643; C07D 257/04; C07D 265/30; C07D 277/22; C07D 317/62; A61K 31/33; A61K 32/23; A61K 38/00; A61P 19/00; C07K 14/585
USPC ....................................................... 514/11.9
See application file for complete search history.

(56) References Cited

U.S. PATENT DOCUMENTS

| | | |
|---|---|---|
| 6,362,231 B1 | 3/2002 | Sakai et al. |
| 2003/0199497 A1 | 10/2003 | Ruat et al. |
| 2005/0032796 A1 | 2/2005 | Shinagawa et al. |
| 2005/0192317 A1 | 9/2005 | Dauban et al. |
| 2006/0069098 A1 | 3/2006 | Miyoshi et al. |
| 2006/0135572 A1 | 6/2006 | Shinagawa et al. |
| 2011/0218160 A1 | 9/2011 | Miyazaki et al. |

FOREIGN PATENT DOCUMENTS

| | | |
|---|---|---|
| EP | 1203761 A2 | 5/2002 |
| EP | 1281702 A2 | 2/2003 |
| EP | 1757582 A1 | 2/2007 |
| WO | WO 93/04373 A1 | 3/1993 |
| WO | WO 95/11221 A1 | 4/1995 |
| WO | WO 96/12697 A2 | 5/1996 |
| WO | WO 97/41090 A1 | 11/1997 |
| WO | WO 98/01417 A1 | 1/1998 |
| WO | WO 00/21910 A2 | 4/2000 |
| WO | WO 01/34562 A1 | 5/2001 |
| WO | WO 01/90069 A1 | 11/2001 |
| WO | WO 02/12181 A1 | 2/2002 |
| WO | WO 02/059102 A3 | 8/2002 |
| WO | WO 03/099776 A1 | 12/2003 |
| WO | WO 03/099814 A1 | 12/2003 |
| WO | WO 2004/056365 A2 | 7/2004 |
| WO | WO 2004/069793 A2 | 8/2004 |
| WO | WO 2004/094362 A1 | 11/2004 |
| WO | WO 2004/106280 A1 | 12/2004 |
| WO | WO 2004/106295 A2 | 12/2004 |
| WO | WO 2004/106296 A2 | 12/2004 |

(Continued)

OTHER PUBLICATIONS

Kitching et al. "Targeting leukocytes in immune glomerular diseases," Curr. Med. Chem. 15:448-458 (2008).*

(Continued)

*Primary Examiner* — Christina Bradley
*Assistant Examiner* — Kristina M Hellman
(74) *Attorney, Agent, or Firm* — Birch, Stewart, Kolasch & Birch, LLP

(57) ABSTRACT

Calcium-sensing receptor (CaSR) modulating substituted cyclopentylene compounds represented in formula I (wherein X is CH or N) and pharmaceutical compositions thereof are useful for treating diseases.

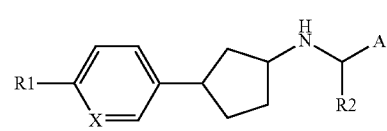

30 Claims, No Drawings

(56) References Cited

FOREIGN PATENT DOCUMENTS

| WO | WO 2005/034928 A1 | 4/2005 |
| WO | WO 2005/065050 A2 | 7/2005 |
| WO | WO 2005/068433 A1 | 7/2005 |
| WO | WO 2005/115975 A1 | 12/2005 |
| WO | WO 2006/001958 A2 | 1/2006 |
| WO | WO 2006001958 A2 * | 1/2006 |
| WO | WO 2006/047195 A2 | 5/2006 |
| WO | WO 2006047195 A2 * | 5/2006 |
| WO | WO 2009/025792 A2 | 2/2009 |
| WO | WO 2009/051718 A2 | 4/2009 |
| WO | WO 2009051718 A2 * | 4/2009 |
| WO | WO 2009/065406 A2 | 5/2009 |
| WO | WO 2010/021351 A1 | 2/2010 |

OTHER PUBLICATIONS

Rifkin et al., "Dialysis Modalities: What the non-nephrologist needs to know," Hosp. Phys. pp. 11-19 (Aug. 2006).*

Canaud, B., et al. "Residual renal function and dialysis modality: is it really beneficial to preserve residual renal function in dialysis patients?," Nephrol. 11:292-296 (2006).*

Beaumont, et, al "Design of Ester Prodrugs to Enhance Oral Absorption of Poorly Permeable Compounds: Challenges to the Discovery Scientist," Current Drug Metabolism 4:461-485 (2003).*

Hashimoto et al., "Enatioselective Intermolecular C—H insertion reactions of α-diazo β-keto esters catalyzed by dirhodium(II) tetrakis[N-phthaloyl(s)-phenylalaniate]: the effect of the substituent at the insertion site on enatioselectivity," Synlett May 1994:353-355 (1994).*

Balfour et al., "Cinacalcet Hydrochloride", Drugs, vol. 65, No. 2, 2005, pp. 271-281.

Brown, "Ca2+-Sensing Receptor", American Society for Bone and Mineral Research, 2008, pp. 134-141.

Chattopadhyay et al., "The Calcium-Sensing Receptor: A Window into the Physiology and Pathophysiology of Mineral Ion Metabolism", Endocrine Reviews, vol. 17, No. 4, 1996, pp. 289-307.

Dong, "Cinacalcet: An Oral Calcimimetic Agent for the Management of Hyperparathyroidism", Clinical Therapeutics, vol. 27, No. 11, 2005, pp. 1725-1751.

Drüeke, "Modulation and action of the calcium-sensing receptor", Nephrol Dial Transplant, vol. 19, Suppl. 5, 2004, pp. v20-v26.

Feng et al., "Easily Accessible C2-Symmetric Chiral Bicyclo[3.3.0] Dienes as Ligands for Rhodium-Catalyzed Asymmetric 1,4-Addition", Chemistry an Asian Journal, vol. 3, 2008, pp. 1511-1516.

Harrington et al., "Calcium Sensing Receptor Activators: Calcimimetics", Current Medicinal Chemistry, vol. 14, 2007, pp. 3027-3034.

Hashimoto et al., "Enantioselective Intramolecular C—H Insertion Reactions of • -Diazo • -Keto Esters Catalyzed by Dirhodium(II) Tetrakis[N-phthaloyl-(S)-phenylalaninate]: The Effect of the Substituent at the Insertion Site on Enantioselectivity", SYNLETT, May 1994, pp. 353-355.

International Search Report dated Dec. 1, 2010, for Application No. PCT/DK2010/000068.

International Search Report dated Dec. 14, 2010, for Application No. PCT/DK2010/000069.

International Search Report dated Sep. 21, 2010, for Application No. PCT/DK2010/000070.

Osigweh et al., "Regulation of colonic crypt fluid and electrolyte secretion by the calcium sensing receptor", Alimentary Tract II, vol. 201, No. 3S, Sep. 2005, p. S17.

Varchi et al., "Copper Catalyzed Conjugate Addition of Highly Functionalized Arylmagnesium Compounds to Enones", Tetrahedron, vol. 56, 2000, pp. 2727-2731.

Wallace et al., "Scalable Synthesis and Isolation of the Four Stereoisomers of Methyl 1-Amino-3-(4-bromophenyl)cyclopentanecarboxylate, Useful Intermediates for the Synthesis of S1P1 Receptor Agonists", J. Org. Chem., vol. 74, 2009, pp. 4886-4889.

Whitfield, "The Bone-Building Action of the Parathyroid Hormone; Implications for the Treatment of Osteoporosis", Drugs & Aging, vol. 15, No. 2, Aug. 1999, pp. 117-129.

Ye et al., "Amyloid-β Protiens Activate Ca2+-Permeable Channels Through Calcium-Sensing Receptors", Journal of Neuroscience Research, vol. 47, 1997, pp. 547-554.

Yu et al., "Rhodium-Catalyzed Asymmetric 1,4-Addition of Heteroaryl Cyclic Triolborate to α,β-Unsaturated Carbonyl Compounds", SYNLETT, No. 6, 2009, pp. 0994-0998.

Yu, et al., "Supporting Information of : Rhodium-Catalyzed Asymmetric 1,4-Addition of Heteroaryl Cyclic Triolborate to α,β-Unsaturated Carbonyl Compounds", SYNLETT, DOI: 10.1055/s-0028-1088198, 2008, pp. 1-15.

* cited by examiner

CALCIUM SENSING RECEPTOR MODULATING COMPOUNDS AND PHARMACEUTICAL USE THEREOF

CROSS REFERENCE TO RELATED APPLICATIONS

This application is a National Phase of International Application No. PCT/DK2010/000070 filed on May 26, 2010 which claims the benefit under 35 U.S.C. §119(e) of U.S. Provisional Application No. 61/181,579 filed on May 27, 2009, and under 35 U.S.C. §119(a) to Patent Application No. PA 2009 00664 filed in Denmark on May 27, 2009. The entire contents of all of the above applications are hereby incorporated by reference into the present application.

FIELD OF THE INVENTION

This invention relates to novel calcium-sensing receptor (CaSR) modulating substituted cyclopentylene compounds and derivatives thereof, to said compounds for use as a medicament, to said compounds for use in therapy, to pharmaceutical compositions comprising said compounds, to methods of treating diseases with said compounds, and to the use of said compounds in the manufacture of medicaments.

BACKGROUND OF THE INVENTION

The calcium-sensing receptor (CaSR) is a G-protein-coupled receptor (GPCR) that signals through the activation of phospholipase C, increasing levels of inositol 1,4,5-triphosphate and cytosolic calcium. The CaSR belongs to the subfamily C of the GPCR superfamily, which also includes receptors for glutamate, gamma aminobutyric acid (GABA), pheromones and odorants that all possess a very large extracellular domain. This domain is highly negatively charged and is involved in binding of calcium and other positively charged molecules. The CaSR is found in the parathyroid glands but has also been identified in the brain, intestine, pituitary, thyroid glands, bone tissue and kidneys [Brown, E., M. Calcium-Sensing Receptor. *Primer of the Metabolic Bone Diseases and Disorders of Mineral Metabolism* Fifth Edition, 2003 by American Society for Bone and Mineral Research, Chapter 17, p. 111.; Drueke, T. E. *Nephrol Dial Transplant* (2004) 19, suppl 5, v20-v26].

The calcium-sensing receptor (CaSR) detects changes in extra-cellular calcium concentration and initiates the functional response of this cell, which is a modulation of the secretion of the parathyroid hormone (PTH). Secretion of PTH increases extra-cellular calcium ion concentration by acting on various cells, such as bone and kidney cells, and the extra-cellular calcium ion concentration reciprocally inhibits the secretion of PTH by acting on parathyroid cells. The reciprocal relationship between calcium concentration and PTH level is an essential mechanism for calcium homeostasis maintenance.

The calcimimetic activity corresponds to the ability to produce or induce biological responses observed through variations in the concentration of extracellular calcium ions $(Ca^{2+})_e$ and extracellular magnesium ions $(Mg^{2+})_e$.

$(Ca^{2+})_e$ and $(Mg^{2+})_e$ ions play a major role in the body since they regulate calcium homeostasis on which the vital functions of the body depend. Thus, hypo- and hypercalcemia, that is to say conditions in which $(Ca^{2+})_e$ ions are below or above the mean threshold, have a major effect on many functions, such as cardiac, renal or intestinal functions. They deeply affect the central nervous system (Chattopadhyay et al. Endocr. Review, 1996).

It has been shown that $Ca^{2+}$ and $Mg^{2+}$ ions, but also $Ba^{2+}$ ions, within millimolar concentration ranges, stimulate CaSRs. Activation of CaSRs might be induced in the brain by β-amyloid peptides, which are involved in neurodegenerative diseases such as Alzheimer's disease [Ye et al, J. Neurosci. Res., 47, 547-554, 1997].

Disturbance of CaSR activity is associated with biological disorders such as primary and secondary hyperparathyroidism, osteoporosis, cardiovascular, gastrointestinal, endocrine and neurodegenerative diseases, or certain cancers in which $(Ca^{2+})_e$ ions are abnormally high.

Primary hyperparathyroidism (primary HPT) is characterised by elevated levels of PTH and serum calcium which is typically caused by adenoma or hyperplasia of the parathyroid gland. It can result in bone pain and excessive bone resorption.

Secondary hyperparathyroidism (secondary HPT) often develops in patients who have reduced kidney function and is characterised by elevated levels of PTH. The underlying causes are complex, but a reduced ability to convert vitamin D to calcitriol and elevated levels of phosphorus play significant roles in the development of secondary HPT. If left untreated, the clinical manifestations of secondary HPT include bone and joint pain and limb deformities [Harrington, P. E. and Fotsch, C. Calcium Sensing Receptor Activators: Calcimimetics. Current Medicinal Chemistry, 2007, 14, 3027-3034].

A reduced kidney function or renal failure is also accompanied by renal osteodystrophy, e.g. osteitis fibrosa, osteomalacia, adynamic bone disease, or osteoporosis. The disorders are characterized by either high or low bone turnover. Osteoporosis is a multifactor disease which depends in particular on age and sex. While menopausal women are very greatly affected, osteoporosis is increasingly proving to be a problem in elderly men, and, for the moment, no really satisfactory treatments exist. Its social cost may become even heavier in the years to come, particularly as life expectancy is becoming longer. Osteoporosis is currently treated with estrogens, calcitonin or biphosphonates which prevent bone resorption without stimulating bone growth. More recent data demonstrate that intermittent increases in PTH or in derivatives thereof are effective in the treatment of osteoporosis and make it possible to remodel bone by stimulating bone formation [Whitfield et al., Drugs & Aging 1999 August; 15 (2): 117-129 1999]. This new therapeutic approach for treatment of osteoporosis appears to be very advantageous, although major problems are associated with the use of PTH hormone, such as the route of injection, but also the appearance of tumours, observed recently during clinical trials in humans. Intermittent secretion of endogenous PTH can be obtained by blocking the calcium sensing receptor. The blocking of PTH secretion with CaSR agonists may be followed by a rapid increase in PTH (rebound effect), which is then beneficial in the treatment of osteoporosis.

A compound having an activating effect on CaSR (CaSR agonist), that is, a compound which selectively acts on CaSR to mimic or strengthen the action of $Ca^{2+}$, is called a calcimimetic. On the other hand, a compound having an antagonistic effect on CaSR (CaSR antagonist, that is, a compound which suppresses or inhibits the action of $Ca^{2+}$), is called a calcilytic.

The calcium-sensing receptor has recently been found to be a potent target for developing therapeutic options such as use of calcimimetics for treatment of diarrhea. [Osigweh et al, J American Coll. of Surgeons, V201, Issue 3, suppl 1, September 2005, p 17.]

Calcimimetics have been shown to be commercially useful for the treatment of hyperparathyroidism (HPT): The calcimimetic compound Cinacalcet® [Balfour, J. A. B. et al. *Drugs* (2005) 65(2), 271-281; Lindberg et. al. *J. Am. Soc. Nephrol* (2005), 16, 800-807, Clinical Therapeutics (2005), 27(11), 1725-1751] is commercially available for the treatment of secondary HPT in chronic kidney disease patients on dialysis and for the treatment of primary HPT in patients with parathyroid carcinoma. Thus, proof of concept for activators of calcium sensing receptor (CaSR) in humans has been achieved and the clinical relevance is well established.

Other calcimimetic compounds were for example described in WO02/059102, WO98/001417, WO05/065050, WO03/099814, WO03/099776, WO00/21910, WO01/34562, WO01/090069, WO97/41090, U.S. Pat. No. 6,001,884, WO96/12697, EP1203761, WO95/11221, WO93/04373, EP1281702, WO02/12181, WO04/56365, WO04/069793, WO04/094362, US2004242602, WO04/106280, WO04/106295, WO04/106296, WO05/068433, WO05/115975, EP 1757582, WO 2009/051718 and WO2010/021351.

SUMMARY OF THE INVENTION

It has been found that the novel compounds of the present invention are modulators, e.g. activators or agonists of the human calcium sensing receptor (CaSR) and may thus be useful in the treatment or prophylaxis of a number of diseases or physiological disorders involving modulation of CaSR activity.

The present invention provides novel substituted cyclopentylene compounds having advantageous pharmacokinetic properties. It has surprisingly been found that cyclopentylene compounds with an ethylamino substituted moiety as defined herein and a (hetero)aryl substituted moiety as defined herein show improved in vitro metabolic stability and improved in vivo pharmacokinetic properties, such as increased volumes of distribution.

Accordingly the present invention relates to a compound of general formula I

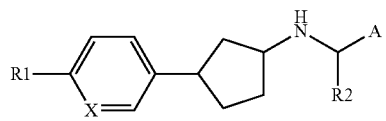

wherein
A represents phenyl, $C_{6-9}$heterocycloalkylphenyl, $C_{1-9}$heteroaryl or $C_{3-7}$cycloalkyl, wherein said phenyl, $C_{6-9}$heterocycloalkylphenyl, $C_{1-9}$heteroaryl or $C_{3-7}$cycloalkyl is optionally further substituted with one or more, same or different substituents represented by halogen, hydroxy, mercapto, trifluoromethyl, cyano, —C(O)H, —NH$_2$, —C(O)NH$_2$, nitro, oxo, —S(O)$_2$NH$_2$, $C_{1-6}$alkyl, $C_{2-6}$alkenyl, $C_{2-6}$alkynyl, $C_{1-6}$hydroxyalkyl, $C_{1-6}$haloalkyl, $C_{1-4}$alkoxy, $C_{1-4}$alkoxycarbonyl, $C_{1-4}$alkylcarbonyloxy, $C_{1-4}$alkoxycarbonyloxy, $C_{1-4}$alkoxysulfonyloxy, $C_{1-4}$alkoxycarbamoyl, $C_{1-4}$aminocarbonyl, $C_{1-4}$alkylthio, $C_{3-7}$cycloalkyl, $C_{3-7}$cycloalkenyl, $C_{1-6}$-amino, iminomethyl, $C_{1-4}$-aminosulfonyl, $C_{1-4}$aminocarbonyloxy, $C_{1-4}$alkylsulfonylamino, hydroxyiminomethyl, $C_{1-4}$alkylcarbonylamino, $C_{1-4}$alkylsulfonyl, $C_{1-6}$heterocycloalkyl, $C_{1-6}$heterocycloalkenyl, $C_{1-5}$heteroaryl or phenyl;
X represents CH or N;
$R_1$ represents halogen, cyano, —NH$_2$, $C_{1-6}$amino, hydroxy, mercapto, —C(O)H, —C(O)NH$_2$, nitro, oxo, hydroxymethyl, $C_{1-6}$alkoxy, $C_{1-6}$alkylcarbonyl, di($C_{1-6}$alkyl)amino $C_{1-6}$alkylaminocarbonyl, $C_{1-6}$aminocarbonyl, hydroxyaminocarbonyl, $C_{1-4}$alkylcarbonylamino$C_{1-6}$alkylaminocarbonyl, $C_{3-6}$cycloalkylaminocarbonyl, $C_{1-6}$heterocycloalkylaminocarbonyl, $C_{1-6}$alkylsulfonylamino $C_{1-6}$aminocarbonyl, NH$_2$—$C_{1-6}$aminocarbonyl, $C_{1-6}$aminoC$_{1-6}$aminocarbonyl, $C_{1-4}$alkylsulfonylaminocarbonyl $C_{1-4}$alkoxy, aminocarbonylC$_{1-6}$alkylaminocarbonyl, aminocarbonylC$_{1-6}$alkoxy, $C_{3-6}$cycloalkylamino, $C_{1-6}$heterocycloalkylcarbonyl, $C_{1-4}$alkylC$_{1-6}$heterocycloalkylcarbonyl, $C_{1-4}$alkylC$_{1-6}$heterocycloalkylaminocarbonyl, $C_{1-4}$alkylsulfonylC$_{1-6}$heterocycloalkylcarbonyl, oxoC$_{1-6}$heterocycloalkylcarbonyl, $C_{1-4}$alkylsulfonylC$_{1-6}$heterocycloalkylcarbonyl, $C_{6-14}$aryl, $C_{1-9}$heteroaryl, $C_{1-6}$heteroarylaminocarbonyl, —S(O)$_2$NH$_2$, $C_{1-6}$ureido, $C_{1-6}$thioureido, $C_{1-4}$alkylcarbonyloxy, $C_{1-6}$alkoxysulfonyloxy, $C_{1-6}$heterocycloalkyloxy, $C_{1-6}$alkylthio, $C_{1-6}$aminosulfonyl, $C_{1-6}$aminocarbonyloxy, $C_{1-6}$alkylsulfonylamino, $C_{1-6}$alkylsulfonylaminoC$_{1-3}$alkyl, $C_{6-10}$arylamino, $C_{6-10}$arylaminocarbonyl, $C_{6-10}$arylcarbonylamino, $C_{1-4}$alkylsulfonylamino, $C_{1-6}$alkylcarbonylamino, $C_{1-3}$alkylcarbonylaminomethyl, $C_{1-6}$alkenylcarbonylamino, $C_{3-6}$cycloalkenylcarbonylamino, $C_{3-6}$cycloalkylcarbonylamino, $C_{1-6}$heterocycloalkylcarbonylamino, $C_{1-6}$alkylsulfonyl, $C_{1-6}$heterocycloalkylsulfonyl, $C_{1-6}$heterocycloalkylsulfonylC$_{1-4}$alkyl, $C_{1-4}$alkylsulfonylaminocarbonyl, aminosulfonylC$_{1-3}$alkylaminocarbonyl, iminomethyl, hydroxyiminomethyl, amidino, trifluoromethyl, $C_{1-6}$alkyl, $C_{2-4}$alkenyl, $C_{2-6}$alkynyl, $C_{1-6}$hydroxyalkyl, aminoC$_{1-6}$alkyl, $C_{1-6}$haloalkyl, $C_{3-6}$cycloalkyl, $C_{3-6}$cycloalkenyl, $C_{1-6}$heterocycloalkyl, or $C_{1-6}$heterocycloalkenyl, wherein said $C_{1-6}$amino, $C_{1-6}$alkoxy, $C_{1-6}$alkylcarbonyl, $C_{1-6}$aminocarbonyl, $C_{3-6}$cycloalkylaminocarbonyl, $C_{1-6}$heterocycloalkylaminocarbonyl, $C_{1-4}$aminoC$_{1-4}$aminocarbonyl, di($C_{1-6}$alkyl)aminoC$_{1-6}$alkylaminocarbonyl, aminocarbonylC$_{1-6}$alkoxy, $C_{3-6}$cycloalkylamino, $C_{1-6}$heterocycloalkylcarbonyl, $C_{1-4}$alkylC$_{1-6}$heterocycloalkylcarbonyl, $C_{6-14}$aryl, $C_{1-9}$heteroaryl, $C_{1-6}$heteroarylaminocarbonyl, $C_{1-6}$ureido, $C_{1-6}$thioureido, $C_{1-4}$alkylcarbonyloxy, $C_{1-4}$alkoxysulfonyloxy, $C_{1-6}$heterocycloalkyloxy, $C_{1-6}$alkylthio, $C_{1-6}$aminosulfonyl, $C_{1-6}$aminocarbonyloxy, $C_{1-6}$alkylsulfonylamino, $C_{1-6}$alkylsulfonylaminoC$_{1-3}$alkyl, $C_{6-10}$arylamino, $C_{6-10}$arylaminocarbonyl, $C_{6-10}$aryloxycarbonyl, $C_{1-4}$alkoxycarbamoyl, $C_{6-10}$arylcarbonylamino, $C_{6-10}$arylsulfonylamino, $C_{1-6}$alkylcarbonylamino, $C_{1-6}$alkenylcarbonylamino, $C_{3-6}$cycloalkenylcarbonylamino, $C_{3-6}$cycloalkylcarbonylamino, $C_{1-6}$heterocycloalkylcarbonylamino, $C_{1-6}$alkylsulfonyl, $C_{1-6}$heterocycloalkylsulfonyl, $C_{1-6}$heterocycloalkylsulfonylC$_{1-4}$alkyl, $C_{1-4}$alkylsulfonylaminocarbonyl, $C_{1-6}$alkyl, $C_{2-6}$alkenyl, $C_{2-6}$alkynyl, $C_{1-6}$hydroxyalkyl, aminoC$_{1-6}$alkyl, $C_{3-6}$cycloalkyl, $C_{3-6}$cycloalkenyl, $C_{1-6}$heterocycloalkyl or $C_{1-6}$heterocycloalkenyl
is optionally substituted with one or more, same or different substituents selected from the group consisting of halogen, trifluoromethyl, hydroxy, cyano, $C_{1-4}$alkyl or —C(O)NH$_2$;
$R_2$ represents $C_{1-6}$alkyl, $C_{2-6}$alkenyl, $C_{2-6}$alkynyl, $C_{1-6}$hydroxyalkyl, $C_{1-6}$haloalkyl, $C_{1-6}$amino, $C_{1-6}$alkoxy or $C_{3-6}$cycloalkyl;
or a pharmaceutically acceptable stereoisomers, salts or in vivo hydrolysable esters thereof.

In another aspect, the present invention relates to the use of a compound of general formula I as defined herein as a medicament in therapy.

In yet another aspect, the invention relates to the use of a compound of general formula I as defined herein in the treatment, amelioration or prophylaxis of physiological disorders or diseases associated with disturbances of CaSR activity, such as hyperparathyroidism.

In a still further aspect, the invention relates to the use of a compound of general formula I as defined herein for the manufacture of a medicament for the treatment, amelioration or prophylaxis of physiological disorders or diseases associated with disturbances of CaSR activity, such as hyperparathyroidism.

In a still further aspect, the invention relates to a pharmaceutical composition comprising a compound of general formula I as defined herein or a pharmaceutically acceptable stereoisomer, salt, or in vivo hydrolysable ester thereof together with a pharmaceutically acceptable vehicle or excipient.

In a still further aspect, the invention relates to a method of preventing, treating or ameliorating parathyroid carcinoma, parathyroid adenoma, primary parathyroid hyperplasia, cardiac, renal or intestinal dysfunctions, diseases of the central nervous system, chronic renal failure, chronic kidney disease, polycystic kidney disorder, podocyte-related diseases, primary hyperparathyroidism, secondary hyperparathyroidism, tertiary hyperparathyroidism, anemia, cardiovascular diseases, osteitis fibrosa, adynamic bone disease, osteoporosis, steroid induced osteoporosis, senile osteoporosis, post menopausal osteoporosis, osteomalacia and related bone disorders, bone loss post renal transplantation, gastrointestinal diseases, endocrine and neurodegenerative diseases, cancer, Alzheimer's disease, IBS, IBD, malassimilation, malneutrition, abnormal intestinal motility such as diarrhea, vascular calcification, abnormal calcium homeostasis, hypercalcemia, or renal bone diseases,
the method comprising administering to a patient in need thereof an effective amount of a compound of general formula I as defined herein, optionally in combination or as supplement with an active vitamin-D sterol or vitamin-D derivative, such as 1-α-hydroxycholecalciferol, ergocalciferol, cholecalciferol, 25-hydroxycholecalciferol, 1-α-25-dihydroxycholecalciferol, or in combination or as supplement with phosphate binders, estrogens, calcitonin or biphosphonates.

DETAILED DESCRIPTION OF THE INVENTION

Definitions

The term "cycloalkyl" is intended to indicate a saturated cycloalkane radical, comprising 3-7 carbon atoms, such as 4-7 or 3-6 carbon atoms, such as 4-6 or 5-6 carbon atoms, e.g. cyclopropyl, cyclobutyl, cyclopentyl, cyclohexyl or cycloheptyl.

The term "cycloalkenyl" is intended to indicate a mono-, or di-unsaturated non-aromatic cyclic hydrocarbon radical, comprising 3-7 carbon atoms, such as 4-7, such as 3-6 carbon atoms, such as 4-6 or preferably 5-6 carbon atoms, e.g. cyclobutenyl, cyclopentenyl, or cyclohexenyl.

The term "heterocycloalkyl" is intended to include a cycloalkyl radical as defined above, comprising 1-6 carbon atoms, in particular a 4-, 5- or 6-membered ring, comprising 1-5 carbon atoms and 1-5 hetero atoms (selected from O, S and N), such as 2-5 carbon atoms and 1-4 hetero atoms, or 3-5 carbon atoms and 1-3 hetero atoms selected from O, S, or N, e.g. piperidyl, piperidino, morpholino, morpholinyl, azetidinyl or isoxazolidinyl.

The term "heterocycloalkenyl" is intended to indicate a cycloalkenyl radical as defined above, comprising 2-6 carbon atoms, such as 2-6 carbon atoms, in particular a 5- or 6-membered ring, comprising 2-5 carbon atoms and 1-5 hetero atoms (selected from O, S and N), such as 3-5 carbon atoms and 1-3 hetero atoms, preferably 4-5 carbon atoms and 1-2 hetero atoms selected from O, S, or N.

The term "heterocycloalkylphenyl" is intended to include radicals of (a) heterocycloalkyl ring(s), in particular 5- or 6-membered ring, comprising 1-5 carbon atoms and 1-4 heteroatoms, selected from O, N or S, such as 2-5 carbon atoms and 1-3 heteroatoms, preferably 3-5 carbon atoms and 1-2 heteroatoms, the heterocycloalkyl ring being fused or annelated with phenyl, e.g. 2,3-dihydro-benzofuranyl, 1,3-benzodioxolyl, 2,3-dihydro-benzo[1,4]dioxinyl, 3,4-dihydro-2H-1,5-benzodioxepinyl or 3,4-dihydro-3-oxo-[2H]-1,4-benzoxazinyl.

The term "aryl" is intended to indicate a radical of (an) aromatic carbocyclic ring(s) comprising 6-20 carbon atoms, such as 6-14 carbon atoms, preferably 6-10 carbon atoms, in particular 6-membered rings, optionally fused or annelated carbocyclic rings with at least one aromatic ring, e.g. phenyl, naphthyl, 1-naphthyl or indanyl.

The term "heteroaryl" is intended to include radicals of (a) heterocyclic aromatic ring(s), comprising 1-4 heteroatoms (selected from O, S and N) and 1-9 carbon atoms, such as 1-4 heteroatoms and 2-9 carbon atoms, such as 1-3 heteroatoms and 3-9 carbon atoms, such as 1-2 heteroatoms and 3-5 carbon atoms, or such as 1-2 heteroatoms and 7-9 carbon atoms, preferably 5- or 6-membered rings with 1-3 heteroatoms and 3-9 carbon atoms, or 1-2 heteroatoms and 7-9 carbon atoms, or 1-2 heteroatoms and 3-5 carbon atoms selected from O, S and N, e.g. quinolinyl, 1H-indolyl, pyrazolyl, imidazo[1,2-a]pyridinyl, thiazolyl, thienyl, 1-benzo[b]thienyl, tetrazolyl, imidazo[1,5-a]pyridinyl, pyrazolo[1,5-a]pyridinyl, thiazolyl or benzo[b]thiophenyl.

The term "halogen" is intended to indicate a substituent from the $7^{th}$ main group of the periodic table, preferably fluoro, chloro, iodo or bromo.

In the present context, the term "alkyl" is intended to indicate the radical obtained when one hydrogen atom is removed from a hydrocarbon. Said alkyl comprises 1-6, preferably 1-4 or 1-3, such as 2-4 or 1-2 carbon atoms. The term includes the subclasses normal alkyl (n-alkyl), secondary and tertiary alkyl, e.g. methyl, ethyl, n-propyl, isopropyl, n-butyl, isobutyl, sec-butyl, tert-butyl, pentyl, isopentyl, hexyl or isohexyl.

The term "alkenyl" is intended to indicate a mono-, di-, or triunsaturated hydrocarbon radical comprising 2-6 carbon atoms, in particular 2-4 carbon atoms, such as 2-3 carbon atoms, e.g. vinyl, allyl, propenyl, butenyl, pentenyl or hexenyl.

The term "alkynyl" is intended to indicate a hydrocarbon radical comprising 1-4 C—C triple bonds, e.g. 1, 2 or 3 triple bonds and 2-6 carbon atoms, the alkane chain typically comprising 2-5 carbon atoms, in particular 2-4 carbon atoms, such as 2-3 carbon atoms, e.g. ethynyl, propynyl, butynyl or pentynyl.

The term "hydroxyalkyl" is intended to indicate an alkyl radical as defined above, wherein one, two, three or more hydrogen atoms are replaced by hydroxy, e.g. hydroxymethyl, hydroxyethyl, hydroxypropyl, hydroxybutyl etc.

The term "haloalkyl" is intended to indicate an alkyl radical as defined above, wherein one, two, three or more hydrogen atoms are replaced by halogen, same or different, such as iodo, chloro, bromo and/or fluoro, e.g. fluoroethyl, difluoroethyl, difluoromethyl or trifluoromethyl.

The term "alkoxy" is intended to indicate a radical of the formula —OR, wherein R is alkyl or alkenyl as indicated above, e.g. methoxy, ethoxy, n-propoxy, isopropoxy, butoxy, tert-butoxy.

The term "carboxyalkoxy" is intended to indicate a radical of the formula —OR—C(O)OH, wherein R is alkyl or alkenyl as indicated above, e.g. carboxymethoxy.

The term "methoxycarbonylalkyl" is intended to indicate a radical of the formula —R—C(O)—O—$CH_3$, wherein R is alkyl as indicated above, e.g. methoxycarbonylmethyl or methoxycarbonylethyl.

The term "alkylcarbonyl" is intended to indicate a radical of the formula —C(O)—R, wherein R represents alkyl as indicated above, e.g. methylcarbonyl, ethylcarbonyl.

The term "alkoxycarbonylalkoxy" is intended to indicate a radical of the formula —OR—C(O)—OR, wherein R is alkyl as indicated above, e.g. methoxycarbonylmethoxy, methoxycarbonylethoxy, ethoxycarbonylmethoxy, or ethoxycarbonylethoxy.

The term "alkylsulfonylaminocarbonylalkoxy" is intended to indicate a radical of the formula —OR—C(O)—NH—S$(O)_2$—R, wherein R is alkyl as indicated above, e.g. methylsulfonylaminocarbonylmethoxy.

The term "alkoxycarbonyl" is intended to indicate a radical of the formula —C(O)—O—R, wherein R is alkyl as indicated above, e.g. methoxycarbonyl, ethoxycarbonyl, n-propoxycarbonyl, isopropoxycarbonyl, or tert-butoxycarbonyl.

The term "methoxycarbonylalkyl" is intended to indicate a radical of the formula —R—C(O)—$OCH_3$, wherein R is alkyl as indicated above, e.g. methoxycarbonylmethyl, methoxycarbonylethyl, methocycarbonylpropyl.

The term "alkylcarbonyloxy" is intended to indicate a radical of the formula —O—C(O)—R, wherein R is alkyl as indicated above, e.g. methylcarbonyloxy, or ethylcarbonyloxy.

The term "alkoxycarbonyloxo" is intended to indicate a radical of the formula —O—C(O)—O—R, wherein R is alkyl as indicated above, e.g. methoxycarbonyloxo or ethoxycarbonyloxo.

The term "alkoxycarbamoyl" is intended to indicate a radical of the formula —C(O)NR'—O—R, wherein R' is hydrogen or alkyl as indicated above, and R is alkyl as indicated above, e.g. methoxycarbamoyl.

The term "amino" is intended to indicate a radical of the formula —NRR', wherein R and R' independently represent hydrogen, alkyl or alkenyl, as indicated above, e.g. methylamino, ethylamino, propylamino, dimethylamino, diethylamino or isopropylamino.

The term "aminoalkyl" in intended to indicate an alkyl radical as defined above wherein one or two hydrogen atoms are replaced by —$NH_2$, e.g. aminomethyl, aminoethyl or aminopropyl.

The term "aminocarbonyloxy" is intended to indicate a radical of the formula —O—C(O)—NRR', wherein R and R' independently represent hydrogen or alkyl as indicated above.

The term "amidino" is intended to indicate the radical —C(=NH)$NH_2$.

The term "iminomethyl" is intended to indicate the radical —CH=NH.

The term "hydroxyiminomethyl" is intended to indicate the radical —CH=N—(OH).

The term "cycloalkylamino" is intended to indicate a radical of the formula —NRR', wherein R represents hydrogen or alkyl and R' represents cycloalkyl as indicated above.

The term "arylamino" is intended to indicate a radical of the formula —NRR', wherein R represents hydrogen or alkyl as indicated above and R' represents aryl as indicated above.

The term "heterocycloalkylcarbonyl" is intended to indicate a radical of the formula —C(O)—R, wherein R is heterocycloalkyl as indicated below, e.g. azetidinylmethanoyl, isoxazolidinylmethanoyl.

The term "aminocarbonyl" is intended to indicate a radical of the formula —C(O)—NR'$_2$, wherein each R' is independently hydrogen, alkyl, alkenyl or cycloalkyl as indicated above, e.g. methylaminocarbonyl or ethylaminocarbonyl.

The term "hydroxyaminocarbonyl" is intended to indicate a radical of the formula —C(O)—NR'—OH, wherein R' is independently hydrogen or alkyl as indicated above.

The term "amino-aminocarbonyl" is intended to indicate a radical of the formula —C(O)—NHR'—NR", wherein R' and R" are independently alkyl or hydrogen as indicated above, e.g. aminoethylaminocarbonyl.

The term "di($C_{1-6}$alkyl)amino$C_{1-6}$alkylaminocarbonyl" is intended to indicate a radical of the formula —C(O)—NHR'—NR'$_2$, wherein R' is independently alkyl as indicated above, e.g. diethylaminoethylaminocarbonyl.

The term "alkylheterocycloalkylcarbonyl," is intended to indicate a radical of the formula —C(O)-heterocycloalkyl-R', wherein heterocycloalkyl is as indicated above and R' is alkyl as indicated above, e.g. ethylpiperazinylcarbonyl.

The term "alkylheterocycloalkylaminocarbonyl" is intended to indicate a radical of the formula —C(O)—NH-heterocycloalkyl-R', wherein heterocycloalkyl is as indicated above and R' is alkyl as indicated above, e.g. ethylpiperidinylaminocarbonyl.

The term "alkylsulfonylheterocycloalkylcarbonyl" is intended to indicate a radical of the formula —C(O)-heterocycloalkyl-S$(O)_2$—R', wherein heterocycloalkyl is as indicated above and R' is alkyl as indicated above, e.g. methylsulfonylpiperazinylcarbonyl.

The term "arylaminocarbonyl" is intended to indicate a radical of the formula —C(O)—NR'-aryl, wherein R' is independently hydrogen or alkyl as indicated above and aryl is as indicated above.

The term "heteroarylaminocarbonyl" is intended to indicate a radical of the formula —C(O)—NR'-heteroaryl, wherein R' is independently hydrogen or alkyl as indicated above and heteroaryl is as indicated above.

The term "cycloalkylaminocarbonyl" is intended to indicate a radical of the formula —C(O)—NR'-cycloalkyl, wherein R' is independently hydrogen or alkyl as indicated above and cycloalkyl is as indicated, above.

The term "heterocycloalkylaminocarbonyl" is intended to indicate a radical of the formula —C(O)—NR'-heterocycloalkyl, wherein R' is independently hydrogen or alkyl as indicated above and heterocycloalkyl is as indicated above, e.g. piperidylaminocarbonyl, oxetanylaminocarbonyl.

The term "heterocycloalkyloxy" is intended to indicate a radical of the formula —O—R, wherein R is a heterocycloalkyl as indicated above.

The term "aminosulfonyl" is intended to indicate a radical of the formula —S$(O)_2$—$NR_2$, wherein each R independently represents hydrogen or alkyl as indicated above, e.g. methylaminosulfonyl or ethylaminosulfonyl.

The term "alkylsulfonylaminocarbonyl" is intended to indicate a radical of the formula —C(O)—NR'—S$(O)_2$—R, wherein R' is independently hydrogen, alkyl or cycloalkyl as indicated above and R is alkyl as indicated above.

The term "aryloxycarbonyl" is intended to indicate a radical of the formula —C(O)—O—R wherein R is aryl as indicated above.

The term "alkylthio" is intended to indicate a radical of the formula —S—R, wherein R is alkyl as indicated above.

The term "alkylsulfonyl" is intended to indicate a radical of the formula —S(O)₂—R, wherein R is alkyl as indicated above, e.g. methylsulfonyl.

The term "heterocycloalkylsulfonyl" is intended to indicate a radical of the formula —S(O)₂—R, wherein R is a heterocycloalkyl as indicated above, e.g. morpholinesulfonyl.

The term "heterocycloalkylsulfonylalkyl" is intended to indicate a radical of the formula —R'—S(O)₂—R, wherein R' is alkyl as indicated above and R is a heterocycloalkyl as indicated above, e.g. morpholinesulfonyl.

The term "alkylcarbonylamino" is intended to indicate a radical of the formula —NR'—C(O)—R, wherein R' is hydrogen or alkyl as indicated above, and R is alkyl as indicated above, e.g. methylcarbonylamino.

The term "alkylcarbonylaminomethyl" is intended to indicate a radical of the formula —R—NR'—C(O)—R, wherein R' is hydrogen or alkyl as indicated above, and R is alkyl as indicated above, e.g. methylcarbonylaminomethyl.

The term "alkoxycarbonylamino" is intended to indicate a radical of the formula —NR'—C(O)—O—R, wherein R' is hydrogen or alkyl as indicated above, and R is alkyl as indicated above.

The term "alkylsulfonylamino" is intended to indicate a radical of the formula —NR'—S(O)₂—R, wherein R is alkyl as indicated above, and R' is hydrogen or alkyl as indicated above, e.g. methylsulfonylamino, ethylsulfonylamino, propylsulfonylamino or butylsulfonylamino.

The term "alkylsulfonylaminoalkyl" is intended to indicate a radical of the formula —R—NR'—S(O)₂—R, wherein R is alkyl as indicated above, and R' is hydrogen or alkyl as indicated above, e.g. methylsulfonylaminomethyl.

The term "arylsulfonylamino" is intended to indicate a radical of the formula —NR'—S(O)₂—R, wherein R is aryl as indicated above, and R' is hydrogen, or alkyl as indicated above.

The term "alkoxysulfonyloxy" is intended to represent a radical of the formula —O—S(O)₂—O—R, wherein R is alkyl as indicated above.

The term "arylcarbonylamino" is intended to indicate a radical of the formula —NR'—C(O)—R, wherein R' is hydrogen or alkyl as indicated above, and R is aryl as indicated above.

The term "alkenylcarbonylamino" is intended to indicate a radical of the formula —NR'—C(O)—R, wherein R' is hydrogen or alkyl as indicated above, and R is alkenyl as indicated above.

The term "cycloalkylcarbonylamino" is intended to indicate a radical of the formula —NR'—C(O)—R, wherein R' is hydrogen or alkyl as indicated above, and R is cycloalkyl as indicated above.

The term "cycloalkenylcarbonylamino" is intended to indicate a radical of the formula —NR'—C(O)—R, wherein R' is hydrogen or alkyl as indicated above, and R is cycloalkenyl as indicated above.

The term "heterocycloalkylcarbonylamino" is intended to indicate a radical of the formula —NR'—C(O)—R, wherein R' is hydrogen or alkyl as indicated above, and R is heterocycloalkyl as indicated above.

The term "ureido" is intended to indicate a radical of the formula "—NR'—C(O)—NH—R, wherein R' is hydrogen or alkyl as indicated above, and R is hydrogen, alkyl, alkenyl, alkynyl, cycloalkyl or aryl as indicated above.

The term "thioureido" is intended to indicate a radical of the formula "—NR'—C(S)—NH—R, wherein R' is hydrogen or alkyl as indicated above, and R is hydrogen, alkyl, or cycloalkyl as indicated above.

The term "pharmaceutically acceptable salt" is intended to indicate salts prepared by reacting a compound of formula I with a suitable inorganic or organic acid, such as hydrochloric, hydrobromic, hydroiodic, sulfuric, nitric, phosphoric, formic, acetic, 2,2-dichloroacetic, choline, adipic, ascorbic, L-aspartic, L-glutamic, galactaric, lactic, maleic, L-malic, phthalic, citric, propionic, benzoic, glutaric, gluconic, D-glucuronic, methanesulfonic, salicylic, succinic, malonic, tartaric, benzenesulfonic, ethane-1,2-disulfonic, 2-hydroxy ethanesulfonic acid, toluenesulfonic, sulfamic or fumaric acid. Pharmaceutically acceptable salts of compounds of formula I may also be prepared by reaction with a suitable base such as sodium hydroxide, potassium hydroxide, magnesium hydroxide, calcium hydroxide, ammonia, or suitable non-toxic amines, such as lower alkylamines, for example triethylamine, hydroxy-lower alkylamines, for example 2-hydroxyethylamine, bis-(2-hydroxyethyl)-amine, cycloalkylamines, for example dicyclohexylamine, or benzylamines, for example N,N'-dibenzylethylene-diamine, and dibenzylamine, or L-arginine or L-lysine.

The term "pharmaceutically acceptable in vivo hydrolysable ester" is intended to indicate easily in vivo hydrolysable esters, i.e. in vivo hydrolysable esters of the compounds of formula I such as alkanoyloxyalkyl, aralkanoyloxyalkyl, aroyloxyalkyl, e.g. acetoxymethyl, pivaloyloxymethyl, benzoyloxymethyl esters and the corresponding 1'-oxyethyl derivatives, or alkoxycarbonyloxyalkyl esters, e.g. methoxycarbonyloxymethyl esters and ethoxycarbonyloxymethyl esters and the corresponding 1'-oxyethyl derivatives, or lactonyl esters, e.g. phthalidyl esters, or dialkylaminoalkyl esters, e.g. dimethylaminoethyl esters. Such esters may be prepared by conventional methods known to persons skilled in the art.

Compounds of formula I may comprise asymmetrically substituted (chiral) carbon atoms and carbon-carbon double bonds which may give rise to the existence of isomeric forms, e.g. enantiomers, diastereomers and geometric isomers. The present invention includes all such isomers, either in pure form or as mixtures thereof. Pure stereoisomeric forms of the compounds and the intermediates of this invention may be obtained by the application of procedures known in the art. Diastereomers may be separated by physical separation methods such as selective crystallization and chromatographic techniques, e.g. liquid chromatography using chiral stationary phases. Enantiomers may be separated from each other by the selective crystallization of their diastereomeric salts with optically active acids. Alternatively, enantiomers may be separated by chromatographic techniques using chiral stationary phases. Said pure stereoisomeric forms may also be derived from the corresponding pure stereoisomeric forms of the appropriate starting materials, provided that the reaction occurs stereoselectively or stereospecifically. Preferably, if a specific stereoisomer is desired, said compound will be synthesized by stereoselective or stereospecific methods of preparation. These methods will advantageously employ chirally pure starting materials. Likewise, pure geometric isomers may be obtained from the corresponding pure geometric isomers of the appropriate starting materials. A mixture of geometric isomers will typically exhibit different physical properties, and they may thus be separated by standard chromatographic techniques well-known in the art.

The present invention further includes prodrugs of compounds of general formula I, such as esters, ethers, complexes or other derivatives which undergo a biotransformation in vivo before exhibiting their pharmacological effects.

The compounds of formula I may be obtained in crystalline form either directly by concentration from an organic solvent or by crystallisation or recrystallisation from an organic solvent or mixture of said solvent and a cosolvent that may be organic or inorganic, such as water. The crystals may be isolated in essentially solvent-free form or as a solvate, such as a hydrate. The invention covers all crystalline modifications and forms and also mixtures thereof.

Embodiments

In one embodiment of the present invention $R_1$ represents halogen, cyano, —$NH_2$, hydroxy, mercapto, —C(O)H, —C(O)$NH_2$, nitro, oxo, iminomethyl, hydroxyiminomethyl, amidino, trifluoromethyl, cyano$C_{1-4}$aminocarbonyl, $C_{1-4}$hydroxyalkyl, $C_{1-6}$amino, $C_{1-4}$alkoxy, hydroxy$C_{1-4}$aminosulfonyl, aminocarbonyl$C_{1-4}$alkoxy, $C_{1-4}$alkylcarbonyl, $C_{1-4}$aminocarbonyl, $NH_2$—$C_{1-4}$aminocarbonyl, $C_{1-4}$amino$C_{1-4}$aminocarbonyl, hydroxy$C_{1-3}$amino$C_{1-3}$aminocarbonyl, di(hydroxy$C_{1-4}$alkyl)amino$C_{1-4}$alkylaminocarbonyl, aminosulfonyl$C_{1-3}$alkylaminocarbonyl, $C_{1-3}$alkylsulfonylaminocarbonyl$C_{1-3}$alkoxy, $C_{1-3}$carbonylamino$C_{1-3}$alkylaminocarbonyl, aminocarbonyl$C_{1-4}$alkylaminocarbonyl, hydroxy$C_{1-4}$aminocarbonyl, $C_{3-6}$cycloalkylaminocarbonyl, $C_{1-5}$heterocycloalkylaminocarbonyl, $C_{1-5}$heterocycloalkyl-N-methyl-aminocarbonyl, $C_{3-6}$cycloalkylamino, $C_{1-5}$heterocycloalkylcarbonyl, hydroxy$C_{1-3}$alkyl$C_{1-6}$heterocycloalkylcarbonyl, hydroxy$C_{1-3}$alkyl$C_{1-6}$heterocycloalkylaminocarbonyl, hydroxy$C_{1-5}$heterocycloalkylcarbonyl, $C_{1-3}$alkylsulfonyl$C_{1-6}$heterocycloalkylcarbonyl, oxo$C_{1-4}$heterocycloalkylcarbonyl, $C_{6-10}$aryl, $C_{1-5}$heteroaryl, $C_{1-5}$heteroarylaminocarbonyl, $C_{1-4}$alkylsulfonylamino$C_{1-4}$aminocarbonyl, —S(O)$_2$$NH_2$, $C_{1-4}$ureido, $C_{1-4}$thioureido, $C_{1-4}$alkoxysulfonyloxy, $C_{1-5}$heterocycloalkyloxy, $C_{1-4}$aminosulfonyl, hydroxy$C_{1-4}$aminosulfonyl, $C_{1-4}$aminocarbonyloxy, $C_{1-4}$alkylsulfonylamino, $C_{1-4}$alkylsulfonylamino$C_{1-3}$alkyl, $C_{6-10}$arylamino, $C_{6-10}$arylaminocarbonyl, $C_{6-10}$aryloxycarbonyl, $C_{1-4}$alkoxycarbamoyl, $C_{6-10}$arylcarbonylamino, $C_{6-10}$arylsulfonylamino, $C_{1-4}$-alkylcarbonylamino, $C_{1-4}$alkenylcarbonylamino, $C_{3-6}$cycloalkenylcarbonylamino, $C_{3-6}$cycloalkylcarbonylamino, $C_{1-5}$heterocycloalkylcarbonylamino, $C_{1-4}$alkylsulfonyl, $C_{1-5}$heterocycloalkylsulfonyl, $C_{1-5}$heterocycloalkylsulfonyl$C_{1-3}$alkyl or $C_{1-4}$alkylsulfonylaminocarbonyl.

In another embodiment of the present invention $R_1$ represents oxo, halogen, trifluoromethyl, C(O)$NH_2$, cyano, cyanomethylaminocarbonyl, $C_{1-3}$hydroxyalkyl, $C_{1-3}$alkoxy, $C_{1-3}$alkylcarbonylamino, $C_{1-3}$alkylcarbonylaminomethyl, $NH_2$—$C_{1-3}$aminocarbonyl, $C_{1-3}$amino$C_{1-3}$aminocarbonyl, di(hydroxy$C_{1-3}$alkyl)amino$C_{1-3}$alkylaminocarbonyl, hydroxy$C_{1-3}$amino$C_{1-3}$aminocarbonyl, methylcarbonylamino$C_{1-3}$aminocarbonyl, $C_{1-3}$alkylsulfonylamino$C_{1-3}$aminocarbonyl, $C_{3-6}$heterocycloalkylaminocarbonyl, $C_{3-5}$heterocycloalkyl-N-methyl-aminocarbonyl, $C_{3-5}$heterocycloalkylcarbonyl, hydroxy$C_{1-3}$alkyl$C_{3-5}$heterocycloalkylcarbonyl, hydroxy$C_{1-3}$alkyl$C_{3-5}$heterocycloalkylaminocarbonyl, hydroxy$C_{3-6}$heterocycloalkylcarbonyl, $C_{1-3}$alkylsulfonyl$C_{3-5}$heterocycloalkylcarbonyl, oxo $C_{1-4}$heterocycloalkylcarbonyl, aminocarbonyl$C_{1-3}$alkoxy, $C_{1-5}$heteroaryl, $C_{1-3}$alkylsulfonyl, hydroxy$C_{1-3}$aminosulfonyl, hydroxy$C_{1-3}$aminocarbonyl, $C_{1-5}$heterocycloalkylsulfonyl, hydroxy$C_{1-3}$aminocarbonyl, $C_{1-5}$heterocycloalkylsulfonyl, $C_{3-5}$heterocycloalkylsulfonyl$C_{1-3}$alkyl, $C_{1-3}$alkylsulfonylamino, aminosulfonyl$C_{1-3}$alkylaminocarbonyl, $C_{1-3}$alkylsulfonylaminocarbonyl$C_{1-33}$alkoxy, aminocarbonyl$C_{1-3}$alkylaminocarbonyl or $C_{1-3}$alkylsulfonylaminomethyl.

In another embodiment of the present invention, $R_1$ represents oxo, hydroxymethyl, piperidylaminocarbonyl, oxetanyl-N-methyl-aminocarbonyl, tetrazolyl, hydroxyethylaminocarbonyl, aminoethylaminocarbonyl, di(hydroxyethyl)aminoethylaminocarbonyl, hydroxyethylaminoethylaminocarbonyl, cyanomethylaminocarbonyl, hydroxyethylaminosulfonyl, hydroxyethylaminocarbonyl, methylsulfonyl, aminocarbonylmethoxy, morpholinosulfonyl, morpholinocarbonyl, azetidinylcarbonyl, isoxazolidinylcarbonyl, hydroxypiperidinocarbonyl, piperazinylcarbonyl, hydroxyethylpiperazinylcarbonyl, hydroxyethylpiperidinylaminocarbonyl, oxopiperazinylcarbonyl, methylsulfonylpiperazinylcarbonyl, hydroxypyrrolidinylcarbonyl, aminosulfonylethylaminocarbonyl, methylsulfonylaminoethylaminocarbonyl, methylsulfonylamino, methylsulfonylaminomethyl, methylsulfonylaminocarbonylmethoxy, morpholinosulfonylethyl, methylcarbonylamino, methylcarbonylaminoethylaminocarbonyl, aminocarbonylmethylaminocarbonyl, aminocarbonylethylaminocarbonyl or methylcarbonylaminomethyl.

In yet another embodiment of the present invention, $R_1$ represents —S(O)$_2$$NH_2$, $C_{1-4}$alkoxysulfonyloxy, $C_{1-6}$aminosulfonyl, $C_{1-6}$alkylsulfonylamino, $C_{1-6}$alkylsulfonylamino$C_{1-3}$alkyl, $C_{6-10}$arylsulfonylamino, $C_{1-6}$alkylsulfonyl, $C_{1-6}$heterocycloalkylsulfonyl or $C_{1-6}$ heterocycloalkylsulfonyl$C_{1-4}$alkyl, wherein said $C_{1-4}$alkoxysulfonyloxy, $C_{1-6}$aminosulfonyl, $C_{1-6}$alkylsulfonylamino, $C_{1-6}$alkylsulfonylamino$C_{1-3}$alkyl, $C_{6-10}$arylsulfonylamino, $C_{1-6}$alkylsulfonyl, $C_{1-6}$heterocycloalkylsulfonyl or $C_{1-6}$ heterocycloalkylsulfonyl$C_{1-4}$alkyl, is optionally substituted with one or more, same or different substituents selected from the group consisting of halogen, trifluoromethyl, hydroxy, cyano, $C_{1-4}$alkyl or —C(O)$NH_2$; such as —S(O)$_2$$NH_2$, $C_{1-6}$aminosulfonyl, $C_{1-6}$alkylsulfonyl or $C_{1-6}$heterocycloalkylsulfonyl, wherein said $C_{1-6}$aminosulfonyl, $C_{1-6}$alkylsulfonyl or $C_{1-6}$heterocycloalkylsulfonyl is optionally substituted with one or more, same or different substituents selected from the group consisting of halogen, trifluoromethyl, hydroxy, cyano, $C_{1-4}$alkyl or —C(O)$NH_2$;

In yet another embodiment of the present invention, $R_1$ represents —C(O)H, —C(O)$NH_2$, $C_{1-6}$alkylcarbonyl, $C_{1-6}$aminocarbonyl, hydroxyaminocarbonyl, $C_{1-4}$alkylcarbonylamino$C_{1-6}$alkylaminocarbonyl, $C_{3-6}$cycloalkylaminocarbonyl, $C_{1-6}$heterocycloalkylaminocarbonyl, $C_{1-6}$alkylsulfonylamino$C_{1-6}$aminocarbonyl, aminocarbonyl $C_{1-6}$alkylaminocarbonyl, $C_{1-6}$heterocycloalkylcarbonyl, oxo$C_{1-6}$heterocycloalkylcarbonyl, $C_{1-6}$heteroarylaminocarbonyl, $C_{6-10}$arylaminocarbonyl, $C_{1-4}$alkoxycarbamoyl, $C_{1-4}$alkylsulfonylaminocarbonyl, aminosulfonyl$C_{1-3}$alkylaminocarbonyl, wherein said $C_{1-6}$alkylcarbonyl, $C_{1-6}$aminocarbonyl, $C_{3-6}$cycloalkylaminocarbonyl, $C_{1-6}$heterocycloalkylaminocarbonyl, $C_{1-6}$heterocycloalkylcarbonyl, $C_{1-6}$heteroarylaminocarbonyl, $C_{6-10}$arylaminocarbonyl, $C_{6-10}$aryloxycarbonyl, $C_{1-4}$alkoxycarbamoyl, $C_{1-4}$alkylsulfonylaminocarbonyl, is optionally substituted with one or more, same or different substituents selected from the group consisting of halogen, trifluoromethyl, hydroxy, cyano, $C_{1-4}$alkyl or —C(O)$NH_2$;

In yet another embodiment of the present invention, A represents phenyl, $C_{6-9}$heterocycloalkylphenyl, $C_{2-9}$heteroaryl or $C_{3-7}$cycloalkyl, wherein said phenyl, $C_{6-9}$heterocycloalkylphenyl, $C_{2-9}$heteroaryl or $C_{3-7}$cycloalkyl is optionally further substituted with one or more, same or different substituents represented by halogen, hydroxy, trifluoromethyl, cyano, carboxy, —C(O)H, —NH$_2$, —C(O)NH$_2$, C$_{2-6}$alkenyl, C$_{2-6}$alkynyl, C$_{1-6}$hydroxyalkyl, C$_{1-6}$haloalkyl, C$_{1-4}$alkoxy, C$_{3-6}$cycloalkyl or phenyl.

In yet another embodiment of the present invention, A represents phenyl or phenyl substituted with one or more, same or different substituents represented by halogen, hydroxy, trifluoromethyl, cyano, carboxy, —C(O)H, —NH$_2$, —C(O)NH$_2$, C$_{1-6}$alkyl, C$_{2-6}$alkenyl, C$_{2-6}$alkynyl, C$_{1-6}$hydroxyalkyl, C$_{1-4}$alkoxy, C$_{3-6}$cycloalkyl or phenyl.

In yet another embodiment of the present invention, A represents phenyl substituted with one or more, same or different substituents selected from fluoro, chloro, bromo, iodo, methoxy, ethoxy, isopropoxy, n-propoxy, n-butoxy, isobutoxy, sec-butoxy, tert-butoxy, cyano or trifluoromethyl.

In yet another embodiment of the present invention, A represents 3-chloro-phenyl, 3,4-dichloro-phenyl, 3-fluoro-phenyl, 3,4-difluoro-phenyl, 3-chloro-4-fluoro-phenyl, 3-trifluoromethyl-phenyl, 3-trifluoromethyl-4-fluoro-phenyl, 3-methoxy-phenyl, 3-ethoxy-phenyl, 3,4-dimethoxy-phenyl, 3,5-dimethoxy-phenyl, 2-fluoro-5-methoxy-phenyl, 3-fluoro-5-methoxy-phenyl, 4-fluoro-3-methoxy-phenyl, 2-fluoro-3-methoxy-phenyl, 3-fluoro-4-methoxy-phenyl, 4-fluoro-2-methoxy-phenyl, 2,3-dimethoxy-phenyl, 3-iso-propoxy-phenyl, 3-ethoxy-phenyl or 3-cyano-4-fluoro-phenyl.

In yet another embodiment of the present invention, A represents C$_3$-C$_9$heteroaryl optionally further substituted with one or more, same or different substituents selected from oxo, halogen, hydroxy, trifluoromethyl, cyano, carboxy, —C(O)H, —NH$_2$, —C(O)NH$_2$, C$_{1-6}$alkyl, C$_{2-6}$alkenyl, C$_{2-6}$alkynyl, C$_{1-6}$hydroxyalkyl, C$_{1-4}$alkoxy, C$_{3-6}$cycloalkyl or phenyl.

In yet another embodiment of the present invention, A represents C$_3$-C$_9$heteroaryl optionally further substituted with one or more, same or different substituents selected from oxo, fluoro, chloro, bromo, iodo, methyl, methoxy, ethoxy, isopropoxy, n-propoxy, n-butoxy, isobutoxy, sec-butoxy, tert-butoxy, cyano, trifluoromethyl or phenyl.

In yet another embodiment of the invention, A represents quinolonyl, imidazo[1,2-a]pyridinyl, 5-fluoro-imidazo[1,2-a]pyridinyl, imidazo[1,5-a]pyridinyl, pyrazolo[1,5-a]pyridinyl, pyrazolyl substituted with phenyl and methyl, thiazolyl substituted with methyl, thiophenyl substituted with chloro or benzo[b]thiophenyl.

In yet another embodiment of the present invention, A represents C$_3$-C$_9$heterocycloalkylphenyl optionally further substituted with one or more, same or different substituents selected from halogen and oxo.

In yet another embodiment of the invention, A represents 2,3-Dihydro-benzofuranyl, 1,3-benzodioxolyl, 2,2-difluoro-benzodioxolyl, 2,3-dihydro-benzo[1,4]dioxinyl, 3,4-dihydro-2H-1,5-benzodioxepinyl, 3,4-dihydro-3-oxo-[2H]-1,4-benzoxazinyl, In yet another embodiment of the present invention, A represents cyclopropyl, cyclobutyl, cyclooentyl, cyclohexyl or cycloheptyl, each of which are optionally further substituted with one or more, same or different substituents selected from halogen, hydroxy, trifluoromethyl, cyano, carboxy, —C(O)H, —NH$_2$, —C(O)NH$_2$, C$_{1-6}$alkyl, C$_{2-6}$alkenyl, C$_{2-6}$alkynyl, C$_{1-6}$hydroxyalkyl, C$_{1-6}$haloalkyl, C$_{1-4}$alkoxy or phenyl.

In yet another embodiment of the present invention, X represents CH.

In yet another embodiment of the present invention, X represents N.

In yet another embodiment of the present invention, X represents N and R$_1$ represents oxo.

In yet another embodiment of the present invention, R$_2$ represents methyl.

Specific examples of compounds of formula I may be selected from the group consisting of (1R)—(N)-[(1R/S,3S)-3-(4-methanesulfonylphenyl)cyclopentyl]-1-(1,3-benzodioxol-4-yl)ethanamine (compound 1000), (1R)—(N)-[(1R/S,3S)-3-(4-methanesulfonylphenyl)cyclopentyl]-1-(1,3-benzodioxol-5-yl)ethanamine (compound 1001), (1R)—(N)-[(1R/S,3S)-3-(4-methanesulfonylphenyl)cyclopentyl]-1-(1-methyl-5-phenyl-pyrazol-3-yl)ethanamine (compound 1002), (1R)—(N)-[(1R/S,3S)-3-(4-methanesulfonylphenyl)cyclopentyl]-1-(2,2-difluoro-1,3-benzodioxol-4-yl)ethanamine (compound 1003), (1R)—(N)-[(1R/S,3S)-3-(4-methanesulfonylphenyl)cyclopentyl]-1-(2,3-dihydro-1,4-benzodioxin-5-yl)ethanamine (compound 1004), (1R)—(N)-[(1R/S,3S)-3-(4-methanesulfonylphenyl)cyclopentyl]-1-(2,3-dihydrobenzofuran-5-yl)ethanamine (compound 1005), (1R)—(N)-[(1R/S,3S)-3-(4-methanesulfonylphenyl)cyclopentyl]-1-(2,3-dimethoxyphenyl)ethanamine (compound 1006), (1R)—(N)-[(1R/S,3S)-3-(4-methanesulfonylphenyl)cyclopentyl]-1-(2-fluoro-3-methoxy-phenyl)ethanamine (compound 1007), (1R)—(N)-[(1R/S,3S)-3-(4-methanesulfonylphenyl)cyclopentyl]-1-(2-fluoro-5-methoxy-phenyl)ethanamine (compound 1008), (1R)—(N)-[(1R/S,3S)-3-(4-methanesulfonylphenyl)cyclopentyl]-1-(2-methylthiazol-4-yl)ethanamine (compound 1009), (1R)—(N)-[(1R/S,3R)-3-(4-methanesulfonylphenyl)cyclopentyl]-1-(3-chloro-4-fluoro-phenyl)ethanamine (compound 1010), (1R)—(N)-[(1R/S,3S)-3-(4-methanesulfonylphenyl)cyclopentyl]-1-(3-ethoxyphenyl)ethanamine (compound 1011), (1R)—(N)-[(1R/S,3S)-3-(4-methanesulfonylphenyl)cyclopentyl]-1-(3-fluoro-5-methoxyphenyl)ethanamine (compound 1012), (1R)—(N)-[(1R/S,3S)-3-(4-methanesulfonylphenyl)cyclopentyl]-1-(4-fluoro-2-methoxyphenyl)ethanamine (compound 1013), (1R)—(N)-[(1R/S,3S)-3-(4-methanesulfonylphenyl)cyclopentyl]-1-(4-fluoro-3-methoxyphenyl)ethanamine (compound 1014), (1R)—(N)-[(1R/S,3R)-3-(4-methanesulfonylphenyl)cyclopentyl]-1-(4-quinolyl)ethanamine (compound 1015), (1R)—(N)-[(1R/S,3R)-3-(4-methanesulfonylphenyl)cyclopentyl]-1-(5-chloro-2-thienyl)ethanamine (compound 1016), (1R)—(N)-[(1R/S,3S)-3-(4-methanesulfonylphenyl)cyclopentyl]-1-(8-quinolyl)ethanamine (compound 1017), (1R)—(N)-[(1R/S,3S)-3-(4-methanesulfonylphenyl)cyclopentyl]-1-[3-(methylethoxy)phenyl]ethanamine (compound 1018), (1R)—(N)-[(1R/S,3S)-3-(4-methanesulfonylphenyl)cyclopentyl]-1-[4-fluoro-3-(trifluoromethyl)phenyl]ethanamine (compound 1019), (1R)—(N)-[(1R/S,3S)-3-(4-methanesulfonylphenyl)cyclopentyl]-1-cyclopropylethanamine (compound 1020), (1R)—(N)-[(1R/S,3S)-3-(4-methanesulfonylphenyl)cyclopentyl]-1-imidazo[1,2-a]pyridin-3-ylethanamine (compound 1021), (1R)—(N)-[(1R/S,3S)-3-(4-methanesulfonylphenyl)cyclopentyl]-1-imidazo[1,5-a]pyridin-3-ylethanamine (compound 1022), (1R)—(N)-[(1R/S,3S)-3-(4-methanesulfonylphenyl)cyclopentyl]-1-pyrazolo[1,5-a]pyridin-3-ylethanamine (compound 1023), (1R)—(N)-[(1R/S,3S)-3-(4-methanesulfonylphenyl)cyclopentyl]-1-cyclohexylethanamine (compound 1024), (1R)—(N)-[(1R/S,3S)-3-(4-methanesulfonylphenyl)cyclopentyl]-1-(3-fluoro-4-methoxyphenyl)ethanamine (compound 1025), (1R)—(N)-[(1R/S,3S)-3-(4-methanesulfonylphenyl)cyclopentyl]-1-(3-fluorophenyl)ethanamine (compound 1026), (1R)—(N)-[(1R/S,3R/S)-3-(4-methanesulfonylphenyl)cyclopentyl]-1-(3-methoxyphenyl)ethanamine (compound 1027), (1R)—(N)-[(1R/S,3S)-3-(4-methanesulfonylphenyl)cyclopentyl]-1-[3-(trifluoromethyl)phenyl]ethanamine (compound 1028), (1R)—(N)-[(1R/S,3S)-3-(4-methanesulfonylphenyl)cyclopentyl]-1-benzo[b]thiophen-3-yl-ethanamine (compound 1029), (1R)—(N)-[(1R/S,3S)-3-(4-methanesulfonylphenyl)cyclopentyl]-1-(3-cyano-4-fluorophenyl)ethanamine (compound 1030), (1R/S)—(N)-[(1R/S,3S)-3-(4-methanesulfonylphenyl)cyclopentyl]-1-(3,4-dihydro-3-oxo-[2H]-1,4-benzoxazin-6-yl)ethanamine (compound 1031), (1R)—(N)-[(1R/S,3S)-3-[4-(1H-tetrazol-5-yl)phenyl]cyclopentyl]-1-(1,3-benzodioxol-4-yl)ethanamine (compound 1032), (1R)—(N)-[(1R/S,3S)-3-[4-(1H-tetrazol-5-yl)phenyl]cyclopentyl]-1-(2,3-dihydro-1,4-benzodioxin-5-yl)ethanamine (compound 1033), (1R)—(N)-[(1R/S,3S)-3-[4-(1H-tetrazol-5-yl)phenyl]cyclopentyl]-1-(4-fluoro-2-methoxyphenyl)ethanamine (compound 1034), (1R)—(N)-[(1R/S,3S)-3-[4-(1H-tetrazol-5-yl)phenyl]cyclopentyl]-1-(4-fluoro-3-methoxyphenyl)ethanamine (compound 1035), (1R)—(N)-[(1R/S,3S)-3-[4-(1H-tetrazol-5-yl)phenyl]cyclopentyl]-1-(3-chlorophenyl)ethanamine (compound 1036), (1R)—(N)-[(1R/S,3S)-3-[4-(4-hydroxypiperidine-1-carbonyl)phenyl]cyclopentyl]-1-(1,3-benzodioxol-4-yl)ethanamine (compound 1037), (1R)—(N)-[(1R/S,3S)-3-[4-(4-hydroxypiperidine-1-carbonyl)phenyl]cyclopentyl]-1-(1-isoquinolyl)ethanamine (compound 1038), (1R)—(N)-[(1R/S,3S)-3-[4-(4-hydroxypiperidine-1-carbonyl)phenyl]cyclopentyl]-1-(3,4-dichlorophenyl)ethanamine (compound 1039), (1R)—(N)-[(1R/S,3S)-3-[4-(4-hydroxypiperidine-1-carbonyl)phenyl]cyclopentyl]-1-(3,4-difluorophenyl)ethanamine (compound 1040), (1R)—(N)-[(1R/S,3S)-3-[4-(4-hydroxypiperidine-1-carbonyl)phenyl]cyclopentyl]-1-(3,4-dihydro-2H-1,5-benzodioxepin-6-yl)ethanamine (compound 1041), (1R)—(N)-[(1R/S,3S)-3-[4-(4-hydroxypiperidine-1-carbonyl)phenyl]cyclopentyl]-1-(3,4-dimethoxyphenyl)ethanamine (compound 1042), (1R)—(N)-[(1R/S,3S)-3-[4-(4-hydroxypiperidine-1-carbonyl)phenyl]cyclopentyl]-1-(3,5-dimethoxyphenyl)ethanamine (compound 1043), (1R)—(N)-[(1R/S,3R)-3-[4-(4-hydroxypiperidine-1-carbonyl)phenyl]cyclopentyl]-1-(3-chloro-4-fluoro-phenyl)ethanamine (compound 1044), (1R)—(N)-[(1R/S,3S)-3-[4-(4-hydroxypiperidine-1-carbonyl)phenyl]cyclopentyl]-1-(3-fluoro-5-methoxyphenyl)ethanamine (compound 1045), (1R)—(N)-[(1R/S,3S)-3-[4-(4-hydroxypiperidine-1-carbonyl)phenyl]cyclopentyl]-1-(4-fluoro-2-methoxyphenyl)ethanamine (compound 1046), (1R)—(N)-[(1R/S,3S)-3-[4-(4-hydroxypiperidine-1-carbonyl)phenyl]cyclopentyl]-1-(4-fluoro-3-methoxyphenyl)ethanamine (compound 1047), (1R)—(N)-[(1R/S,3S)-3-[4-(4-hydroxypiperidine-1-carbonyl)phenyl]cyclopentyl]-1-pyrazolo[1,5-a]pyridin-3-ylethanamine (compound 1048), (1R)—(N)-[(1R/S,3S)-3-[4-(4-hydroxypiperidine-1-carbonyl)phenyl]cyclopentyl]-1-benzo[b]thiophen-3-yl-ethanamine (compound 1049), (1R)—(N)-[(3S)-(1R/S,3S)-3-[4-[3-hydroxypyrrolidin-1-ylcarbonyl]phenyl]-cyclopentyl]-1-(3-ethoxyphenyl)ethanamine (compound 1050), (1R)—(N)-[(3S)-(1R/S,3S)-3-[4-[3-hydroxypyrrolidin-1-ylcarbonyl]phenyl]-cyclopentyl]-1-(4-fluoro-3-methoxyphenyl)ethanamine (compound 1051), (1R)—(N)-[(3S)-(1R/S,3S)-3-[4-[3-hydroxypyrrolidin-1-ylcarbonyl]phenyl]-cyclopentyl]-1-(3-chlorophenyl)ethanamine (compound 1052), (1R)—(N)-[(3S)-(1R/S,3S)-3-[4-[3-hydroxypyrrolidin-1-ylcarbonyl]phenyl]-cyclopentyl]-1-benzo[b]thiophen-3-yl-ethanamine (compound 1053), (1R)—(N)-[(1R/S,3R/S)-3-[4-acetamidophenyl]cyclopentyl]-1-(3-methoxyphenyl)-ethanamine (compound 1054), (1R)—(N)-[(1R/S,3R/S)-3-[4-methanesulfonylaminophenyl]cyclopentyl]-1-(3-methoxyphenyl)ethanamine (compound 1055), (1R)—(N)-[(1R/S,3R)-3-[4-[aminocarbonylmethoxy]phenyl]cyclopentyl]-1-(1,3-benzodioxol-4-yl)ethanamine (compound 1056), (1R)—(N)-[(1R/S,3R)-3-[4-[aminocarbonylmethoxy]phenyl]cyclopentyl]-1-(3-chloro-4-fluoro-phenyl)ethanamine (compound 1057), (1R)—(N)-[(1R/S,3R)-3-[4-[aminocarbonylmethoxy]phenyl]cyclopentyl]-1-(3-ethoxyphenyl)ethanamine (compound 1058), (1R)—(N)-[(1R/S,3R)-3-[4-(aminocarbonylmethoxy)-phenyl]cyclopentyl]-1-(4-fluoro-2-methoxyphenyl)ethanamine (compound 1059), (1R)—(N)-[(1R/S,3R)-3-[4-(aminocarbonylmethoxy)-phenyl]cyclopentyl]-1-(4-fluoro-3-methoxyphenyl)ethanamine (compound 1060), (1R)—(N)-[(1R/S,3R)-3-[4-[aminocarbonylmethoxy]phenyl]cyclopentyl]-1-(3-chlorophenyl)ethanamine (compound 1061), (1R)—(N)-[(1R/S,3R/S)-3-[3-methylsulfonylaminophenyl]cyclopentyl]-1-(3-methoxyphenyl)ethanamine (compound 1062), (1R)—(N)-[(1R/S,3R/S)-3-[4-morpholinosulfonylphenyl]cyclopentyl]-1-(3-methoxyphenyl)ethanamine (compound 1063), (1R)—(N)-[(1R/S,3R/S)-3-[4-hydroxymethylphenyl]cyclopentyl]-1-(3-methoxyphenyl)ethanamine (compound 1064), (1R)—(N)-[(1R/S,3R/S)-3-[4-methanesulfonylaminophenyl]cyclopentyl]-1-(3-methoxyphenyl)ethanamine (compound 1065), (1R)—(N)-[(1R/S,3S)-3-[4-(2-(aminosulfonyl)ethylaminocarbonyl)phenyl]-cyclopentyl]-1-(1,3-benzodioxol-4-yl)ethanamine (compound 1066), (1R)—(N)-[(1R/S,3S)-3-[4-(2-(aminosulfonyl)ethylaminocarbonyl)phenyl]-cyclopentyl]-1-(3-ethoxyphenyl)ethanamine (compound 1067), (1R)—(N)-[(1R/S,3S)-3-[4-(2-(aminosulfonyl)ethylaminocarbonyl)phenyl]-cyclopentyl]-1-(4-fluoro-2-methoxyphenyl)ethanamine (compound 1068), (1R)—(N)-[(1R/S,3S)-3-[4-(2-(aminosulfonyl)ethylaminocarbonyl)phenyl]-cyclopentyl]-1-(4-fluoro-3-methoxyphenyl)ethanamine (compound 1069), (1R)—(N)-[(1R/S,3S)-3-[4-(2-(aminosulfonyl)ethylaminocarbonyl)phenyl]-cyclopentyl]-1-(3-chlorophenyl)ethanamine (compound 1070), (1R)—(N)-[(1R/S,3S)-3-[4-(2-(aminosulfonyl)ethylaminocarbonyl)phenyl]cyclopentyl]-1-benzo[b]thiophen-3-yl-ethanamine (compound 1071), (1R)—(N)-[(1R/S,3S)-3-[4-(3-oxo-piperazinylcarbonyl)phenyl]cyclopentyl]-1-(1,3-benzodioxol-4-yl)ethanamine (compound 1072), (1R)—(N)-[(1R/S,3S)-3-[4-(3-oxo-piperazinylcarbonyl)phenyl]cyclopentyl]-1-(3-ethoxyphenyl)ethanamine (compound 1073), (1R)—(N)-[(1R/S,3S)-3-[4-(3-oxo-piperazinylcarbonyl)phenyl]cyclopentyl]-1-(4-fluoro-3-methoxyphenyl)ethanamine (compound 1074), (1R)—(N)-[(1R/S,3S)-3-[4-(3-oxo-piperazinylcarbonyl)phenyl]cyclopentyl]-1-(3-chlorophenyl)ethanamine (compound 1075), (1R)—(N)-[(1R/S,3S)-3-[4-(3-oxo-piperazinylcarbonyl)phenyl]cyclopentyl]-1-benzo[b]thiophen-3-yl-ethanamine (compound 1076), (1R)—(N)-[(1R/S,3R/S)-3-[4-(acetamidomethyl)phenyl]cyclopentyl]-1-(3-methoxyphenyl)ethanamine (compound 1077), (1R)—(N)-[(1R/S,3S)-3-[2-hydroxypyridin-5-yl]cyclopentyl]-1-(1,3-benzodioxol-4-yl)ethanamine (compound 1078), (1R)—(N)-[(1R/S,3S)-3-[2-hydroxypyridin-5-yl]cyclopentyl]-1-(1,3-benzodioxol-5-yl)ethanamine (compound 1079), (1R)—(N)-[(1R/S,3S)-3-[2-hydroxypyridin-5-yl]cyclopentyl]-1-(1-methyl-5-phenyl-pyrazol-3-yl)ethanamine (compound 1080), (1R)—(N)-[(1R/S,3S)-3-[2-hydroxypyridin-5-yl]cyclopentyl]-1-(2,3-dihydro-1,4-benzodioxin-5-yl)ethanamine (compound 1081), (1R)—(N)-[(1R/S,3S)-3-[2-hydroxypyridin-5-yl]cyclopentyl]-1-(2,3-dihydrobenzofuran-5-yl)ethanamine (compound 1082), (1R)—(N)-[(1R/S,3S)-3-[2-hydroxypyridin-5-yl]cyclopentyl]-1-(2,3-dimethoxyphenyl)ethanamine (compound 1083), (1R)—(N)-[(1R/S,3S)-3-[2-hydroxypyridin-5-yl]cyclopentyl]-1-(2-fluoro-3-methoxy-phenyl)ethanamine (compound 1084), (1R)—(N)-[(1R/S,3S)-3-[2-hydroxypyridin-5-yl]cyclopentyl]-1-(2-fluoro-5-methoxy-phenyl)ethanamine (compound 1085), (1R)—(N)-[(1R/S,3S)-3-[2-hydroxypyridin-5-yl]cyclopentyl]-1-(2-methylthiazol-4-yl)ethanamine (compound 1086), (1R)—(N)-[(1R/S,3S)-3-[2-hydroxypyridin-5-yl]cyclopentyl]-1-(3-fluoro-5-methoxyphenyl)ethanamine (compound 1087), (1R)—(N)-[(1R/S,3S)-3-[2-hydroxypyridin-5-yl]cyclopentyl]-1-(4-fluoro-2-methoxyphenyl)ethanamine (compound 1088), (1R)—(N)-[(1R/S,3S)-3-[2-hydroxypyridin-5-yl]cyclopentyl]-1-(4-fluoro-3-methoxyphenyl)ethanamine (compound 1089), (1R)—(N)-[(1R/S,3S)-3-[2-hydroxypyridin-5-yl]cyclopentyl]-1-(8-quinolyl)ethanamine (compound 1090), (1R)—(N)-[(1R/S,3S)-3-[2-hydroxypyridin-5-yl]cyclopentyl]-1-cyclopropylethanamine (compound 1091), (1R)—(N)-[(1R/S,3S)-3-[2-hydroxypyridin-5-yl]cyclopentyl]-1-imidazo[1,2-a]pyridin-3-ylethanamine (compound 1092), (1R)—(N)-[(1R/S,3S)-3-[2-hydroxypyridin-5-yl]cyclopentyl]-1-pyrazolo[1,5-a]pyridin-3-ylethanamine (compound 1093), (1R)—(N)-[(1R/S,3S)-3-[2-hydroxypyridin-5-yl]cyclopentyl]-1-cyclohexylethanamine (compound 1094), (1R)—(N)-[(1R/S,3S)-3-[2-hydroxypyridin-5-yl]cyclopentyl]-1-(3-chlorophenyl)ethanamine (compound 1095), (1R)—(N)-[(1R/S,3S)-3-[2-hydroxypyridin-5-yl]cyclopentyl]-1-(3-fluoro-4-methoxyphenyl)ethanamine (compound 1096), (1R)—(N)-[(1R/S,3S)-3-[2-hydroxypyridin-5-yl]cyclopentyl]-1-(3-fluorophenyl)ethanamine (compound 1097), (1R)—(N)-[(1R/S,3S)-3-[2-hydroxypyridin-5-yl]cyclopentyl]-1-[3-(trifluoromethyl)phenyl]ethanamine (compound 1098), (1R)—(N)-[(1R/S,3S)-3-[2-hydroxypyridin-5-yl]cyclopentyl]-1-benzo[b]thiophen-3-yl-ethanamine (compound 1099), (1R/S)—(N)-[(1R/S,3S)-3-[2-hydroxypyridin-5-yl]cyclopentyl]-1-pyrimidin-4-ylethanamine (compound 1100), (1R)—(N)-[(1R/S,3S)-3-[2-hydroxypyridin-5-yl]cyclopentyl]-1-(3-cyano-4-fluorophenyl)ethanamine (compound 1101), (1R)—(N)-[(1R/S,3S)-3-(4-(2-(acetamido)ethylaminocarbonyl)phenyl)-cyclopentyl]-1-(1,3-benzodioxol-4-yl)ethanamine (compound 1102), (1R)—(N)-[(1R/S,3S)-3-(4-(2-(acetamido)ethylaminocarbonyl)phenyl)-cyclopentyl]-1-(3-ethoxyphenyl)ethanamine (compound 1103), (1R)—(N)-[(1R/S,3S)-3-(4-(2-(acetamido)ethylaminocarbonyl)phenyl)-cyclopentyl]-1-(4-fluoro-2-methoxyphenyl)ethanamine (compound 1104), (1R)—(N)-[(1R/S,3S)-3-(4-(2-(acetamido)ethylaminocarbonyl)phenyl)-cyclopentyl]-1-(4-fluoro-3-methoxyphenyl)ethanamine (compound 1105), (1R)—(N)-[(1R/S,3S)-3-(4-(2-(acetamido)ethylaminocarbonyl)phenyl)-cyclopentyl]-1-(3-chlorophenyl)ethanamine (compound 1106), (1R)—(N)-[(1R/S,3S)-3-(4-(2-(acetamido)ethylaminocarbonyl)phenyl)-cyclopentyl]-1-benzo[b]thiophen-3-yl-ethanamine (compound 1107), (1R)—(N)-[(1R/S,3S)-3-[4-(aminocarbonylmethylaminocarbonyl)phenyl]-cyclopentyl]-1-(3-ethoxyphenyl)ethanamine (compound 1108), (1R)—(N)-[(1R/S,3S)-3-[4-(aminocarbonylmethylaminocarbonyl)phenyl]-cyclopentyl]-1-(4-fluoro-2-methoxyphenyl)ethanamine (compound 1109), (1R)—(N)-[(1R/S,3S)-3-[4-(aminocarbonylmethylaminocarbonyl)phenyl]-cyclopentyl]-1-(4-fluoro-3-methoxyphenyl)ethanamine (compound 1110), (1R)—(N)-[(1R/S,3S)-3-[4-(aminocarbonylmethylaminocarbonyl)phenyl]-cyclopentyl]-1-benzo[b]thiophen-3-yl-ethanamine (compound 1111), (1R)—(N)-[(1R/S,3S)-3-[4-(2-hydroxyethylaminosulfonyl)phenyl]cyclopentyl]-1-(3,4-difluorophenyl)ethanamine (compound 1112

(1R)—(N)-[(1R/S,3S)-3-[4-(2-hydroxyethylaminosulfonyl)phenyl]cyclopentyl]-1-(3,4-dihydro-2H-1,5-benzodioxepin-6-yl)ethanamine (compound 1113), (1R)—(N)-[(1R/S,3S)-3-[4-(2-hydroxyethylaminosulfonyl)phenyl]cyclopentyl]-1-(3,4-dimethoxyphenyl)ethanamine (compound 1114), (1R)—(N)-[(1R/S,3S)-3-[4-(2-hydroxyethylaminosulfonyl)phenyl]cyclopentyl]-1-(3-fluoro-5-methoxyphenyl)ethanamine (compound 1115), (1R)—(N)-[(1R/S,3S)-3-[4-(2-hydroxyethylaminosulfonyl)phenyl]cyclopentyl]-1-(4-fluoro-2-methoxyphenyl)ethanamine (compound 1116), (1R)—(N)-[(1R/S,3S)-3-[4-(2-hydroxyethylaminosulfonyl)phenyl]cyclopentyl]-1-(4-fluoro-3-methoxyphenyl)ethanamine (compound 1117), (1R)—(N)-[(1R/S,3S)-3-[4-(2-hydroxyethylaminocarbonyl)phenyl]cyclopentyl]-1-(3-chloro-4-fluoro-phenyl)ethanamine (compound 1118), (1R)—(N)-[(1R/S,3S)-3-[4-(2-hydroxyethylaminocarbonyl)phenyl]cyclopentyl]-1-(3-ethoxyphenyl)ethanamine (compound 1119), (1R)—(N)-[(1R/S,3S)-3-[4-(2-hydroxyethylaminocarbonyl)phenyl]cyclopentyl]-1-(3-fluoro-5-methoxyphenyl)ethanamine (compound 1120), (1R)—(N)-[(1R/S,3S)-3-[4-(2-hydroxyethylaminocarbonyl)phenyl]cyclopentyl]-1-(4-fluoro-3-methoxyphenyl)ethanamine (compound 1121), (1R)—(N)-[(1R/S,3S)-3-[4-(2-hydroxyethylaminocarbonyl)phenyl]cyclopentyl]-1-(3-chlorophenyl)ethanamine (compound 1122), (1R)—(N)-[(1R/S,3S)-3-[4-(2-hydroxyethylaminocarbonyl)phenyl]cyclopentyl]-1-benzo[b]thiophen-3-yl-ethanamine (compound 1123), (1R)—(N)-[(1R/S,3S)-3-[4-(cyanomethylaminocarbonyl)phenyl]cyclopentyl]-1-(3-chloro-4-fluoro-phenyl)ethanamine (compound 1124), (1R)—(N)-[(1R/S,3S)-3-[4-(cyanomethylaminocarbonyl)phenyl]cyclopentyl]-1-(3-ethoxyphenyl)ethanamine (compound 1125), (1R)—(N)-[(1R/S,3S)-3-[4-(cyanomethylaminocarbonyl)phenyl]cyclopentyl]-1-(3-fluoro-5-methoxyphenyl)ethanamine (compound 1126), (1R)—(N)-[(1R/S,3S)-3-[4-(cyanomethylaminocarbonyl)phenyl]cyclopentyl]-1-(4-fluoro-2-methoxyphenyl)ethanamine (compound 1127), (1R)—(N)-[(1R/S,3S)-3-[4-(cyanomethylaminocarbonyl)phenyl]cyclopentyl]-1-(4-fluoro-3-methoxyphenyl)ethanamine (compound 1128), (1R)—(N)-[(1R/S,3S)-3-[4-(cyanomethylaminocarbonyl)phenyl]cyclopentyl]-1-(3-chlorophenyl)ethanamine (compound 1129), (1R)—(N)-[(1R/S,3S)-3-[4-(cyanomethylaminocarbonyl)phenyl]cyclopentyl]-1-benzo[b]thiophen-3-yl-ethanamine (compound 1130), (1R)—(N)-[(1R/S,3S)-3-[4-(2-(methanesulfonylamino)-ethylaminocarbonyl)-phenyl]cyclopentyl]-1-(3-ethoxyphenyl)ethanamine (compound 1131), (1R)—(N)-[(1R/S,3S)-3-[4-(2-(methanesulfonylamino)-ethylaminocarbonyl)-phenyl]cyclopentyl]-1-(3-fluoro-5-methoxyphenyl)ethanamine (compound 1132), (1R)—(N)-[(1R/S,3S)-3-[4-(2-(methanesulfonylamino)-ethylaminocarbonyl)-phenyl]cyclopentyl]-1-(4-fluoro-2-methoxyphenyl)ethanamine (compound 1133), (1R)—(N)-[(1R/S,3S)-3-[4-(2-(methanesulfonylamino)-ethylaminocarbonyl)-phenyl]cyclopentyl]-1-(4-fluoro-3-methoxyphenyl)ethanamine (compound 1134), (1R)—(N)-[(1R/S,3S)-3-[4-(2-(methanesulfonylamino)-ethylaminocarbonyl)-phenyl]cyclopentyl]-1-(3-chlorophenyl)ethanamine (compound 1135), (1R)—(N)-[(1R/S,3S)-3-[4-(2-(methanesulfonylamino)-ethylaminocarbonyl)-phenyl]cyclopentyl]-1-benzo[b]thiophen-3-yl-ethanamine (compound 1136), (1R)—(N)-[(1R/S,3R)-3-[4-[methanesulfonylaminocarbonylmethoxy]phenyl]-cyclopentyl]-1-(1,3-benzodioxol-4-yl)ethanamine (compound 1137), (1R)—(N)-[(1R/S,3R)-3-[4-[methanesulfonylaminocarbonylmethoxy]phenyl]-cyclopentyl]-1-(3-chloro-4-fluorophenyl)ethanamine (compound 1138), (1R)—(N)-[(1R/S,3R)-3-[4-[methanesulfonylaminocarbonylmethoxy]phenyl]-cyclopentyl]-1-(3-ethoxyphenyl)ethanamine (compound 1139), (1R)—(N)-[(1R/S,3R)-3-[4-(methanesulfonylaminocarbonylmethoxy)-phenyl]cyclopentyl]-1-(3-fluoro-5-methoxyphenyl)ethanamine (compound 1140), (1R)—(N)-[(1R/S,3R)-3-[4-(methanesulfonylaminocarbonylmethoxy)-phenyl]cyclopentyl]-1-(4-fluoro-2-methoxyphenyl)ethanamine (compound 1141), (1R)—(N)-[(1R/S,3R)-3-[4-(methanesulfonylaminocarbonylmethoxy)-phenyl]cyclopentyl]-1-(4-fluoro-3-methoxyphenyl)ethanamine (compound 1142), (1R)—(N)-[(1R/S,3S)-3-[4-[piperidin-4-ylaminocarbonyl]phenyl]cyclopentyl]-1-(1,3-benzodioxol-4-yl)ethanamine (compound 1143), (1R)—(N)-[(1R/S,3S)-3-[4-[piperidin-4-ylaminocarbonyl]phenyl]cyclopentyl]-1-(1,3-benzodioxol-5-yl)ethanamine (compound 1144), (1R)—(N)-[(1R/S,3S)-3-[4-[piperidin-4-ylaminocarbonyl]phenyl]cyclopentyl]-1-(1-methyl-5-phenyl-pyrazol-3-yl)ethanamine (compound 1145), (1R)—(N)-[(1R/S,3S)-3-[4-[piperidin-4-ylaminocarbonyl]phenyl]cyclopentyl]-1-(2,2-difluoro-1,3-benzodioxol-4-yl)ethanamine (compound 1146), (1R)—(N)-[(1R/S,3S)-3-[4-[piperidin-4-ylaminocarbonyl]phenyl]cyclopentyl]-1-(2,3-dihydro-1,4-benzodioxin-5-yl)ethanamine (compound 1147), (1R)—(N)-[(1R/S,3S)-3-[4-[piperidin-4-ylaminocarbonyl]phenyl]cyclopentyl]-1-(2,3-dihydrobenzofuran-5-yl)ethanamine (compound 1148), (1R)—(N)-[(1R/S,3S)-3-[4-[piperidin-4-ylaminocarbonyl]phenyl]cyclopentyl]-1-(2,3-dimethoxyphenyl)ethanamine (compound 1149), (1R)—(N)-[(1R/S,3S)-3-[4-[piperidin-4-ylaminocarbonyl]phenyl]cyclopentyl]-1-(2-fluoro-3-methoxy-phenyl)ethanamine (compound 1150), (1R)—(N)-[(1R/S,3S)-3-[4-[piperidin-4-ylaminocarbonyl]phenyl]cyclopentyl]-1-(2-fluoro-5-methoxy-phenyl)ethanamine (compound 1151), (1R)—(N)-[(1R/S,3S)-3-[4-[piperidin-4-ylaminocarbonyl]phenyl]cyclopentyl]-1-(2-methylthiazol-4-yl)ethanamine (compound 1152), (1R)—(N)-[(1R/S,3S)-3-[4-[piperidin-4-ylaminocarbonyl]phenyl]cyclopentyl]-1-(3-chloro-4-fluoro-phenyl)ethanamine (compound 1153), (1R)—(N)-[(1R/S,3S)-3-[4-[piperidin-4-ylaminocarbonyl]phenyl]cyclopentyl]-1-(3-ethoxyphenyl)ethanamine (compound 1154), (1R)—(N)-[(1R/S,3S)-3-[4-[piperidin-4-ylaminocarbonyl]phenyl]cyclopentyl]-1-(3-fluoro-5-methoxyphenyl)ethanamine (compound 1155), (1R)—(N)-[(1R/S,3S)-3-[4-[piperidin-4-ylaminocarbonyl]phenyl]cyclopentyl]-1-(4-fluoro-2-methoxyphenyl)ethanamine (compound 1156),
(1R)—(N)-[(1R/S,3S)-3-[4-[piperidin-4-ylaminocarbonyl]phenyl]cyclopentyl]-1-(4-fluoro-3-methoxyphenyl)ethanamine (compound 1157),
(1R)—(N)-[(1R/S,3S)-3-[4-[piperidin-4-ylaminocarbonyl]phenyl]cyclopentyl]-1-(5-chloro-2-thienyl)ethanamine (compound 1158),
(1R)—(N)-[(1R/S,3S)-3-[4-[piperidin-4-ylaminocarbonyl]phenyl]cyclopentyl]-1-(5-fluoroimidazo[1,2-a]pyridin-2-yl)ethanamine (compound 1159),
(1R)—(N)-[(1R/S,3S)-3-[4-[piperidin-4-ylaminocarbonyl]phenyl]cyclopentyl]-1-(8-quinolyl)ethanamine (compound 1160),
(1R)—(N)-[(1R/S,3S)-3-[4-[piperidin-4-ylaminocarbonyl]phenyl]cyclopentyl]-1-[3-(methylethoxy)phenyl]ethanamine (compound 1161),
(1R)—(N)-[(1R/S,3S)-3-[4-[piperidin-4-ylaminocarbonyl]phenyl]cyclopentyl]-1-[4-fluoro-3-(trifluoromethyl)phenyl]ethanamine (compound 1162),
(1R)—(N)-[(1R/S,3S)-3-[4-[piperidin-4-ylaminocarbonyl]phenyl]cyclopentyl]-1-cyclopropylethanamine (compound 1163),
(1R)—(N)-[(1R/S,3S)-3-[4-[piperidin-4-ylaminocarbonyl]phenyl]cyclopentyl]-1-imidazo[1,5-a]pyridin-3-ylethanamine (compound 1164),
(1R)—(N)-[(1R/S,3S)-3-[4-[piperidin-4-ylaminocarbonyl]phenyl]cyclopentyl]-1-pyrazolo[1,5-a]pyridin-3-ylethanamine (compound 1165),
(1R)—(N)-[(1R/S,3S)-3-[4-[piperidin-4-ylaminocarbonyl]phenyl]cyclopentyl]-1-(3-chlorophenyl)ethanamine (compound 1166),
(1R)—(N)-[(1R/S,3S)-3-[4-[piperidin-4-ylaminocarbonyl]phenyl]cyclopentyl]-1-(3-fluoro-4-methoxyphenyl)ethanamine (compound 1167),
(1R)—(N)-[(1R/S,3S)-3-[4-[piperidin-4-ylaminocarbonyl]phenyl]cyclopentyl]-1-(3-fluorophenyl)ethanamine (compound 1168),
(1R)—(N)-[(1R/S,3S)-3-[4-[piperidin-4-ylaminocarbonyl]phenyl]cyclopentyl]-1-[3-(trifluoromethyl)phenyl]ethanamine (compound 1169),
(1R)—(N)-[(1R/S,3S)-3-[4-[piperidin-4-ylaminocarbonyl]phenyl]cyclopentyl]-1-benzo[b]thiophen-3-yl-ethanamine (compound 1170),
(1R/S)—(N)-[(1R/S,3S)-3-[4-[piperidin-4-ylaminocarbonyl]phenyl]cyclopentyl]-1-pyrimidin-4-ylethanamine (compound 1171), or
(1R)—(N)-[(1R/S,3S)-3-[4-[piperidin-4-ylaminocarbonyl]phenyl]cyclopentyl]-1-(3-cyano-4-fluorophenyl)ethanamine (compound 1172).
(4-{(1R,3S)-3-[(1R)-1-(4-Fluoro-3-methoxy-phenyl)-ethylamino]-cyclopentyl}-phenyl)-(3-hydroxy-azetidin-1-yl)-methanone (compound 1173),
4-{(1R,3S)-3-[(1R)-1-(4-Fluoro-3-methoxy-phenyl)-ethylamino]-cyclopentyl}-N-methyl-N-oxetan-3-yl-benzamide (compound 1174),
(4-{(1R,3S)-3-[(1R)-1-(4-Fluoro-3-methoxy-phenyl)-ethylamino]-cyclopentyl}-phenyl)-isoxazolidin-2-yl-methanone (compound 1175),
4-{(1R,3S)-3-[(1R)-1-(4-Fluoro-3-methoxy-phenyl)-ethylamino]-cyclopentyl}-N-(2-hydroxy-ethyl)-benzamide (Compound 1176),
(4-{(1R,3S)-3-[(1R)-1-(4-Fluoro-3-methoxy-phenyl)-ethylamino]-cyclopentyl}-phenyl)-(3-hydroxy-pyrrolidin-1-yl)-methanone (compound 1177),
4-{(1R,3S)-3-[(1R)-1-(4-Fluoro-3-methoxy-phenyl)-ethylamino]-cyclopentyl}-N-(2-methanesulfonylamino-ethyl)-benzamide hydrochloride (compound 1178),
4-(4-{(1R,3S)-3-[(1R)-1-(4-Fluoro-3-methoxy-phenyl)-ethylamino]-cyclopentyl}-benzoyl)-piperazin-2-one (compound 1179),
(1R/S,3R)—N-[(1R)-1-(4-fluoro-3-methoxy-phenyl)ethyl]-3-[4-(2-morpholinosulfonylethyl)-phenyl]cyclopentanamine (mixture of 2 isomers) (compound 1180),
N-[[4-[(1R/S,3R/S)-3-[[(1R)-1-(4-fluoro-3-methoxy-phenyl)ethyl]amino]cyclopentyl]phenyl]methyl]methanesulfonamide (mixture of 4 isomers) (compound 1181),
(1S,3R)—N-[(1R)-1-(4-fluoro-3-methoxy-phenyl)ethyl]-3-[4-(1H-tetrazol-5-yl)phenyl]cyclopentanamine (compound 1182),
[4-[(1S,3R/S)-3-[[(1R)-1-(3-ethoxyphenyl)ethyl]amino]cyclopentyl]phenyl]-morpholino-methanone (compound 1183),
[4-[(1S,3R/S)-3-[[(1R)-1-(3-chlorophenyl)ethyl]amino]cyclopentyl]phenyl]-morpholino-methanone (compound 1184),
[4-[(1S,3R/S)-3-[[(1R)-1-(4-fluoro-3-methoxy-phenyl)ethyl]amino]cyclopentyl]phenyl]-morpholino-methanone (compound 1185),
N-(3-amino-3-oxo-propyl)-4-[(1S,3R/S)-3-[[(1R)-1-(1,3-benzodioxol-4-yl)ethyl]amino]cyclopentyl]benzamide (compound 1186),
4-[(1R,3S)-3-[[(1R)-1-(4-fluoro-3-methoxy-phenyl)ethyl]amino]cyclopentyl]-N-(2-hydroxyethyl)benzenesulfonamide (compound 1187),
N-(3-amino-3-oxo-propyl)-4-[(1S,3R/S)-3-[[(1R)-1-(3-ethoxyphenyl)ethyl]amino]-cyclopentyl]benzamide (compound 1188),
N-(3-amino-3-oxo-propyl)-4-[(1S,3R/S)-3-[[(1R)-1-(4-fluoro-3-methoxy-phenyl)ethyl]amino]cyclopentyl]benzamide (compound 1189),
N-{2-[Bis-(2-hydroxy-ethyl)-amino]-ethyl}-4-{(1R,3S)-3-[(1R)-1-(4-fluoro-3-methoxy-phenyl)-ethylamino]-cyclopentyl}-benzamide (Compound 1190),
(N)-[(1S,3R)-3-[4-(4-hydroxypiperidine-1-carbonyl)phenyl]cyclopentyl]-(1R)-1-(4-fluoro-3-methoxyphenyl)ethylamine (Compound 1191),
(N)-[(1S,3R)-3-[4-(4-hydroxypiperidine-1-carbonyl)phenyl]cyclopentyl]-(1R)-1-(3-ethoxyphenyl)-ethanamine (Compound 1192),
(N)-[(1S,3R)-3-[4-(4-hydroxypiperidine-1-carbonyl)phenyl]cyclopentyl]-(1R)-1-(3-chlorophenyl)ethanamine (Compound 1193),
(N)-[(1S,3R)-3-[4-(4-hydroxypiperidine-1-carbonyl)phenyl]cyclopentyl]-(1R)-1-(1,3-benzodioxol-4-yl)ethanamine (Compound 1194),
(N)-[(1S,3R)-3-[4-(4-hydroxypiperidine-1-carbonyl)phenyl]cyclopentyl]-(1R)-1-(3-fluoro-5-methoxy-phenyl)-ethanamine (Compound 1195),
(N)-[(1S,3R)-3-[4-(4-hydroxypiperidine-1-carbonyl)phenyl]cyclopentyl]-(1R)-1-(2,3-Dihydro-benzo[1,4]dioxin-5-yl)-ethylamine (Compound 1196),
(N)-[(1S,3R)-3-[4-[(3S)-3-hydroxypyrrolidin-1-ylcarbonyl]phenyl]cyclopentyl]-(1R)-1-(4-fluoro-3-methoxyphenyl)ethylamine (Compound 1197),
(N)-[(1S,3R)-3-[4-[(3S)-3-hydroxypyrrolidin-1-ylcarbonyl]phenyl]cyclopentyl]-(1R)-1-(3-ethoxyphenyl)-ethanamine (Compound 1198),
(N)-[(1S,3R)-3-[4-[(3S)-3-hydroxypyrrolidin-1-ylcarbonyl]phenyl]cyclopentyl]-(1R)-1-(3-chlorophenyl)ethanamine (Compound 1199), (N)-[(1S,3R)-3-[4-[(3S)-3-hydroxypyrrolidin-1-ylcarbonyl]phenyl]cyclopentyl]-(1R)-1-(1,3-benzodioxol-4-yl)ethanamine (Compound 1200), (N)-[(1S,3R)-3-[4-[(3S)-3-hydroxypyrrolidin-1-ylcarbonyl]phenyl]cyclopentyl]-(1R)-1-(3-fluoro-5-methoxy-phenyl)-ethanamine (Compound 1201), (N)-[(1S,3R)-3-[4-[(3S)-3-hydroxypyrrolidin-1-ylcarbonyl]phenyl]cyclopentyl]-(1R)-1-(2,3-Dihydro-benzo[1,4]dioxin-5-yl)-ethylamine (Compound 1202), (N)-[(1S,3R)-3-[4-(2-(aminosulfonyl)ethylaminocarbonyl)phenyl]cyclopentyl]-(1R)-1-(4-fluoro-3-methoxyphenyl)ethylamine (Compound 1203), (N)-[(1S,3R)-3-[4-(2-(aminosulfonyl)ethylaminocarbonyl)phenyl]cyclopentyl]-(1R)-1-(3-ethoxyphenyl)-ethanamine (Compound 1204), (N)-[(1S,3R)-3-[4-(2-(aminosulfonyl)ethylaminocarbonyl)phenyl]cyclopentyl]-(1R)-1-(3-chlorophenyl)ethanamine (Compound 1205), (N)-[(1S,3R)-3-[4-(2-(aminosulfonyl)ethylaminocarbonyl)phenyl]cyclopentyl]-(1R)-1-(1,3-benzodioxol-4-yl)ethanamine (Compound 1206), (N)-[(1S,3R)-3-[4-(2-(aminosulfonyl)ethylaminocarbonyl)phenyl]cyclopentyl]-(1R)-1-(3-fluoro-5-methoxy-phenyl)-ethanamine (Compound 1207), (N)-[(1S,3R)-3-[4-(2-(aminosulfonyl)ethylaminocarbonyl)phenyl]cyclopentyl]-(1R)-1-(2,3-Dihydro-benzo[1,4]dioxin-5-yl)-ethylamine (Compound 1208), (N)-[(1S,3R)-3-[4-(3-oxo-piperazinylcarbonyl)phenyl]cyclopentyl]-(1R)-1-(3-fluoro-5-methoxy-phenyl)-ethanamine (Compound 1209), (N)-[(1S,3R)-3-[4-(3-oxo-piperazinylcarbonyl)phenyl]cyclopentyl]-(1R)-1-(3-ethoxyphenyl)-ethanamine (Compound 1210), (N)-[(1S,3R)-3-[4-(3-oxo-piperazinylcarbonyl)phenyl]cyclopentyl]-(1R)-1-(3-chlorophenyl)ethanamine (Compound 1211), (N)-[(1S,3R)-3-[4-(3-oxo-piperazinylcarbonyl)phenyl]cyclopentyl]-(1R)-1-(1,3-benzodioxol-4-yl)ethanamine (Compound 1212), (N)-[(1S,3R)-3-[4-(3-oxo-piperazinylcarbonyl)phenyl]cyclopentyl]-(1R)-1-(2,3-Dihydro-benzo[1,4]dioxin-5-yl)-ethylamine (Compound 1213), (N)-[(1S,3R)-3-[4-(aminocarbonylmethylaminocarbonyl)phenyl]cyclopentyl]-(1R)-1-(4-fluoro-3-methoxyphenyl)ethylamine (Compound 1214), (N)-[(1S,3R)-3-[4-(aminocarbonylmethylaminocarbonyl)phenyl]cyclopentyl]-(1R)-1-(3-ethoxyphenyl)-ethanamine (Compound 1215), (N)-[(1S,3R)-3-[4-(aminocarbonylmethylaminocarbonyl)phenyl]cyclopentyl]-(1R)-1-(3-chlorophenyl)ethanamine (Compound 1216), (N)-[(1S,3R)-3-[4-(aminocarbonylmethylaminocarbonyl)phenyl]cyclopentyl]-(1R)-1-(1,3-benzodioxol-4-yl)ethanamine (Compound 1217), (N)-[(1S,3R)-3-[4-(aminocarbonylmethylaminocarbonyl)phenyl]cyclopentyl]-(1R)-1-(3-fluoro-5-methoxy-phenyl)-ethanamine (Compound 1218), (N)-[(1S,3R)-3-[4-(aminocarbonylmethylaminocarbonyl)phenyl]cyclopentyl]-(1R)-1-(2,3-Dihydro-benzo[1,4]dioxin-5-yl)-ethylamine (Compound 1219), (N)-[(1S,3R)-3-[4-(2-(methanesulfonylamino)-ethylaminocarbonyl)phenyl]cyclopentyl]-(1R)-1-(3-ethoxyphenyl)-ethanamine (Compound 1220), (N)-[(1S,3R)-3-[4-(2-(methanesulfonylamino)-ethylaminocarbonyl)phenyl]cyclopentyl]-(1R)-1-(3-chlorophenyl)ethanamine (Compound 1221), (N)-[(1S,3R)-3-[4-(2-(methanesulfonylamino)-ethylaminocarbonyl)phenyl]cyclopentyl]-(1R)-1-(1,3-benzodioxol-4-yl)ethanamine (Compound 1222), (N)-[(1S,3R)-3-[4-(2-(methanesulfonylamino)-ethylaminocarbonyl)phenyl]cyclopentyl]-(1R)-1-(3-fluoro-5-methoxy-phenyl)-ethanamine (Compound 1223), (N)-[(1S,3R)-3-[4-(2-(methanesulfonylamino)-ethylaminocarbonyl)phenyl]cyclopentyl]-(1R)-1-(2,3-Dihydro-benzo[1,4]dioxin-5-yl)-ethylamine (Compound 1224), (N)-[(1S,3R)-3-[4-[piperidin-4-ylaminocarbonyl]phenyl]cyclopentyl]-(1R)-1-(4-fluoro-3-methoxyphenyl)ethylamine (Compound 1225), (N)-[(1S,3R)-3-[4-[piperidin-4-ylaminocarbonyl]phenyl]cyclopentyl]-(1R)-1-(3-ethoxyphenyl)-ethanamine (Compound 1226), (N)-[(1S,3R)-3-[4-[piperidin-4-ylaminocarbonyl]phenyl]cyclopentyl]-(1R)-1-(3-chlorophenyl)ethanamine (Compound 1227), (N)-[(1S,3R)-3-[4-[piperidin-4-ylaminocarbonyl]phenyl]cyclopentyl]-(1R)-1-(1,3-benzodioxol-4-yl)ethanamine (Compound 1228), (N)-[(1S,3R)-3-[4-[piperidin-4-ylaminocarbonyl]phenyl]cyclopentyl]-(1R)-1-(3-fluoro-5-methoxy-phenyl)-ethanamine (Compound 1229), (N)-[(1S,3R)-3-[4-[piperidin-4-ylaminocarbonyl]phenyl]cyclopentyl]-(1R)-1-(2,3-Dihydro-benzo[1,4]dioxin-5-yl)-ethylamine (Compound 1230), 4-{(1R,3S)-3-[(1R)-1-(4-Fluoro-3-methoxy-phenyl)-ethylamino]-cyclopentyl}-N-[2-(2-hydroxy-ethylamino)-ethyl]-benzamide (Compound 1231), (4-{(1R,3S)-3-[(1R)-1-(4-Fluoro-3-methoxy-phenyl)-ethylamino]-cyclopentyl}-phenyl)-[4-(2-hydroxy-ethyl)-piperazin-1-yl]-methanone (Compound 1232), (4-{(1R,3S)-3-[(1R)-1-(4-Fluoro-3-methoxy-phenyl)-ethylamino]-cyclopentyl}-phenyl)-piperazin-1-yl-methanone (Compound 1233), (4-{(1R,3S)-3-[(1R)-1-(4-Fluoro-3-methoxy-phenyl)-ethylamino]-cyclopentyl}-phenyl)-(4-methanesulfonyl-piperazin-1-yl)-methanone (Compound 1234), N-(2-Amino-ethyl)-4-{(1R,3S)-3-[(1R)-1-(4-fluoro-3-methoxy-phenyl)-ethylamino]-cyclopentyl}-benzamide (Compound 1235), or 4-{(1R,3S)-3-[(1R)-1-(4-Fluoro-3-methoxy-phenyl)-ethylamino]-cyclopentyl}-N-[1-(2-hydroxy-ethyl)-piperidin-4-yl]-benzamide (Compound 1236).

Specific examples of intermediates for the preparation of compounds of formula I may be selected from the group consisting of (3S)-3-(4-methylsulfonylphenyl)cyclopentanone (preparation 1), tert-butyl 4-[[4-[(1S)-3-oxocyclopentyl]benzoyl]amino]piperidine-1-carboxylate (preparation 2), (3S)-3-(6-methoxy-3-pyridyl)cyclopentanone (preparation 3), 5-[(1S)-3-oxocyclopentyl]-1H-pyridin-2-one (preparation 4), (3S)-3-[4-(1H-tetrazol-5-yl)phenyl]cyclopentanone (preparation 5), N-(2-Hydroxyethyl)-4-[(1S)-3-oxocyclopentyl]benzenesulfonamide (preparation 6), (3S)-3-[4-(4-hydroxypiperidine-1-carbonyl)phenyl]cyclopentanone (preparation 7), N-methylsulfonyl-2-[4-[(1R)-3-oxocyclopentyl]phenoxy]acetamide (preparation 8), 2-[4-[(1R)-3-oxocyclopentyl]phenoxy]acetamide (preparation 9), N-(2-acetamidoethyl)-4-[(1S)-3-oxocyclopentyl]benzamide (preparation 10), 4-[(1S)-3-oxocyclopentyl]-N-(2-sulfamoylethyl)benzamide (preparation 11),
4-[4-[(1S)-3-oxocyclopentyl]benzoyl]piperazin-2-one (preparation 12),
(3S)-3-[4-[(3S)-3-hydroxypyrrolidine-1-carbonyl]phenyl] cyclopentanone (preparation 13),
N-(2-amino-2-oxo-ethyl)-4-[(1S)-3-oxocyclopentyl]benzamide (preparation 14),
(3S)-3-[4-(morpholine-4-carbonyl)phenyl]cyclopentanone (preparation 15),
N-(2-hydroxyethyl)-4-[(1S)-3-oxocyclopentyl]benzamide (preparation 16),
N-[2-(methanesulfonamido)ethyl]-4-[(1S)-3-oxocyclopentyl]benzamide (preparation 17),
N-(cyanomethyl)-4-[(1S)-3-oxocyclopentyl]benzamide (preparation 18),
methyl 4-[(1S)-3-oxocyclopentyl]benzoate (preparation 19),
4-[(1S)-3-oxocyclopentyl]benzoic acid hydrochloride (preparation 20),
(R)-1-Isoquinolin-1-yl-ethylamine dihydrochloride (preparation 21),
(R)-1-(2,3-Dihydro-benzo[1,4]dioxin-5-yl)-ethylamine hydrochloride (preparation 22),
(R)-1-Pyrazolo[1,5-a]pyridin-3-yl-ethylamine hydrochloride (preparation 23),
(R)-1-(2,2-Difluoro-benzo[1,3]dioxol-4-yl)-ethylamine hydrochloride (preparation 24),
(R)-1-(3,4-Dihydro-2H-benzo[b][1,4]dioxepin-6-yl)-ethylamine hydrochloride (preparation 25),
(R)-1-(1-Methyl-5-phenyl-1H-pyrazol-3-yl)-ethylamine (preparation 26),
(R)-1-Imidazo[1,2-a]pyridin-3-yl-ethylamine hydrochloride (preparation 27),
(R)-1-(5-Fluoro-imidazo[1,2-a]pyridin-2-yl)-ethylamine hydrochloride (preparation 28),
(R)-1-Imidazo[1,5-a]pyridin-3-yl-ethylamine hydrochloride (preparation 29),
[4-(3-Oxo-cyclopentyl)-phenoxy]-acetic acid ethyl ester (Preparation 30),
(R)-[4-(3-Oxo-cyclopentyl)-phenoxy]-acetic acid (Preparation 31),
Methyl 4-[(1R)-3-oxocyclopentyl]benzoate (preparation 32),
Methyl 4-[(1R,3S)-3-[[(1R)-1-(4-fluoro-3-methoxy-phenyl) ethyl]amino]cyclopentyl]-benzoate (preparation 33),
4-[(1R,3S)-3-[[(1R)-1-(4-Fluoro-3-methoxy-phenyl)ethyl] amino]-cyclopentyl]benzoic acid (preparation 34),
4-[(1R)-3-Oxocyclopentyl]benzonitrile (preparation 35),
4-[(1R,3S)-3-[[(1R)-1-(4-Fluoro-3-methoxy-phenyl)ethyl] amino]cyclopentyl]benzonitrile (preparation 36),
N-(3-Amino-3-oxo-propyl)-4-[(1S)-3-oxocyclopentyl]benzamide (preparation 37),
(3R)-3-(4-Bromo-phenyl)-cyclopentanone (Preparation 38),
4-[(1R)-3-oxocyclopentyl]benzoic acid (Preparation 39),
4-[4-[(1R)-3-oxocyclopentyl]benzoyl]piperazin-2-one (Preparation 40),
N-(2-acetamidoethyl)-4-[(1R)-3-oxocyclopentyl]benzamide (Preparation 41),
4-[(1R)-3-oxocyclopentyl]-N-(2-sulfamoylethyl)benzamide (Preparation 42),
(3R)-3-[4-(4-hydroxypiperidine-1-carbonyl)phenyl]cyclopentanone (Preparation 43),
N-[2-(methanesulfonamido)ethyl]-4-[(1R)-3-oxocyclopentyl]benzamide (Preparation 44),
(3R)-3-[4-[(3S)-3-hydroxypyrrolidine-1-carbonyl]phenyl] cyclopentanone (Preparation 45),
tert-butyl 4-[[4-[(1R)-3-oxocyclopentyl]benzoyl]amino]piperidine-1-carboxylate (Preparation 46)
([(1S,3R)-3-(4-Bromo-phenyl)-cyclopentyl]-(1R)-[1-(4-fluoro-3-methoxy-phenyl)-ethyl]-amine (Preparation 50).

Pharmaceutical Compositions

For use in therapy, compounds of the present invention are typically in the form of a pharmaceutical composition. The invention therefore relates to a pharmaceutical composition comprising a compound of formula I, optionally together with one or more other therapeutically active compound(s), together with a pharmaceutically acceptable excipient or vehicle. The excipient must be "acceptable" in the sense of being compatible with the other ingredients of the composition and not deleterious to the recipient thereof.

Conveniently, the active ingredient comprises from 0.05-99.9% by weight of the formulation.

Pharmaceutical compositions of the invention may be in unit dosage form such as tablets, pills, capsules, powders, granules, elixirs, syrups, emulsions, ampoules, suppositories or parenteral solutions or suspensions; for oral, parenteral, opthalmic, transdermal, intra-articular, topical, pulmonal, nasal, buccal or rectal administration or in any other manner appropriate for the formulation of compounds used in nephrology and in accordance with accepted practices such as those disclosed in Remington: The Science and Practice of Pharmacy, $21^{st}$ ed., 2000, Lippincott Williams & Wilkins. In the composition of the invention, the active component may be present in an amount of from about 0.01 to about 99%, such as 0.1% to about 10% by weight of the composition.

For oral administration in the form of a tablet or capsule, a compound of formula I may suitably be combined with an oral, non-toxic, pharmaceutically acceptable carrier such as ethanol, glycerol, water or the like. Furthermore, suitable binders, lubricants, disintegrating agents, flavouring agents and colourants may be added to the mixture, as appropriate. Suitable binders include, e.g., lactose, glucose, starch, gelatin, acacia gum, tragacanth gum, sodium alginate, carboxymethylcellulose, polyethylene glycol, waxes or the like. Lubricants include, e.g., sodium oleate, sodium stearate, magnesium stearate, sodium benzoate, sodium acetate, sodium chloride or the like. Disintegrating agents include, e.g., starch, methyl cellulose, agar, bentonite, xanthan gum or the like. Additional excipients for capsules include macrogols or lipids.

For the preparation of solid compositions such as tablets, the active compound of formula I is mixed with one or more excipients, such as the ones described above, and other pharmaceutical diluents such as water to make a solid preformulation composition containing a homogenous mixture of a compound of formula I. The term "homogenous" is understood to mean that the compound of formula I is dispersed evenly throughout the composition so that the composition may readily be subdivided into equally effective unit dosage forms such as tablets or capsules. The preformulation composition may then be subdivided into unit dosage forms containing from about 0.05 to about 1000 mg, in particular from about 0.1 to about 500 mg, e.g. 10-200 mg, such as 30-180 mg, such as 20-50 mg of the active compound of the invention.

In the form of a dosage unit, the compound may be administered one or more times a day at appropriate intervals, always depending, however, on the condition of the patient, and in accordance with the prescription made by the medical practitioner. Conveniently, a dosage unit of a formulation contain between 0.1 mg and 1000 mg, preferably between 1 mg and 100 mg, such as 5-50 mg of a compound of formula I.

A suitable dosage of the compound of the invention will depend, inter alia, on the age and condition of the patient, the severity of the disease to be treated and other factors well known to the practising physician. The compound may be administered either orally, parenterally or topically according to different dosing schedules, e.g. daily or with weekly intervals. In general a single dose will be in the range from 0.01 to 400 mg/kg body weight. The compound may be administered as a bolus (i.e. the entire daily dosis is administered at once) or in divided doses two or more times a day.

If the treatment involves administration of another therapeutically active compound it is recommended to consult *Goodman & Gilman's The Pharmacological Basis of Therapeutics*, 9$^{th}$ Ed., J. G. Hardman and L. E. Limbird (Eds.), McGraw-Hill 1995, for useful dosages of said compounds. The administration of a compound of the present invention with one or more other active compounds may be either concomitantly or sequentially.

Liquid formulations for either oral or parenteral administration of the compound of the invention include, e.g., aqueous solutions, syrups, aqueous or oil suspensions and emulsion with edible oils such as cottonseed oil, sesame oil, coconut oil or peanut oil. Suitable dispersing or suspending agents for aqueous suspensions include synthetic or natural gums such as tragacanth, alginate, acacia, dextran, sodium carboxymethylcellulose, gelatin, methylcellulose or polyvinylpyrrolidone.

For parenteral administration, e.g. intramuscular, intraperitoneal, subcutaneous or intravenous injection or infusion, the pharmaceutical composition preferably comprises a compound of formula I dissolved or solubilised in an appropriate, pharmaceutically acceptable solvent. For parenteral administration, the composition of the invention may include a sterile aqueous or non-aqueous solvent, in particular water, isotonic saline, isotonic glucose solution, buffer solution or other solvent conventionally used for parenteral administration of therapeutically active substances. The composition may be sterilised by, for instance, filtration through a bacteria-retaining filter, addition of a sterilising agent to the composition, irradiation of the composition, or heating the composition. Alternatively, the compound of the invention may be provided as a sterile, solid preparation, e.g. a freeze-dried powder, which is dissolved in sterile solvent immediately prior to use.

The composition intended for parenteral administration may additionally comprise conventional additives such as stabilisers, buffers or preservatives, e.g. antioxidants such as methyl hydroxybenzoate or the like.

Compositions for rectal administration may be in the form of a suppository incorporating the active ingredient and a carrier such as cocoa butter, or in the form of an enema.

Compositions suitable for intra-articular administration may be in the form of a sterile aqueous preparation of the active ingredient which may be in microcrystalline form, for example, in the form of an aqueous microcrystalline suspension. Liposomal formulations or biodegradable polymer systems may also be used to present the active ingredient for both intra-articular and ophthalmic administration.

Compositions suitable for topical administration, including ophthalmic treatment, include liquid or semi-liquid preparations such as liniments, lotions, gels, applicants, oil-in-water or water-in-oil emulsions such as creams, ointments or pastes; or solutions or suspensions such as drops. For topical administration, the compound of formula I may typically be present in an amount of from 0.01 to 20% by weight of the composition, such as 0.1% to about 10%, but may also be present in an amount of up to about 50% of the composition. Compositions for ophthalmic treatment may preferably additionally contain a cyclodextrin. Compositions suitable for administration to the nasal or buccal cavity or for inhalation include powder, self-propelling and spray formulations, such as aerosols and atomizers. Such compositions may comprise a compound of formula I in an amount of 0.01-20%, e.g. 2%, by weight of the composition.

The composition may additionally comprise one or more other active components conventionally used in the treatment of physiological disorders or diseases associated with disturbances of CaSR activity, such as hyperparathyroidism.

A suitable dosage of the compound of the invention will depend, inter alia, on the age and condition of the patient, the severity of the disease to be treated and other factors well known to the practising physician. The compound may be administered either orally, parenterally or topically according to different dosing schedules, e.g. daily or with weekly intervals. In general a single dose will be in the range from 0.01 to 400 mg/kg body weight. The compound may be administered as a bolus (i.e. the entire daily dosage is administered at once) or in divided doses two or more times a day.

Pharmacological Methods

The calcium sensing receptor (CaSR) and its use in identifying or screening for calcimimetic compounds has been described in EP 637 237, EP 1 296 142, EP 1 100 826, EP 1 335 978, and EP 1 594 446.

In vitro and vivo methods for testing the compounds of the present invention are well established and may be found in the references listed above, or e.g. in Journal of Biological Chemistry (2004), 279(8), 7254-7263 or in U.S. Pat. No. 5,858,684 and references cited therein.

Biological Assay for Analysis of In Vitro Activity

The assay investigates a compound's functional ability to act as a biological positive modulator on the human CaSR. Activation of the receptor expressed on CHO-K1 cells is detected through the G alpha q pathway, the activation of phospholipase C and the accumulation of intracellular inositol phosphate (IP) as described earlier [Sandrine Ferry, Bruno Chatel, Robert H. Dodd, Christine Lair, Danielle Gully, Jean-Pierre, Maffrand, and Martial Ruat. *Effects of Divalent Cations and of a Calcimimetic on Adrenocorticotropic Hormone Release in Pituitary Tumor Cells*. BIOCHEMICAL AND BIOPHYSICAL RESEARCH COMMUNICATIONS 238, 866-873 (1997)]. The human CaSR is stably expressed on a CHO-K1 cell clone, stimulated with a basal level of calcium and challenged with the tested compound. The level of IP1 is determined using the IP-One htrf kit (Cisbio, France). CHO-K1 cells not transfected with the CaSR fail to elicit an IP1 response upon calcium and/or compound stimulation.

Cloning of the Human CaSR Gene

The ORF coding for the human CaSR (genebank: NM_000388) was acquired from Invitrogen Corp, USA and subsequently cloned into the mammalian expression vector pCDA3.1.

Generation of Cell Line Expressing CaSR

CHO-K1 cells were transfected using Lipofectamine according to manufacturer's protocol (400.000 cells/well were seeded in a 6-well plate and transfected after 24 hours using 2 μg DNA and 5 μl lipofectamine). After another 24 hours the cells were detached, seeded and subjected to 1 mg/ml of G-418. Following 7 days growth single clones were picked, the CaSR expression evaluated using the 5C10 antibody against CaSR, the clones with the highest expression were selected and tested for functional response. The preferred clone was continuously cultured according to standard procedures described in ATCC (American Type Culture Collection) protocols for CHO-K1 with the addition of 500 μg/ml G-418.

Functional Whole Cell Assay

On the assay day cells were harvested and resuspended to $13*10^6$ cells/ml in stimulation buffer (containing: Hepes 10 mM, $MgCl_2$ 0.5 mM, KCl 4.2 mM, NaCl 146 mM, glucose 5.5 mM, LiCl 50 mM at pH 7.4). Five µl cell solution were pipetted into a well (white 384-well plate, Perkin Elmer Optiplate) followed by 5 µl compound diluted in a $Ca^{2+}$-containing (to the final concentration of 2 mM) buffer. After compound stimulation for 1 hour at 37° C. 10 ul of IP-One assay reagents were added and incubated for another 1 hour at room temperature. Finally the plate was read using a Perkin Elmer EnVision, according to protocol supplied by the IP-One assay kit manufacturer. The FRET ratio was calculated by dividing the 665 nm emission signal with that of the 615 nm.

Testing data of compounds of the present invention indicate that compounds of the present invention are potent modulators of CaSR, thus making them potentially useful in the treatment of diseases related to kidneys or bones.

As described above, the compounds described in the present invention are modulators of CaSR activity. The CaSR can be found in the parathyroid gland, the thyroid, bone cells, the stomach, the lung, the kidney, pituitary gland, the brain, the hypothalamus, the olfactory areas or the hippocampus. Compounds according to the present invention may preferably be more selective, in their use, with respect to the receptors of the parathyroid compared with those of the thyroid gland.

The compounds according to the invention, and the pharmaceutical compositions comprising them, may be used as a medicinal product, in particular for the treatment of physiological disorders or diseases associated with disturbances of CaSR activity. Even more particularly, these physiological disorders or diseases of the type including primary or secondary hyperparathyroidism, osteoporosis, cardiovascular, gastrointestinal, endocrine or neurodegenerative diseases or certain cancers in which $(Ca^{2+})_e$ ions are abnormally high. The secondary hyperparathyroidism is more particularly observed in chronic renal failure.

Screening for P450 2D6 Inhibition

The assay rapidly screen for potential inhibitors of human P450 2D6 catalytic activity, by using recombinant human P450 2D6. The IC50 determination is performed in duplicate at eight concentrations.

Incubations were conducted in 96 well microtiter plates based on a method described by BD Biosciences. To the first well in each row, a NADPH regenerating system and test compound was added. In the second well and all remaining wells, NADPH regenerating system and acetonitrile (final concentration of 2%) was added. The final assay concentration of the NADPH regenerating system was 8.2 µM $NADP^+$, 0.41 mM glucose-6-phosphate, 0.41 mM magnesium chloride hexahydrate and 0.4 U/ml glucose-6-phosphate dehydrogenase and 0.01 mg/mL control insect cell membrane protein. The test compound solution was serially diluted 1:3 through the eighth wells. The final concentration of the test compounds were in the range 100 µM to 45.7 nM in the eight rows. Wells 9 and 10 contained no test compound (only NADPH regenerating system and enzyme/substrate mix) and wells 11 and 12 were used as controls for background fluorescence (enzyme and substrate were added after the reaction was terminated). The plate was then pre-incubated at 37° C. for 10 min, and the reaction was initiated by the addition of pre-warmed enzyme/substrate mix. The assay concentration of the enzyme/substrate mix was 100 mM potassium phosphate, pH 7.4, 1.5 pmol recombinant human P450 CYP2D6 and 1.5 µM of the fluorescent substrate 3-[2-(N,N diethyl-N-methylamino)ethyl]-7-methoxy-4-methylcoumarin (AMMC). The assay was conducted in duplicate in a final volume of 200 µL per well. Reactions were terminated after 30 min by addition of a 4:1, acetonitrile:0.5 M Tris base solution. Quinidine was used as positive control, 0.5 µM as highest concentration. Fluorescence per well was measured using a fluorescence plate reader (excitation: 390 nm, emission: 460 nm). The IC50 values were calculated.

Testing data of compounds of the present invention indicate that compounds of the present invention show low or no inhibition towards human P450 2D6 (pIC50-value below 6).

Biological Assay for Analysis of Clearance in Human Liver Microsomes

Test compound concentration is 0.5 µM, microsome concentration is 0.5 mg/mL and NADPH concentration is 1 mM in the incubation. The described method is performed by the liquid handling system Tecan RSP and is based on a 96-well format.

Control incubations with test compound without NADPH and test compound without microsomes are conducted to investigate non-CYP mediated metabolism and stability in phosphate buffer at 37° C., respectively.

Incubation Conditions

The human liver microsomal suspension in phosphate buffer is mixed with NADPH. The mixture is pre-heated (7 min) to 37° C. Test compound is added, and the mixture is incubated for 30 minutes. Incubations are run in duplicate. Samples are withdrawn at predetermined stop times and mixed with methanol containing internal standard (IS) to terminate all enzyme activity and precipitate proteins. A control without NADPH (to detect problems such as nonspecific protein binding, heat instability or non-CYP mediated metabolism) and a control without microsomes (for assessing compound stability in the absence of any active enzymes) are tested.

The percentage of organic solvent in the incubations is less than 1%. Careful inspections of reagents are performed prior to the start of any experiment to ensure all reagents are in solution.

Sample Analysis

The 96-well plates are centrifuged. Test compound depletion, using a compound specific LC/MS/MS method, is determined.

The logarithm of the peak area ratios of test compound to internal standard (IS) versus incubation time is plotted in a graph.

The rate constant (k) ($min^{-1}$) of test compound depletion is calculated from the linear part of the curve and the half-time ($t_{1/2}$) in minutes can be calculated from the rate constant (Eq. 1).

$$t_{1/2} = (\ln 2)/k \quad \text{(Eq. 1)}$$

Intrinsic clearance ($Cl_{int}$) (mL/min/mg protein) is calculated from:

$$Cl_{int} = k/c \quad \text{(Eq. 2)}$$

where c is the microsomal protein concentration in mg/mL.

Intrinsic clearance is the maximum ability of the liver to extract a drug in the absence of blood flow restrictions.

Conversion to apparent clearance ($Cl_{app}$) (mL/min/kg) is done by Eq. 3:

$$Cl_{app} = Cl_{int} \times a \times b/d \quad \text{(Eq. 3)}$$

where a, b and d are the scaling factors for normalizing $Cl_{int}$ to human body weight.

The following human scaling factors are used:
a: 45 (microsomal protein/liver weight (mg/g))
b: 1500 (liver weight (g))
d: 70 (body weight (kg))

Apparent clearance below approximately 10 mL/min/kg human body weight (corresponding to extraction ratio of approx. 30%) is considered as low clearance (high metabolic stability). Apparent intrinsic clearance above approximately 60 mL/min/kg human body weight (corresponding to extraction ratio of approx. 75%) is considered as high clearance (low metabolic stability).

Estimation of Pharmacokinetic Profile Following Intravenous Administration in Rats.

A rat is dosed intravenously with a solution of test compound (0.5 mg/kg) in DMSO/EtOH/H$_2$O/propylene glycol [0.2:0.8:5:4] and blood samples are taken from the sublingual venous plexus after 2 min, 10 min, 30 min, 1 h, 2 h, 4 h and 6 h.

Blood samples are taken in BD Vacutainer SST serum separation tubes, serum is isolated by centrifugation, transferred to micronics tubes and analyzed. Samples are kept at −18° C. pending analysis.

Mass spectrometer (API5000 series) parameters are optimised to analyse for the specific compounds and test injections are performed to confirm the validity of the established generic chromatography method. The generic method is based on fast gradient (2.5 min) analysis on C18 column with mobile phases consisting methanol, ammonium acetate, formic acid and water.

Standards are prepared in rat serum to cover the analytical range 0.1 to 300 ng/ml. Standards, blank serum and study samples are applied to 96 deepwell plate and proteins are precipitated by addition of acetonitrile containing internal standard. Samples are analysed on LC-MS/MS usually over night.

As standard, the 2 and 10 min samples are diluted 10 times with rat serum prior to analysis. Other samples may need similar dilution to keep quantification below 300 ng/ml.

Data Analysis and Calculations

Quantification is performed based on the ratio between analyte and internal standard. The curve should preferably fit a linear curve using a 1/x weighting factor. At least a factor of two is needed to distinguish between blank serum and lowest standard. If this is not the case the quantification of the specific experiment may be raised.

Calculation of T½ requires at least three datapoints describing a true elimination phase. If such three points are not available AUC (0-inf) can not be estimated. In these cases F(0-6 h) is calculated instead.

Total clearance of drug from serum (Cl_iv) is calculated from:

$$Cl\_iv = Dose/AUC$$

Terminal volume of distribution (Vd) is defined as the volume in which the amount of drug would need to be uniformly distributed to produce the observed serum concentration and is calculated from:

$$Vd = T½ \times Cl\_iv/(\ln 2)$$

Among the compounds of the present invention, compounds can be found with improved in vitro and in vivo pharmacokinetic properties, i.e. low clearance as determined by the human liver microsome assay described above, and/or increased volume of distribution in rats as determined by the in vivo experiment described above (see table 1).

TABLE 1

Pharmacokinetic data fro compounds according to the present invention.

| Compound no. | Functional whole cell assay (modulation of human CaSR) A: <500 nM; B: 500-2000 nM; C: 2-5 μM | Clearance (Cl$_{app}$) in human liver microsomes A: <20 mL/min/kg; B: 20-60 mL/min/kg; C: >60 mL/min/kg | Vd following iv administration (0.5 mg/kg) in rats A: >50 L/kg; B: 10-50 L/kg; C: <10 L/kg |
|---|---|---|---|
| 1014 | A | A | |
| 1157 | A | A | B |
| 1176 | A | A | |
| 1178 | A | A | A |
| 1179 | A | A | B |
| 1181 | A | A | |
| 1182 | A | A | C |
| 1187 | A | A | A |

The invention is described in further detail in the following non-limiting examples which are not in any way intended to limit the scope of the invention as claimed.

Methods of Preparation

The compounds of general formula I can be prepared in a number of ways well known to those skilled in the art of organic synthesis. The compounds of formula I can be synthesised using the methods outlined below, together with methods known in the art of synthetic organic chemistry, or variations thereof as appreciated by those skilled in the art. Preferred methods include, but are not limited to, those described below.

The compounds of formula I can be prepared by techniques and procedures readily available to one of ordinary skill in the art, for example by following the procedures as set forth in the following schemes. The reactions are performed in solvents appropriate to the reagents and materials employed and suitable for the transformations being effected. Also, in the synthetic methods described below, it is to be understood that all proposed reaction conditions, including choice of solvent, reaction atmosphere, reaction temperature, duration of experiment and work-up procedures, are chosen to be conditions of standard for that reaction, which should be readily recognised by one skilled in the art. It is understood by one skilled in the art of organic synthesis that the functionalities present on various portions of the starting molecules in a reaction must be compatible with the reagents and reactions proposed. Not all compounds of formula I falling into a given class may be compatible with some of the reaction conditions required in some of the methods described. Such restrictions to the substituents which are compatible with the reaction conditions will be readily apparent to one skilled in the art and alternative methods can be used.

The schemes described in this section are not intended to limit the scope of the invention in any way. All substituents, unless otherwise indicated, are previously defined. The reagents and starting materials are either available from commercial suppliers or prepared by methods known to one of ordinary skill in the art following procedures set forth in references such as *Fieser and Fieser's Reagents for Organic Synthesis*, Volumes 1-22 (John Wiley and Sons, 2004); *Rodd's Chemistry of Carbon Compounds*, Volumes 1-5 and Supplements (Elsevier Science Publishers, 2000); *Organic Reactions*, Volumes 1-64 (John Wiley and Sons, 2004); *March's Advanced Organic Chemistry* (John Wiley and Sons, 5$^{th}$ Edition) and *Larock's Comprehensive Organic Transformations* (VCH Publishers Inc., 1999). These schemes are merely illustrative of some methods by which the compounds of this invention can be synthesised, and various modifications to these schemes can be made and will be suggested to one skilled in the art having referred to this disclosure. The starting materials and the intermediates of the reactions may be isolated and purified if desired using conventional techniques, including but not limited to filtration, distillation, crystallisation, chromatography and the like. Such materials may be characterised using conventional means, including physical constants and spectral data.

Compounds of general formula I may be obtained by reductive amination between a cyclopentanone of general formula II and an amine of general formula III. The reaction between ketone II and amine III may be carried out either by one-pot reductive amination or with isolation of the imine followed by reduction.

d. When LG is a leaving group such as chloride, bromide, iodide, tosylate or triflate, alkylation is performed in the presence of a base such as NEt$_3$, DIPEA, NaH, NaOH, KOH, carbonates in an appropriate solvent such as DMF, pyridine, DMSO, CH$_3$CN, acetone, toluene. Alternatively reaction with an alcohol (LG=OH) may also be considered. Such Mitsunobu-like reaction is performed in the presence of a phosphine such as PBu$_3$, PPh$_3$ and the like, an azodicarboxylate or an azodicarboxamide in an aprotic solvent, typically THF. For this

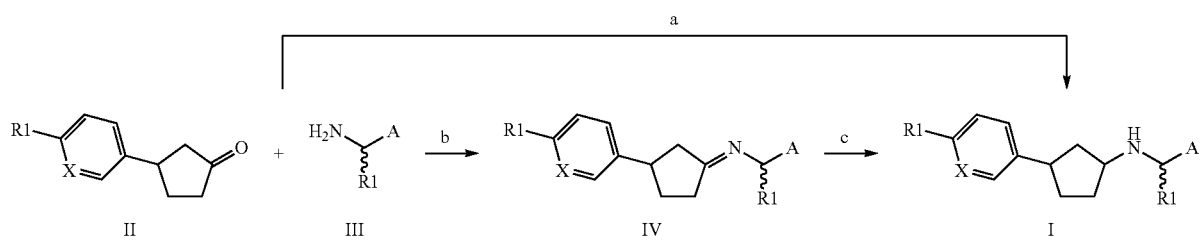

a. The formation of the intermediate iminium IV may be promoted by addition of a protic or aprotic acid such as, but not limited to acetic acid and Ti(Oi-Pr)$_4$ respectively. The reducing agent may be but is not limited to Na(CN)BH$_3$, NaBH$_4$, Na(OAc)$_3$BH (for other non-limiting conditions see *Org. React.* 2002, 59, 1-714 and references cited therein).

b. The formation of the imine is promoted either by Lewis acids such as TiCl$_4$, ZnCl$_2$, AlCl$_3$ or by bases such as pyridine, optionally in the presence of a drying agent such as TiCl$_4$ or molecular sieve (see *Comprehensive Organic Functionnal Group Transformations* 3, 403 (1995) Pergamon).

c. Reduction may be performed by hydrogenation in the presence of a catalyst such as Pd/C, Pt/C or a chiral rhodium complex to perform the reaction in a stereoselective manner or by hydride transfer from a reducing agent such as BH$_3$, NaBH$_4$, NaBH$_3$CN, LiAlH$_4$, L-selectride (see Larock R. C. *Comprehensive Organic Transformations* 1989, VCH; *Comprehensive Organic Functionnal Group Transformations* 2, 268-269 (2005) Pergamon and references cited therein).

Compounds of general formula I may also be prepared through alkylation of the amine III.

purpose the amine III is protected/activated as a carbamate or a sulphonamide. The resulting compound is deprotected using standard conditions (*Protective Groups in Organic Synthesis*, T. W. Greene and P. G., M. Wuts, John Wiley and Sons, 3$^{rd}$ Edition 1999 and reference sited therein) to afford I.

The cyclopentanone II may be prepared in various manners:

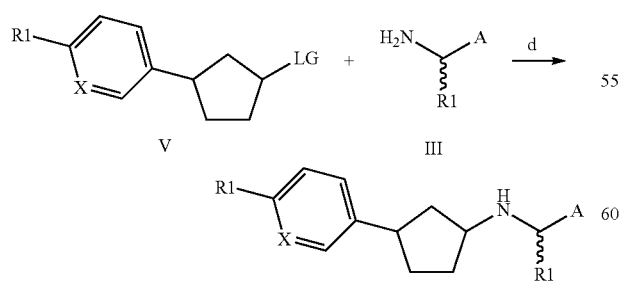

LG = leaving group

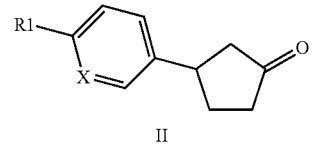

e. An alcohol Va may be oxidised to afford II. Oxidation may be performed with many different reagents. A few of them are H$_2$Cr$_2$O$_7$, Al$_2$O$_3$, MnO$_2$, periodinanes, DMSO in combination with DCC, acetic anhydride, oxalyl chloride and the like.

2-Cyclopentenones may be used as starting materials.

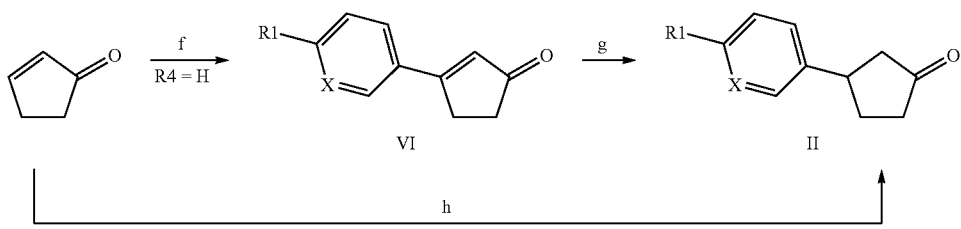

f. Coupling reaction with an aryl/heteroaryl halide or pseudo halide such as triflate in the presence of a palladium source such as Pd(OAc)$_2$, PdCl$_2$(PPh$_3$)$_2$, a base such as NEt$_3$, K$_2$CO$_3$, NaHCO$_3$, optionally with a phosphine such PPh$_3$, P(o-Tol)$_3$, 1,3-bis(diphenylphosphino)propane (dppp), optionally in the presence of a salt like NBu$_4$Cl, AgNO$_3$ in a solvent such as DMF or acetonitrile. Alternatively a decarboxylative Heck-type coupling may be performed using an aryl/heteroaryl carboxylic acid (*Org. Lett.* 2004, 6, 433).

g. Chemospecific reduction of the double bond may be performed under numerous conditions. The hydrogen source may be H$_2$, water, Hantzsch esters. Metal-based catalysts such as Pd/C, Pd(PPh$_3$)$_4$, supported PdCl$_2$, Rh-, Co-, Cu-, Ir-based catalysts may be used. Stereoselectivity may be achieved by addition of a chiral auxiliary such as but not limited to enantiopure binaphthol phosphate derivatives/valine, imidazolidinone iminiums, bidentate phosphines.

Alternatively cyclopentenones may be subjected to 1,4-addition.

h. Reaction with an aryl/heteroaryl metal in which the metal may be Li, Mg halide, trialkyltin, boronic acid, boronic acid ester, optionally in the presence of a metal complex such as PdCl$_2$, Pd(OAc)$_2$, Pd(PPh$_3$)$_4$, (acac)Rh(CO)$_2$, Ni(acac)$_2$, (COD)Rh(1,4-dihydroquinone)BF$_4$ with a ligand typically phosphine-based such as PBu$_3$, PPh$_3$, 1,3-bis(diphenylphosphino)propane (dppp), 1,3-hydroquinone or 1,4-hydroquinone in solvents such as DMF, THF, water, toluene, dioxane, dimethoxyethane. In the presence of a chiral ligand as a pure enantiomer such as BINAP, phosphoramidite, Me-DuPHOS and the like the reaction may be performed stereoselectively.

1,4-Addition of heteroatom nucleophiles leads to compounds of general formula I. The reaction may be catalysed by reagents such as but not limited to NEt$_3$, ScCl$_3$, CAN, RuCl$_3$, PtCl$_4$ in solvents like CH$_2$Cl$_2$, CH$_3$CN, DMF, toluene.

Cyclopentan-1,3-dione may be used as a starting material.

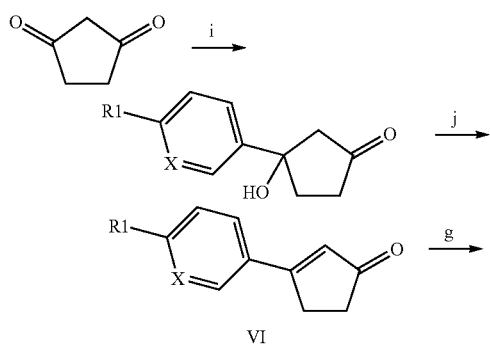

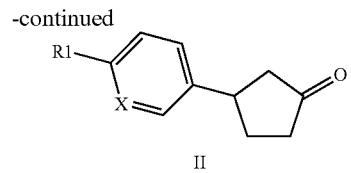

i. Addition of an organometallic species such as GLi or GMgHal (Hal=Cl, Br) affords a ketoalcohol. Alternatively addition of GBr under indium catalysis may lead to analogous ketoalcohols. The ketoalcohols may be dehydrated to afford cyclopentenones VI using dehydrating agents such as but not limited to triflic anhydride and MsCl in the presence of a base such as NEt$_3$, or by using acids such as but not limited to HBr, HCl, H$_2$SO$_4$, H$_3$PO$_4$, p-TsOH, AcOH in solvents such as dioxane, DCM, benzene, methanol, water, diethyl ether. The cyclopentenone VI may then be transformed to cyclopentanone II as described above.

Chiral amines of the general formula III are commercially available or may be prepared from more readily available aldehydes by catalytic asymmetric synthesis using tert-butanesulfinamide according to Liu, G.; Cogan, D. A.; Ellmann, J. A., J. Amer. Chem. Soc., 1997, 114, 9913.

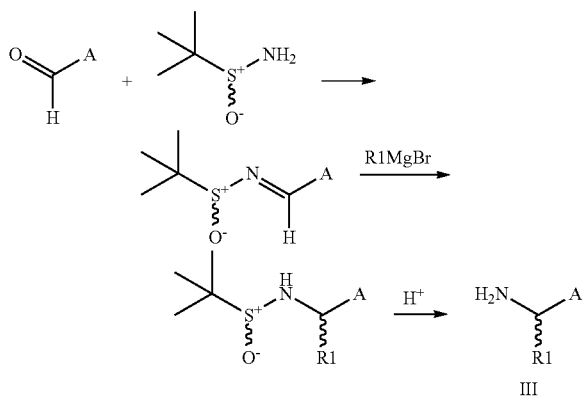

Many of the general methods described above may be used in a different order whenever appropriate.

EXAMPLES

General

For $^1$H nuclear magnetic resonance (NMR) spectra (300 MHz) and $^{13}$C NMR (75.6, MHz) chemical shift values (δ) (in ppm) are quoted for dimethyl-d$_6$ sulfoxide (DMSO-d$_6$) or CDCl$_3$ solutions relative to internal tetramethylsilane (δ=0) standard. The value of a multiplet, either defined (doublet (d), triplet (t), quartet (q), doublet of doublets (dd), doublet of triplets (dt)) or not (m) at the approximate mid point is given unless a range is quoted, (bs) indicates a broad singlet. The ES mass spectra were obtained on a VG Quattro II triple quadrapole mass spectrometer (Micromass, Manchester, UK) operating in either positive or negative electrospray mode with a cone voltage of 30V.

The microwave oven used was the model Initiator™ from Biotage.

The organic solvents used were anhydrous unless otherwise specified. Flash chromatography was performed on silica gel from Fluke Chemie GmbH, Switzerland. The phase separation cartridges used were Chromabond® from Macherey-Nagel GmbH.

Chemicals unless otherwise noted were from commercial sources, e.g. Aldrich, Maybridge Chemical, Fluke or ABCR.

Abbreviations aq. aqueous
BINAP 2,2'-bis(diphenylphosphino)-1,1'-binaphthyl
Boc tert-butoxycarbonyl
CDI 1,1'-carbonyldiimidazole
COD 1,5-cyclooctadiene
DCC N,N'-dicyclohexylcarbodiimide
DCE 1,2-dichloroethane
DCM dichloromethane
DIPEA ethyl diisopropylamine
DMAP dimethyl aminopyridine
DMF N,N-Dimethylformamide
DME 1,2-dimethoxyethane
DMSO dimethyl sulfoxide
EDCI 1-(3-dimethylaminopropyl)-3-ethylcarbodiimide; hydrochloride
eq. equivalent(s)
ES Electro Spray
EtOAc ethyl acetate
h hour(s)
Me-DuPhos 1,2-Bis[2,5-dimethylphospholano]benzene
nbd norbornadiene
$NBu_4Cl$ tetrabutylammoniumchloride
$NEt_3$ triethylamine
NMR nuclear magnetic resonance
$PBu_3$ tributylphosphin
$P(o-Tol)_3$ tri(o-tolyl)-phosphin
r.t. room temperature
RT retention time
sat. saturated
THF tetrahydrofuran
$Ti(Oi-Pr)_4$ titanium tetraisopropoxide
TMSCl chloro trimethylsilane Flash chromatography was performed on silica gel. Appropriate mixtures of ethyl acetate, dichloromethane, methanol, and petroleum ether (40-60) were used as eluents unless otherwise noted.

[Rh(R-BINAP)(nbd)]$BF_4$ was prepared according to the procedure described in Itooka, R.; Iguchi, Y.; Miyaura, N.; J. Org. Chem., 2003, 68, 6000. [Rh(S-BINAP)(nbd)]$BF_4$ was prepared following the same procedure, but using (S)-BINAP instead of (R)-BINAP. (COD)Rh(1,4-dihydroquinone)$BF_4$ was prepared according to the procedure described in Son et al., *J. Am. Chem. Soc.* 2005, 127, 12238.

HPLC purifications of the crude products were performed by using Waters LC-MS system [column: Waters X Terra C18, 5 µm or Luna C18 100 Å 5 µm; Size: 250×10.00 mm (Phenomenex) or XBridge C18 5 Size: 150×19 mm]; Sample Manager: Waters 2767; Pump: Waters 2525; Single Quadrupole: Waters ZQ; PDA-detector: Waters 2996), solventsystem: A=50 mM Ammonium hydrogencarbonate and B=acetonitrile; flow rate=18 mL/min.

Alternatively, a solvent system consisting of A=water (0.1% formic acid) and B=acetonitrile (0.1% formic acid); flow rate=18 mL/min was used.

Unless otherwise noted, analytical LC/MS was performed on a Dionex APS-system with a P680A analytical pump and a Thermo, MSQ Plus mass spectrometer (ionisation mode: ES+/ES−). Column: Waters XBridge, 150 mm×4.6 mm, 5 µm; mobile phase: A=50 mM $NH_4HCO_3$ (aq.) and B=acetonitrile; flow rate=1.2 mL/min; method (10 min): Linear gradient method going from 10% B to 90% B in 4.5 minutes and staying at 90% B for another 1.5 minutes.

When stated, the analytical LC/MS was instead carried out by the following method:

LC/MS Method B

Analytical HPLC/MS was performed on a Dionex APS-system with a P680A analytical pump and a Thermo, MSQ Plus mass spectrometer (ionisation mode: ES+/ES−). Column: Waters XTerra C-18, 150 mm×4.6 mm, 5 µm; mobile phase: A=water (0.1% formic acid) and B=acetonitrile (0.1% formic acid); flow rate=1.0 mL/min; method (10 min): Linear gradient method going from 10% B to 100% B in 6.6 minutes and staying at 100% B for another 1.5 minutes.

General Procedure A

[Rh(R-BINAP)(nbd)]$BF_4$ or [Rh(S-BINAP)(nbd)]$BF_4$ (0.03 mmol) and arylboronic acid (1.5 mmol) were added to a 25 mL-flask containing a magnetic stirring bar and a septum inlet. The flask was flushed with argon. Triethylamine (1.5 mmol) and 2-cyclopenten-1-one (1.0 mmol) dissolved in 1,4-dioxane-$H_2O$ (6:1, 3 mL) were then added. The mixture was stirred for 6 h at 25° C. Brine was added, and the mixture was extracted with ethyl acetate. If necessary the product was purified by chromatography over silica gel.

General Procedure B

To a solution of ketone (1 eq.) in DMF (0.38M) were added the amine (1.1 eq.), glacial AcOH (1.2 eq.) and $NaBH(OAc)_3$ (1.4 eq.). The mixture was stirred at r.t. overnight and filtered. Purification was performed by preparative HPLC-MS.

General Procedure C

To a solution of ketone (1 eq.) in acetonitrile (0.38M) were added the amine (1.1 eq.), glacial AcOH (1.2 eq.) and NaBH $(OAc)_3$ (1.4 eq.). The mixture was stirred at r.t. overnight, filtered and concentrated in vacuo. The reaction was dissolved in 1.7M HCl in MeOH (0.38M). The mixture was stirred at r.t. overnight, filtered and concentrated in vacuo. Purification was performed by preparative HPLC-MS.

General Procedure D

To a solution of 4-[(1S)-3-oxocyclopentyl]benzoic acid in acetonitrile (3 mL) were added an amine (1.2 eq.), DMAP (1.5 eq.) and EDCI (1.5 eq.). The resulting slurry was heated in a microwave reactor at 150° C. for 10 min. The mixture was diluted with DCM, washed twice with water and twice with aqueous $NH_4Cl$. The solvents were removed in vacuo. The compound was used without further purification.

General Procedure E

To a solution of 2-cyclopenten-1-one (400 µmol) in 400 µL DME were added boronic acid (480 µmol, 1.2 eq.), (COD) Rh(1,4-dihydroquinone)$BF_4$ (1 mol %) in 100 µL DME, and LiOH (4 mol %) in 600 µL water. After shaking the mixture overnight at 50° C., the solvent was removed in vacuo. The crude intermediate ketone was dissolved in DCE containing acetic acid (1.2 eq.). An amine (1 eq.) in DCE was added followed by $NaBH(OAc)_3$ (1.2 eq.) The mixture was shaken overnight at r. t., filtered and the solvents were removed in vacuo. The residue was redissolved in 750 μL DMSO and purified by preparative HPLC-MS.

General Procedure F (S)-2-Methyl-propane-2-sulfinic acid amide (1 equiv) was taken up in DCM (2 mL/mmol) in a, MW vial, then copper sulphate (2.2 equiv) and aldehyde (1.1 equiv) was added and the vial capped. Heated at 90° C. for 5 min, then filtered and cooled under argon to −50° C. before slow addition of methyl magnesium bromide (2 equiv). The reaction mixture was allowed to warm to r.t. over night. Quenched with ammonium chloride (aq) and extracted with EtOAc, then dried over Na$_2$SO$_4$ and concentrated in vacuo. The intermediate was purified by flash chromatography. Taken up in methanol (1 mL/mmol), then HCl in dioxane (4M, 1 mL/mmol) was added and the reaction mixture stirred at r.t. for 30 min. The methanol was evaporated and the product precipitated with ether. The title compound was collected by filtration and dried in vacuo.

General Procedure G

To a solution of 4-[(1R,3S)-3-[[(1R)-1-(4-fluoro-3-methoxy-phenyl)ethyl]amino]-cyclopentyl]benzoic acid (preparation 34, 0.05 mmol) in acetonitrile (3 mL) were added an amine (1.5 eq.), DMAP (1.5 eq.) and EDCI (1.5 eq.). If the amine is supplied as a hydrochloride salt, DIPEA (1 eq.) is added as well. The resulting slurry was heated in a microwave reactor at 150° C. for 5 min. The solvents were removed in vacuo. The residue was redissolved in DMSO, filtered, and purified by preparative HPLC-MS.

General Procedure H

To a solution of 4-[(1R)-3-oxocyclopentyl]benzoic acid (0.05 mmol) in acetonitrile (3 mL) were added an amine (1.2 eq.), DMAP (1.5 eq.) and EDCI (1.5 eq.). The resulting slurry was heated in a microwave reactor at 150° C. for 10 min. The mixture was diluted with DCM, washed twice with water and twice with aqueous NH$_4$Cl. The solvents were removed in vacuo. The compound was used without further purification.

Preparation 1

(3S)-3-(4-Methylsulfonylphenyl)cyclopentanone

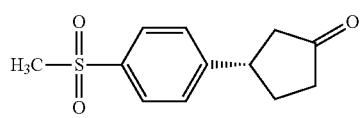

General procedure A was followed using [Rh(S-BINAP)(nbd)]BF$_4$ and 4-(methanesulphonyl)benzeneboronic acid as the arylboronic acid. $^1$H NMR (300 MHz, DMSO) δ 7.91-7.84 (m, 2H), 7.65-7.59 (m, 2H), 3.60-3.44 (m, 1H), 3.19 (s, 3H), 2.65-2.53 (m, 1H), 2.44-2.24 (m, 4H), 2.04-1.86 (m, 1H).

Preparation 2 tert-Butyl 4-[[4-[(1S)-3-oxocyclopentyl]benzoyl]amino]piperidine-1-carboxylate

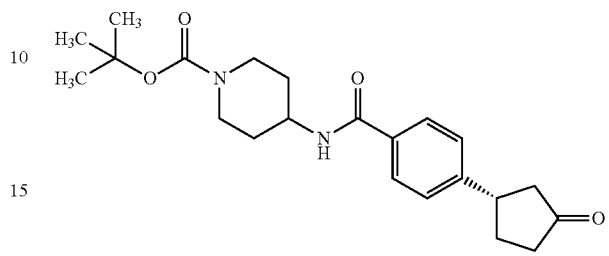

General procedure D was followed using tert-butyl 4-aminopiperidine-1-carboxylate as the amine. $^1$H NMR (300 MHz, DMSO) δ 8.18 (d, 1H), 7.79 (d, 2H), 7.40 (d, 2H), 4.07-3.83 (m, 3H), 3.53-3.35 (m, 1H), 2.95-2.67 (m, 2H), 2.62-2.49 (m, 1H), 2.42-2.22 (m, 4H), 2.02-1.85 (m, 1H), 1.84-1.70 (m, 2H), 1.52-1.29 (m, 11H).

Preparation 3

(3S)-3-(6-Methoxy-3-pyridyl)cyclopentanone

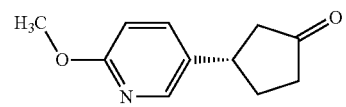

General procedure A was followed using [Rh(S-BINAP)(nbd)]BF$_4$ and 2-methoxypyridine-5-boronic acid as the arylboronic acid. $^1$H NMR (300 MHz, DMSO) δ 8.10 (d, 1H), 7.70 (dd, 1H), 6.79 (d, 1H), 3.82 (s, 3H), 3.31 (m, 1H), 2.50 (m, 1H), 2.38-2.19 (m, 4H), 1.98-1.79 (m, 1H).

Preparation 4

5-[(1S)-3-Oxocyclopentyl]-1H-pyridin-2-one

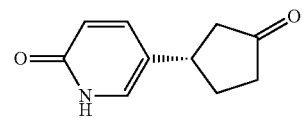 [SMILES: O=C1CC[C@H](c2ccc(=O)[nH]c2)C1]

(3S)-3-(6-methoxy-3-pyridyl)cyclopentanone (preparation 3) (560 mg, 2.9 mmol) was dissolved in acetonitrile (12 mL) and treated with NaI (1.32 g, 8.8 mmol) followed by chlorotrimethylsilane (0.74 mL, 5.9 mmol). The reaction mixture was heated in a microwave reactor at 100° C. for 5 min. Following the addition of DCM and aqueous NaHSO$_3$, the mixture was washed with water. The organic phase was dried over MgSO$_4$ and concentrated under reduced pressure to afford the title compound. $^1$H NMR (300 MHz, DMSO) δ

11.43 (s, 1H), 7.50 (dd, 1H), 7.19 (d, 1H), 6.32 (d, 1H), 3.21-3.06 (m, 1H), 2.46-2.35 (m, 1H), 2.33-2.11 (m, 4H), 1.90-1.69 (m, 1H).

Preparation 5

(3S)-3-[4-(1H-Tetrazol-5-yl)phenyl]cyclopentanone

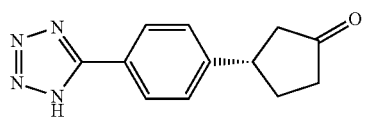 [SMILES: O=C1CC[C@H](c2ccc(-c3nnn[nH]3)cc2)C1]

General procedure A was followed using [Rh(S-BINAP)(nbd)]BF$_4$ and 4-cyanophenylboronic acid as the arylboronic acid, affording 4-[(1S)-3-oxocyclopentyl]benzonitrile. This intermediate (250 mg) was dissolved in toluene (7.5 mL) and treated with azidotrimethylsilane (0.48 mL, 5 eq.) followed by dibutyltin oxide (174 mg, 0.2 eq). The reaction mixture was heated to 110° C. for 16 h and then filtered through a pad of silica gel, which was washed with DCM. The filtrate was concentrated in vacuo to afford the title compound. $^1$H NMR (300 MHz, DMSO) δ 7.99 (d, 2H), 7.55 (d, 2H), 3.53-3.38 (m, 1H), 2.67-2.53 (m, 1H), 2.45-2.26 (m, 4H), 2.05-1.87 (m, 1H).

Preparation 6

N-(2-Hydroxyethyl)-4-[(1S)-3-oxocyclopentyl]benzenesulfonamide

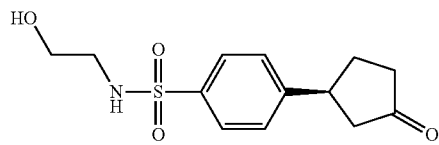 [SMILES: O=C1CC[C@H](c2ccc(S(=O)(=O)NCCO)cc2)C1]

General procedure A was followed using [Rh(S-BINAP)(nbd)]BF$_4$ and 4-(2-hydroxyethylsulfamoyl)benzeneboronic acid as the arylboronic acid. $^1$H NMR (300 MHz, CDCl$_3$) δ 7.91-7.80 (m, 2H), 7.41 (d, 2H), 4.99 (t, 1H), 3.77-3.67 (m, 2H), 3.58-3.42 (m, 1H), 3.18-3.08 (m, 2H), 2.71 (dd, 1H), 2.58-2.26 (m, 4H), 2.10-1.88 (m, 1H).

Preparation 7

(3S)-3-[4-(4-Hydroxypiperidine-1-carbonyl)phenyl]cyclopentanone

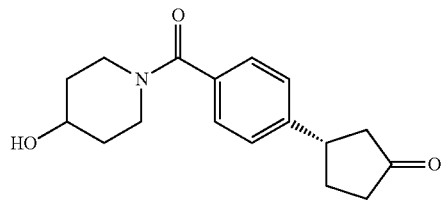 [SMILES: O=C1CC[C@H](c2ccc(C(=O)N3CCC(O)CC3)cc2)C1]

General procedure D was followed using 4-hydroxypiperidine as the amine. $^1$H NMR (300 MHz, DMSO) δ 7.46-7.27 (m, 4H), 3.79-3.69 (m, 1H), 3.53-3.37 (m, 2H), 3.35-3.30 (m, 2H), 3.15 (s, 2H), 2.43-2.19 (m, 4H), 2.01-1.86 (m, 1H), 1.85-1.61 (m, 2H), 1.46-1.23 (m, 2H).

Preparation 8

N-Methylsulfonyl-2-[4-[(1R)-3-oxocyclopentyl]phenoxy]acetamide

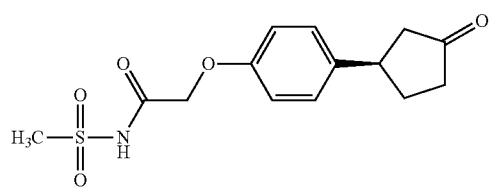 [SMILES: CS(=O)(=O)NC(=O)COc1ccc([C@@H]2CCC(=O)C2)cc1]

(R)-[4-(3-Oxo-cyclopentyl)-phenoxy]-acetic acid (preparation 31) (2.5 mmol, 585 mg) was dissolved in DCM (30 mL) and cooled to 0° C. on an icebath. EDCI.HCl (3.75 mmol, 720 mg), methanesulfonamide (2.75 mmol, 261 mg) and DMAP (3.75 mmol, 458 mg) was added and the reaction mixture left an additional 15 min on the ice bath. The ice bath was then removed and the reaction was allowed to warm to r.t. over night. Quenched with citric acid (10% aq.) and extracted with DCM, then dried over Na$_2$SO$_4$ and concentrated in vacuo to yield the title compound (745 mg, 95%). $^1$H NMR (300 MHz, CDCl$_3$) δ 8.84 (bs, 1H), 7.25-7.19 (m, 2H), 6.95-6.85 (m, 3H), 4.58 (s, 2H), 3.58-3.08 (m, 5H), 2.78-2.58 (m, 1H), 2.58-2.15 (m, 5H), 2.15-1.78 (m, 1H).

Preparation 9

2-[4-[(1R)-3-Oxocyclopentyl]phenoxy]acetamide

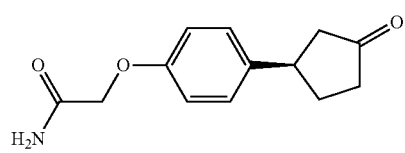 [SMILES: NC(=O)COc1ccc([C@@H]2CCC(=O)C2)cc1]

(R)-[4-(3-Oxo-cyclopentyl)-phenoxy]-acetic acid (preparation 31) (1.6 mmol, 375 mg) was dissolved in DMF (3 mL), then CDI (1.84 mmol, 299 mg) was added and the reaction mixture stirred at r.t. for 90 min. Ammonium hydroxide (25% aq, 7 mL) was added and a precipitate formed. Water (7 mL) was added and the precipitate filtered off and dried in vacuo to yield the title compound (302 mg, 81%). $^1$H NMR (300 MHz, CDCl$_3$) δ 7.25-7.14 (m, 2H), 6.97-6.83 (m, 2H), 6.78 (bs, 1H), 5.91 (bs, 1H), 4.49 (s, 2H), 3.52-3.28 (m, 1H), 2.77-2.57 (m, 1H), 2.57-2.11 (m, 5H), 2.09-1.79 (m, 1H).

Preparation 10

N-(2-Acetamidoethyl)-4-[(1S)-3-oxocyclopentyl]benzamide

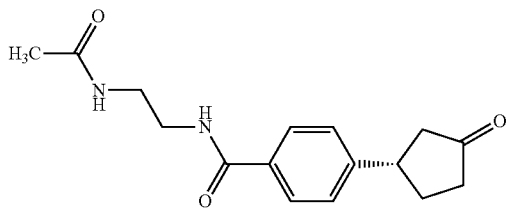 [SMILES: CC(=O)NCCNC(=O)c1ccc([C@H]2CCC(=O)C2)cc1]

General procedure D was followed using N-(2-aminoethyl)acetamide as the amine. ¹H NMR (300 MHz, DMSO) δ 8.46-8.38 (m, 1H), 7.99-7.89 (m, 1H), 7.80 (d, 2H), 7.41 (d, 2H), 3.53-3.35 (m, 1H), 3.35-3.24 (m, 2H), 3.24-3.13 (m, 2H), 2.98 (s, 3H), 2.50 (m, 1H), 2.41-2.23 (m, 4H), 1.92 (m, 1H).

Preparation 11

4-[(1S)-3-Oxocyclopentyl]-N-(2-sulfamoylethyl)benzamide

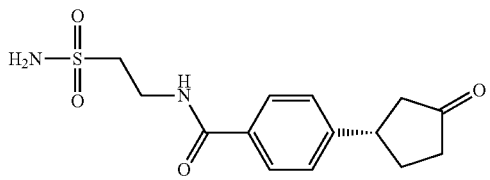 [SMILES: NS(=O)(=O)CCNC(=O)c1ccc([C@H]2CCC(=O)C2)cc1]

General procedure D was followed using 2-amino-ethanesulfonic acid amide hydrochloride as the amine. ¹H NMR (300 MHz, DMSO) δ 8.60-8.48 (m, 1H), 7.79 (d, 2H), 7.42 (d, 2H), 6.92 (s, 2H), 3.69-3.59 (m, 2H), 3.54-3.35 (m, 1H), 3.23 (dd, 2H), 2.50 (dd, 1H), 2.42-2.24 (m, 4H), 2.02-1.84 (m, 1H).

Preparation 12

4-[4-[(1S)-3-Oxocyclopentyl]benzoyl]piperazin-2-one

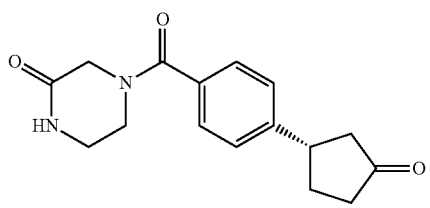 [SMILES: O=C1CC[C@H](c2ccc(C(=O)N3CCNC(=O)C3)cc2)C1]

General procedure D was followed using piperazin-2-one as the amine.

Preparation 13

(3S)-3-[4-[(3S)-3-Hydroxypyrrolidine-1-carbonyl]phenyl]-cyclopentanone

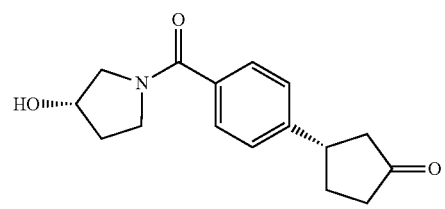 [SMILES: O=C1CC[C@H](c2ccc(C(=O)N3CC[C@H](O)C3)cc2)C1]

General procedure D was followed using (S)-3-hydroxypyrrolidine as the amine.

Preparation 14

N-(2-Amino-2-oxo-ethyl)-4-[(1S)-3-oxocyclopentyl]benzamide

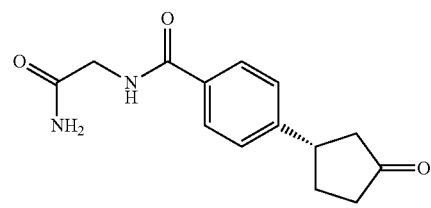 [SMILES: NC(=O)CNC(=O)c1ccc([C@H]2CCC(=O)C2)cc1]

General procedure D was followed using 2-aminoacetamide hydrochloride as the amine. ¹H NMR (300 MHz, DMSO) δ 8.58 (t, 1H), 7.84 (d, 2H), 7.42 (d, 2H), 7.33 (s, 1H), 7.00 (s, 1H), 3.80 (d, 2H), 3.55-3.37 (m, 1H), 2.63-2.50 (m, 1H), 2.41-2.24 (m, 4H), 1.99-1.85 (m, 1H).

Preparation 15

(3S)-3-[4-(Morpholine-4-carbonyl)phenyl]cyclopentanone

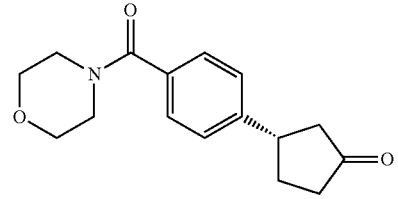 [SMILES: O=C1CC[C@H](c2ccc(C(=O)N3CCOCC3)cc2)C1]

General procedure D was followed using morpholine as the amine. ¹H NMR (300 MHz, DMSO) δ 7.49-7.28 (m, 4H), 3.67-3.55 (m, 4H), 3.55-3.48 (m, 2H), 3.48-3.35 (m, 3H), 2.62-2.52 (m, 1H), 2.42-2.23 (m, 4H), 2.00-1.82 (m, 1H).

Preparation 16

N-(2-Hydroxyethyl)-4-[(1S)-3-oxocyclopentyl]benzamide

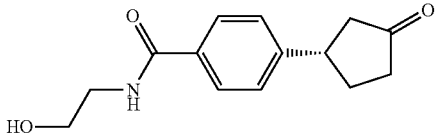 [SMILES: O=C1CC[C@H](c2ccc(C(=O)NCCO)cc2)C1]

General procedure D was followed using 2-aminoethanol as the amine. $^1$H NMR (300 MHz, DMSO) δ 8.34 (t, 1H), 7.80 (d, 2H), 7.42 (d, 2H), 4.69 (t, 1H), 3.55-3.39 (m, 3H), 3.39-3.23 (m, 2H), 2.63-2.50 (m, 1H), 2.43-2.23 (m, 4H), 2.06-1.85 (m, 1H).

Preparation 17

N-[2-(Methanesulfonamido)ethyl]-4-[(1S)-3-oxocyclopentyl]benzamide

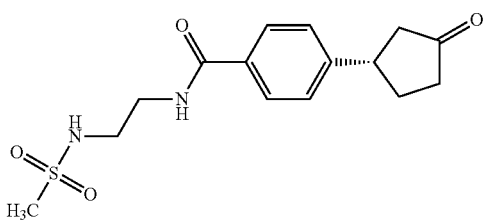 [SMILES: CS(=O)(=O)NCCNC(=O)c1ccc([C@H]2CCC(=O)C2)cc1]

General procedure D was followed using N-(2-aminoethyl)methanesulfonamide as the amine. $^1$H NMR (300 MHz, DMSO) δ 8.45 (t, 1H), 7.81 (d, 2H), 7.42 (d, 2H), 7.13 (t, 1H), 3.53-3.25 (m, 3H), 3.11 (q, 2H), 2.90 (s, 3H), 2.63-2.49 (m, 1H), 2.41-2.24 (m, 4H), 2.02-1.85 (m, 1H).

Preparation 18

N-(Cyanomethyl)-4-[(1S)-3-oxocyclopentyl]benzamide

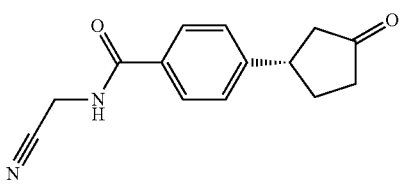 [SMILES: N#CCNC(=O)c1ccc([C@H]2CCC(=O)C2)cc1]

General procedure D was followed using 2-aminoacetonitrile as the amine. $^1$H NMR (300 MHz, DMSO) δ 9.13 (t, 1H), 7.83 (d, 2H), 7.46 (d, 2H), 4.30 (d, 2H), 3.57-3.35 (m, 1H), 2.66-2.51 (m, 1H), 2.43-2.24 (m, 4H), 2.02-1.84 (m, 1H).

Preparation 19

Methyl 4-[(1S)-3-oxocyclopentyl]benzoate

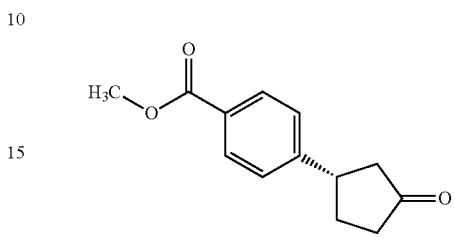

General procedure A was followed using [Rh(S-BINAP)(nbd)]BF$_4$ and 4-methoxycarbonylphenylboronic acid. $^1$H NMR (300 MHz, DMSO) δ 7.92 (d, 2H), 7.48 (d, 2H), 3.84 (s, 3H), 3.57-3.40 (m, 1H), 2.65-2.52 (m, 1H), 2.42-2.24 (m, 4H), 2.02-1.85 (m, 1H).

Preparation 20

4-[(1S)-3-Oxocyclopentyl]benzoic acid

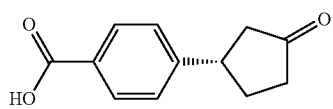

(S)-4-(3-Oxo-cyclopentyl)-benzoic acid methyl ester (preparation 19) (10.2 mmol, 2.25 g) was taken up in MeOH (6 mL) and NaOH (2N, 6 mL), the reaction mixture stirred at r.t. for 2 h. Then the MeOH was evaporated and the reaction mixture diluted with water, then neutralized with HCl (2N) to pH 5 and extracted with DCM. Dried over Na$_2$SO$_4$ and concentrated in vacuo to yield the title compound (2.09 g, 99%). $^1$H NMR (300 MHz, DMSO) δ 12.83 (br s, 1H), 7.94-7.84 (m, 2H), 7.45 (d, 2H), 3.55-3.39 (m, 1H), 2.65-2.52 (m, 1H), 2.41-2.21 (m, 4H), 2.03-1.84 (m, 1H).

Preparation 21

(R)-1-Isoquinolin-1-yl-ethylamine dihydrochloride

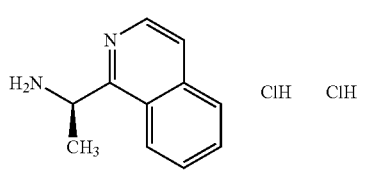

General procedure F was followed using isoquinoline-1-carbaldehyde as the aldehyde. $^1$H NMR (300 MHz, DMSO) δ 8.68 (s, 3H), 8.55 (d, J=5.7, 1H), 8.36 (d, J=7.9, 1H), 8.08 (d, J=7.9, 1H), 7.88 (ddd, J=3.4, 8.4, 9.3, 2H), 7.77 (ddd, J=1.3, 6.9, 8.2, 1H), 5.64-5.08 (m, 7H), 1.59 (d, J=6.8, 3H).

Preparation 22

(R)-1-(2,3-Dihydro-benzo[1,4]dioxin-5-yl)-ethylamine hydrochloride

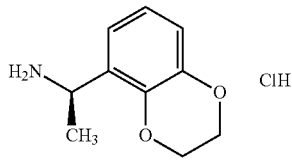

General procedure F was followed using 2,3-dihydro-benzo[1,4]dioxine-5-carbaldehyde as the aldehyde. $^1$H NMR (300 MHz, DMSO) δ 8.51 (s, 3H), 7.13-6.99 (m, 1H), 6.95-6.79 (m, 2H), 4.52 (q, J=6.8, 1H), 4.37-4.28 (m, 2H), 4.28-4.20 (m, 2H), 1.48 (d, J=6.8, 3H).

Preparation 23

(R)-1-Pyrazolo[1,5-a]pyridin-3-yl-ethylamine hydrochloride

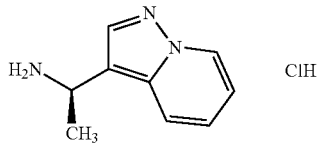

General procedure F was followed using pyrazolo[1,5-a]pyridine-3-carbaldehyde as the aldehyde. $^1$H NMR (300 MHz, DMSO) δ 8.88 (s, 3H), 8.13 (d, J=2.3, 1H), 7.79 (dd, J=1.2, 8.9, 1H), 7.32 (dd, J=7.0, 8.9, 1H), 7.16 (d, J=6.4, 1H), 6.77 (d, J=2.3, 1H), 5.14 (dt, J=6.2, 12.4, 1H), 1.70 (d, J=6.8, 3H).

Preparation 24

(R)-1-(2,2-Difluoro-benzo[1,3]dioxol-4-yl)-ethylamine hydrochloride

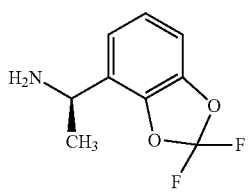

General procedure F was followed using 2,2-difluoro-benzo[1,3]dioxole-4-carbaldehyde as the aldehyde. $^1$H NMR (300 MHz, CDCl$_3$) δ 7.23-6.38 (m, 3H), 4.24 (t, J=20.7, 1H), 1.94 (s, 2H), 1.45 (d, J=5.8, 3H).

Preparation 25

(R)-1-(3,4-Dihydro-2H-benzo[b][1,4]dioxepin-6-yl)-ethylamine hydrochloride

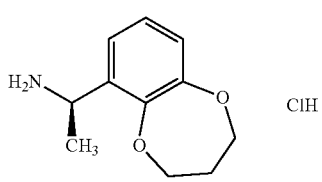

General procedure F was followed using 3,4-dihydro-2H-benzo[b][1,4]dioxepine-6-carbaldehyde as the aldehyde. $^1$H NMR (300 MHz, DMSO) δ 8.43 (s, 3H), 7.18 (dd, J=2.8, 6.5, 1H), 7.07-6.93 (m, 2H), 4.69-4.50 (m, 1H), 4.28-4.16 (m, 2H), 4.12 (t, J=5.4, 2H), 2.21-2.05 (m, 2H), 1.47 (d, J=6.8, 3H).

Preparation 26

(R)-1-(1-Methyl-5-phenyl-1H-pyrazol-3-yl)-ethylamine

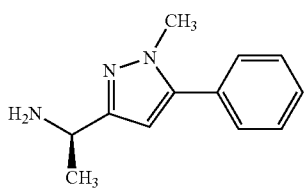

General procedure F was followed using 1-methyl-5-phenyl-1H-pyrazole-3-carbaldehyde as the aldehyde. $^1$H NMR (300 MHz, DMSO) δ 7.55-7.35 (m, 5H), 6.31 (s, 1H), 3.94 (q, J=6.7, 1H), 3.77 (s, 3H), 1.30 (d, J=6.6, 3H).

Preparation 27

(R)-1-Imidazo[1,2-a]pyridin-3-yl-ethylamine hydrochloride

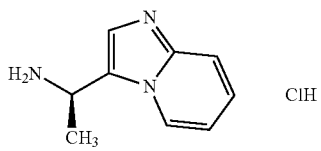

General procedure F was followed using imidazo[1,2-a]pyridine-3-carbaldehyde as the aldehyde. $^1$H NMR (300

MHz, DMSO) δ 9.18 (d, J=6.5, 1H), 9.04 (s, 3H), 8.47 (s, 1H), 8.02 (d, J=6.5, 2H), 7.58 (t, J=6.4, 1H), 5.21 (s, 1H), 1.76 (d, J=6.8, 3H).

Preparation 28

(R)-1-(5-Fluoro-imidazo[1,2-a]pyridin-2-yl)-ethylamine hydrochloride

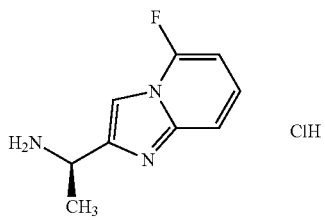

General procedure F was followed using 5-fluoro-imidazo[1,2-a]pyridine-2-carbaldehyde as the aldehyde. ¹H NMR (300 MHz, DMSO) δ 8.64 (s, 3H), 8.18 (s, 1H), 8.02-7.28 (m, 4H), 6.99 (ddd, J=1.5, 5.3, 7.1, 1H), 4.91-4.39 (m, 1H), 1.63 (d, J=6.8, 3H).

Preparation 29

(R)-1-Imidazo[1,5-a]pyridin-3-yl-ethylamine hydrochloride

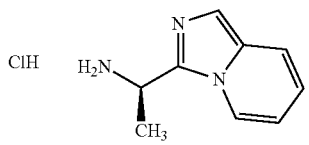

General procedure F was followed using imidazo[1,5-a]pyridine-3-carbaldehyde as the aldehyde. ¹H NMR (300 MHz, DMSO) δ 8.76 (s, 3H), 8.53 (d, J=6.3, 1H), 7.76-7.58 (m, 2H), 6.95 (dd, J=5.8, 9.1, 1H), 6.91-6.82 (m, 1H), 5.17 (s, 7H), 1.68 (d, J=6.8, 3H).

Preparation 30

[4-((1R)-3-Oxo-cyclopentyl)-phenoxy]-acetic acid ethyl ester

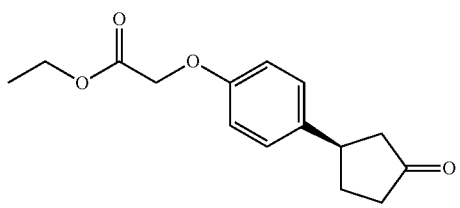 [SMILES: CCOC(=O)COc1ccc([C@@H]2CCC(=O)C2)cc1]

General procedure A was followed using [Rh(R-BINAP)(nbd)]BF₄ and 4-(2-ethoxy-2-oxoethoxy)benzeneboronic acid as the arylboronic acid. ¹H NMR (600 MHz, DMSO) δ 7.25-7.22 (m, 2H), 6.89-6.86 (m, 2H), 4.74 (s, 2H), 4.16 (q, 2H), 3.36-3.28 (m, 1H), 2.53-2.47 (m, 1H), 2.33-2.20 (m, 4H), 1.91-1.82 (m, 1H), 1.21 (t, 3H).

Preparation 31

(R)-[4-(3-Oxo-cyclopentyl)-phenoxy]-acetic acid

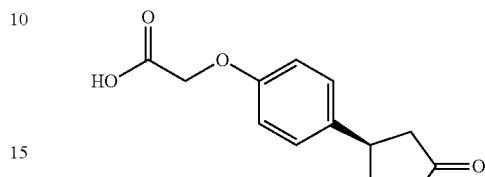

(R)-[4-(3-Oxo-cyclopentyl)-phenoxy]-acetic acid ethyl ester (preparation 30) (6.0 mmol, 1.57 g) was taken up in EtOH (6 mL) and NaOH (2N, 6 mL), the reaction mixture stirred at r.t. for 2 h. Then the EtOH was evaporated and the reaction mixture diluted with water, then neutralized with HCl (2N) to pH 5 and extracted with DCM. Dried over Na₂SO₄ and concentrated in vacuo to yield the title compound (1.24 g, 89%). ¹H NMR (300 MHz, CDCl₃) δ 7.23-7.06 (m, 2H), 6.98-6.72 (m, 2H), 4.66 (s, 2H), 3.53-3.13 (m, 1H), 2.64 (dd, J=7.5, 18.2, 1H), 2.56-2.17 (m, 4H), 2.14-1.69 (m, 1H).

Preparation 32

Methyl 4-[(1R)-3-oxocyclopentyl]benzoate

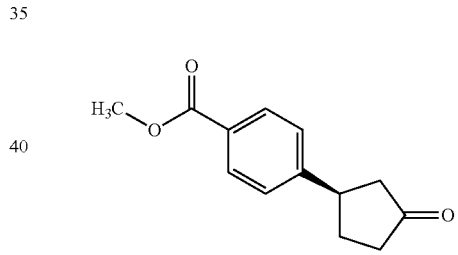

General procedure A was followed using [Rh(R-BINAP)(nbd)]BF₄ and 4-methoxycarbonylphenylboronic acid. ¹H NMR (300 MHz, DMSO) δ 7.96-7.88 (m, 2H), 7.49 (d, J=8.2 Hz, 2H), 3.84 (s, 3H), 3.56-3.41 (m, 1H), 2.64-2.52 (m, 1H), 2.42-2.22 (m, 4H), 2.03-1.83 (m, 1H).

Preparation 33

Methyl 4-[(1R,3S)-3-[[(1R)-1-(4-fluoro-3-methoxyphenyl)ethyl]-amino]cyclopentyl]benzoate

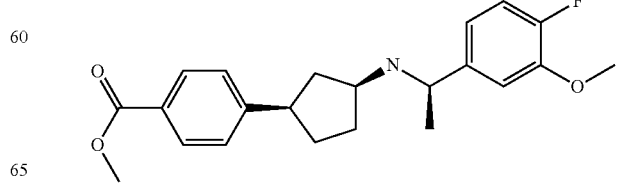

General procedure B was followed using methyl 4-[(1R)-3-oxocyclopentyl]benzoate (preparation 32) as the ketone and (1R)-1-(4-fluoro-3-methoxyphenyl)ethylamine hydrochloride as the amine. The resulting isomers were separated by flash chromatography (gradient of 0-50% EtOAc in heptane containing 3% NEt₃). The faster eluting peak was isolated to afford the title compound. ¹H NMR (300 MHz, DMSO) 7.86 (d, J=8.3 Hz, 2H), 7.38 (d, J=8.3 Hz, 2H), 7.15 (dd, J=8.7, 1.8 Hz, 1H), 7.09 (dd, J=11.5, 8.3 Hz, 1H), 6.91-6.85 (m, 1H), 3.83 (2s, 6H), 3.80-3.70 (m, 1H), 3.05-2.86 (m, 2H), 2.22-1.52 (m, 5H), 1.41-1.27 (m, 1H), 1.23 (d, J=6.6 Hz, 3H).

Preparation 34

4-[(1R,3S)-3-[[(1R)-1-(4-fluoro-3-methoxy-phenyl)ethyl]amino]-cyclopentyl]benzoic acid

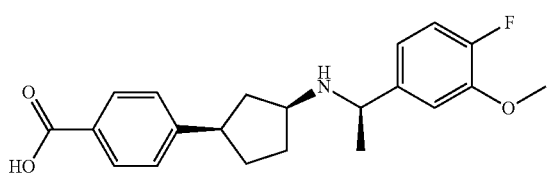 [SMILES: COc1cc([C@@H](C)N[C@H]2CC[C@@H](c3ccc(C(=O)O)cc3)C2)ccc1F]

Methyl 4-[(1R,3S)-3-[[(1R)-1-(4-fluoro-3-methoxyphenyl)ethyl]amino]-cyclopentyl]benzoate (preparation 33) (89 mg) in methanol (1 mL) was treated with 2M NaOH at r.t. for 2 h. After removal of the solvent in vacuo, 2M acetic acid was added to pH 4. The resulting precipitate was collected on a filter, washed with water and dried to afford the title compound. ¹H NMR (300 MHz, DMSO) δ 7.78 (d, J=8.1 Hz, 2H), 7.18 (d, J=8.2 Hz, 3H), 7.10 (dd, J=11.5, 8.3 Hz, 1H), 6.89 (ddd, J=8.2, 4.5, 1.9 Hz, 1H), 3.85-3.73 (m, 4H), 2.98-2.82 (m, 2H), 2.14-2.01 (m, 1H), 1.97-1.54 (m, 4H), 1.36 (td, J=11.7, 8.9 Hz, 1H), 1.25 (d, J=6.6 Hz, 3H).

Preparation 35

4-[(1R)-3-oxocyclopentyl]benzonitrile

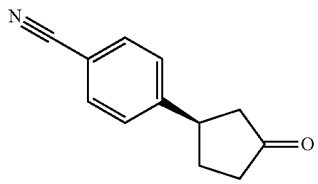 [SMILES: N#Cc1ccc([C@@H]2CCC(=O)C2)cc1]

General procedure A was followed using [Rh(R-BINAP)(nbd)]BF₄ and 4-cyanophenylboronic acid. ¹H NMR (300 MHz, DMSO) δ 7.83-7.76 (m, 2H), 7.55 (d, J=8.3 Hz, 2H), 3.58-3.42 (m, 1H), 2.57 (dd, J=17.5, 7.5 Hz, 1H), 2.43-2.21 (m, 4H), 2.02-1.83 (m, 1H).

Preparation 36

4-[(1R,3S)-3-[[(1R)-1-(4-fluoro-3-methoxy-phenyl)ethyl]amino]-cyclopentyl]benzonitrile

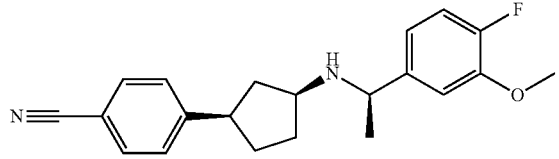 [SMILES: COc1cc([C@@H](C)N[C@H]2CC[C@@H](c3ccc(C#N)cc3)C2)ccc1F]

General procedure B was followed using 4-[(1R)-3-oxocyclopentyl]benzonitrile as the ketone and (1R)-1-(4-fluoro-3-methoxyphenyl)ethylamine hydrochloride as the amine. ¹H NMR (300 MHz, DMSO) δ 7.76-7.69 (m, 2H), 7.44 (d, J=8.3 Hz, 2H), 7.15 (dd, J=8.6, 1.9 Hz, 1H), 7.09 (dd, J=11.5, 8.3 Hz, 1H), 6.88 (ddd, J=8.2, 4.5, 1.9 Hz, 1H), 3.82 (s, 3H), 3.75 (d, J=6.2 Hz, 1H), 3.07-2.85 (m, 2H), 2.23-2.03 (m, 2H), 2.00-1.54 (m, 3H), 1.40-1.19 (m, 1H), 1.23 (d, J=6.6 Hz, 3H).

Preparation 37

N-(3-amino-3-oxo-propyl)-4-[(1S)-3-oxocyclopentyl]benzamide

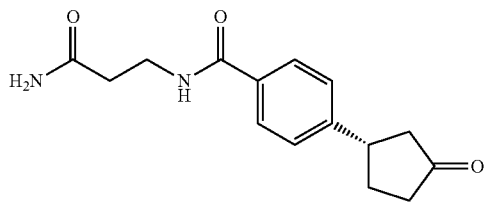 [SMILES: NC(=O)CCNC(=O)c1ccc([C@H]2CCC(=O)C2)cc1]

General procedure D was followed using 3-aminopropionamide hydrochloride as the amine.

Preparation 38

(3R)-3-(4-Bromo-phenyl)-cyclopentanone

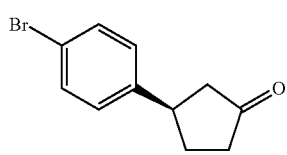 [SMILES: O=C1CC[C@@H](c2ccc(Br)cc2)C1]

General procedure A was followed using [Rh(R-BINAP)(nbd)]BF₄ and 4-bromophenylboronic acid. ¹H NMR (300

MHz, DMSO) δ 7.54-7.47 (m, 2H), 7.33-7.26 (m, 2H), 3.46-3.29 (m, 1H), 2.59-2.48 (m, 1H), 2.38-2.18 (m, 4H), 1.99-1.78 (m, 1H).

Preparation 39

4-[(1R)-3-oxocyclopentyl]benzoic acid

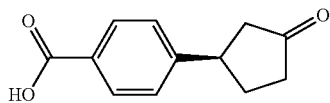

The title compound is prepared from methyl 4-[(1R)-3-oxocyclopentyl]benzoate in a manner similar to the one described for Preparation 20.

Preparation 40

4-[4-[(1R)-3-oxocyclopentyl]benzoyl]piperazin-2-one

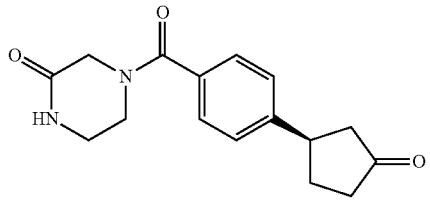 [SMILES: O=C1CC[C@@H](c2ccc(C(=O)N3CCNC(=O)C3)cc2)C1]

General procedure H is followed using piperazin-2-one as the amine.

Preparation 41

N-(2-acetamidoethyl)-4-[(1R)-3-oxocyclopentyl]benzamide

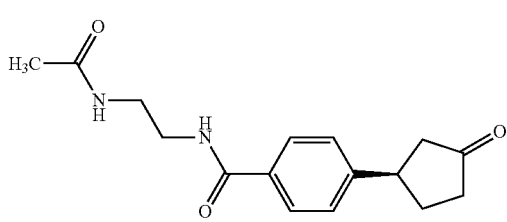 [SMILES: CC(=O)NCCNC(=O)c1ccc([C@@H]2CCC(=O)C2)cc1]

General procedure H was followed using N-(2-aminoethyl)acetamide as the amine.

Preparation 42

4-[(1R)-3-oxocyclopentyl]-N-(2-sulfamoylethyl)benzamide

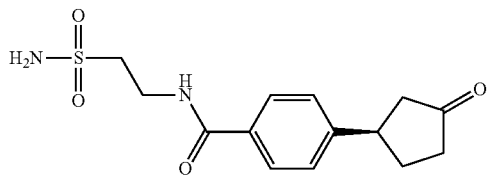 [SMILES: NS(=O)(=O)CCNC(=O)c1ccc([C@@H]2CCC(=O)C2)cc1]

General procedure H is followed using 2-amino-ethanesulfonic acid amide hydrochloride as the amine.

Preparation 43

(3R)-3-[4-(4-hydroxypiperidine-1-carbonyl)phenyl]cyclopentanone

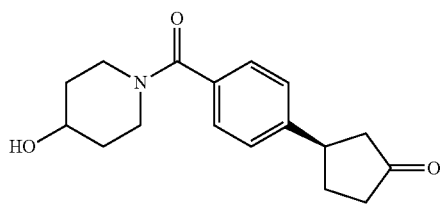 [SMILES: O=C1CC[C@@H](c2ccc(C(=O)N3CCC(O)CC3)cc2)C1]

General procedure H is followed using 4-hydroxypiperidine as the amine.

Preparation 44

N-[2-(methanesulfonamido)ethyl]-4-[(1R)-3-oxocyclopentyl]benzamide

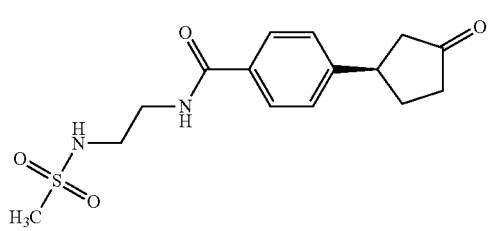 [SMILES: CS(=O)(=O)NCCNC(=O)c1ccc([C@@H]2CCC(=O)C2)cc1]

Preparation 45

(3R)-3-[4-[(3S)-3-hydroxypyrrolidine-1-carbonyl]phenyl]-cyclopentanone

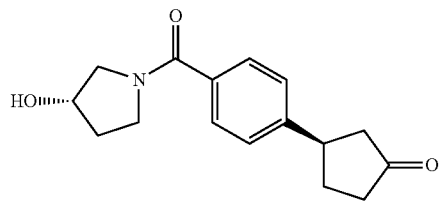 [SMILES: O=C1CC[C@@H](c2ccc(C(=O)N3CC[C@H](O)C3)cc2)C1]

General procedure H was followed using (S)-3-hydroxypyrrolidine as the amine.

Preparation 46 tert-butyl 4-[[4-[(1R)-3-oxocyclopentyl]benzoyl]amino]piperidine-1-carboxylate

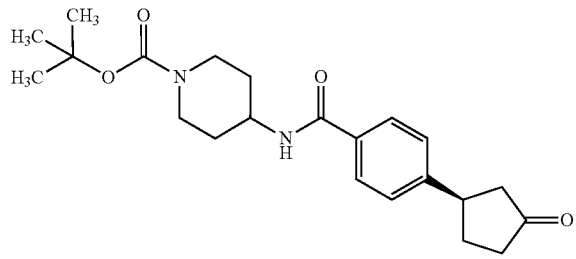 [SMILES: CC(C)(C)OC(=O)N1CCC(NC(=O)c2ccc([C@@H]3CCC(=O)C3)cc2)CC1]

General procedure H is followed using tert-butyl 4-aminopiperidine-1-carboxylate as the amine.

Preparation 47

(3R)-3-(4-Iodo-phenyl)-cyclopentanone

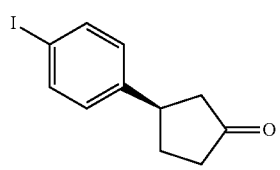 [SMILES: O=C1CC[C@@H](c2ccc(I)cc2)C1]

General procedure A was followed using [Rh(R-BINAP)(nbd)]BF$_4$ and 4-iodophenylboronic acid.

General procedure H is followed using N-(2-aminoethyl)methanesulfonamide as the amine.

Preparation 48

(3R)-3-{4-[2-(Morpholine-4-sulfonyl)-vinyl]-phenyl}-cyclopentanone

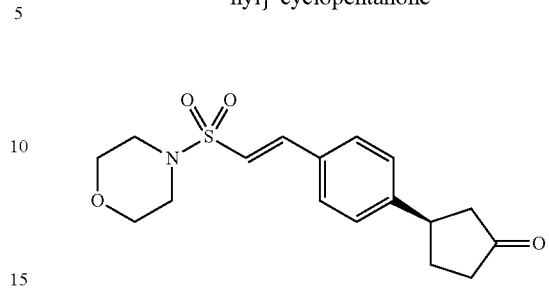

A mixture of (3R)-3-(4-iodo-phenyl)-cyclopentanone (286 mg, 1 mmol), 4-(vinylsulfonyl)morpholine (265 mg, 1.5 mmol), tri(o-tolyl)-phosphin (20 mg), Pd(OAc)$_2$ (8 mg) and NaOAc (164 mg) in DMF (4 mL) was heated at 130 C for 1.5 h. After cooling, the mixture $^1$H NMR (300 MHz, DMSO) δ 7.73 (d, J=8.2 Hz, 2H), 7.45-7.36 (m, 3H), 7.26 (d, J=15.5 Hz, 1H), 3.71-3.61 (m, 4H), 3.52-3.37 (m, 1H), 3.10-3.02 (m, 4H), 2.61-2.49 (m, 1H), 2.41-2.21 (m, 4H), 2.01-1.84 (m, 1H).

Preparation 49

(3R)-3-{4-[2-(Morpholine-4-sulfonyl)-ethyl]-phenyl}-cyclopentanone

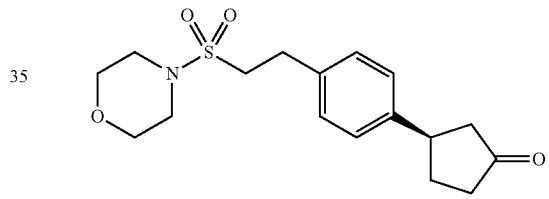

A solution of (3R)-3-{4-[2-(morpholine-4-sulfonyl)-vinyl]-phenyl}-cyclopentanone (210 mg) in EtOAc (10 ml) containing Pd/C (10%, 50 mg) was hydrogenated over night at r.t. The mixture is filtered and solvents are removed in vacuo to afford the $^1$H NMR (300 MHz, CDCl$_3$) δ 7.25-7.17 (m, 4H), 3.75 (m, 4H), 3.48-3.34 (m, 1H), 3.32-3.23 (m, 4H), 3.21-3.07 (m, 4H), 2.72-2.61 (m, 1H), 2.53-2.22 (m, 4H), 2.01-1.89 (m, 1H).

Preparation 50

{[(1S,3R)-3-(4-Bromo-phenyl)-cyclopentyl]-(1R)-[1-(4-fluoro-3-methoxy-phenyl)-ethyl]-amine

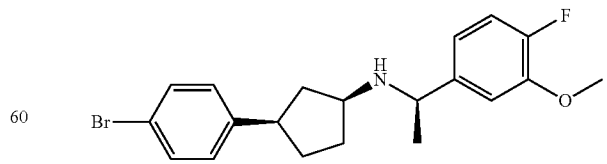

General procedure B was followed using (3R)-3-(4-Bromo-phenyl)-cyclopentanone as the ketone and (1R)-1-(4-fluoro-3-methoxyphenyl)ethylamine hydrochloride as the amine. The product was purified by flash chromatography (gradient of 20-80% EtOAc in heptane containing 2.5% NEt₃), and the faster eluting peaks were collected to afford the title compound. ¹H NMR (300 MHz, CDCl₃) δ 7.37 (d, J=8.4 Hz, 2H), 7.10-6.94 (m, 4H), 6.85-6.78 (m, 1H), 3.90 (s, 3H), 3.83 (q, 1H), 3.12-3.00 (m, 1H), 2.96-2.81 (m, 1H), 2.24-2.13 (m, 1H), 2.08-1.91 (m, 2H), 1.80-1.29 (m, 6H).

The compounds listed in the examples below are single isomers unless otherwise stated.

Stereochemistry (R and S) is assigned to the best of our knowledge.

The term "R/S" in the examples indicates that the stereochemistry is unknown in the sense, that when the compound is not indicated as a "mixture of stereoisomers" (the compound is a mixture of R and S stereoisomers), then only a single stereoisomeric form is present, but the stereochemistry of the form is not determined or is uncertain.

Example 1

(1R)—(N)-[(1R/S,3S)-3-(4-methanesulfonylphenyl) cyclopentyl]-1-(1,3-benzodioxol-4-yl)ethanamine (mixture of stereoisomers) (compound 1000)

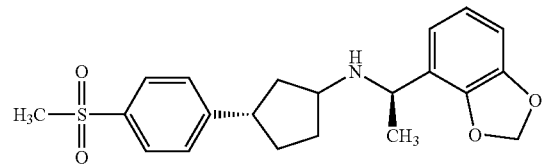 [SMILES: C[C@@H](NC1CC[C@H](c2ccc(S(C)(=O)=O)cc2)C1)c1cccc2c1OCO2]

General procedure B was followed using (3S)-3-(4-methylsulfonylphenyl)-cyclopentanone (preparation 1) as the ketone and (1R)-1-(1,3-benzodioxol-4-yl)ethanamine hydrochloride as the amine. LC-MS: RT=4.92, M=387.

Example 2

(1R)—(N)-[(1R/S,3S)-3-(4-methanesulfonylphenyl) cyclopentyl]-1-(1,3-benzodioxol-5-yl)ethanamine (compound 1001)

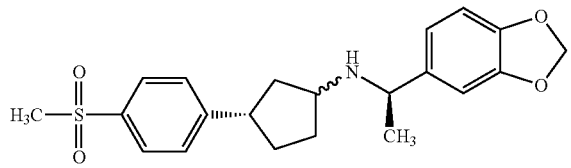 [SMILES: C[C@@H](NC1CC[C@H](c2ccc(S(C)(=O)=O)cc2)C1)c1ccc2c(c1)OCO2]

General procedure B was followed using (3S)-3-(4-methylsulfonylphenyl)-cyclopentanone (preparation 1) as the ketone and (1R)-1-(1,3-benzodioxol-5-yl)ethanamine as the amine. LC-MS: RT=4.14, M=387.

Example 3

(1R)—(N)-[(1R/S,3S)-3-(4-methanesulfonylphenyl) cyclopentyl]-1-(1-methyl-5-phenyl-pyrazol-3-yl) ethanamine (compound 1002)

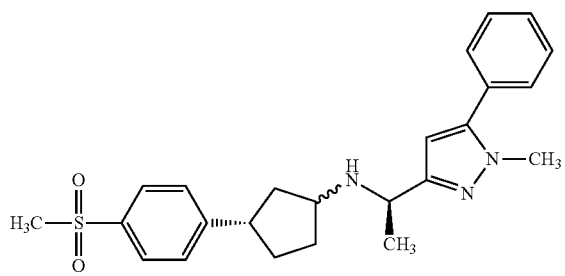 [SMILES: C[C@@H](NC1CC[C@H](c2ccc(S(C)(=O)=O)cc2)C1)c1cc(-c2ccccc2)n(C)n1]

General procedure B was followed using (3S)-3-(4-methylsulfonylphenyl)-cyclopentanone (preparation 1) as the ketone and (1R)-1-(1-methyl-5-phenyl-pyrazol-3-yl)ethanamine (preparation 26) as the amine. LC-MS: RT=4.02, M=423.

Example 4

(1R)—(N)-[(1R/S,3S)-3-(4-methanesulfonylphenyl) cyclopentyl]-1-(2,2-difluoro-1,3-benzodioxol-4-yl) ethanamine (compound 1003

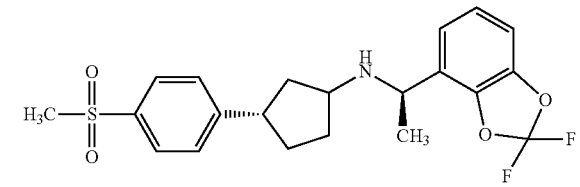 [SMILES: C[C@@H](NC1CC[C@H](c2ccc(S(C)(=O)=O)cc2)C1)c1cccc2c1OC(F)(F)O2]

General procedure B was followed using (3S)-3-(4-methylsulfonylphenyl)-cyclopentanone (preparation 1) as the ketone and (1R)-1-(2,2-difluoro-1,3-benzodioxol-4-yl)ethanamine (preparation 24) as the amine. LC-MS: RT=2.63, M=423.

Example 5

(1R)—(N)-[(1R/S,3S)-3-(4-methanesulfonylphenyl) cyclopentyl]-1-(2,3-dihydro-1,4-benzodioxin-5-yl) ethanamine (compound 1004)

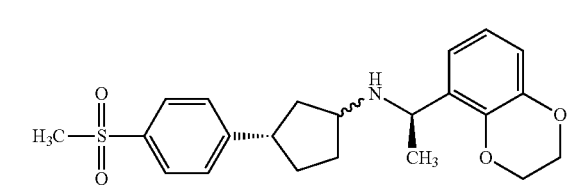 [SMILES: C[C@@H](NC1CC[C@H](c2ccc(S(C)(=O)=O)cc2)C1)c1cccc2c1OCCO2]

General procedure B was followed using (3S)-3-(4-methylsulfonylphenyl)-cyclopentanone (preparation 1) as the ketone and (1R)-1-(2,3-dihydro-1,4-benzodioxin-5-yl)ethanamine hydrochloride (preparation 22) as the amine. LC-MS: RT=3.96, M=401.

Example 6

(1R)—(N)-[(1R/S,3S)-3-(4-methanesulfonylphenyl)cyclopentyl]-1-(2,3-dihydrobenzofuran-5-yl)ethanamine (mixture of stereoisomers) (compound 1005)

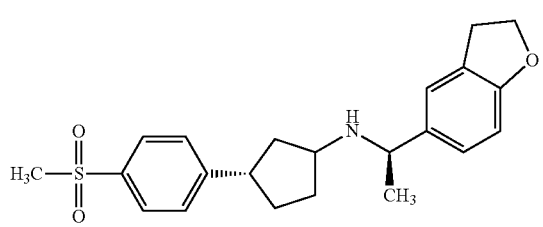 [SMILES: C[C@@H](NC1CC[C@H](c2ccc(S(C)(=O)=O)cc2)C1)c1ccc2c(c1)CCO2]

General procedure B was followed using (3S)-3-(4-methylsulfonylphenyl)-cyclopentanone (preparation 1) as the ketone and (1R)-1-(2,3-dihydrobenzofuran-5-yl)ethanamine as the amine. LC-MS: RT=3.94, M=385.

Example 7

(1R)—(N)-[(1R/S,3S)-3-(4-methanesulfonylphenyl)cyclopentyl]-1-(2,3-dimethoxyphenyl)ethanamine (mixture of stereoisomers) (compound 1006)

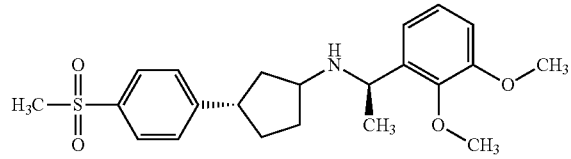

General procedure B was followed using (3S)-3-(4-methylsulfonylphenyl)-cyclopentanone (preparation 1) as the ketone and (1R)-1-(2,3-dimethoxyphenyl)ethylamine hydrochloride as the amine. LC-MS: RT=4.56, M=403.

Example 8

(1R)—(N)-[(1R/S,3S)-3-(4-methanesulfonylphenyl)cyclopentyl]-1-(2-fluoro-3-methoxy-phenyl)ethanamine (compound 1007)

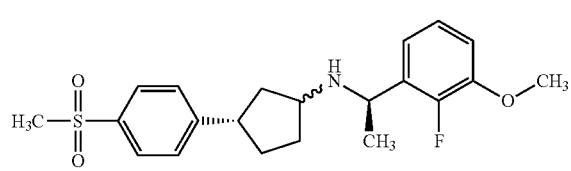

General procedure B was followed using (3S)-3-(4-methylsulfonylphenyl)-cyclopentanone (preparation 1) as the ketone and (1R)-1-(2-fluoro-3-methoxy-phenyl)-ethanamine as the amine. LC-MS: RT=3.92, M=391.

Example 9

(1R)—(N)-[(1R/S,3S)-3-(4-methanesulfonylphenyl)cyclopentyl]-1-(2-fluoro-5-methoxy-phenyl)ethanamine (compound 1008)

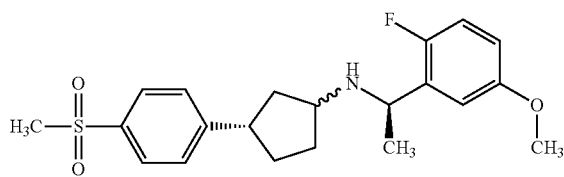 [SMILES: COc1ccc(F)c([C@@H](C)NC2CC[C@H](c3ccc(S(C)(=O)=O)cc3)C2)c1]

General procedure B was followed using (3S)-3-(4-methylsulfonylphenyl)-cyclopentanone (preparation 1) as the ketone and (1R)-1-(2-fluoro-5-methoxy-phenyl)-ethanamine as the amine. LC-MS: RT=3.97, M=391.

Example 10

(1R)—(N)-[(1R/S,3S)-3-(4-methanesulfonylphenyl)cyclopentyl]-1-(2-methylthiazol-4-yl)ethanamine (compound 1009)

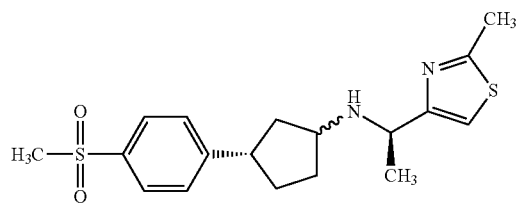 [SMILES: Cc1nc([C@@H](C)NC2CC[C@H](c3ccc(S(C)(=O)=O)cc3)C2)cs1]

General procedure B was followed using (3S)-3-(4-methylsulfonylphenyl)-cyclopentanone (preparation 1) as the ketone and (1R)-1-(2-methylthiazol-4-yl)ethanamine hydrochloride as the amine. LC-MS: RT=4.51, M=364.

Example 11

(1R)—(N)-[(1R/S,3R)-3-(4-methanesulfonylphenyl)cyclopentyl]-1-(3-chloro-4-fluoro-phenyl)ethanamine (mixture of stereoisomers) (compound 1010)

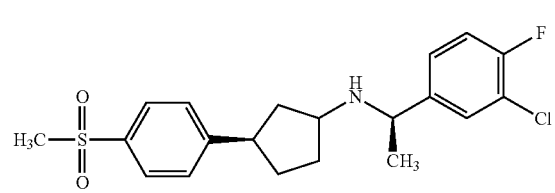 [SMILES: C[C@@H](NC1CC[C@@H](c2ccc(S(C)(=O)=O)cc2)C1)c1ccc(F)c(Cl)c1]

General procedure B was followed using (3S)-3-(4-methylsulfonylphenyl)-cyclopentanone (preparation 1) as the ketone and (1R)-1-(3-chloro-4-fluoro-phenyl)ethanamine hydrochloride as the amine. LC-MS: RT=2.05, M=396.

Example 12

(1R)—(N)-[(1R/S,3S)-3-(4-methanesulfonylphenyl) cyclopentyl]-1-(3-ethoxyphenyl)ethanamine formiate (mixture of stereoisomers) (compound 1011)

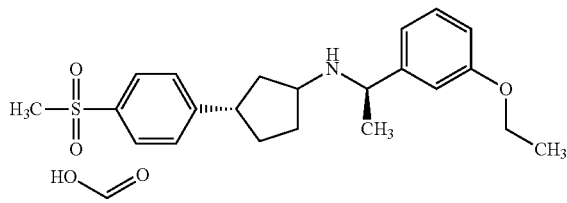

General procedure B was followed using (3S)-3-(4-methylsulfonylphenyl)-cyclopentanone (preparation 1) as the ketone and (1R)-1-(3-ethoxyphenyl)-ethanamine hydrochloride as the amine. LC-MS: RT=2.01, M=434.

Example 13

(1R)—(N)-[(1R/S,3S)-3-(4-methanesulfonylphenyl) cyclopentyl]-1-(3-fluoro-5-methoxyphenyl)ethanamine (mixture of stereoisomers) (compound 1012)

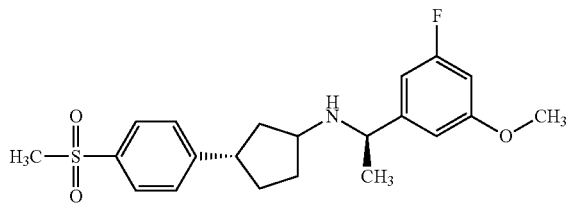

General procedure B was followed using (3S)-3-(4-methylsulfonylphenyl)-cyclopentanone (preparation 1) as the ketone and (1R)-1-(3-fluoro-5-methoxy-phenyl)-ethanamine as the amine. LC-MS: RT=5.57, M=391.

Example 14

(1R)—(N)-[(1R/S,3S)-3-(4-methanesulfonylphenyl) cyclopentyl]-1-(4-fluoro-2-methoxyphenyl)ethanamine (compound 1013)

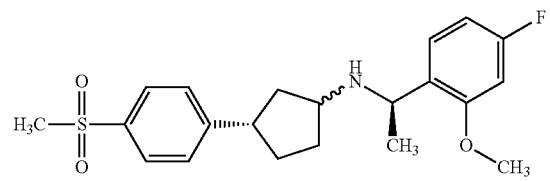 [SMILES: COc1cc(F)ccc1[C@@H](C)NC1CC[C@H](c2ccc(S(C)(=O)=O)cc2)C1]

General procedure B was followed using (3S)-3-(4-methylsulfonylphenyl)-cyclopentanone (preparation 1) as the ketone and (1R)-1-(4-fluoro-2-methoxy-phenyl)-ethanamine as the amine. LC-MS: RT=5.17, M=391.

Example 15

(1R)—(N)-[(1R/S,3S)-3-(4-methanesulfonylphenyl) cyclopentyl]-1-(4-fluoro-3-methoxyphenyl)ethanamine (compound 1014)

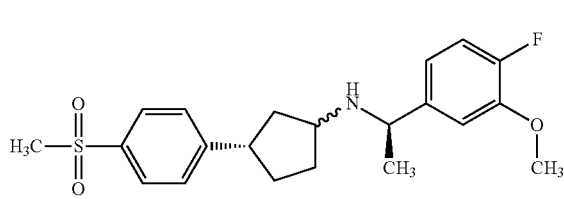 [SMILES: COc1cc([C@@H](C)NC2CC[C@H](c3ccc(S(C)(=O)=O)cc3)C2)ccc1F]

General procedure B was followed using (3S)-3-(4-methylsulfonylphenyl)-cyclopentanone (preparation 1) as the ketone and (1R)-1-(4-fluoro-3-methoxyphenyl)ethylamine hydrochloride as the amine. LC-MS: RT=3.97, M=391.

Example 16

(1R)—(N)-[(1R/S,3R)-3-(4-methanesulfonylphenyl) cyclopentyl]-1-(4-quinolyl)ethanamine (mixture of stereoisomers) (compound 1015)

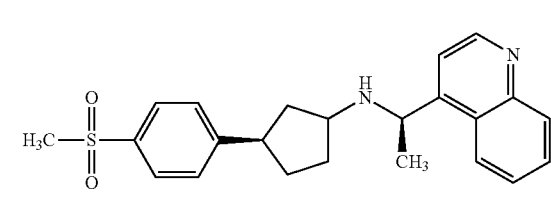 [SMILES: C[C@@H](NC1CC[C@@H](c2ccc(S(C)(=O)=O)cc2)C1)c1ccnc2ccccc12]

General procedure B was followed using (3S)-3-(4-methylsulfonylphenyl)-cyclopentanone (preparation 1) as the ketone and (1R)-1-(4-quinolyl)ethanamine hydrochloride as the amine. LC-MS: RT=1.86, M=395.

Example 17

(1R)—(N)-[(1R/S,3R)-3-(4-methanesulfonylphenyl) cyclopentyl]-1-(5-chloro-2-thienyl)ethanamine (mixture of stereoisomers) (compound 1016)

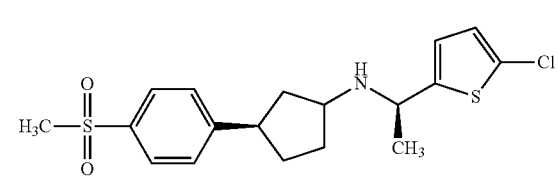 [SMILES: C[C@@H](NC1CC[C@@H](c2ccc(S(C)(=O)=O)cc2)C1)c1ccc(Cl)s1]

General procedure B was followed using (3S)-3-(4-methylsulfonylphenyl)-cyclopentanone (preparation 1) as the ketone and (1R)-1-(5-chloro-2-thienyl)ethanamine hydrochloride as the amine. LC-MS: RT=2.01, M=384.

Example 18

(1R)—(N)-[(1R/S,3S)-3-(4-methanesulfonylphenyl)cyclopentyl]-1-(8-quinolyl)ethanamine (compound 1017)

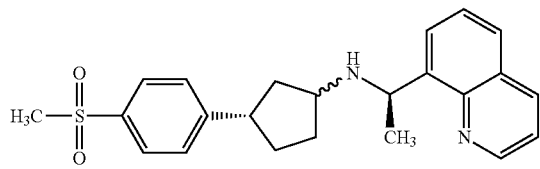 [SMILES: C[C@@H](NC1CC[C@H](c2ccc(S(C)(=O)=O)cc2)C1)c1cccc2cccnc12]

General procedure B was followed using (3S)-3-(4-methylsulfonylphenyl)-cyclopentanone (preparation 1) as the ketone and (1R)-1-(8-quinolyl)ethanamine as the amine. LC-MS: RT=4.04, M=394.

Example 19

(1R)—(N)-[(1R/S,3S)-3-(4-methanesulfonylphenyl)cyclopentyl]-1-[3-(methylethoxy)phenyl]ethanamine (compound 1018)

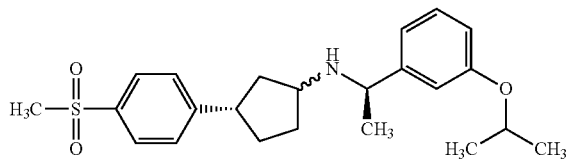 [SMILES: CC(C)Oc1cccc([C@@H](C)NC2CC[C@H](c3ccc(S(C)(=O)=O)cc3)C2)c1]

General procedure B was followed using (3S)-3-(4-methylsulfonylphenyl)-cyclopentanone (preparation 1) as the ketone and (1R)-1-[3-(methylethoxy)phenyl]ethylamine hydrochloride as the amine. LC-MS: RT=5.77, M=401.

Example 20

(1R)—(N)-[(1R/S,3S)-3-(4-methanesulfonylphenyl)cyclopentyl]-1-[4-fluoro-3-(trifluoromethyl)phenyl]ethanamine (mixture of stereoisomers) (compound 1019)

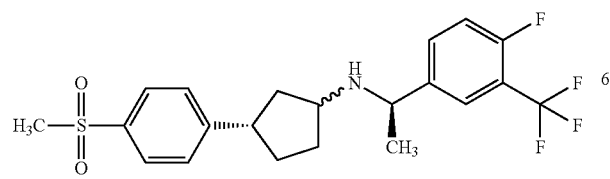

General procedure B was followed using (3S)-3-(4-methylsulfonylphenyl)-cyclopentanone (preparation 1) as the ketone and (1R)-1-[4-fluoro-3-(trifluoromethyl)phenyl]ethanamine hydrochloride as the amine: LC-MS: RT=2.07, M=429.

Example 21

(1R)—(N)-[(1R/S,3S)-3-(4-methanesulfonylphenyl)cyclopentyl]-1-cyclopropylethanamine (mixture of stereoisomers) (compound 1020)

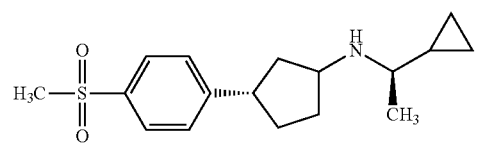 [SMILES: C[C@@H](NC1CC[C@H](c2ccc(S(C)(=O)=O)cc2)C1)C1CC1]

General procedure B was followed using (3S)-3-(4-methylsulfonylphenyl)-cyclopentanone (preparation 1) as the ketone and (1R)-1-cyclopropylethanamine as the amine. LC-MS: RT=3.96, M=307.

Example 22

(1R)—(N)-[(1R/S,3S)-3-(4-methanesulfonylphenyl)cyclopentyl]-1-imidazo[1,2-a]pyridin-3-ylethanamine (mixture of stereoisomers) (compound 1021)

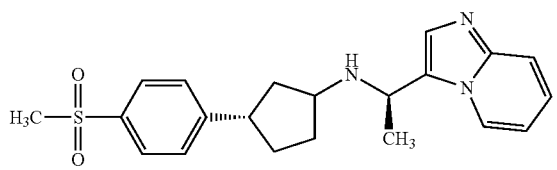 [SMILES: C[C@@H](NC1CC[C@H](c2ccc(S(C)(=O)=O)cc2)C1)c1cnc2ccccn12]

General procedure B was followed using (3S)-3-(4-methylsulfonylphenyl)-cyclopentanone (preparation 1) as the ketone and (1R)-1-imidazo[1,2-a]pyridin-3-ylethanamine hydrochloride (preparation 27) as the amine. LC-MS: RT=4.04, M=383.

Example 23

(1R)—(N)-[(1R/S,3S)-3-(4-methanesulfonylphenyl)cyclopentyl]-1-imidazo[1,5-a]pyridin-3-ylethanamine (mixture of stereoisomers) (compound 1022)

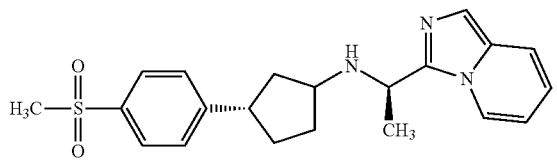 [SMILES: C[C@@H](NC1CC[C@H](c2ccc(S(C)(=O)=O)cc2)C1)c1ncc2ccccn12]

General procedure B was followed using (3S)-3-(4-methylsulfonylphenyl)-cyclopentanone (preparation 1) as the ketone and (1R)-1-imidazo[1,5-a]pyridin-3-ylethanamine hydrochloride (preparation 29) as the amine. LC-MS: RT=(n/d), M=(n/d).

Example 24

(1R)—(N)-[(1R/S,3S)-3-(4-methanesulfonylphenyl)cyclopentyl]-1-pyrazolo[1,5-a]pyridin-3-ylethanamine formiate (mixture of stereoisomers) (compound 1023)

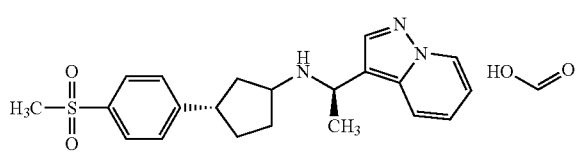

General procedure B was followed using (3S)-3-(4-methylsulfonylphenyl)-cyclopentanone (preparation 1) as the ketone and (1R)-1-pyrazolo[1,5-a]pyridin-3-ylethanamine hydrochloride (preparation 23) as the amine. LC-MS: RT=2.36, M=383.

Example 25

(1R)—(N)-[(1R/S,3S)-3-(4-methanesulfonylphenyl)cyclopentyl]-1-cyclohexylethanamine (mixture of stereoisomers) (compound 1024)

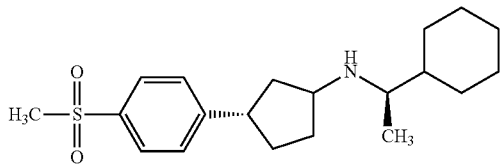 [SMILES: C[C@@H](NC1CC[C@H](c2ccc(S(C)(=O)=O)cc2)C1)C1CCCCC1]

General procedure B was followed using (3S)-3-(4-methylsulfonylphenyl)-cyclopentanone (preparation 1) as the ketone and (R)-(−)-1-cyclohexylethylamine as the amine. LC-MS: RT=5.06, M=349.

Example 26

(1R)—(N)-[(1R/S,3S)-3-(4-methanesulfonylphenyl)cyclopentyl]-1-(3-fluoro-4-methoxyphenyl)ethanamine (compound 1025)

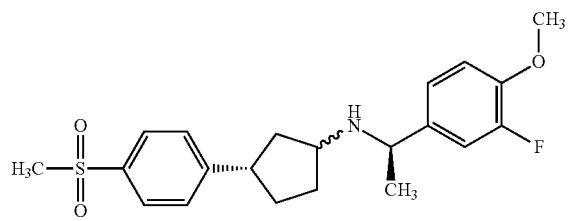

General procedure B was followed using (3S)-3-(4-methylsulfonylphenyl)-cyclopentanone (preparation 1) as the ketone and (R)-1-(3-fluoro-4-methoxyphenyl)ethanamine hydrochloride as the amine. LC-MS: RT=5.26, M=391.

Example 27

(1R)—(N)-[(1R/S,3S)-3-(4-methanesulfonylphenyl)cyclopentyl]-1-(3-fluorophenyl)ethanamine (mixture of stereoisomers) (compound 1026)

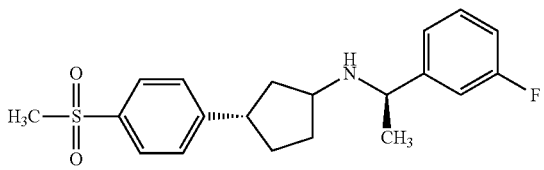 [SMILES: C[C@@H](NC1CC[C@H](c2ccc(S(C)(=O)=O)cc2)C1)c1cccc(F)c1]

General procedure B was followed using (3S)-3-(4-methylsulfonylphenyl)-cyclopentanone (preparation 1) as the ketone and (R)-1-(3-fluorophenyl)ethanamine as the amine. LC-MS: RT=5.16, M=361.

Example 28

(1R)—(N)-[(1R/S,3R/S)-3-(4-methanesulfonylphenyl)cyclopentyl]-1-(3-methoxyphenyl)ethanamine (mixture of stereoisomers) (compound 1027)

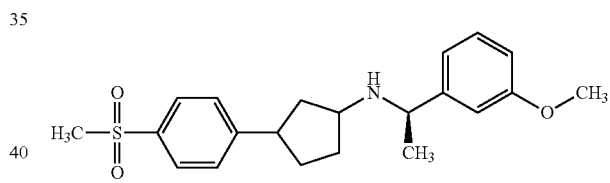

General procedure B was followed using (3S)-3-(4-methylsulfonylphenyl)-cyclopentanone (preparation 1) as the ketone and (R)-1-(3-methoxyphenyl)-ethylamine as the amine. LC-MS: RT=4.04, M=373.

Example 29

(1R)—(N)-[(1R/S,3S)-3-(4-methanesulfonylphenyl)cyclopentyl]-1-[3-(trifluoromethyl)phenyl]ethanamine (compound 1028)

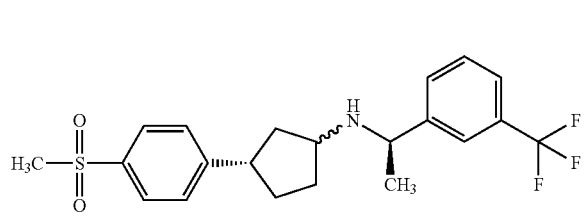 [SMILES: C[C@@H](NC1CC[C@H](c2ccc(S(C)(=O)=O)cc2)C1)c1cccc(C(F)(F)F)c1]

General procedure B was followed using (3S)-3-(4-methylsulfonylphenyl)-cyclopentanone (preparation 1) as the ketone and (R)-1-[3-(trifluoromethyl)phenyl]ethylamine as the amine. LC-MS: RT=4.11, M=411.

Example 30

(1R)—(N)-[(1R/S,3S)-3-(4-methanesulfonylphenyl)cyclopentyl]-1-benzo[b]thiophen-3-yl-ethanamine (compound 1029)

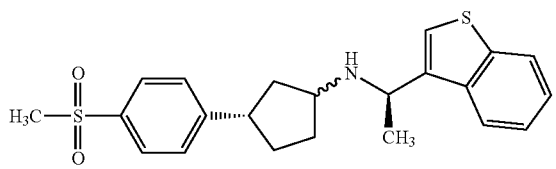 [SMILES: C[C@@H](NC1CC[C@H](c2ccc(S(C)(=O)=O)cc2)C1)c1csc2ccccc12]

General procedure B was followed using (3S)-3-(4-methylsulfonylphenyl)-cyclopentanone (preparation 1) as the ketone and (R)-1-benzo[b]thiophen-3-yl-ethylamine as the amine. LC-MS: RT=4.11, M=399.

Example 31

(1R)—(N)-[(1R/S,3S)-3-(4-methanesulfonylphenyl)cyclopentyl]-1-(3-cyano-4-fluorophenyl)ethanamine (mixture of stereoisomers) (compound 1030)

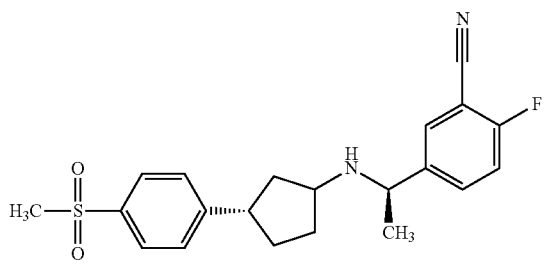 [SMILES: C[C@@H](NC1CC[C@H](c2ccc(S(C)(=O)=O)cc2)C1)c1ccc(F)c(C#N)c1]

General procedure B was followed using (3S)-3-(4-methylsulfonylphenyl)-cyclopentanone (preparation 1) as the ketone and 5-[(1R)-1-aminoethyl]-2-fluoro-benzonitrile hydrochloride as the amine. LC-MS: RT=5.41, M=386.

Example 32

(1R/S)—(N)-[(1R/S,3S)-3-(4-methanesulfonylphenyl)cyclopentyl]-1-(3,4-dihydro-3-oxo-[2H]-1,4-benzoxazin-6-yl)ethanamine (mixture of stereoisomers) (compound 1031)

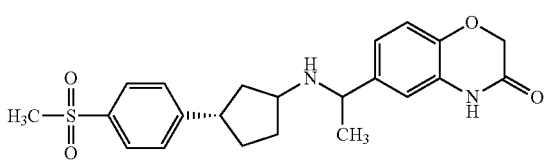 [SMILES: CC(NC1CC[C@H](c2ccc(S(C)(=O)=O)cc2)C1)c1ccc2c(c1)NC(=O)CO2]

General procedure B was followed using (3S)-3-(4-methylsulfonylphenyl)-cyclopentanone (preparation 1) as the ketone and 6-(1-aminoethyl)-2H-1,4-benzoxazin-3(4H)-one as the amine. LC-MS: RT=4.44, M=414.

Example 33

(1R)—(N)-[(1R/S,3S)-3-[4-(1H-tetrazol-5-yl)phenyl]cyclopentyl]-1-(1,3-benzodioxol-4-yl)ethanamine (mixture of stereoisomers) (compound 1032)

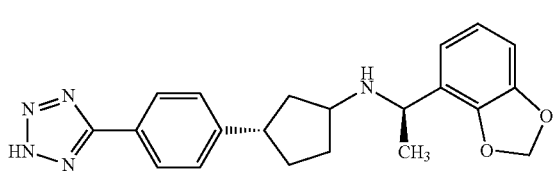 [SMILES: C[C@@H](NC1CC[C@H](c2ccc(-c3nn[nH]n3)cc2)C1)c1cccc2c1OCO2]

General procedure B was followed using (3S)-3-[4-(1H-tetrazol-5-yl)phenyl]-cyclopentanone as the ketone and (1R)-1-(1,3-benzodioxol-4-yl)ethanamine hydrochloride as the amine. LC-MS: RT=1.93, M=377.

Example 34

(1R)—(N)-[(1R/S,3S)-3-[4-(1H-tetrazol-5-yl)phenyl]cyclopentyl]-1-(2,3-dihydro-1,4-benzodioxin-5-yl)ethanamine (mixture of stereoisomers) (compound 1033)

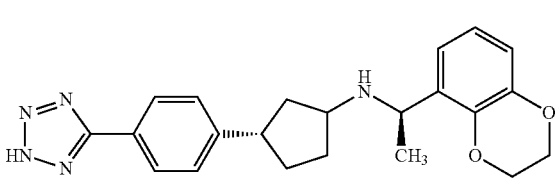 [SMILES: C[C@@H](NC1CC[C@H](c2ccc(-c3nn[nH]n3)cc2)C1)c1cccc2c1OCCO2]

General procedure B was followed using (3S)-3-[4-(1H-tetrazol-5-yl)phenyl]-cyclopentanone (preparation 5) as the ketone and (1R)-1-(2,3-dihydro-1,4-benzodioxin-5-yl)ethanamine hydrochloride (preparation 22) as the amine. LC-MS: RT=(n/d), M=(n/d).

Example 35

(1R)—(N)-[(1R/S,3S)-3-[4-(1H-tetrazol-5-yl)phenyl]cyclopentyl]-1-(4-fluoro-2-methoxyphenyl)ethanamine (mixture of stereoisomers) (compound 1034)

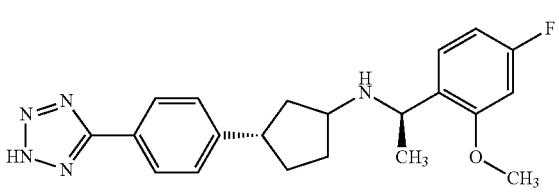 [SMILES: COc1cc(F)ccc1[C@@H](C)NC1CC[C@H](c2ccc(-c3nn[nH]n3)cc2)C1]

General procedure B was followed using (3S)-3-[4-(1H-tetrazol-5-yl)phenyl]-cyclopentanone (preparation 5) as the ketone and (1R)-1-(4-fluoro-2-methoxy-phenyl)-ethanamine as the amine. LC-MS: RT=1.46, M=381.

Example 36

(1R)—(N)-[(1R/S,3S)-3-[4-(1H-tetrazol-5-yl)phenyl]cyclopentyl]-1-(4-fluoro-3-methoxyphenyl)ethanamine (mixture of stereoisomers) (compound 1035)

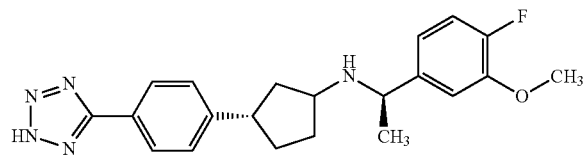 [SMILES: COc1cc([C@@H](C)NC2CC[C@H](c3ccc(-c4nn[nH]n4)cc3)C2)ccc1F]

General procedure B was followed using (3S)-3-[4-(1H-tetrazol-5-yl)phenyl]-cyclopentanone (preparation 5) as the ketone and (1R)-1-(4-fluoro-3-methoxyphenyl)ethylamine hydrochloride as the amine. LC-MS: RT=1.43, M=381.

Example 37

(1R)—(N)-[(1R/S,3S)-3-[4-(1H-tetrazol-5-yl)phenyl]cyclopentyl]-1-(3-chlorophenyl)ethanamine (mixture of stereoisomers) (compound 1036)

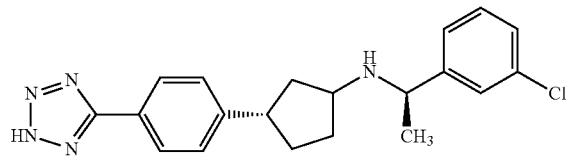 [SMILES: C[C@@H](NC1CC[C@H](c2ccc(-c3nn[nH]n3)cc2)C1)c1cccc(Cl)c1]

General procedure B was followed using (3S)-3-[4-(1H-tetrazol-5-yl)phenyl]-cyclopentanone (preparation 5) as the ketone and (R)-1-(3-chlorophenyl)ethanamine as the amine. LC-MS: RT=2.00, M=368.

Example 38

(1R)—(N)-[(1R/S,3S)-3-[4-(4-hydroxypiperidine-1-carbonyl)phenyl]-cyclopentyl]-1-(1,3-benzodioxol-4-yl)ethanamine (compound 1037)

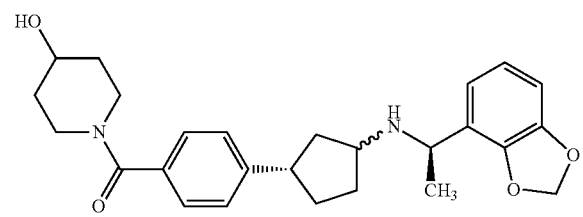 [SMILES: C[C@@H](NC1CC[C@H](c2ccc(C(=O)N3CCC(O)CC3)cc2)C1)c1cccc2c1OCO2]

General procedure B was followed using (3S)-3-[4-(4-hydroxypiperidine-1-carbonyl)phenyl]cyclopentanone (preparation 7) as the ketone and (1R)-1-(1,3-benzodioxol-4-yl)ethanamine hydrochloride as the amine. LC-MS: RT=4.54, M=436.

Example 39

(1R)—(N)-[(1R/S,3S)-3-[4-(4-hydroxypiperidine-1-carbonyl)phenyl]-cyclopentyl]-1-(1-isoquinolyl)ethanamine hydrochloride (compound 1038)

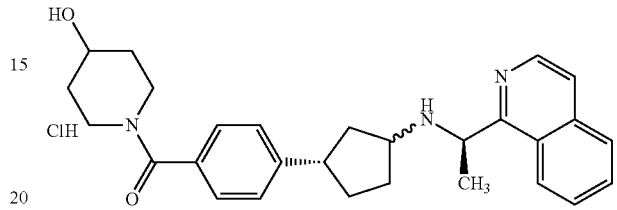

General procedure B was followed using (3S)-3-[4-(4-hydroxypiperidine-1-carbonyl)phenyl]cyclopentanone (preparation 7) as the ketone and (1R)-1-(1-isoquinolyl)-ethanamine dihydrochloride (preparation 21) as the amine. LC-MS: RT=4.44, M=443.

Example 40

(1R)—(N)-[(1R/S,3S)-3-[4-(4-hydroxypiperidine-1-carbonyl)phenyl]-cyclopentyl]-1-(3,4-dichlorophenyl)ethanamine hydrochloride (compound 1039)

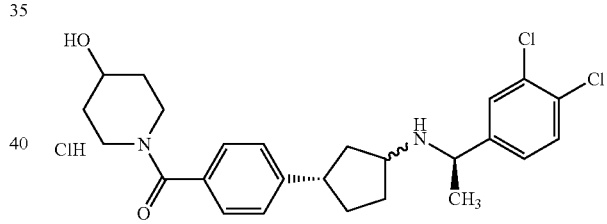

General procedure B was followed using (3S)-3-[4-(4-hydroxypiperidine-1-carbonyl)phenyl]cyclopentanone (preparation 7) as the ketone and (1R)-1-(3,4-dichlorophenyl)-ethanamine hydrochloride as the amine. LC-MS: RT=5.62, M=460.

Example 41

(1R)—(N)-[(1R/S,3S)-3-[4-(4-hydroxypiperidine-1-carbonyl)phenyl]-cyclopentyl]-1-(3,4-difluorophenyl)ethanamine hydrochloride (compound 1040)

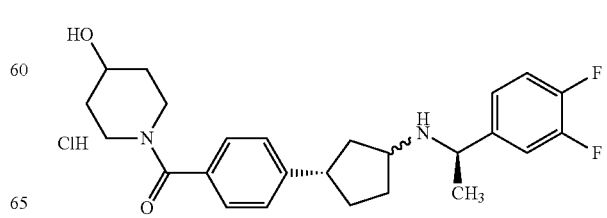

General procedure B was followed using (3S)-3-[4-(4-hydroxypiperidine-1-carbonyl)phenyl]cyclopentanone (preparation 7) as the ketone and (1R)-1-(3,4-difluorophenyl)-ethanamine hydrochloride as the amine. LC-MS: RT=4.96, M=428.

Example 42

(1R)—N)-[(1R/S,3S)-3-[4-(4-hydroxypiperidine-1-carbonyl)phenyl]-cyclopentyl]-1-(3,4-dihydro-2H-1,5-benzodioxepin-6-yl)ethanamine hydrochloride (compound 1041

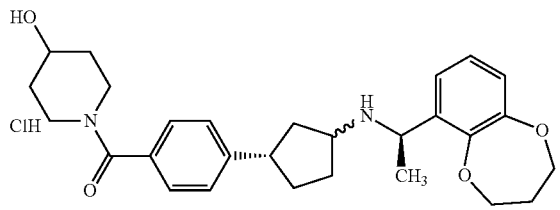 [SMILES: Cl ; C[C@@H](NC1CC[C@H](c2ccc(C(=O)N3CCC(O)CC3)cc2)C1)c1cccc2c1OCCCO2]

General procedure B was followed using (3S)-3-[4-(4-hydroxypiperidine-1-carbonyl)phenyl]cyclopentanone (preparation 7) as the ketone and (1R)-1-(3,4-dihydro-2H-1,5-benzodioxepin-6-yl)ethanamine hydrochloride (preparation 25) as the amine. LC-MS: RT=4.37, M=464.

Example 43

(1R)—N)-[(1R/S,3S)-3-[4-(4-hydroxypiperidine-1-carbonyl)phenyl]-cyclopentyl]-1-(3,4-dimethoxyphenyl)ethanamine hydrochloride (compound 1042)

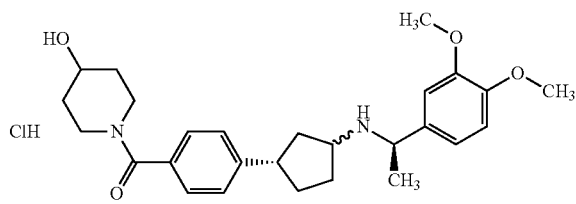 [SMILES: Cl ; COc1ccc([C@@H](C)NC2CC[C@H](c3ccc(C(=O)N4CCC(O)CC4)cc3)C2)cc1OC]

General procedure B was followed using (3S)-3-[4-(4-hydroxypiperidine-1-carbonyl)phenyl]cyclopentanone (preparation 7) as the ketone and (1R)-1-(3,4-dimethoxyphenyl)ethanamine hydrochloride as the amine. LC-MS: RT=4.06, M=452.

Example 44

(1R)—N)-[(1R/S,3S)-3-[4-(4-hydroxypiperidine-1-carbonyl)phenyl]-cyclopentyl]-1-(3,5-dimethoxyphenyl)ethanamine hydrochloride (compound 1043)

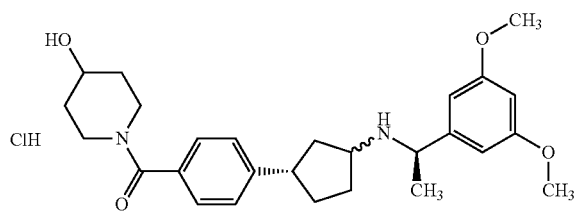 [SMILES: Cl ; COc1cc(OC)cc([C@@H](C)NC2CC[C@H](c3ccc(C(=O)N4CCC(O)CC4)cc3)C2)c1]

General procedure B was followed using (3S)-3-[4-(4-hydroxypiperidine-1-carbonyl)phenyl]cyclopentanone (preparation 7) as the ketone and (1R)-1-(3,5-dimethoxyphenyl)ethanamine hydrochloride as the amine. LC-MS: RT=4.52, M=452.

Example 45

(1R)—N)-[(1R/S,3R)-3-[4-(4-hydroxypiperidine-1-carbonyl)phenyl]-cyclopentyl]-1-(3-chloro-4-fluorophenyl)ethanamine (compound 1044)

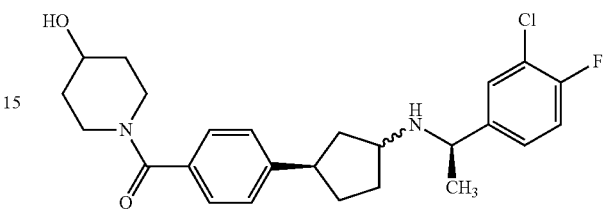

General procedure B was followed using (3S)-3-[4-(4-hydroxypiperidine-1-carbonyl)phenyl]cyclopentanone (preparation 7) as the ketone and (1R)-1-(3-chloro-4-fluoro-phenyl)ethanamine hydrochloride as the amine. LC-MS: RT=5.22, M=444.

Example 46

(1R)—N)-[(1R/S,3S)-3-[4-(4-hydroxypiperidine-1-carbonyl)phenyl]-cyclopentyl]-1-(3-fluoro-5-methoxyphenyl)ethanamine hydrochloride (compound 1045)

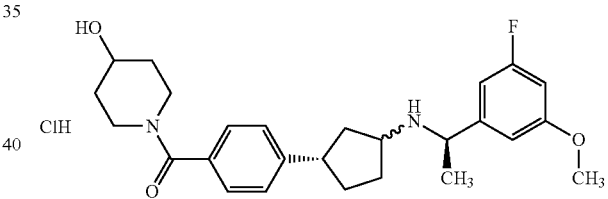

General procedure B was followed using (3S)-3-[4-(4-hydroxypiperidine-1-carbonyl)phenyl]cyclopentanone (preparation 7) as the ketone and (1R)-1-(3-fluoro-5-methoxy-phenyl)ethanamine as the amine. LC-MS: RT=4.86, M=440.

Example 47

(1R)—N)-[(1R/S,3S)-3-[4-(4-hydroxypiperidine-1-carbonyl)phenyl]-cyclopentyl]-1-(4-fluoro-2-methoxyphenyl)ethanamine hydrochloride (compound 1046)

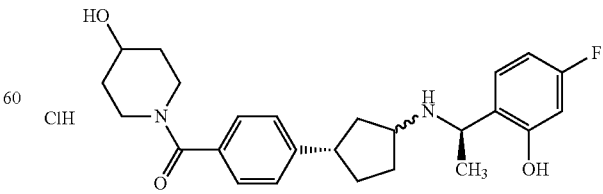

General procedure B was followed using (3S)-3-[4-(4-hydroxypiperidine-1-carbonyl)phenyl]cyclopentanone (preparation 7) as the ketone and (1R)-1-(4-fluoro-2-methoxy-phenyl)ethanamine as the amine. LC-MS: RT=4.44, M=440.

Example 48

(1R)—(N)-[(1R/S,3S)-3-[4-(4-hydroxypiperidine-1-carbonyl)phenyl]-cyclopentyl]-1-(4-fluoro-3-methoxyphenyl)ethanamine hydrochloride (compound 1047)

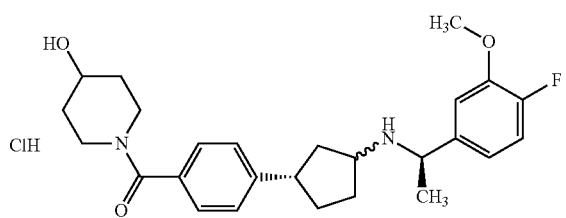 [SMILES: Cl ; COc1cc([C@@H](C)NC2CC[C@H](c3ccc(C(=O)N4CCC(O)CC4)cc3)C2)ccc1F]

General procedure B was followed using (3S)-3-[4-(4-hydroxypiperidine-1-carbonyl)phenyl]cyclopentanone (preparation 7) as the ketone and (1R)-1-(4-fluoro-3-methoxyphenyl)ethylamine hydrochloride as the amine. LC-MS: RT=4.62, M=440.

Example 49

(1R)—(N)-[(1R/S,3S)-3-[4-(4-hydroxypiperidine-1-carbonyl)phenyl]-cyclopentyl]-1-pyrazolo[1,5-a]pyridin-3-ylethanamine (mixture of stereoisomers) (compound 1048)

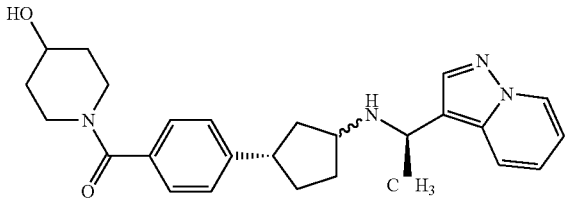

General procedure B was followed using (3S)-3-[4-(4-hydroxypiperidine-1-carbonyl)phenyl]cyclopentanone (preparation 7) as the ketone and (1R)-1-pyrazolo[1,5-a]pyridin-3-ylethanamine hydrochloride (preparation 23) as the amine. LC-MS: RT=4.71, M=432.

Example 50

(1R)—(N)-[(1R/S,3S)-3-[4-(4-hydroxypiperidine-1-carbonyl)phenyl]cyclopentyl]-1-benzo[b]thiophen-3-yl-ethanamine hydrochloride (compound 1049)

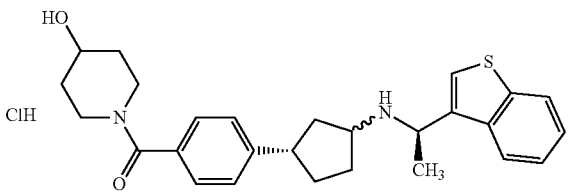 [SMILES: Cl ; C[C@@H](NC1CC[C@H](c2ccc(C(=O)N3CCC(O)CC3)cc2)C1)c1csc2ccccc12]

General procedure B was followed using (3S)-3-[4-(4-hydroxypiperidine-1-carbonyl)phenyl]cyclopentanone (preparation 7) as the ketone and (R)-1-benzo[b]thiophen-3-yl-ethylamine as the amine. LC-MS: RT=5.16, M=448.

Example 51

(1R)—(N)-[(1R/S,3S)-3-[4-[(3S)-3-hydroxypyrrolidin-1-ylcarbonyl]phenyl]cyclopentyl]-1-(3-ethoxyphenyl)ethanamine (compound 1050)

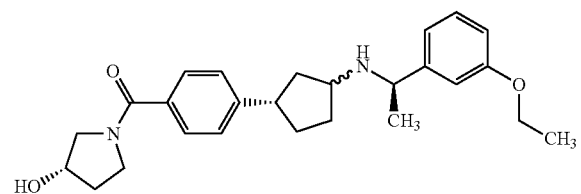 [SMILES: CCOc1cccc([C@@H](C)NC2CC[C@H](c3ccc(C(=O)N4CC[C@H](O)C4)cc3)C2)c1]

General procedure B was followed using (3S)-3-[4-[(3S)-3-hydroxypyrrolidine-1-carbonyl]phenyl]cyclopentanone (preparation 13) as the ketone and (1R)-1-(3-ethoxyphenyl)-ethanamine hydrochloride as the amine. LC-MS: RT=4.64, M=422.

Example 52

(1R)—(N)-[(1R/S,3S)-3-[4-[(3S)-3-hydroxypyrrolidin-1-ylcarbonyl]phenyl]cyclopentyl]-1-(4-fluoro-3-methoxyphenyl)ethanamine (compound 1051)

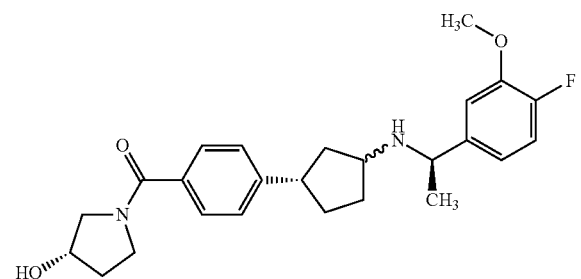 [SMILES: COc1cc([C@@H](C)NC2CC[C@H](c3ccc(C(=O)N4CC[C@H](O)C4)cc3)C2)ccc1F]

General procedure B was followed using (3S)-3-[4-[(3S)-3-hydroxypyrrolidine-1-carbonyl]phenyl]cyclopentanone (preparation 13) as the ketone and (1R)-1-(4-fluoro-3-methoxyphenyl)ethanamine hydrochloride as the amine. LC-MS: RT=4.49, M=426.

Example 53

(1R)—(N)-[(1R/S,3S)-3-[4-[(3S)-3-hydroxypyrrolidin-1-ylcarbonyl]phenyl]cyclopentyl]-1-(3-chlorophenyl)ethanamine (compound 1052)

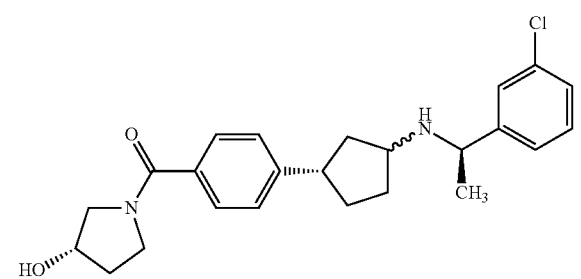 [SMILES: C[C@@H](NC1CC[C@H](c2ccc(C(=O)N3CC[C@H](O)C3)cc2)C1)c1cccc(Cl)c1]

General procedure B was followed using (3S)-3-[4-[(3S)-3-hydroxypyrrolidine-1-carbonyl]phenyl]cyclopentanone (preparation 13) as the ketone and (R)-1-(3-chlorophenyl)-ethanamine as the amine. LC-MS: RT=5.01, M=412.

Example 54

(1R)—(N)-[(1R/S,3S)-3-[4-[(3S)-3-hydroxypyrrolidin-1-ylcarbonyl]phenyl]cyclopentyl]-1-benzo[b]thiophen-3-yl-ethanamine (compound 1053)

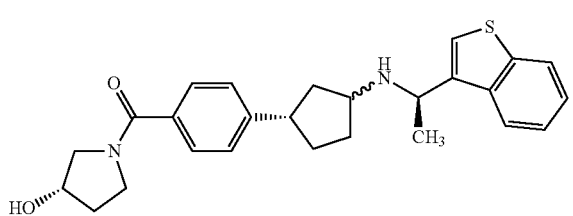 [SMILES: C[C@@H](NC1CC[C@H](c2ccc(C(=O)N3CC[C@H](O)C3)cc2)C1)c1csc2ccccc12]

General procedure B was followed using (3S)-3-[4-[(3S)-3-hydroxypyrrolidine-1-carbonyl]phenyl]cyclopentanone (preparation 13) as the ketone and (R)-1-benzo[b]thiophen-3-yl-ethylamine as the amine. LC-MS: RT=5.05, M=434.

Example 55

(1R)—(N)-[(1R/S,3R/S)-3-[4-acetamidophenyl]cyclopentyl]-1-(3-methoxyphenyl)ethanamine (mixture of stereoisomers) (compound 1054)

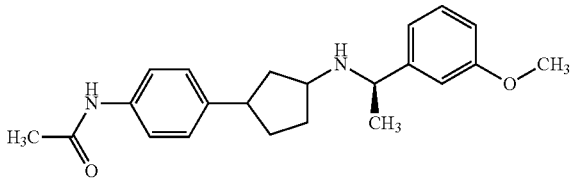 [SMILES: COc1cccc([C@@H](C)NC2CCC(c3ccc(NC(C)=O)cc3)C2)c1]

General procedure E was followed using (4-acetylaminophenyl)boronic acid as the boronic acid and (R)-1-(3-methoxyphenyl)ethylamine as the amine. LC-MS (method B): RT=3.99, M=352.

Example 56

(1R)—(N)-[(1R/S,3R/S)-3-[4-methanesulfonylaminophenyl]-cyclopentyl]-1-(3-methoxyphenyl)ethanamine (mixture of stereoisomers) (compound 1055)

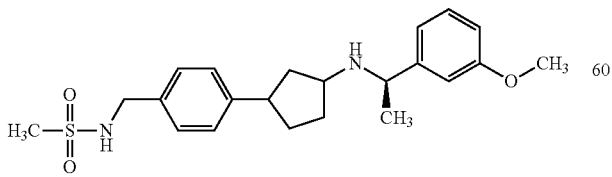

General procedure E was followed using (4-methanesulfonylaminomethyl)-phenylboronic acid as the boronic acid and (R)-1-(3-methoxyphenyl)ethylamine as the amine. LC-MS (method B): RT=4.07, M=402.

Example 57

(1R)—(N)-[(1R/S,3R)-3-[4-[aminocarbonylmethoxy]phenyl]-cyclopentyl]-1-(1,3-benzodioxol-4-yl)ethanamine (compound 1056)

General procedure B was followed using 2-[4-[(1R)-3-oxocyclopentyl]phenoxy]-acetamide (preparation 9) as the ketone and (1R)-1-(1,3-benzodioxol-4-yl)ethanamine hydrochloride as the amine. LC-MS: RT=4.96, M=382.

Example 58

(1R)—(N)-[(1R/S,3R)-3-[4-[aminocarbonylmethoxy]phenyl]-cyclopentyl]-1-(3-chloro-4-fluorophenyl)ethanamine (compound 1057)

General procedure B was followed using 2-[4-[(1R)-3-oxocyclopentyl]phenoxy]-acetamide (preparation 9) as the ketone and (1R)-1-(3-chloro-4-fluoro-phenyl)ethanamine hydrochloride as the amine. LC-MS: RT=5.71, M=390.

Example 59

(1R)—(N)-[(1R/S,3R)-3-[4-[aminocarbonylmethoxy]phenyl]-cyclopentyl]-1-(3-ethoxyphenyl)ethanamine (compound 1058)

General procedure B was followed using 2-[4-[(1R)-3-oxocyclopentyl]phenoxy]-acetamide (preparation 9) as the ketone and (1R)-1-(3-ethoxyphenyl)ethanamine hydrochloride as the amine. LC-MS: RT=5.21, M=382.

Example 60

(1R)—(N)-[(1R/S,3R)-3-[4-(aminocarbonyl-methoxy)-phenyl]-cyclopentyl]-1-(4-fluoro-2-methoxyphenyl)ethanamine (compound 1059)

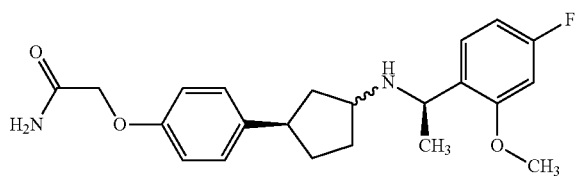 [SMILES: COc1cc(F)ccc1[C@@H](C)NC1CC[C@@H](c2ccc(OCC(N)=O)cc2)C1]

General procedure B was followed using 2-[4-[(1R)-3-oxocyclopentyl]phenoxy]-acetamide (preparation 9) as the ketone and (1R)-1-(4-fluoro-2-methoxy-phenyl)ethanamine as the amine. LC-MS: RT=5.27, M=386.

Example 61

(1R)—(N)-[(1R/S,3R)-3-[4-(aminocarbonyl-methoxy)-phenyl]-cyclopentyl]-1-(4-fluoro-3-methoxyphenyl)ethanamine (compound 1060)

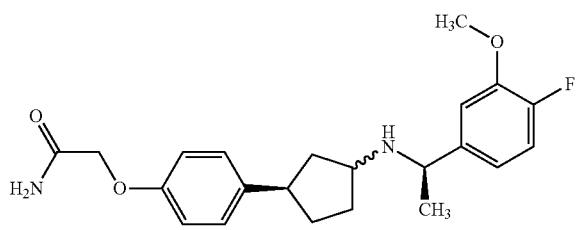 [SMILES: COc1cc([C@@H](C)NC2CC[C@@H](c3ccc(OCC(N)=O)cc3)C2)ccc1F]

General procedure B was followed using 2-[4-[(1R)-3-oxocyclopentyl]phenoxy]-acetamide (preparation 9) as the ketone and (1R)-1-(4-fluoro-3-methoxyphenyl)ethylamine hydrochloride as the amine. LC-MS: RT=1.40, M=386.

Example 62

(1R)—(N)-[(1R/S,3R)-3-[4-[aminocarbonyl-methoxy]phenyl]-cyclopentyl]-1-(3-chlorophenyl)ethanamine (compound 1061)

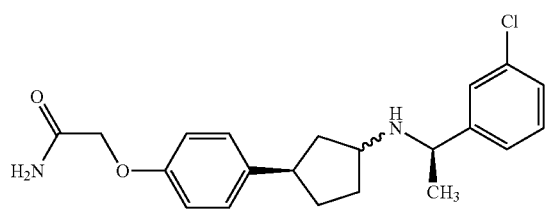 [SMILES: C[C@@H](NC1CC[C@@H](c2ccc(OCC(N)=O)cc2)C1)c1cccc(Cl)c1]

General procedure B was followed using 2-[4-[(1R)-3-oxocyclopentyl]phenoxy]-acetamide (preparation 9) as the ketone and (R)-1-(3-chlorophenyl)ethanamine as the amine. LC-MS: RT=5.62, M=372.

Example 63

(1R)—(N)-[(1R/S,3R/S)-3-[3-methylsulfonylaminophenyl]-cyclopentyl]-1-(3-methoxyphenyl)ethanamine (mixture of stereoisomers) (compound 1062)

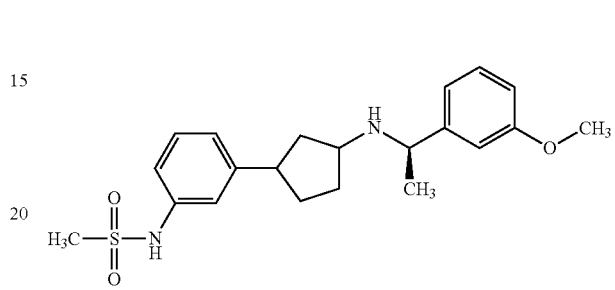

General procedure E was followed using 3-(methylsulfonylamino)phenylboronic acid as the boronic acid and (R)-1-(3-methoxyphenyl)ethylamine as the amine. LC-MS (method B): RT=(n/d), M=388.

Example 64

(1R)—(N)-[(1R/S,3R/S)-3-[4-morpholinosulfonylphenyl]cyclopentyl]-1-(3-methoxyphenyl)ethanamine (mixture of stereoisomers) (compound 1063)

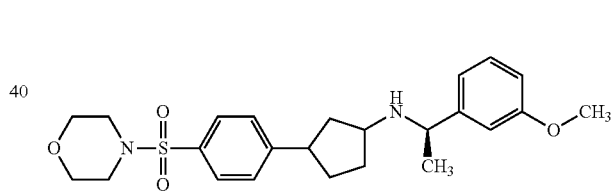

General procedure E was followed using 4-(4-morpholinylsulfonyl)phenylboronic acid as the boronic acid and (R)-1-(3-methoxyphenyl)ethylamine as the amine. LC-MS (method B): RT=4.19, M=444.

Example 65

(1R)—(N)-[(1R/S,3R/S)-3-[4-hydroxymethylphenyl]cyclopentyl]-1-(3-methoxyphenyl)ethanamine (mixture of stereoisomers) (compound 1064

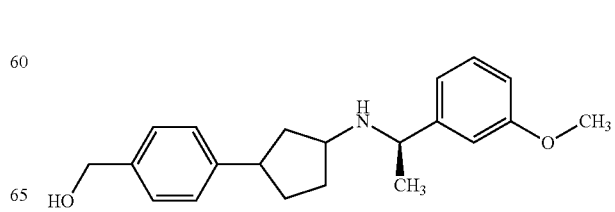

General procedure E was followed using 4-(hydroxymethyl)phenylboronic acid as the boronic acid and (R)-1-(3-methoxyphenyl)ethylamine as the amine. LC-MS (method B): RT=4.01, M=325.

Example 66

(1R)—(N)-[(1R/S,3R/S)-3-[4-methanesulfonylaminophenyl]-cyclopentyl]-1-(3-methoxyphenyl)ethanamine (mixture of stereoisomers) (compound 1065)

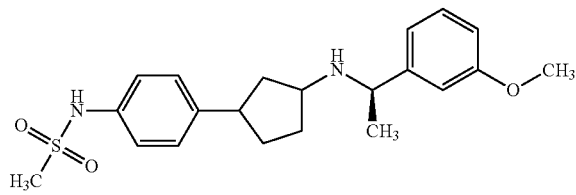

General procedure E was followed using 4-(methylsulfonylamino)phenylboronic acid as the boronic acid and (R)-1-(3-methoxyphenyl)ethylamine as the amine. LC-MS (method B): RT=4.07, M=388.

Example 67

(1R)—(N)-[(1R/S,3S)-3-[4-(2-(aminosulfonyl)ethylaminocarbonyl)-phenyl]cyclopentyl]-1-(1,3-benzodioxol-4-yl)ethanamine (compound 1066)

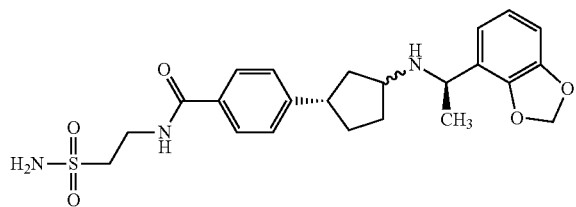 [SMILES: C[C@@H](NC1CC[C@H](c2ccc(C(=O)NCCS(N)(=O)=O)cc2)C1)c1cccc2c1OCO2]

General procedure B was followed using 4-[(1S)-3-oxocyclopentyl]-N-(2-sulfamoylethyl)benzamide (preparation 11) as the ketone and (1R)-1-(1,3-benzodioxol-4-yl)ethanamine hydrochloride as the amine. LC-MS: RT=4.59, M=459.

Example 68

(1R)—(N)-[(1R/S,3S)-3-[4-(2-(aminosulfonyl)ethylaminocarbonyl)-phenyl]cyclopentyl]-1-(3-ethoxyphenyl)ethanamine (compound 1067)

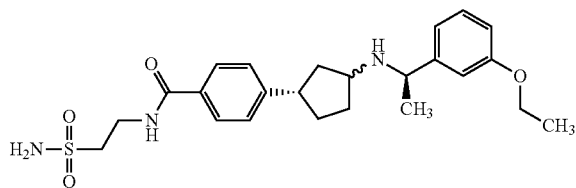 [SMILES: CCOc1cccc([C@@H](C)NC2CC[C@H](c3ccc(C(=O)NCCS(N)(=O)=O)cc3)C2)c1]

General procedure B was followed using 4-[(1S)-3-oxocyclopentyl]-N-(2-sulfamoylethyl)benzamide (preparation 11) as the ketone and (1R)-1-(3-ethoxyphenyl)ethanamine hydrochloride as the amine. LC-MS: RT=4.79, M=459.

Example 69

(1R)—(N)-[(1R/S,3S)-3-[4-(2-(aminosulfonyl)ethylaminocarbonyl)-phenyl]cyclopentyl]-1-(4-fluoro-2-methoxyphenyl)ethanamine (compound 1068)

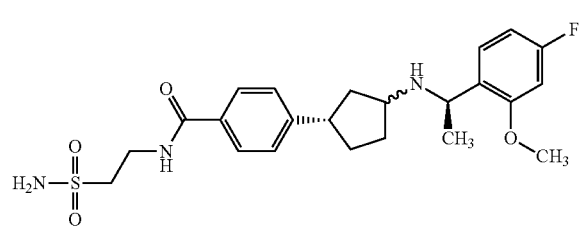 [SMILES: COc1cc(F)ccc1[C@@H](C)NC1CC[C@H](c2ccc(C(=O)NCCS(N)(=O)=O)cc2)C1]

General procedure B was followed using 4-[(1S)-3-oxocyclopentyl]-N-(2-sulfamoylethyl)benzamide (preparation 11) as the ketone and (1R)-1-(4-fluoro-2-methoxy-phenyl)ethanamine as the amine. LC-MS: RT=4.47, M=463.

Example 70

(1R)—(N)-[(1R/S,3S)-3-[4-(2-(aminosulfonyl)ethylaminocarbonyl)-phenyl]cyclopentyl]-1-(4-fluoro-3-methoxyphenyl)ethanamine (compound 1069)

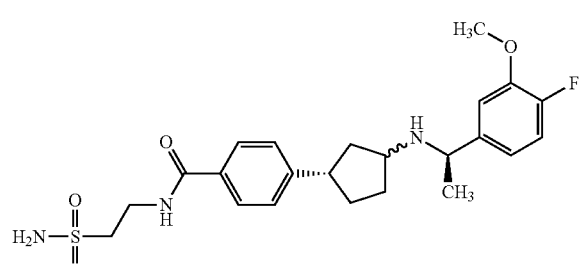

General procedure B was followed using 4-[(1S)-3-oxocyclopentyl]-N-(2-sulfamoylethyl)benzamide (preparation 11) as the ketone and (1R)-1-(4-fluoro-3-methoxyphenyl)ethylamine hydrochloride as the amine. LC-MS: RT=4.62, M=463.

Example 71

(1R)—(N)-[(1R/S,3S)-3-[4-(2-(aminosulfonyl)ethylaminocarbonyl)-phenyl]cyclopentyl]-1-(3-chlorophenyl)ethanamine (compound 1070)

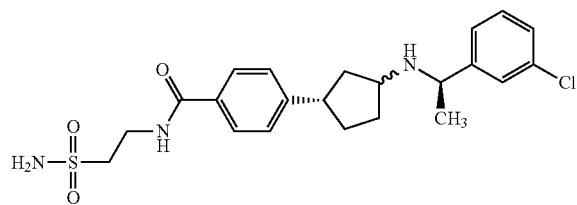 [SMILES: C[C@@H](NC1CC[C@H](c2ccc(C(=O)NCCS(N)(=O)=O)cc2)C1)c1cccc(Cl)c1]

General procedure B was followed using 4-[(1S)-3-oxocyclopentyl]-N-(2-sulfamoylethyl)benzamide (preparation 11) as the ketone and (R)-1-(3-chlorophenyl)ethanamine as the amine. LC-MS: RT=5.12, M=449.

Example 72

(1R)—(N)-[(1R/S,3S)-3-[4-(2-(aminosulfonyl)ethylaminocarbonyl)-phenyl]cyclopentyl]-1-benzo[b]thiophen-3-yl-ethanamine (compound 1071)

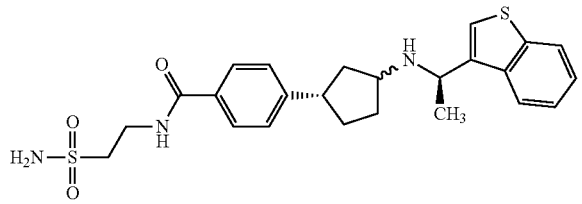 [SMILES: C[C@@H](NC1CC[C@H](c2ccc(C(=O)NCCS(N)(=O)=O)cc2)C1)c1csc2ccccc12]

General procedure B was followed using 4-[(1S)-3-oxocyclopentyl]-N-(2-sulfamoylethyl)benzamide (preparation 11) as the ketone and (R)-1-benzo[b]thiophen-3-yl-ethylamine as the amine. LC-MS: RT=5.16, M=471.

Example 73

(1R)—(N)-[(1R/S,3S)-3-[4-(3-oxo-piperazinylcarbonyl)phenyl]-cyclopentyl]-1-(1,3-benzodioxol-4-yl)ethanamine (compound 1072)

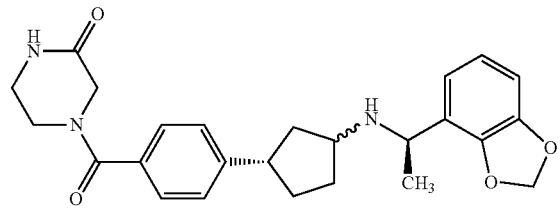 [SMILES: C[C@@H](NC1CC[C@H](c2ccc(C(=O)N3CCNC(=O)C3)cc2)C1)c1cccc2c1OCO2]

General procedure B was followed using 4-[4-[(1S)-3-oxocyclopentyl]benzoyl]-piperazin-2-one (preparation 12) as the ketone and (1R)-1-(1,3-benzodioxol-4-yl)ethanamine hydrochloride as the amine. LC-MS: RT=4.36, M=435.

Example 74

(1R)—(N)-[(1R/S,3S)-3-[4-(3-oxo-piperazinylcarbonyl)phenyl]-cyclopentyl]-1-(3-ethoxyphenyl)ethanamine (compound 1073)

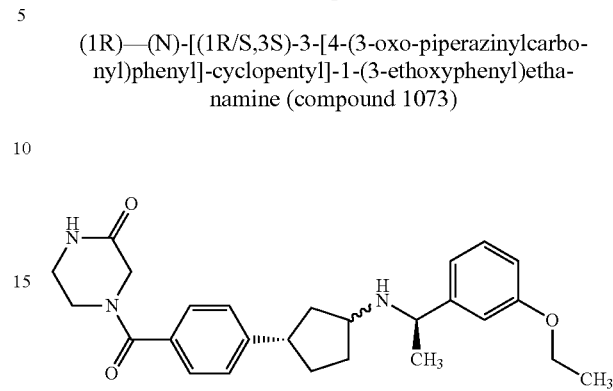

General procedure B was followed using 4-[4-[(1S)-3-oxocyclopentyl]benzoyl]-piperazin-2-one (preparation 12) as the ketone and (1R)-1-(3-ethoxyphenyl)ethanamine hydrochloride as the amine. LC-MS: RT=4.61, M=435.

Example 75

(1R)—(N)-[(1R/S,3S)-3-[4-(3-oxo-piperazinylcarbonyl)phenyl]-cyclopentyl]-1-(4-fluoro-3-methoxyphenyl)ethanamine (compound 1074)

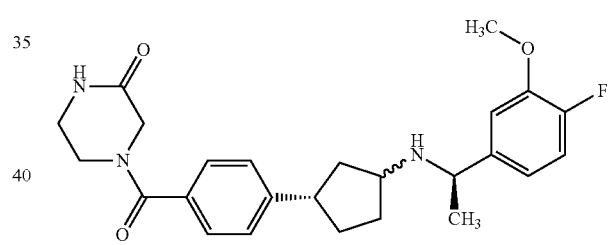

General procedure B was followed using 4-[4-[(1S)-3-oxocyclopentyl]benzoyl]-piperazin-2-one (preparation 12) as the ketone and (1R)-1-(4-fluoro-3-methoxyphenyl)ethylamine hydrochloride as the amine. LC-MS: RT=4.52, M=439.

Example 76

(1R)—(N)-[(1R/S,3S)-3-[4-(3-oxo-piperazinylcarbonyl)phenyl]-cyclopentyl]-1-(3-chlorophenyl)ethanamine (compound 1075)

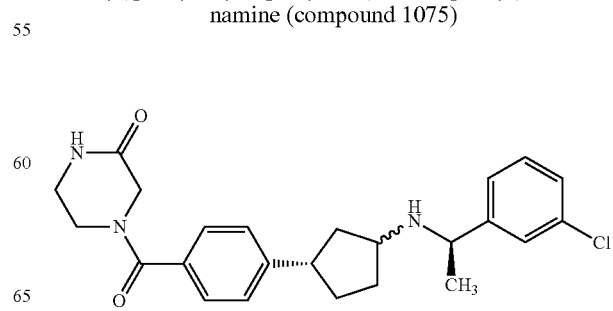

General procedure B was followed using 4-[4-[(1S)-3-oxocyclopentyl]benzoyl]-piperazin-2-one (preparation 12) as the ketone and (R)-1-(3-chlorophenyl)ethanamine as the amine. LC-MS: RT=4.87, M=425.

Example 77

(1R)—(N)-[(1R/S,3S)-3-[4-(3-oxo-piperazinylcarbonyl)phenyl]-cyclopentyl]-1-benzo[b]thiophen-3-yl-ethanamine (compound 1076)

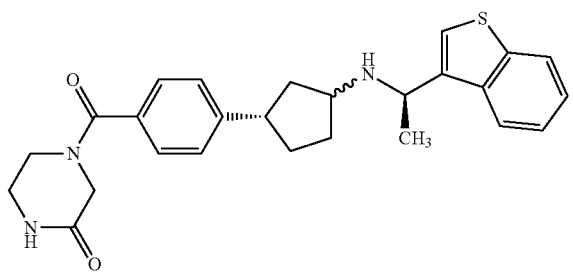 [SMILES: C[C@@H](NC1CC[C@H](c2ccc(C(=O)N3CCNC(=O)C3)cc2)C1)c1csc2ccccc12]

General procedure B was followed using 4-[4-[(1S)-3-oxocyclopentyl]benzoyl]-piperazin-2-one (preparation 12) as the ketone and (R)-1-benzo[b]thiophen-3-yl-ethylamine as the amine. LC-MS: RT=4.92, M=447.

Example 78

(1R)—(N)-[(1R/S,3R/S)-3-[4-(acetamidomethyl)phenyl]cyclopentyl]-1-(3-methoxyphenyl)ethanamine (mixture of stereoisomers) (compound 1077

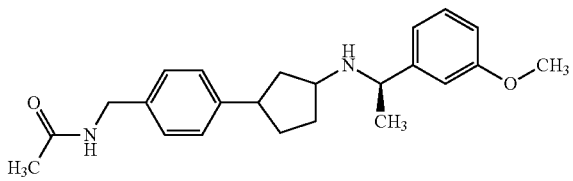 [SMILES: COc1cccc([C@@H](C)NC2CCC(c3ccc(CNC(C)=O)cc3)C2)c1]

General procedure E was followed using 4-acetamidomethylphenylboronic acid as the boronic acid and (R)-1-(3-methoxyphenyl)ethylamine as the amine. LC-MS (method B): RT=3.97, M=366.

Example 79

(1R)—(N)-[(1R/S,3S)-3-[2-hydroxypyridin-5-yl]cyclopentyl]-1-(1,3-benzodioxol-4-yl)ethanamine (mixture of stereoisomers) (compound 1078)

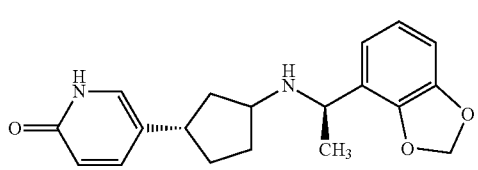 [SMILES: C[C@@H](NC1CC[C@H](c2ccc(=O)[nH]c2)C1)c1cccc2c1OCO2]

General procedure B was followed using 5-[(1S)-3-oxocyclopentyl]-1H-pyridin-2-one (preparation 4) as the ketone and (1R)-1-(1,3-benzodioxol-4-yl)ethanamine hydrochloride as the amine. LC-MS: RT=4.07, M=326.

Example 80

(1R)—(N)-[(1R/S,3S)-3-[2-hydroxypyridin-5-yl]cyclopentyl]-1-(1,3-benzodioxol-5-yl)ethanamine (mixture of stereoisomers) (compound 1079)

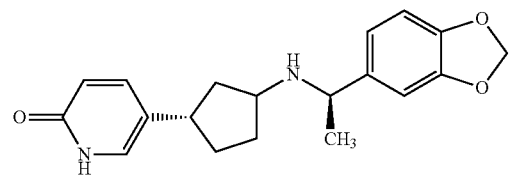 [SMILES: C[C@@H](NC1CC[C@H](c2ccc(=O)[nH]c2)C1)c1ccc2c(c1)OCO2]

General procedure B was followed using 5-[(1S)-3-oxocyclopentyl]-1H-pyridin-2-one (preparation 4) as the ketone and (1R)-1-(1,3-benzodioxol-5-yl)ethanamine as the amine. LC-MS: RT=3.87, M=326.

Example 81

(1R)—(N)-[(1R/S,3S)-3-[2-hydroxypyridin-5-yl]cyclopentyl]-1-(1-methyl-5-phenyl-pyrazol-3-yl)ethanamine (compound 1080)

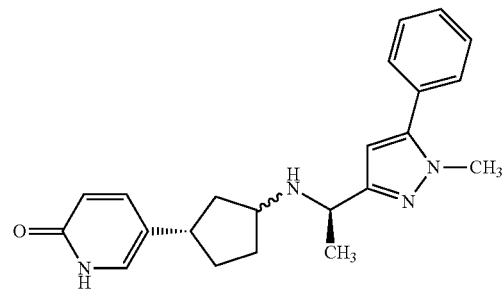 [SMILES: C[C@@H](NC1CC[C@H](c2ccc(=O)[nH]c2)C1)c1cc(-c2ccccc2)n(C)n1]

General procedure B was followed using 5-[(1S)-3-oxocyclopentyl]-1H-pyridin-2-one (preparation 4) as the ketone and (1R)-1-(1-methyl-5-phenyl-pyrazol-3-yl)ethanamine (preparation 26) as the amine. LC-MS: RT=3.99, M=362.

Example 82

(1R)—(N)-[(1R/S,3S)-3-[2-hydroxypyridin-5-yl]cyclopentyl]-1-(2,3-dihydro-1,4-benzodioxin-5-yl)ethanamine (compound 1081)

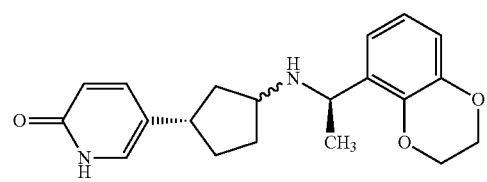 [SMILES: C[C@@H](NC1CC[C@H](c2ccc(=O)[nH]c2)C1)c1cccc2c1OCCO2]

General procedure B was followed using 5-[(1S)-3-oxocyclopentyl]-1H-pyridin-2-one (preparation 4) as the ketone and (1R)-1-(2,3-dihydro-1,4-benzodioxin-5-yl)ethanamine hydrochloride (preparation 22) as the amine. LC-MS: RT=3.77, M=340.

Example 83

(1R)—(N)-[(1R/S,3S)-3-[2-hydroxypyridin-5-yl]cyclopentyl]-1-(2,3-dihydrobenzofuran-5-yl)ethanamine (compound 1082)

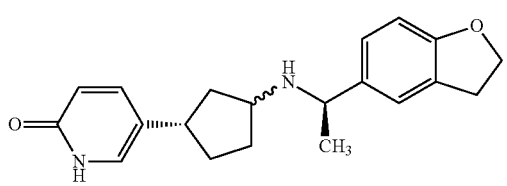 [SMILES: C[C@@H](NC1CC[C@H](c2ccc(=O)[nH]c2)C1)c1ccc2c(c1)CCO2]

General procedure B was followed using 5-[(1S)-3-oxocyclopentyl]-1H-pyridin-2-one (preparation 4) as the ketone and (1R)-1-(2,3-dihydrobenzofuran-5-yl)ethanamine as the amine. LC-MS: RT=3.74, M=324.

Example 84

(1R)—(N)-[(1R/S,3S)-3-[2-hydroxypyridin-5-yl]cyclopentyl]-1-(2,3-dimethoxyphenyl)ethanamine (compound 1083)

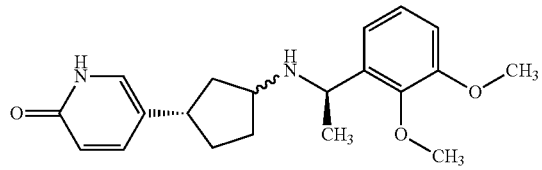 [SMILES: COc1cccc([C@@H](C)NC2CC[C@H](c3ccc(=O)[nH]c3)C2)c1OC]

General procedure B was followed using 5-[(1S)-3-oxocyclopentyl]-1H-pyridin-2-one (preparation 4) as the ketone and (1R)-1-(2,3-dimethoxyphenyl)ethylamine hydrochloride as the amine. LC-MS: RT=3.92, M=342.

Example 85

(1R)—(N)-[(1R/S,3S)-3-[2-hydroxypyridin-5-yl]cyclopentyl]-1-(2-fluoro-3-methoxy-phenyl)ethanamine (compound 1084)

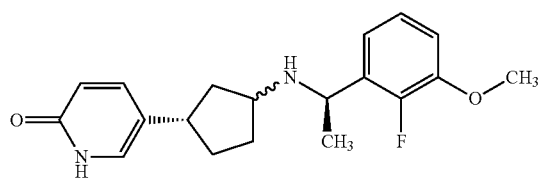 [SMILES: COc1cccc([C@@H](C)NC2CC[C@H](c3ccc(=O)[nH]c3)C2)c1F]

General procedure B was followed using 5-[(1S)-3-oxocyclopentyl]-1H-pyridin-2-one (preparation 4) as the ketone and (1R)-1-(2-fluoro-3-methoxy-phenyl)ethanamine as the amine. LC-MS: RT=4.16, M=330.

Example 86

(1R)—(N)-[(1R/S,3S)-3-[2-hydroxypyridin-5-yl]cyclopentyl]-1-(2-fluoro-5-methoxy-phenyl)ethanamine (compound 1085)

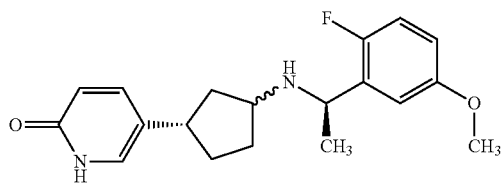 [SMILES: COc1ccc(F)c([C@@H](C)NC2CC[C@H](c3ccc(=O)[nH]c3)C2)c1]

General procedure B was followed using 5-[(1S)-3-oxocyclopentyl]-1H-pyridin-2-one (preparation 4) as the ketone and (1R)-1-(2-fluoro-5-methoxy-phenyl)ethanamine as the amine. LC-MS: RT=4.31, M=330.

Example 87

(1R)—(N)-[(1R/S,3S)-3-[2-hydroxypyridin-5-yl]cyclopentyl]-1-(2-methylthiazol-4-yl)ethanamine (compound 1086)

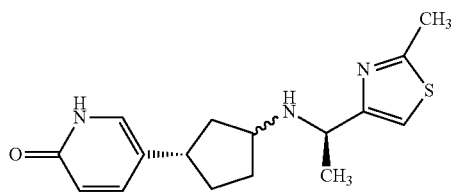 [SMILES: Cc1nc([C@@H](C)NC2CC[C@H](c3ccc(=O)[nH]c3)C2)cs1]

General procedure B was followed using 5-[(1S)-3-oxocyclopentyl]-1H-pyridin-2-one (preparation 4) as the ketone and (1R)-1-(2-methylthiazol-4-yl)ethanamine hydrochloride as the amine. LC-MS: RT=3.54, M=303.

Example 88

(1R)—(N)-[(1R/S,3S)-3-[2-hydroxypyridin-5-yl]cyclopentyl]-1-(3-fluoro-5-methoxyphenyl)ethanamine (mixture of stereoisomers) (compound 1087)

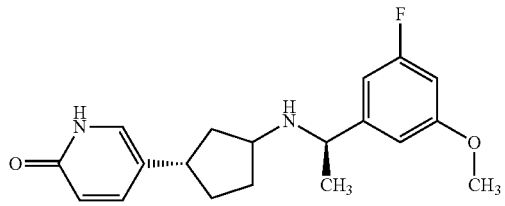 [SMILES: COc1cc(F)cc([C@@H](C)NC2CC[C@H](c3ccc(=O)[nH]c3)C2)c1]

General procedure B was followed using 5-[(1S)-3-oxocyclopentyl]-1H-pyridin-2-one (preparation 4) as the ketone and (1R)-1-(3-fluoro-5-methoxy-phenyl)ethanamine as the amine. LC-MS: RT=4.36, M=330.

Example 89

(1R)—(N)-[(1R/S,3S)-3-[2-hydroxypyridin-5-yl]cyclopentyl]-1-(4-fluoro-2-methoxyphenyl)ethanamine (mixture of stereoisomers) (compound 1088

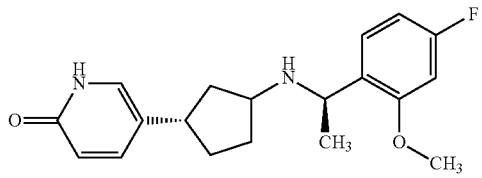 [SMILES: COc1cc(F)ccc1[C@@H](C)NC1CC[C@H](c2ccc(=O)[nH]c2)C1]

General procedure B was followed using 5-[(1S)-3-oxocyclopentyl]-1H-pyridin-2-one (preparation 4) as the ketone and (1R)-1-(4-fluoro-2-methoxy-phenyl)ethanamine as the amine. LC-MS: RT=4.02, M=330.

Example 90

(1R)—(N)-[(1R/S,3S)-3-[2-hydroxypyridin-5-yl]cyclopentyl]-1-(4-fluoro-3-methoxyphenyl)ethanamine (compound 1089)

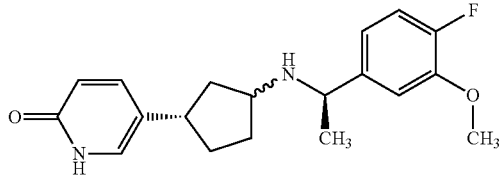 [SMILES: COc1cc([C@@H](C)NC2CC[C@H](c3ccc(=O)[nH]c3)C2)ccc1F]

General procedure B was followed using 5-[(1S)-3-oxocyclopentyl]-1H-pyridin-2-one (preparation 4) as the ketone and (1R)-1-(4-fluoro-3-methoxyphenyl)ethylamine hydrochloride as the amine. LC-MS: RT=4.07, M=330.

Example 91

(1R)—(N)-[(1R/S,3S)-3-[2-hydroxypyridin-5-yl]cyclopentyl]-1-(8-quinolyl)ethanamine (compound 1090)

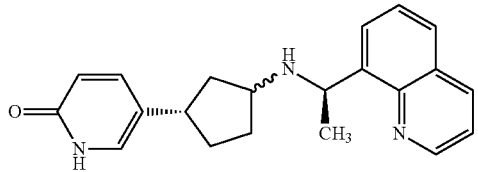 [SMILES: C[C@@H](NC1CC[C@H](c2ccc(=O)[nH]c2)C1)c1cccc2cccnc12]

General procedure B was followed using 5-[(1S)-3-oxocyclopentyl]-1H-pyridin-2-one (preparation 4) as the ketone and (1R)-1-(8-quinolyl)ethanamine as the amine. LC-MS: RT=3.79, M=333.

Example 92

(1R)—(N)-[(1R/S,3S)-3-[2-hydroxypyridin-5-yl]cyclopentyl]-1-cyclopropylethanamine (mixture of stereoisomers) (compound 1091)

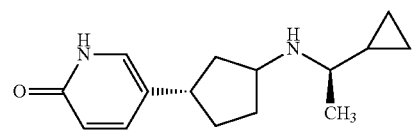

General procedure B was followed using 5-[(1S)-3-oxocyclopentyl]-1H-pyridin-2-one (preparation 4) as the ketone and (1R)-1-cyclopropylethanamine as the amine. LC-MS: RT=3.02, M=246.

Example 93

(1R)—(N)-[(1R/S,3S)-3-[2-hydroxypyridin-5-yl]cyclopentyl]-1-imidazo[1,2-a]pyridin-3-ylethanamine (mixture of stereoisomers) (compound 1092)

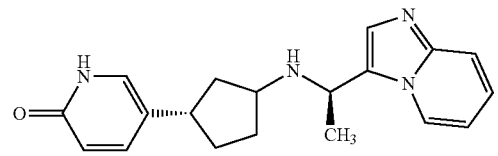 [SMILES: C[C@@H](NC1CC[C@H](c2ccc(=O)[nH]c2)C1)c1cnc2ccccn12]

General procedure B was followed using 5-[(1S)-3-oxocyclopentyl]-1H-pyridin-2-one (preparation 4) as the ketone and (1R)-1-imidazo[1,2-a]pyridin-3-ylethanamine hydrochloride (preparation 27) as the amine. LC-MS: RT=3.04, M=322.

Example 94

(1R)—(N)-[(1R/S,3S)-3-[2-hydroxypyridin-5-yl]cyclopentyl]-1-pyrazolo[1,5-a]pyridin-3-ylethanamine formiate (mixture of stereoisomers) (compound 1093)

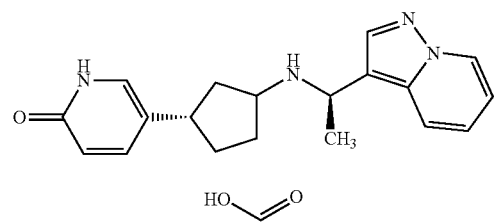

General procedure B was followed using 5-[(1S)-3-oxocyclopentyl]-1H-pyridin-2-one (preparation 4) as the ketone and (1R)-1-pyrazolo[1,5-a]pyridin-3-ylethanamine hydrochloride (preparation 23) as the amine. LC-MS: RT=1.96, M=322.

Example 95

(1R)—(N)-[(1R/S,3S)-3-[2-hydroxypyridin-5-yl]cyclopentyl]-1-cyclohexylethanamine (mixture of stereoisomers) (compound 1094)

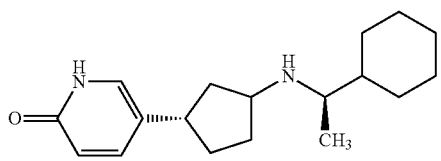 [SMILES: C[C@@H](NC1CC[C@H](c2ccc(=O)[nH]c2)C1)C1CCCCC1]

General procedure B was followed using 5-[(1S)-3-oxocyclopentyl]-1H-pyridin-2-one (preparation 4) as the ketone and (R)-(−)-1-cyclohexylethylamine as the amine. LC-MS: RT=3.51, M=288.

Example 96

(1R)—(N)-[(1R/S,3S)-3-[2-hydroxypyridin-5-yl]cyclopentyl]-1-(3-chlorophenyl)ethanamine (mixture of stereoisomers) (compound 1095)

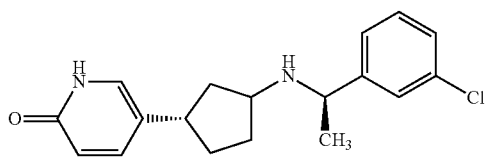 [SMILES: C[C@@H](NC1CC[C@H](c2ccc(=O)[nH]c2)C1)c1cccc(Cl)c1]

General procedure B was followed using 5-[(1S)-3-oxocyclopentyl]-1H-pyridin-2-one (preparation 4) as the ketone and (R)-1-(3-chlorophenyl)ethanamine as the amine. LC-MS: RT=4.52, M=316.

Example 97

(1R)—(N)-[(1R/S,3S)-3-[2-hydroxypyridin-5-yl]cyclopentyl]-1-(3-fluoro-4-methoxyphenyl)ethanamine (mixture of stereoisomers) (compound 1096

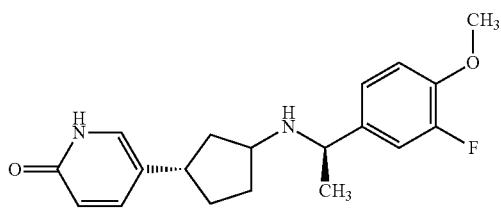 [SMILES: COc1ccc([C@@H](C)NC2CC[C@H](c3ccc(=O)[nH]c3)C2)cc1F]

General procedure B was followed using 5-[(1S)-3-oxocyclopentyl]-1H-pyridin-2-one (preparation 4) as the ketone and (R)-1-(3-fluoro-4-methoxyphenyl)ethanamine hydrochloride as the amine. LC-MS: RT=4.06, M=330.

Example 98

(1R)—(N)-[(1R/S,3S)-3-[2-hydroxypyridin-5-yl]cyclopentyl]-1-(3-fluorophenyl)ethanamine (mixture of stereoisomers) (compound 1097)

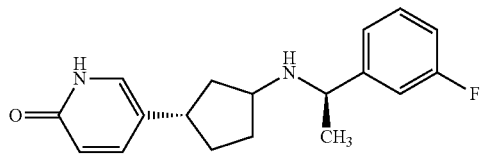 [SMILES: C[C@@H](NC1CC[C@H](c2ccc(=O)[nH]c2)C1)c1cccc(F)c1]

General procedure B was followed using 5-[(1S)-3-oxocyclopentyl]-1H-pyridin-2-one (preparation 4) as the ketone and (R)-1-(3-fluorophenyl)ethanamine as the amine. LC-MS: RT=4.22, M=300.

Example 99

(1R)—(N)-[(1R/S,3S)-3-[2-hydroxypyridin-5-yl]cyclopentyl]-1-[3-(trifluoromethyl)phenyl]ethanamine formiate (mixture of stereoisomers) (compound 1098)

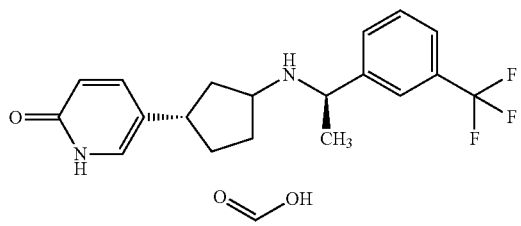

General procedure B was followed using 5-[(1S)-3-oxocyclopentyl]-1H-pyridin-2-one (preparation 4) as the ketone and (R)-1-[3-(trifluoromethyl)phenyl]ethylamine as the amine. LC-MS: RT=2.37, M=396.

Example 100

(1R)—(N)-[(1R/S,3S)-3-[2-hydroxypyridin-5-yl]cyclopentyl]-1-benzo[b]thiophen-3-yl-ethanamine formiate (mixture of stereoisomers) (compound 1099)

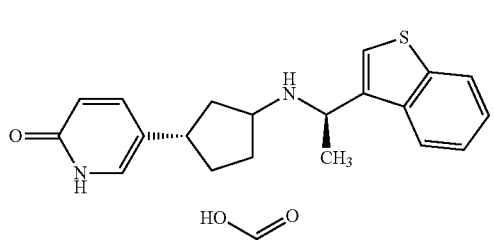

General procedure B was followed using 5-[(1S)-3-oxocyclopentyl]-1H-pyridin-2-one (preparation 4) as the ketone and (R)-1-benzo[b]thiophen-3-yl-ethylamine as the amine. LC-MS: RT=2.44, M=384.

Example 101

(1R/S)—(N)-[(1R/S,3S)-3-[2-hydroxypyridin-5-yl]cyclopentyl]-1-pyrimidin-4-ylethanamine (mixture of stereoisomers) (compound 1100)

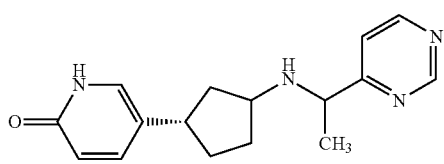 [SMILES: CC(NC1CC[C@H](c2ccc(=O)[nH]c2)C1)c1ccncn1]

General procedure B was followed using 5-[(1S)-3-oxocyclopentyl]-1H-pyridin-2-one (preparation 4) as the ketone and 1-pyrimidin-4-ylethanamine dihydrochloride as the amine. LC-MS: RT=3.09, M=284.

Example 102

(1R)—(N)-[(1R/S,3S)-3-[2-hydroxypyridin-5-yl]cyclopentyl]-1-(3-cyano-4-fluorophenyl)ethanamine (mixture of stereoisomers) (compound 1101)

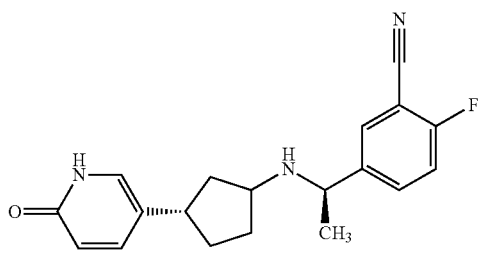 [SMILES: C[C@@H](NC1CC[C@H](c2ccc(=O)[nH]c2)C1)c1ccc(F)c(C#N)c1]

General procedure B was followed using 5-[(1S)-3-oxocyclopentyl]-1H-pyridin-2-one (preparation 4) as the ketone and 5-[(1R)-1-aminoethyl]-2-fluoro-benzonitrile hydrochloride as the amine. LC-MS: RT=4.27, M=325.

Example 103

(1R)—(N)-[(1R/S,3S)-3-(4-(2-(acetamido)ethylaminocarbonyl)-phenyl)cyclopentyl]-1-(1,3-benzodioxol-4-yl)ethanamine (compound 1102)

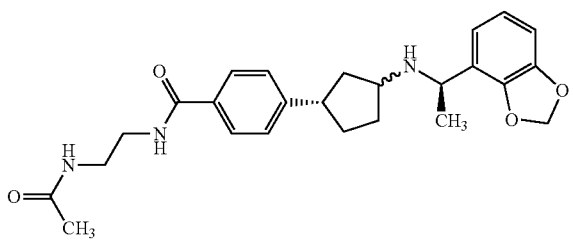 [SMILES: CC(=O)NCCNC(=O)c1ccc([C@H]2CCC(N[C@H](C)c3cccc4c3OCO4)C2)cc1]

General procedure B was followed using N-(2-acetamidoethyl)-4-[(1S)-3-oxocyclopentyl]benzamide (preparation 10) as the ketone and (1R)-1-(1,3-benzodioxol-4-yl)ethanamine hydrochloride as the amine. LC-MS: RT=4.41, M=437.

Example 104

(1R)—(N)-[(1R/S,3S)-3-(4-(2-(acetamido)ethylaminocarbonyl)-phenyl)cyclopentyl]-1-(3-ethoxyphenyl)ethanamine (compound 1103)

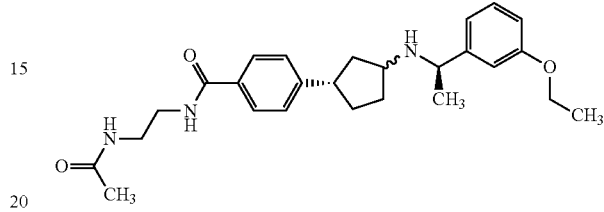

General procedure B was followed using N-(2-acetamidoethyl)-4-[(1S)-3-oxocyclopentyl]benzamide (preparation 10) as the ketone and (1R)-1-(3-ethoxyphenyl)-ethanamine hydrochloride as the amine. LC-MS: RT=4.61, M=437.

Example 105

(1R)—(N)-[(1R/S,3S)-3-(4-(2-(acetamido)ethylaminocarbonyl)-phenyl)cyclopentyl]-1-(4-fluoro-2-methoxyphenyl)ethanamine (compound 1104)

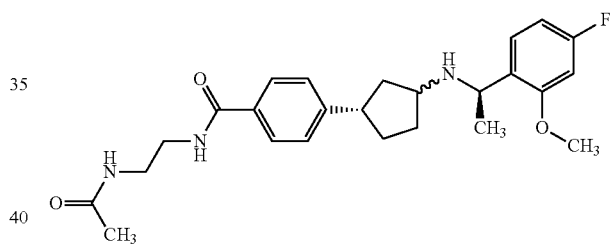

General procedure B was followed using N-(2-acetamidoethyl)-4-[(1S)-3-oxocyclopentyl]benzamide (preparation 10) as the ketone and (1R)-1-(4-fluoro-2-methoxy-phenyl)ethanamine as the amine. LC-MS: RT=4.31, M=441.

Example 106

(1R)—(N)-[(1R/S,3S)-3-(4-(2-(acetamido)ethylaminocarbonyl)-phenyl)cyclopentyl]-1-(4-fluoro-3-methoxyphenyl)ethanamine (compound 1105)

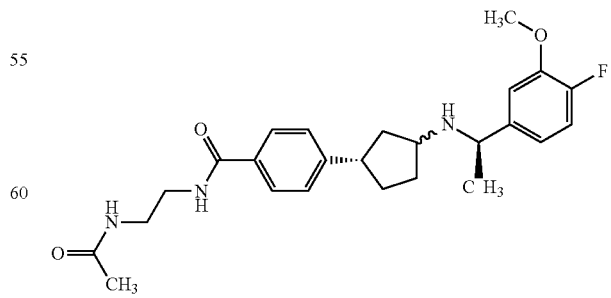

General procedure B was followed using N-(2-acetamidoethyl)-4-[(1S)-3-oxocyclopentyl]benzamide (preparation 10) as the ketone and (1R)-1-(4-fluoro-3-methoxyphenyl)-ethylamine hydrochloride as the amine. LC-MS: RT=4.46, M=441.

Example 107

(1R)—(N)-[(1R/S,3S)-3-(4-(2-(acetamido)ethylaminocarbonyl)-phenyl)cyclopentyl]-1-(3-chlorophenyl)ethanamine (compound 1106)

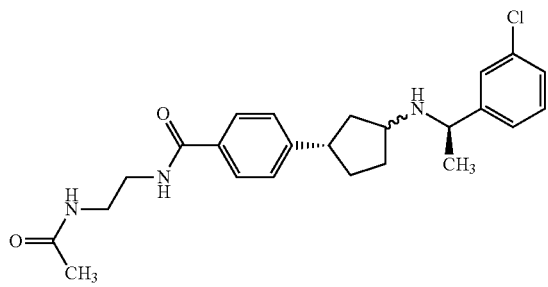 [SMILES: CC(=O)NCCNC(=O)c1ccc([C@H]2CCC(N[C@H](C)c3cccc(Cl)c3)C2)cc1]

General procedure B was followed using N-(2-acetamido-ethyl)-4-[(1S)-3-oxocyclopentyl]benzamide (preparation 10) as the ketone and (R)-1-(3-chlorophenyl)ethanamine as the amine. LC-MS: RT=4.92, M=427.

Example 108

(1R)—(N)-[(1R/S,3S)-3-(4-(2-(acetamido)ethylaminocarbonyl)-phenyl)cyclopentyl]-1-benzo[b]thiophen-3-yl-ethanamine (compound 1107)

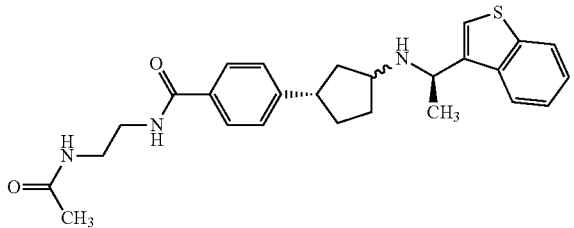 [SMILES: CC(=O)NCCNC(=O)c1ccc([C@H]2CCC(N[C@H](C)c3csc4ccccc34)C2)cc1]

General procedure B was followed using N-(2-acetamido-ethyl)-4-[(1S)-3-oxocyclopentyl]benzamide (preparation 10) as the ketone and (R)-1-benzo[b]thiophen-3-yl-ethylamine as the amine. LC-MS: RT=4.97, M=449.

Example 109

(1R)—(N)-[(1R/S,3S)-3-[4-(aminocarbonylmethylaminocarbonyl)-phenyl]cyclopentyl]-1-(3-ethoxyphenyl)ethanamine (compound 1108)

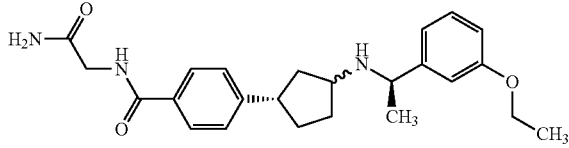 [SMILES: CCOc1cccc([C@@H](C)NC2CC[C@H](c3ccc(C(=O)NCC(N)=O)cc3)C2)c1]

General procedure B was followed using N-(2-amino-2-oxo-ethyl)-4-[(1S)-3-oxocyclopentyl]benzamide (preparation 14) as the ketone and (1R)-1-(3-ethoxyphenyl)-ethanamine hydrochloride as the amine. LC-MS: RT=4.51, M=409.

Example 110

(1R)—(N)-[(1R/S,3S)-3-[4-(aminocarbonylmethylaminocarbonyl)-phenyl]cyclopentyl]-1-(4-fluoro-2-methoxyphenyl)ethanamine (compound 1109)

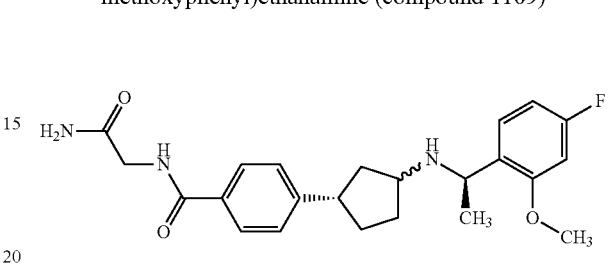

General procedure B was followed using N-(2-amino-2-oxo-ethyl)-4-[(1S)-3-oxocyclopentyl]benzamide (preparation 14) as the ketone and (1R)-1-(4-fluoro-2-methoxy-phenyl)ethanamine as the amine. LC-MS: RT=4.22, M=413.

Example 111

(1R)—(N)-[(1R/S,3S)-3-[4-(aminocarbonylmethylaminocarbonyl)-phenyl]cyclopentyl]-1-(4-fluoro-3-methoxyphenyl)ethanamine (compound 1110)

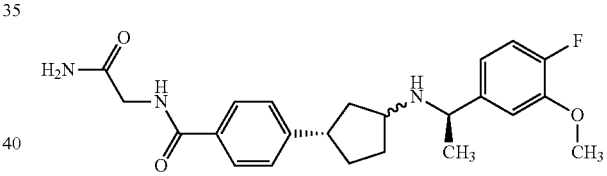

General procedure B was followed using N-(2-amino-2-oxo-ethyl)-4-[(1S)-3-oxocyclopentyl]benzamide (preparation 14) as the ketone and (1R)-1-(4-fluoro-3-methoxyphenyl)-ethanamine hydrochloride as the amine. LC-MS: RT=4.37, M=413.

Example 112

(1R)—(N)-[(1R/S,3S)-3-[4-(aminocarbonylmethylaminocarbonyl)-phenyl]cyclopentyl]-1-benzo[b]thiophen-3-yl-ethanamine (compound 1111)

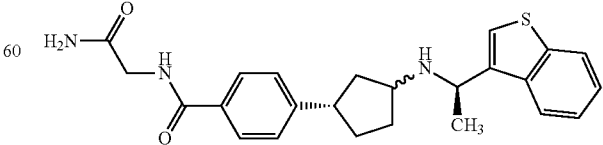

General procedure B was followed using N-(2-amino-2-oxo-ethyl)-4-[(1S)-3-oxocyclopentyl]benzamide (preparation 14) as the ketone and (R)-1-benzo[b]thiophen-3-yl-ethylamine as the amine. LC-MS: RT=4.87, M=421.

Example 113

(1R)—(N)-[(1R/S,3S)-3-[4-(2-hydroxyethylaminosulfonyl)-phenyl]cyclopentyl]-1-(3,4-difluorophenyl)ethanamine hydrochloride (mixture of stereoisomers) (compound 1112)

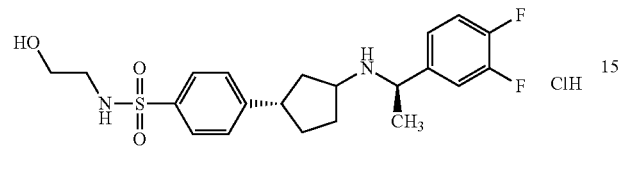

General procedure B was followed using N-(2-hydroxyethyl)-4-[(1R)-3-oxocyclopentyl]benzenesulfonamide (preparation 6) as the ketone and (1R)-1-(3,4-difluorophenyl)ethanamine hydrochloride as the amine. LC-MS: RT=5.17, M=424.

Example 114

(1R)—(N)-[(1R/S,3S)-3-[4-(2-hydroxyethylaminosulfonyl)-phenyl]cyclopentyl]-1-(3,4-dihydro-2H-1,5-benzodioxepin-6-yl)ethanamine hydrochloride (mixture of stereoisomers) (compound 1113)

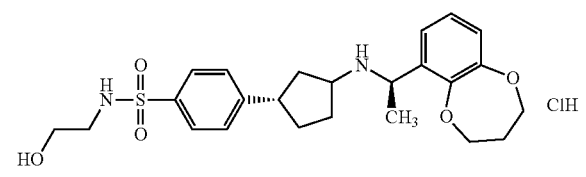 [SMILES: C[C@@H](NC1CC[C@H](c2ccc(S(=O)(=O)NCCO)cc2)C1)c1cccc2c1OCCCO2 ; Cl]

General procedure B was followed using N-(2-hydroxyethyl)-4-[(1R)-3-oxocyclopentyl]benzenesulfonamide (preparation 6) as the ketone and (1R)-1-(3,4-dihydro-2H-1,5-benzodioxepin-6-yl)ethanamine hydrochloride (preparation 25) as the amine. LC-MS: RT=4.61, M=460.

Example 115

(1R)—(N)-[(1R/S,3S)-3-[4-(2-hydroxyethylaminosulfonyl)-phenyl]cyclopentyl]-1-(3,4-dimethoxyphenyl)ethanamine hydrochloride (mixture of stereoisomers) (compound 1114)

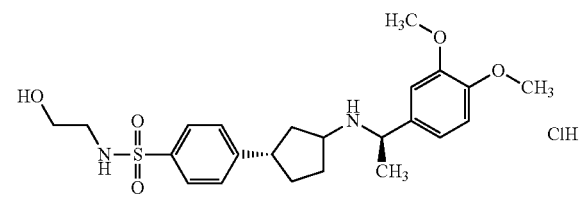 [SMILES: COc1ccc([C@@H](C)NC2CC[C@H](c3ccc(S(=O)(=O)NCCO)cc3)C2)cc1OC ; Cl]

General procedure B was followed using N-(2-hydroxyethyl)-4-[(1R)-3-oxocyclopentyl]benzenesulfonamide (preparation 6) as the ketone and (1R)-1-(3,4-dimethoxyphenyl)ethanamine hydrochloride as the amine. LC-MS: RT=4.27, M=448.

Example 116

(1R)—(N)-[(1R/S,3S)-3-[4-(2-hydroxyethylaminosulfonyl)-phenyl]cyclopentyl]-1-(3-fluoro-5-methoxyphenyl)ethanamine hydrochloride (mixture of stereoisomers) (compound 1115)

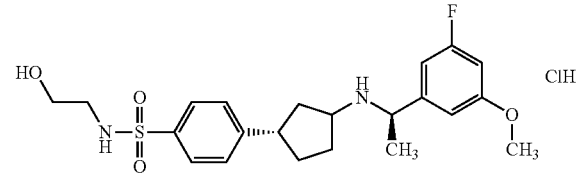 [SMILES: COc1cc(F)cc([C@@H](C)NC2CC[C@H](c3ccc(S(=O)(=O)NCCO)cc3)C2)c1 ; Cl]

General procedure B was followed using N-(2-hydroxyethyl)-4-[(1R)-3-oxocyclopentyl]benzenesulfonamide (preparation 6) as the ketone and (1R)-1-(3-fluoro-5-methoxy-phenyl)ethanamine as the amine. LC-MS: RT=5.11, M=436.

Example 117

(1R)—(N)-[(1R/S,3S)-3-[4-(2-hydroxyethylaminosulfonyl)-phenyl]cyclopentyl]-1-(4-fluoro-2-methoxyphenyl)ethanamine hydrochloride (mixture of stereoisomers) (compound 1116)

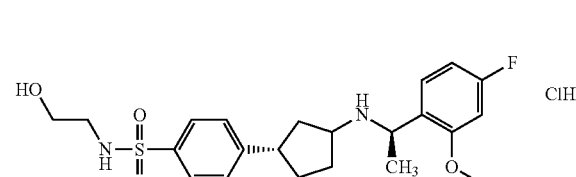

General procedure B was followed using N-(2-hydroxyethyl)-4-[(1R)-3-oxocyclopentyl]benzenesulfonamide (preparation 6) as the ketone and (1R)-1-(4-fluoro-2-methoxy-phenyl)ethanamine as the amine. LC-MS: RT=4.71, M=436.

Example 118

(1R)—(N)-[(1R/S,3S)-3-[4-(2-hydroxyethylaminosulfonyl)-phenyl]cyclopentyl]-1-(4-fluoro-3-methoxyphenyl)ethanamine hydrochloride (mixture of stereoisomers) (compound 1117)

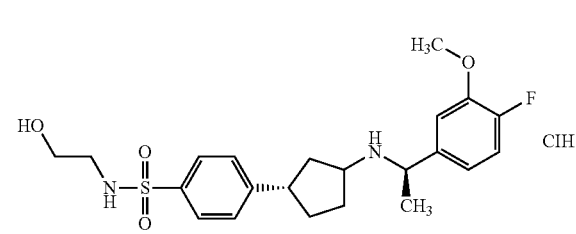

General procedure B was followed using N-(2-hydroxyethyl)-4-[(1R)-3-oxocyclopentyl]benzenesulfonamide (preparation 6) as the ketone and (1R)-1-(4-fluoro-3-methoxyphenyl)ethylamine hydrochloride as the amine. LC-MS: RT=4.89, M=436.

Example 119

(1R)—(N)-[(1R/S,3S)-3-[4-(2-hydroxyethylaminocarbonyl)phenyl]-cyclopentyl]-1-(3-chloro-4-fluoro-phenyl)ethanamine (compound 1118)

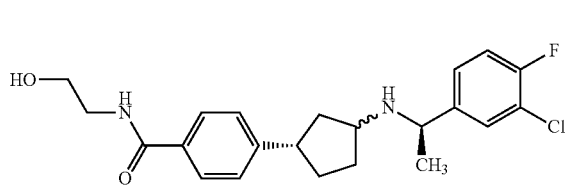 [SMILES: C[C@@H](NC1CC[C@H](c2ccc(C(=O)NCCO)cc2)C1)c1ccc(F)c(Cl)c1]

General procedure B was followed using N-(2-hydroxyethyl)-4-[(1S)-3-oxocyclopentyl]benzamide (preparation 16) as the ketone and (1R)-1-(3-chloro-4-fluoro-phenyl)ethanamine hydrochloride as the amine. LC-MS: RT=5.19, M=404.

Example 120

(1R)—(N)-[(1R/S,3S)-3-[4-(2-hydroxyethylaminocarbonyl)phenyl]-cyclopentyl]-1-(3-ethoxyphenyl)ethanamine (compound 1119)

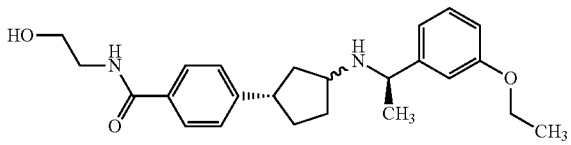

General procedure B was followed using N-(2-hydroxyethyl)-4-[(1S)-3-oxocyclopentyl]benzamide (preparation 16) as the ketone and (1R)-1-(3-ethoxyphenyl)-ethanamine hydrochloride as the amine. LC-MS: RT=4.66, M=396.

Example 121

(1R)—(N)-[(1R/S,3S)-3-[4-(2-hydroxyethylaminocarbonyl)phenyl]-cyclopentyl]-1-(3-fluoro-5-methoxyphenyl)ethanamine (mixture of stereoisomers) (compound 1120)

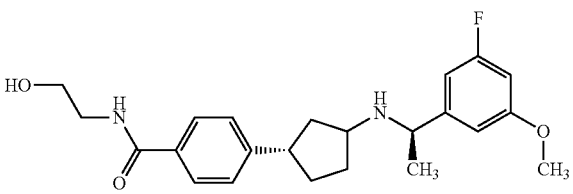 [SMILES: COc1cc(F)cc([C@@H](C)NC2CC[C@H](c3ccc(C(=O)NCCO)cc3)C2)c1]

General procedure B was followed using N-(2-hydroxyethyl)-4-[(1S)-3-oxocyclopentyl]benzamide (preparation 16) as the ketone and (1R)-1-(3-fluoro-5-methoxy-phenyl)ethanamine as the amine. LC-MS: RT=4.79, M=400.

Example 122

(1R)—(N)-[(1R/S,3S)-3-[4-(2-hydroxyethylaminocarbonyl)phenyl]-cyclopentyl]-1-(4-fluoro-3-methoxyphenyl)ethanamine (compound 1121)

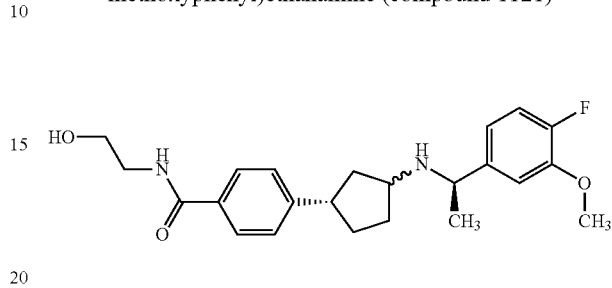

General procedure B was followed using N-(2-hydroxyethyl)-4-[(1S)-3-oxocyclopentyl]benzamide (preparation 16) as the ketone and (1R)-1-(4-fluoro-3-methoxyphenyl)-ethylamine hydrochloride as the amine. LC-MS: RT=4.54, M=400.

Example 123

(1R)—(N)-[(1R/S,3S)-3-[4-(2-hydroxyethylaminocarbonyl)phenyl]-cyclopentyl]-1-(3-chlorophenyl)ethanamine (compound 1122)

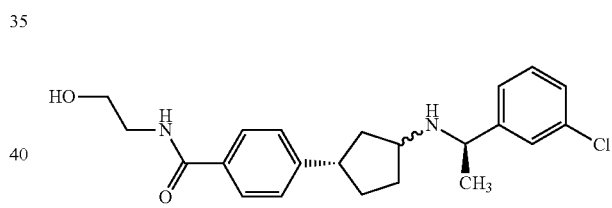

General procedure B was followed using N-(2-hydroxyethyl)-4-[(1S)-3-oxocyclopentyl]benzamide (preparation 16) as the ketone and (R)-1-(3-chlorophenyl)ethanamine as the amine. LC-MS: RT=5.06, M=386.

Example 124

(1R)—(N)-[(1R/S,3S)-3-[4-(2-hydroxyethylaminocarbonyl)phenyl]-cyclopentyl]-1-benzo[b]thiophen-3-yl-ethanamine (compound 1123)

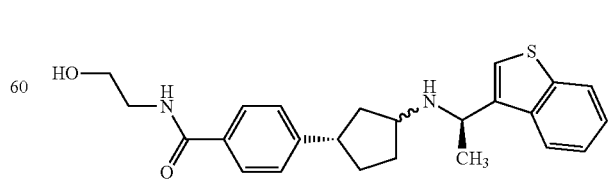

General procedure B was followed using N-(2-hydroxyethyl)-4-[(1S)-3-oxocyclopentyl]benzamide (preparation 16) as the ketone and (R)-1-benzo[b]thiophen-3-yl-ethylamine as the amine. LC-MS: RT=5.04, M=408.

Example 125

(1R)—(N)-[(1R/S,3S)-3-[4-(cyanomethylaminocarbonyl)phenyl]-cyclopentyl]-1-(3-chloro-4-fluorophenyl)ethanamine (compound 1124)

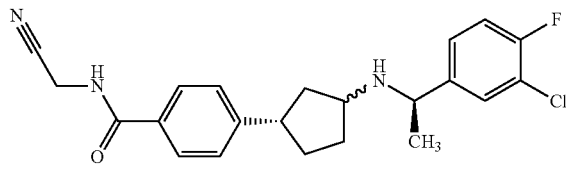

General procedure B was followed using N-(cyanomethyl)-4-[(1S)-3-oxocyclopentyl]benzamide (preparation 18) as the ketone and (1R)-1-(3-chloro-4-fluoro-phenyl)ethanamine hydrochloride as the amine. LC-MS: RT=5.72, M=399.

Example 126

(1R)—N-[(1R/S,3S)-3-[4-(cyanomethylaminocarbonyl)phenyl]-cyclopentyl]-1-(3-ethoxyphenyl)ethanamine (compound 1125)

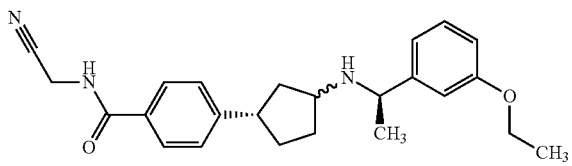 [SMILES: CCOc1cccc([C@@H](C)NC2CC[C@H](c3ccc(C(=O)NCC#N)cc3)C2)c1]

General procedure B was followed using N-(cyanomethyl)-4-[(1S)-3-oxocyclopentyl]benzamide (preparation 18) as the ketone and (1R)-1-(3-ethoxyphenyl)-ethanamine hydrochloride as the amine. LC-MS: RT=5.29, M=391.

Example 127

(1R)—(N)-[(1R/S,3S)-3-[4-(cyanomethylaminocarbonyl)phenyl]-cyclopentyl]-1-(3-fluoro-5-methoxyphenyl)ethanamine (mixture of stereoisomers) (compound 1126)

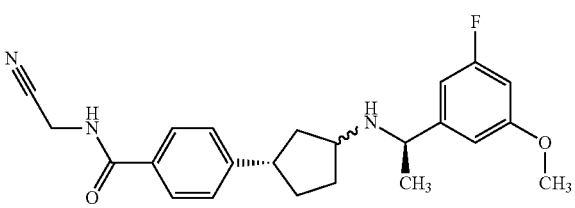 [SMILES: COc1cc(F)cc([C@@H](C)NC2CC[C@H](c3ccc(C(=O)NCC#N)cc3)C2)c1]

General procedure B was followed using N-(cyanomethyl)-4-[(1S)-3-oxocyclopentyl]benzamide (preparation 18) as the ketone and (1R)-1-(3-fluoro-5-methoxy-phenyl)ethanamine as the amine. LC-MS: RT=5.37, M=395.

Example 128

(1R)—N-[(1R/S,3S)-3-[4-(cyanomethylaminocarbonyl)phenyl]-cyclopentyl]-1-(4-fluoro-2-methoxyphenyl)ethanamine (compound 1127)

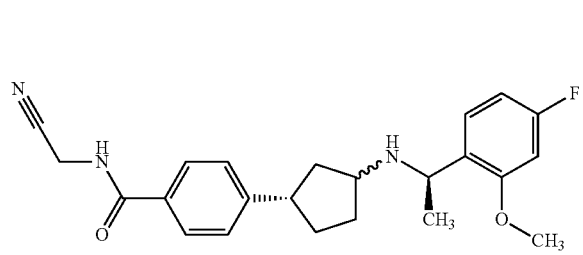 [SMILES: COc1cc(F)ccc1[C@@H](C)NC1CC[C@H](c2ccc(C(=O)NCC#N)cc2)C1]

General procedure B was followed using N-(cyanomethyl)-4-[(1S)-3-oxocyclopentyl]benzamide (preparation 18) as the ketone and (1R)-1-(4-fluoro-2-methoxy-phenyl)ethanamine as the amine. LC-MS: RT=4.96, M=395.

Example 129

(1R)—(N)-[(1R/S,3S)-3-[4-(cyanomethylaminocarbonyl)phenyl]-cyclopentyl]-1-(4-fluoro-3-methoxyphenyl)ethanamine (compound 1128)

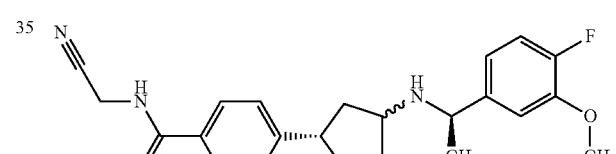

General procedure B was followed using N-(cyanomethyl)-4-[(1S)-3-oxocyclopentyl]benzamide (preparation 18) as the ketone and (1R)-1-(4-fluoro-3-methoxyphenyl) ethylamine hydrochloride as the amine. LC-MS: RT=5.09, M=395.

Example 130

(1R)—(N)-[(1R/S,3S)-3-[4-(cyanomethylaminocarbonyl)phenyl]-cyclopentyl]-1-(3-chlorophenyl)ethanamine (compound 1129)

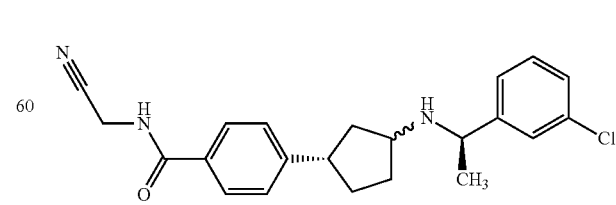

General procedure B was followed using N-(cyanomethyl)-4-[(1S)-3-oxocyclopentyl]benzamide (preparation 18) as the ketone and (R)-1-(3-chlorophenyl)ethanamine as the amine. LC-MS: RT=5.71, M=381.

Example 131

(1R)—(N)-[(1R/S,3S)-3-[4-(cyanomethylaminocarbonyl)phenyl]-cyclopentyl]-1-benzo[b]thiophen-3-yl-ethanamine (compound 1130

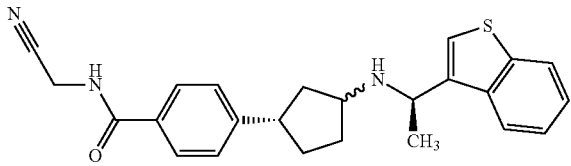 [SMILES: C[C@@H](NC1CC[C@H](c2ccc(C(=O)NCC#N)cc2)C1)c1csc2ccccc12]

General procedure B was followed using N-(cyanomethyl)-4-[(1S)-3-oxocyclopentyl]benzamide (preparation 18) as the ketone and (R)-1-benzo[b]thiophen-3-yl-ethylamine as the amine. LC-MS: RT=5.69, M=403.

Example 132

(1R)—N)-[(1R/S,3S)-3-[4-(2-(methanesulfonylamino)-ethylaminocarbonyl)phenyl]cyclopentyl]-1-(3-ethoxyphenyl)ethanamine (compound 1131)

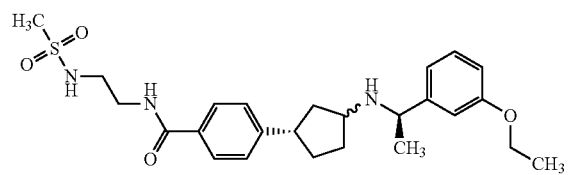 [SMILES: CCOc1cccc([C@@H](C)NC2CC[C@H](c3ccc(C(=O)NCCNS(C)(=O)=O)cc3)C2)c1]

General procedure B was followed using N-[2-(methanesulfonamido)ethyl]-4-[(1S)-3-oxocyclopentyl]benzamide (preparation 17) as the ketone and (1R)-1-(3-ethoxyphenyl)ethanamine hydrochloride as the amine. LC-MS: RT=4.91, M=473.

Example 133

(1R)—(N)-[(1R/S,3S)-3-[4-(2-(methanesulfonylamino)-ethylaminocarbonyl)phenyl]cyclopentyl]-1-(3-fluoro-5-methoxyphenyl)-ethanamine (compound 1132)

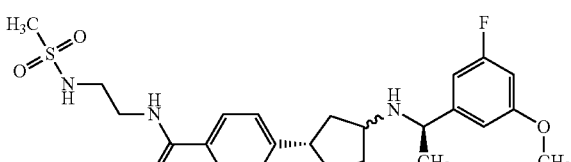

General procedure B was followed using N-[2-(methanesulfonamido)ethyl]-4-[(1S)-3-oxocyclopentyl]benzamide (preparation 17) as the ketone and (1R)-1-(3-fluoro-5-methoxy-phenyl)ethanamine as the amine. LC-MS: RT=4.99, M=477.

Example 134

(1R)—(N)-[(1R/S,3S)-3-[4-(2-(methanesulfonylamino)-ethylaminocarbonyl)phenyl]cyclopentyl]-1-(4-fluoro-2-methoxyphenyl)-ethanamine (compound 1133)

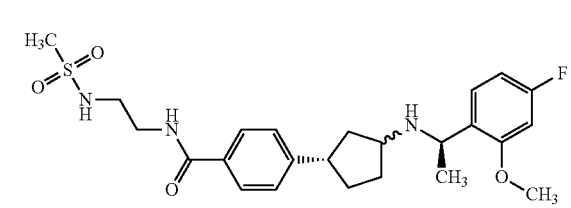 [SMILES: COc1cc(F)ccc1[C@@H](C)NC1CC[C@H](c2ccc(C(=O)NCCNS(C)(=O)=O)cc2)C1]

General procedure B was followed using N-[2-(methanesulfonamido)ethyl]-4-[(1S)-3-oxocyclopentyl]benzamide (preparation 17) as the ketone and (1R)-1-(4-fluoro-2-methoxy-phenyl)ethanamine as the amine. LC-MS: RT=4.59, M=477.

Example 135

(1R)—(N)-[(1R/S,3S)-3-[4-(2-(methanesulfonylamino)-ethylaminocarbonyl)phenyl]cyclopentyl]-1-(4-fluoro-3-methoxyphenyl)-ethanamine

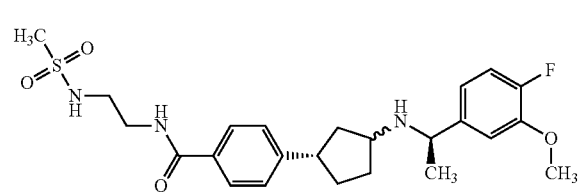 [SMILES: COc1cc([C@@H](C)NC2CC[C@H](c3ccc(C(=O)NCCNS(C)(=O)=O)cc3)C2)ccc1F]

General procedure B was followed using N-[2-(methanesulfonamido)ethyl]-4-[(1S)-3-oxocyclopentyl]benzamide (preparation 17) as the ketone and (1R)-1-(4-fluoro-3-methoxyphenyl)ethylamine hydrochloride as the amine. LC-MS: RT=4.74, M=477.

Example 136

(1R)—(N)-[(1R/S,3S)-3-[4-(2-(methanesulfonylamino)-ethylaminocarbonyl)phenyl]cyclopentyl]-1-(3-chlorophenyl)ethanamine (compound 1135)

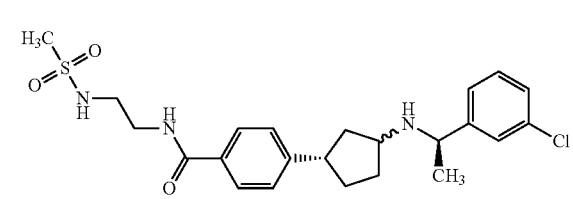 [SMILES: C[C@@H](NC1CC[C@H](c2ccc(C(=O)NCCNS(C)(=O)=O)cc2)C1)c1cccc(Cl)c1]

General procedure B was followed using N-[2-(methanesulfonamido)ethyl]-4-[(1S)-3-oxocyclopentyl]benzamide (preparation 17) as the ketone and (R)-1-(3-chlorophenyl)-ethanamine as the amine. LC-MS: RT=5.31, M=463.

Example 137

(1R)—(N)-[(1R/S,3S)-3-[4-(2-(methanesulfonylamino)-ethylaminocarbonyl)phenyl]cyclopentyl]-1-benzo[b]thiophen-3-yl-ethanamine (compound 1136)

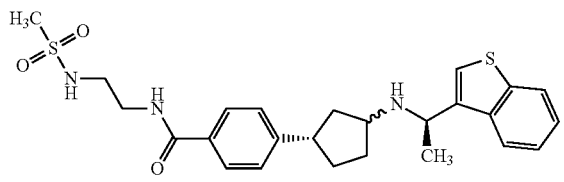 [SMILES: C[C@@H](NC1CC[C@H](c2ccc(C(=O)NCCNS(C)(=O)=O)cc2)C1)c1csc2ccccc12]

General procedure B was followed using N-[2-(methanesulfonamido)ethyl]-4-[(1S)-3-oxocyclopentyl]benzamide (preparation 17) as the ketone and (R)-1-benzo[b]thiophen-3-yl-ethylamine as the amine. LC-MS: RT=5.29, M=485.

Example 138

(1R)—(N)-[(1R/S,3R)-3-[4-[methanesulfonylaminocarbonyl-methoxy]phenyl]cyclopentyl]-1-(1,3-benzodioxol-4-yl)ethanamine (mixture of stereoisomers) (compound 1137)

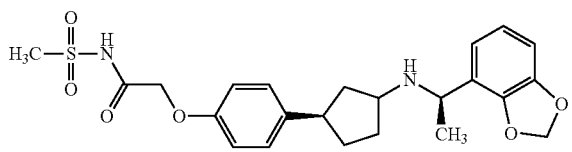 [SMILES: C[C@@H](NC1CC[C@@H](c2ccc(OCC(=O)NS(C)(=O)=O)cc2)C1)c1cccc2c1OCO2]

General procedure B was followed using N-methylsulfonyl-2-[4-[(1R)-3-oxocyclopentyl]phenoxy]acetamide (preparation 8) as the ketone and (1R)-1-(1,3-benzodioxol-4-yl)ethanamine hydrochloride as the amine. LC-MS: RT=4.07, M=460.

Example 139

(1R)—(N)-[(1R/S,3R)-3-[4-[methanesulfonylaminocarbonyl-methoxy]phenyl]cyclopentyl]-1-(3-chloro-4-fluoro-phenyl)ethanamine (compound 1138)

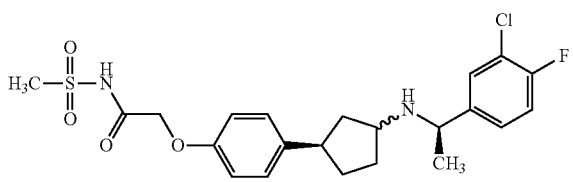 [SMILES: C[C@@H](NC1CC[C@@H](c2ccc(OCC(=O)NS(C)(=O)=O)cc2)C1)c1ccc(F)c(Cl)c1]

General procedure B was followed using N-methylsulfonyl-2-[4-[(1R)-3-oxocyclopentyl]phenoxy]acetamide (preparation 8) as the ketone and (1R)-1-(3-chloro-4-fluorophenyl)ethanamine hydrochloride as the amine. LC-MS: RT=4.49, M=468.

Example 140

(1R)—(N)-[(1R/S,3R)-3-[4-[methanesulfonylaminocarbonyl-methoxy]phenyl]cyclopentyl]-1-(3-ethoxyphenyl)ethanamine (mixture of stereoisomers) (compound 1139)

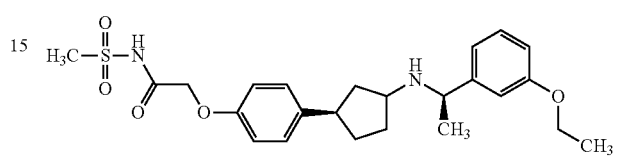

General procedure B was followed using N-methylsulfonyl-2-[4-[(1R)-3-oxocyclopentyl]phenoxy]acetamide (preparation 8) as the ketone and (1R)-1-(3-ethoxyphenyl)-ethanamine hydrochloride as the amine. LC-MS: RT=4.24, M=460.

Example 141

(1R)—(N)-[(1R/S,3R)-3-[4-(methanesulfonylaminocarbonyl-methoxy)-phenyl]cyclopentyl]-1-(3-fluoro-5-methoxyphenyl)ethanamine (mixture of stereoisomers) (compound 1140

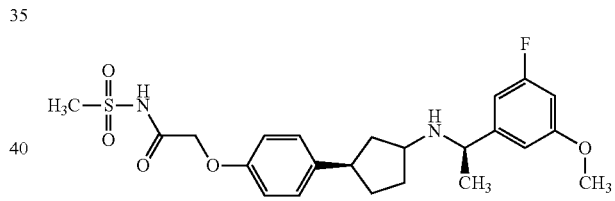

General procedure B was followed using N-methylsulfonyl-2-[4-[(1R)-3-oxocyclopentyl]phenoxy]acetamide (preparation 8) as the ketone and (1R)-1-(3-fluoro-5-methoxy-phenyl)ethanamine as the amine. LC-MS: RT=4.16, M=464.

Example 142

(1R)—(N)-[(1R/S,3R)-3-[4-(methanesulfonylaminocarbonyl-methoxy)-phenyl]cyclopentyl]-1-(4-fluoro-2-methoxyphenyl)ethanamine (compound 1141)

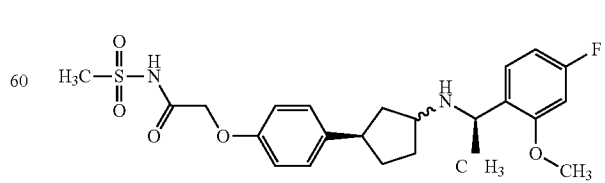

General procedure B was followed using N-methylsulfonyl-2-[4-[(1R)-3-oxocyclopentyl]phenoxy]acetamide (preparation 8) as the ketone and (1R)-1-(4-fluoro-2-methoxy-phenyl)ethanamine as the amine. LC-MS: RT=4.07, M=464.

Example 143

(1R)—(N)-[(1R/S,3R)-3-[4-(methanesulfonylaminocarbonyl-methoxy)-phenyl]cyclopentyl]-1-(4-fluoro-3-methoxyphenyl)ethanamine (mixture of stereoisomers) (compound 1142)

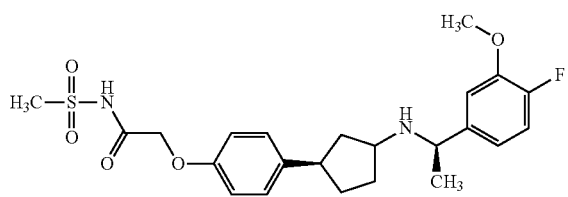 [SMILES: COc1cc([C@@H](C)NC2CC[C@@H](c3ccc(OCC(=O)NS(C)(=O)=O)cc3)C2)ccc1F]

General procedure B was followed using N-methylsulfonyl-2-[4-[(1R)-3-oxocyclopentyl]phenoxy]acetamide (preparation 8) as the ketone and (1R)-1-(4-fluoro-3-methoxyphenyl)ethylamine hydrochloride as the amine. LC-MS: RT=4.14, M=464.

Example 144

(1R)—(N)-[(1R/S,3S)-3-[4-[piperidin-4-ylaminocarbonyl]phenyl]-cyclopentyl]-1-(1,3-benzodioxol-4-yl)ethanamine (mixture of stereoisomers)

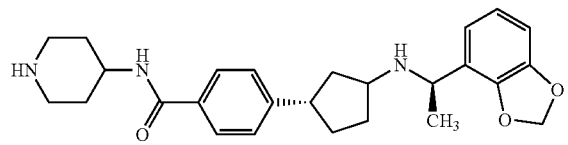 [SMILES: C[C@@H](NC1CC[C@H](c2ccc(C(=O)NC3CCNCC3)cc2)C1)c1cccc2c1OCO2]

General procedure C was followed using tert-butyl 4-[[4-[(1S)-3-oxocyclopentyl]benzoyl]amino]piperidine-1-carboxylate (preparation 2) as the ketone and (1R)-1-(1,3-benzodioxol-4-yl)ethanamine hydrochloride as the amine. LC-MS: RT=4.31, M=435.

Example 145

(1R)—(N)-[(1R/S,3S)-3-[4-[piperidin-4-ylaminocarbonyl]phenyl]-cyclopentyl]-1-(1,3-benzodioxol-5-yl)ethanamine (compound 1144)

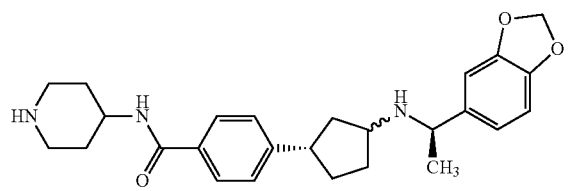 [SMILES: C[C@@H](NC1CC[C@H](c2ccc(C(=O)NC3CCNCC3)cc2)C1)c1ccc2c(c1)OCO2]

General procedure C was followed using tert-butyl 4-[[4-[(1S)-3-oxocyclopentyl]benzoyl]amino]piperidine-1-carboxylate (preparation 2) as the ketone and (1R)-1-(1,3-benzodioxol-5-yl)ethanamine as the amine. LC-MS: RT=4.16, M=435.

Example 146

(1R)—(N)-[(1R/S,3S)-3-[4-[piperidin-4-ylaminocarbonyl]phenyl]-cyclopentyl]-1-(1-methyl-5-phenylpyrazol-3-yl)ethanamine (compound 1145)

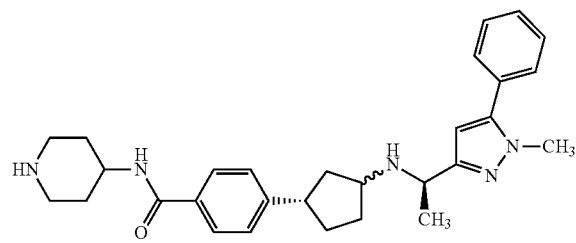 [SMILES: C[C@@H](NC1CC[C@H](c2ccc(C(=O)NC3CCNCC3)cc2)C1)c1cc(-c2ccccc2)n(C)n1]

General procedure C was followed using tert-butyl 4-[[4-[(1S)-3-oxocyclopentyl]benzoyl]amino]piperidine-1-carboxylate (preparation 2) as the ketone and (1R)-1-(1-methyl-5-phenyl-pyrazol-3-yl)ethanamine (preparation 26) as the amine. LC-MS: RT=4.04, M=471.

Example 147

(1R)—(N)-[(1R/S,3S)-3-[4-[piperidin-4-ylaminocarbonyl]phenyl]-cyclopentyl]-1-(2,2-difluoro-1,3-benzodioxol-4-yl)ethanamine hydrochloride (mixture of stereoisomers) (compound 1146)

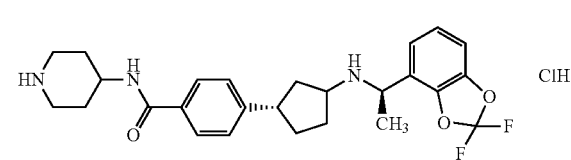 [SMILES: C[C@@H](NC1CC[C@H](c2ccc(C(=O)NC3CCNCC3)cc2)C1)c1cccc2c1OC(F)(F)O2 ; Cl]

General procedure C was followed using tert-butyl 4-[[4-[(1S)-3-oxocyclopentyl]-benzoyl]amino]piperidine-1-carboxylate (preparation 2) as the ketone and (1R)-1-(2,2-difluoro-1,3-benzodioxol-4-yl)ethanamine (preparation 24) as the amine. LC-MS: RT=4.99, M=471.

Example 148

(1R)—(N)-[(1R/S,3S)-3-[4-[piperidin-4-ylaminocarbonyl]phenyl]-cyclopentyl]-1-(2,3-dihydro-1,4-benzodioxin-5-yl)ethanamine (compound 1147)

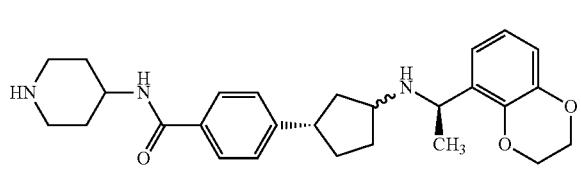 [SMILES: C[C@@H](NC1CC[C@H](c2ccc(C(=O)NC3CCNCC3)cc2)C1)c1cccc2c1OCCO2]

General procedure C was followed using tert-butyl 4-[[4-[(1S)-3-oxocyclopentyl]-benzoyl]amino]piperidine-1-carboxylate (preparation 2) as the ketone and (1R)-1-(2,3-dihydro-1,4-benzodioxin-5-yl)ethanamine hydrochloride (preparation 22) as the amine. LC-MS: RT=3.97, M=449.

Example 149

(1R)—(N)-[(1R/S,3S)-3-[4-[piperidin-4-ylaminocarbonyl]phenyl]-cyclopentyl]-1-(2,3-dihydrobenzofuran-5-yl)ethanamine (compound 1148

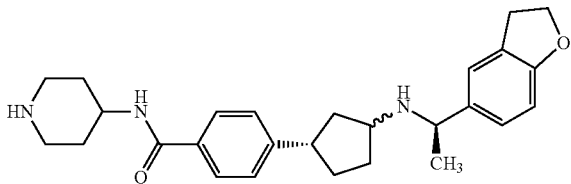 [SMILES: C[C@@H](NC1CC[C@H](c2ccc(C(=O)NC3CCNCC3)cc2)C1)c1ccc2c(c1)CCO2]

General procedure C was followed using tert-butyl 4-[[4-[(1S)-3-oxocyclopentyl]benzoyl]amino]piperidine-1-carboxylate (preparation 2) as the ketone and (1R)-1-(2,3-dihydrobenzofuran-5-yl)ethanamine as the amine. LC-MS: RT=3.87, M=433.

Example 150

(1R)—(N)-[(1R/S,3S)-3-[4-[piperidin-4-ylaminocarbonyl]phenyl]-cyclopentyl]-1-(2,3-dimethoxyphenyl)ethanamine (mixture of stereoisomers) (compound 1149)

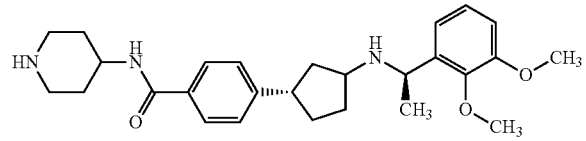 [SMILES: COc1cccc([C@@H](C)NC2CC[C@H](c3ccc(C(=O)NC4CCNCC4)cc3)C2)c1OC]

General procedure C was followed using tert-butyl 4-[[4-[(1S)-3-oxocyclopentyl]-benzoyl]amino]piperidine-1-carboxylate (preparation 2) as the ketone and (1R)-1-(2,3-dimethoxyphenyl)ethylamine hydrochloride as the amine. LC-MS: RT=4.12, M=451.

Example 151

(1R)—(N)-[(1R/S,3S)-3-[4-[piperidin-4-ylaminocarbonyl]phenyl]-cyclopentyl]-1-(2-fluoro-3-methoxy-phenyl)ethanamine (compound 1150)

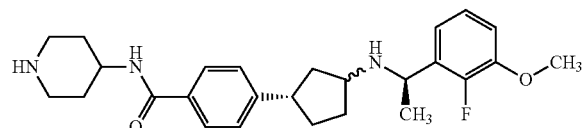

General procedure C was followed using tert-butyl 4-[[4-[(1S)-3-oxocyclopentyl]-benzoyl]amino]piperidine-1-carboxylate (preparation 2) as the ketone and (1R)-1-(2-fluoro-3-methoxy-phenyl)ethanamine as the amine. LC-MS: RT=4.31, M=439.

Example 152

(1R)—(N)-[(1R/S,3S)-3-[4-[piperidin-4-ylaminocarbonyl]phenyl]-cyclopentyl]-1-(2-fluoro-5-methoxy-phenyl)ethanamine (compound 1151)

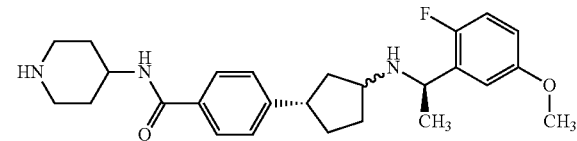 [SMILES: COc1ccc(F)c([C@@H](C)NC2CC[C@H](c3ccc(C(=O)NC4CCNCC4)cc3)C2)c1]

General procedure C was followed using tert-butyl 4-[[4-[(1S)-3-oxocyclopentyl]-benzoyl]amino]piperidine-1-carboxylate (preparation 2) as the ketone and (1R)-1-(2-fluoro-5-methoxy-phenyl)ethanamine as the amine. LC-MS: RT=4.44, M=439.

Example 153

(1R)—(N)-[(1R/S,3S)-3-[4-[piperidin-4-ylaminocarbonyl]phenyl]-cyclopentyl]-1-(2-methylthiazol-4-yl)ethanamine (compound 1152)

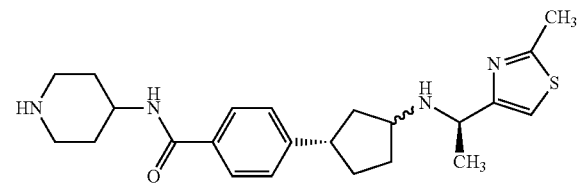 [SMILES: Cc1nc([C@@H](C)NC2CC[C@H](c3ccc(C(=O)NC4CCNCC4)cc3)C2)cs1]

General procedure C was followed using tert-butyl 4-[[4-[(1S)-3-oxocyclopentyl]-benzoyl]amino]piperidine-1-carboxylate (preparation 2) as the ketone and (1R)-1-(2-methylthiazol-4-yl)ethanamine hydrochloride as the amine. LC-MS: RT=3.91, M=439.

Example 154

(1R)—(N)-[(1R/S,3S)-3-[4-[piperidin-4-ylaminocarbonyl]phenyl]-cyclopentyl]-1-(3-chloro-4-fluorophenyl)ethanamine hydrochloride (mixture of stereoisomers) (compound 1153)

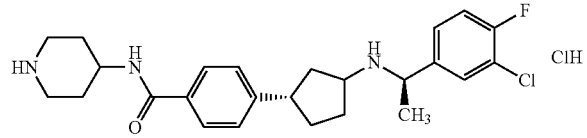

General procedure C was followed using tert-butyl 4-[[4-[(1S)-3-oxocyclopentyl]-benzoyl]amino]piperidine-1-carboxylate (preparation 2) as the ketone and (1R)-1-(3-chloro-4-fluoro-phenyl)ethanamine hydrochloride as the amine. LC-MS: RT=4.87, M=443.

Example 155

(1R)—(N)-[(1R/S,3S)-3-[4-[piperidin-4-ylaminocarbonyl]phenyl]-cyclopentyl]-1-(3-ethoxyphenyl)ethanamine hydrochloride (mixture of stereoisomers) (compound 1154)

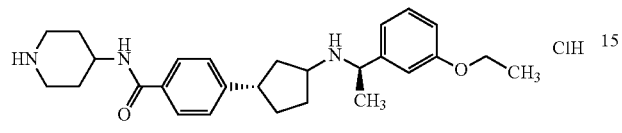

General procedure C was followed using tert-butyl 4-[[4-[(1S)-3-oxocyclopentyl]-benzoyl]amino]piperidine-1-carboxylate (preparation 2) as the ketone and (1R)-1-(3-ethoxyphenyl)ethanamine hydrochloride as the amine. LC-MS: RT=3.94, M=435.

Example 156

(1R)—(N)-[(1R/S,3S)-3-[4-[piperidin-4-ylaminocarbonyl]phenyl]-cyclopentyl]-1-(3-fluoro-5-methoxyphenyl)ethanamine (compound 1155

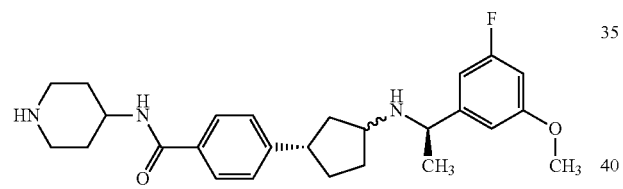

General procedure C was followed using tert-butyl 4-[[4-[(1S)-3-oxocyclopentyl]-benzoyl]amino]piperidine-1-carboxylate (preparation 2) as the ketone and (1R)-1-(3-fluoro-5-methoxy-phenyl)ethanamine as the amine. LC-MS: RT=4.51, M=439.

Example 157

(1R)—(N)-[(1R/S,3S)-3-[4-[piperidin-4-ylaminocarbonyl]phenyl]-cyclopentyl]-1-(4-fluoro-2-methoxyphenyl)ethanamine (mixture of stereoisomers) (compound 1156)

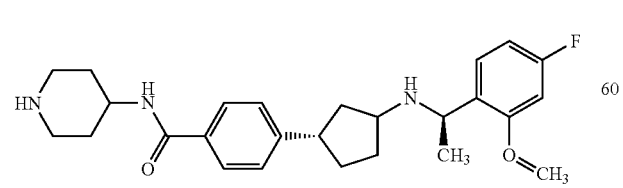

General procedure C was followed using tert-butyl 4-[[4-[(1S)-3-oxocyclopentyl]-benzoyl]amino]piperidine-1-carboxylate (preparation 2) as the ketone and (1R)-1-(4-fluoro-2-methoxy-phenyl)ethanamine as the amine. LC-MS: RT=2.00, M=440.

Example 158

(1R)—(N)-[(3S)-3-[4-[piperidin-4-ylaminocarbonyl]phenyl]-cyclopentyl]-1-(4-fluoro-3-methoxyphenyl)ethanamine (mixture of stereoisomers) (compound 1157)

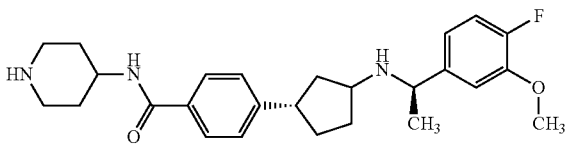 [SMILES: COc1cc([C@@H](C)NC2CC[C@H](c3ccc(C(=O)NC4CCNCC4)cc3)C2)ccc1F]

General procedure C was followed using tert-butyl 4-[[4-[(1S)-3-oxocyclopentyl]-benzoyl]amino]piperidine-1-carboxylate (preparation 2) as the ketone and (1R)-1-(4-fluoro-3-methoxyphenyl)ethylamine hydrochloride as the amine. LC-MS: RT=4.26, M=439.

Example 159

(1R)—(N)-[(1R/S,3S)-3-[4-[piperidin-4-ylaminocarbonyl]phenyl]-cyclopentyl]-1-(5-chloro-2-thienyl)ethanamine hydrochloride (mixture of stereoisomers) (compound 1158)

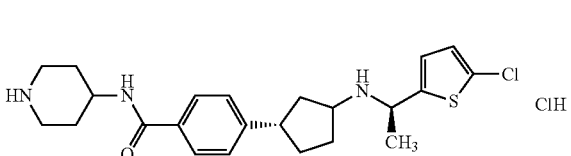

General procedure C was followed using tert-butyl 4-[[4-[(1S)-3-oxocyclopentyl]-benzoyl]amino]piperidine-1-carboxylate (preparation 2) as the ketone and (1R)-1-(5-chloro-2-thienyl)ethanamine hydrochloride as the amine. LC-MS: RT=4.97, M=431.

Example 160

(1R)—(N)-[(1R/S,3S)-3-[4-[piperidin-4-ylaminocarbonyl]phenyl]-cyclopentyl]-1-(5-fluoroimidazo[1,2-a]pyridin-2-yl)ethanamine formiate (mixture of stereoisomers) (compound 1159)

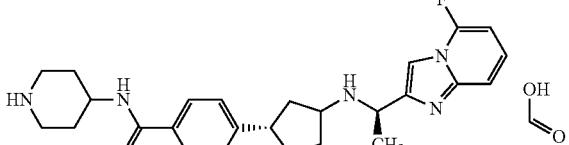

General procedure C was followed using tert-butyl 4-[[4-[(1S)-3-oxocyclopentyl]-benzoyl]amino]piperidine-1-carboxylate (preparation 2) as the ketone and (1R)-1-(5-fluoroimidazo[1,2-a]pyridin-2-yl)ethanamine hydrochloride (preparation 28) as the amine. LC-MS: RT=1.65, M=496.

3-(trifluoromethyl)phenyl]ethanamine hydrochloride as the amine. LC-MS: RT=5.01, M=477.

Example 161

(1R)—(N)-[(1R/S,3S)-3-[4-[piperidin-4-ylaminocarbonyl]phenyl]-cyclopentyl]-1-(8-quinolyl)ethanamine (compound 1160)

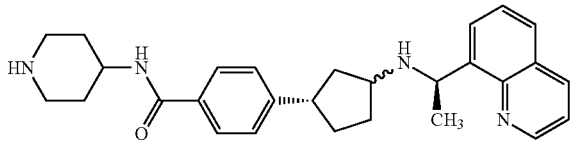 [SMILES: C[C@@H](NC1CC[C@H](c2ccc(C(=O)NC3CCNCC3)cc2)C1)c1cccc2cccnc12]

General procedure C was followed using tert-butyl 4-[[4-[(1S)-3-oxocyclopentyl]-benzoyl]amino]piperidine-1-carboxylate (preparation 2) as the ketone and (1R)-1-(8-quinolyl)ethanamine as the amine. LC-MS: RT=3.91, M=442.

Example 162

(1R)—(N)-[(1R/S,3S)-3-[4-[piperidin-4-ylaminocarbonyl]phenyl]-cyclopentyl]-1-[3-(methylethoxy)phenyl]ethanamine (mixture of stereoisomers) (compound 1161)

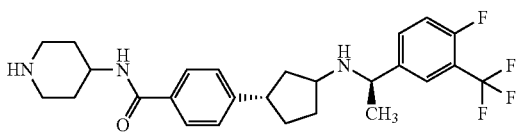

General procedure C was followed using tert-butyl 4-[[4-[(1S)-3-oxocyclopentyl]-benzoyl]amino]piperidine-1-carboxylate (preparation 2) as the ketone and (1R)-1-[3-(methylethoxy)phenyl]ethylamine hydrochloride as the amine. LC-MS: RT=4.57, M=449.

Example 163

(1R)—(N)-[(1R/S,3S)-3-[4-[piperidin-4-ylaminocarbonyl]phenyl]-cyclopentyl]-1-[4-fluoro-3-(trifluoromethyl)phenyl]ethanamine hydrochloride (mixture of stereoisomers) (compound 1162)

General procedure C was followed using tert-butyl 4-[[4-[(1S)-3-oxocyclopentyl]-benzoyl]amino]piperidine-1-carboxylate (preparation 2) as the ketone and (1R)-1-[4-fluoro-

Example 164

(1R)—(N)-[(1R/S,3S)-3-[4-[piperidin-4-ylaminocarbonyl]phenyl]-cyclopentyl]-1-cyclopropylethanamine (compound 1163)

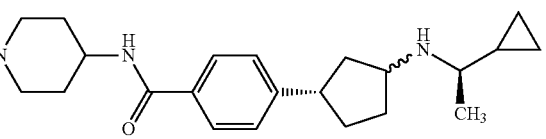

General procedure C was followed using tert-butyl 4-[[4-[(1S)-3-oxocyclopentyl]-benzoyl]amino]piperidine-1-carboxylate (preparation 2) as the ketone and (1R)-1-cyclopropylethanamine as the amine. LC-MS: RT=2.77, M=355.

Example 165

(1R)—(N)-[(1R/S,3S)-3-[4-[piperidin-4-ylaminocarbonyl]phenyl]-cyclopentyl]-1-imidazo[1,5-a]pyridin-3-ylethanamine (mixture of stereoisomers) (compound 1164)

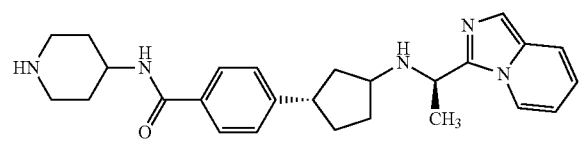 [SMILES: C[C@@H](NC1CC[C@H](c2ccc(C(=O)NC3CCNCC3)cc2)C1)c1ncc2ccccn12]

General procedure C was followed using tert-butyl 4-[[4-[(1S)-3-oxocyclopentyl]-benzoyl]amino]piperidine-1-carboxylate (preparation 2) as the ketone and (1R)-1-imidazo[1,5-a]pyridin-3-ylethanamine hydrochloride (preparation 29) as the amine. LC-MS: RT=3.87, M=431.

Example 166

(1R)—(N)-[(1R/S,3S)-3-[4-[piperidin-4-ylaminocarbonyl]phenyl]-cyclopentyl]-1-pyrazolo[1,5-a]pyridin-3-ylethanamine (mixture of stereoisomers) (compound 1165)

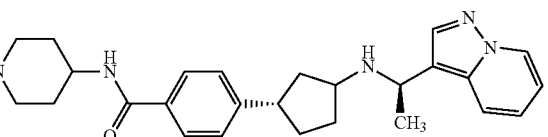

General procedure C was followed using tert-butyl 4-[[4-[(1S)-3-oxocyclopentyl]-benzoyl]amino]piperidine-1-carboxylate (preparation 2) as the ketone and (1R)-1-pyrazolo

[1,5-a]pyridin-3-ylethanamine hydrochloride (preparation 23) as the amine. LC-MS: RT=2.11, M=432.

Example 167

(1R)—(N)-[(1R/S,3S)-3-[4-[piperidin-4-ylaminocarbonyl]phenyl]-cyclopentyl]-1-(3-chlorophenyl)ethanamine (compound 1166)

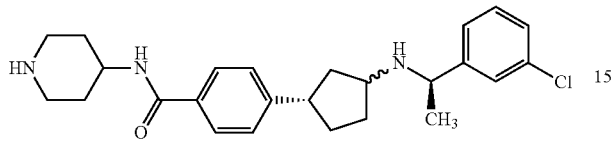

General procedure C was followed using tert-butyl 4-[[4-[(1S)-3-oxocyclopentyl]-benzoyl]amino]piperidine-1-carboxylate (preparation 2) as the ketone and (R)-1-(3-chlorophenyl)ethanamine as the amine. LC-MS: RT=4.31, M=425.

Example 168

(1R)—(N)-[(1R/S,3S)-3-[4-[piperidin-4-ylaminocarbonyl]phenyl]-cyclopentyl]-1-(3-fluoro-4-methoxyphenyl)ethanamine (mixture of stereoisomers) (compound 1167)

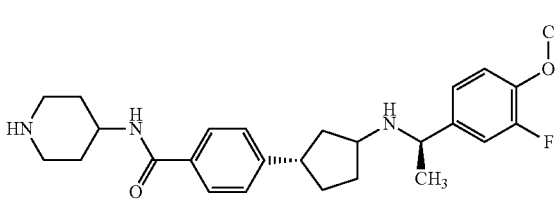

General procedure C was followed using tert-butyl 4-[[4-[(1S)-3-oxocyclopentyl]-benzoyl]amino]piperidine-1-carboxylate (preparation 2) as the ketone and (R)-1-(3-fluoro-4-methoxyphenyl)ethanamine hydrochloride as the amine. LC-MS: RT=4.24, M=439.

Example 169

(1R)—(N)-[(1R/S,3S)-3-[4-[piperidin-4-ylaminocarbonyl]phenyl]-cyclopentyl]-1-(3-fluorophenyl)ethanamine (mixture of stereoisomers) (compound 1168)

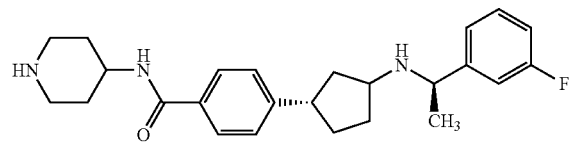 [SMILES: C[C@@H](NC1CC[C@H](c2ccc(C(=O)NC3CCNCC3)cc2)C1)c1cccc(F)c1]

General procedure C was followed using tert-butyl 4-[[4-[(1S)-3-oxocyclopentyl]-benzoyl]amino]piperidine-1-carboxylate (preparation 2) as the ketone and (R)-1-(3-fluorophenyl)ethanamine as the amine. LC-MS: RT=4.41, M=409.

Example 170

(1R)—(N)-[(1R/S,3S)-3-[4-[piperidin-4-ylaminocarbonyl]phenyl]-cyclopentyl]-1-[3-(trifluoromethyl)phenyl]ethanamine formiate (mixture of stereoisomers) (compound 1169)

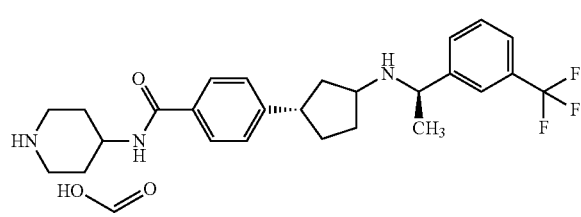

General procedure C was followed using tert-butyl 4-[[4-[(1S)-3-oxocyclopentyl]-benzoyl]amino]piperidine-1-carboxylate (preparation 2) as the ketone and (R)-1-[3-(trifluoromethyl)phenyl]ethylamine as the amine. LC-MS: RT=1.60, M=506.

Example 171

(1R)—(N)-[(1R/S,3S)-3-[4-[piperidin-4-ylaminocarbonyl]phenyl]-cyclopentyl]-1-benzo[b]thiophen-3-yl-ethanamine (mixture of stereoisomers)

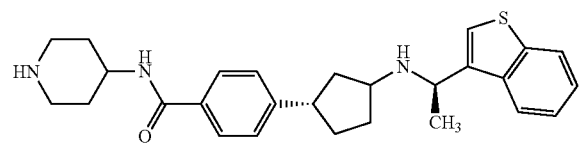 [SMILES: C[C@@H](NC1CC[C@H](c2ccc(C(=O)NC3CCNCC3)cc2)C1)c1csc2ccccc12]

General procedure C was followed using tert-butyl 4-[[4-[(1S)-3-oxocyclopentyl]-benzoyl]amino]piperidine-1-carboxylate (preparation 2) as the ketone and (R)-1-benzo[b]thiophen-3-yl-ethylamine as the amine. LC-MS: RT=1.84, M=448.

Example 172

(1R/S)—(N)-[(1R/S,3S)-3-[4-[piperidin-4-ylaminocarbonyl]phenyl]-cyclopentyl]-1-pyrimidin-4-ylethanamine (mixture of stereoisomers) (compound 1171)

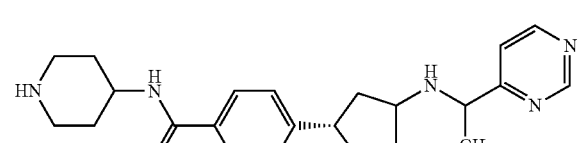

General procedure C was followed using tert-butyl 4-[[4-[(1S)-3-oxocyclopentyl]-benzoyl]amino]piperidine-1-carboxylate (preparation 2) as the ketone and 1-pyrimidin-4-ylethanamine dihydrochloride as the amine. LC-MS: RT=2.96, M=393.

Example 173

(1R)—(N)-[(1R/S,3S)-3-[4-[piperidin-4-ylaminocarbonyl]phenyl]-cyclopentyl]-1-(3-cyano-4-fluorophenyl)ethanamine (compound 1172)

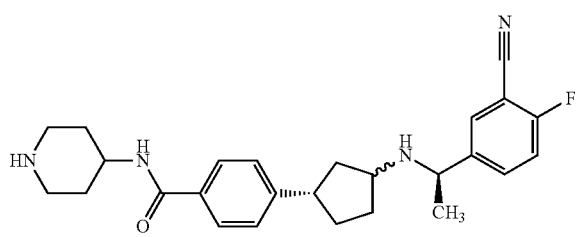 [SMILES: C[C@@H](NC1CC[C@H](c2ccc(C(=O)NC3CCNCC3)cc2)C1)c1ccc(F)c(C#N)c1]

General procedure C was followed using tert-butyl 4-[[4-[(1S)-3-oxocyclopentyl]-benzoyl]amino]piperidine-1-carboxylate (preparation 2) as the ketone and 5-[(1R)-1-aminoethyl]-2-fluoro-benzonitrile hydrochloride as the amine. LC-MS: RT=4.41, M=434.

Example 174

(4-{(1R,3S)-3-[(1R)-1-(4-Fluoro-3-methoxy-phenyl)-ethylamino]-cyclopentyl}-phenyl)-(3-hydroxy-azetidin-1-yl)-methanone (Compound 1173)

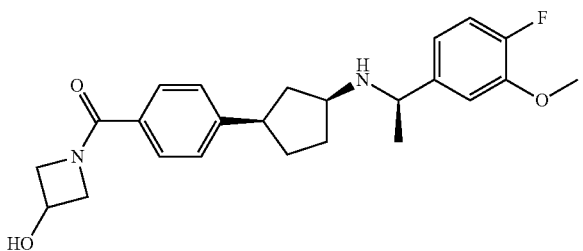 [SMILES: COc1cc([C@@H](C)N[C@H]2CC[C@@H](c3ccc(C(=O)N4CC(O)C4)cc3)C2)ccc1F]

General procedure G was followed using 3-hydroxyazetidine hydrochloride as the amine. $^1$H NMR (300 MHz, DMSO) δ 7.53 (d, J=8.2 Hz, 2H), 7.30 (d, J=8.3 Hz, 2H), 7.24 (dd, J=8.5, 1.9 Hz, 1H), 7.15 (dd, J=11.5, 8.2 Hz, 1H), 6.95 (ddd, J=8.3, 4.4, 2.0 Hz, 1H), 4.52-3.92 (m, 6H), 3.84 (s, 3H), 3.01 (m, 2H), 2.21-2.08 (m, 1H), 2.00-1.80 (m, 2H), 1.78-1.64 (m, 2H), 1.45 (m, 1H), 1.34 (d, J=6.6 Hz, 3H).

Example 175

4-{(1R,3S)-3-[(1R)-1-(4-Fluoro-3-methoxy-phenyl)-ethylamino]-cyclopentyl}-N-methyl-N-oxetan-3-yl-benzamide (Compound 1174)

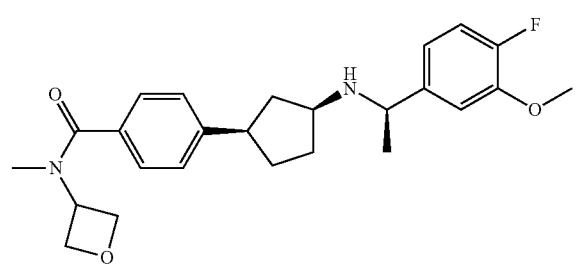

General procedure G was followed using N-methyl-3-oxetanamine-dihydrogenphosphate as the amine. $^1$H NMR (300 MHz, DMSO) δ 7.91 (d, J=8.3 Hz, 2H), 7.39 (d, J=8.3 Hz, 2H), 7.23 (dd, J=8.6, 1.9 Hz, 1H), 7.14 (dd, J=11.5, 8.2 Hz, 1H), 6.99-6.89 (m, 1H), 4.30 (ddd, J=20.5, 11.5, 5.3 Hz, 2H), 3.96-3.48 (m, 6H), 3.09-2.92 (m, 3H), 2.45 (s, 3H), 2.20-2.07 (m, 1H), 2.02-1.61 (m, 4H), 1.54-1.37 (m, 1H), 1.32 (d, J=6.6 Hz, 3H).

Example 176

(4-{(1R,3S)-3-[(1R)-1-(4-Fluoro-3-methoxy-phenyl)-ethylamino]-cyclopentyl}-phenyl)-isoxazolidin-2-yl-methanone (Compound 1175)

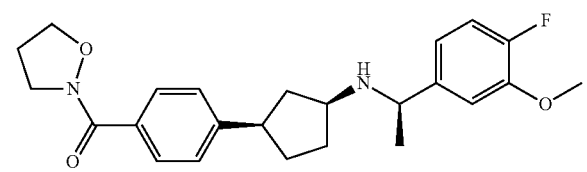 [SMILES: COc1cc([C@@H](C)N[C@H]2CC[C@@H](c3ccc(C(=O)N4CCCO4)cc3)C2)ccc1F]

General procedure G was followed using isoxazolidine hydrochloride as the amine. $^1$H NMR (300 MHz, DMSO) δ 7.61 (d, J=8.2 Hz, 2H), 7.30 (d, J=8.3 Hz, 2H), 7.22 (dd, J=8.5, 1.7 Hz, 1H), 7.14 (dd, J=11.5, 8.2 Hz, 1H), 6.98-6.90 (m, 1H), 3.94-3.80 (m, 6H), 3.78-3.70 (m, 2H), 3.08-2.89 (m, 2H), 2.32-1.61 (m, 7H), 1.52-1.36 (m, 1H), 1.31 (d, J=6.6 Hz, 3H).

Example 177

4-{(1R,3S)-3-[(1R)-1-(4-Fluoro-3-methoxy-phenyl)-ethylamino]-cyclopentyl}-N-(2-hydroxy-ethyl)-benzamide (Compound 1176)

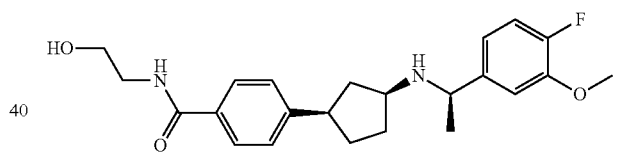

General procedure G was followed using aminoethanol as the amine. $^1$H NMR (300 MHz, DMSO) δ 8.54 (t, J=5.3 Hz, 1H), 7.80 (d, J=8.3 Hz, 2H), 7.40-7.25 (m, 4H), 7.13-7.04 (m, 1H), 4.39 (q, J=6.8 Hz, 1H), 3.92-3.83 (m, 5H), 3.51-3.38 (m, 3H), 3.15-3.01 (m, 1H), 2.44-2.29 (m, 1H), 2.13-1.58 (m, 5H), 1.54 (d, J=6.7 Hz, 3H).

Example 178

(4-{(1R,3S)-3-[(1R)-1-(4-Fluoro-3-methoxy-phenyl)-ethylamino]-cyclopentyl}-phenyl)-(3-hydroxy-pyrrolidin-1-yl)-methanone (Compound 1177)

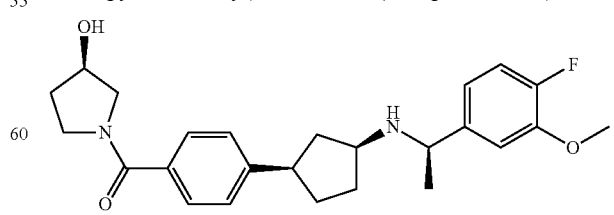

General procedure G was followed using (3R)-pyrrolidin-3-ol as the amine. $^1$H NMR (300 MHz, DMSO) δ 8.22 (s, 1H), 7.46-7.38 (m, 2H), 7.28 (d, J=8.2 Hz, 2H), 7.23 (dd, J=8.5, 1.9

Hz, 1H), 7.15 (dd, J=11.5, 8.3 Hz, 1H), 6.94 (ddd, J=8.3, 4.4, 2.0 Hz, 1H), 4.35-4.18 (m, 1H), 3.93 (q, J=6.6 Hz, 1H), 3.84 (s, 3H), 3.61-2.88 (m, 6H), 2.22-2.08 (m, 1H), 2.01-1.63 (m, 6H), 1.52-1.37 (m, 1H), 1.33 (d, J=6.6 Hz, 3H).

Example 179

4-{(1R,3S)-3-[(1R)-1-(4-Fluoro-3-methoxy-phenyl)-ethylamino]-cyclopentyl}-N-(2-methanesulfonylamino-ethyl)-benzamide hydrochloride (Compound

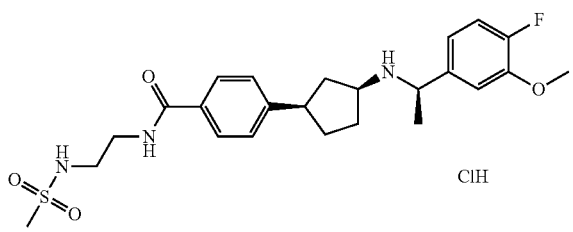 [SMILES: COc1cc([C@@H](C)N[C@H]2CC[C@@H](c3ccc(C(=O)NCCNS(C)(=O)=O)cc3)C2)ccc1F ; Cl]

General procedure G was followed using N-(2-aminoethyl)methanesulfonamide as the amine. The product was dissolved in dioxane and treated with 4N HCl in dioxane. Solvents were removed in vacuo to afford the title compound. $^1$H NMR (300 MHz, DMSO) δ 9.82 (br s, 1H), 9.48 (br s, 1H), 8.48 (t, J=5.7 Hz, 1H), 7.80 (d, J=8.3 Hz, 2H), 7.61 (dd, J=8.3, 1.9 Hz, 1H), 7.34 (d, J=8.3 Hz, 2H), 7.28 (dd, J=11.4, 8.3 Hz, 1H), 7.20-7.10 (m, 2H), 4.47-4.35 (m, 1H), 3.88 (s, 3H), 3.42-3.32 (m, 3H), 3.16-2.98 (m, 3H), 2.90 (s, 3H), 2.39-2.26 (m, 1H), 2.08-1.74 (m, 5H), 1.62 (d, J=6.7 Hz, 3H).

Example 180

4-(4-{(1R,3S)-3-[(1R)-1-(4-Fluoro-3-methoxy-phenyl)-ethylamino]-cyclopentyl}-benzoyl)-piperazin-2-one (Compound 1179)

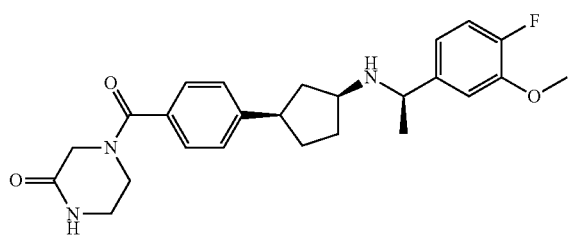 [SMILES: COc1cc([C@@H](C)N[C@H]2CC[C@@H](c3ccc(C(=O)N4CCNC(=O)C4)cc3)C2)ccc1F]

General procedure G was followed using piperazin-2-one as the amine. $^1$H NMR (300 MHz, MeOH) δ 8.45 (s, 1H), 7.78 (d, J=8.3 Hz, 2H), 7.35 (d, J=8.3 Hz, 2H), 7.28 (dd, J=8.0, 2.0 Hz, 1H), 7.19 (dd, J=11.0, 8.3 Hz, 1H), 7.06 (ddd, J=8.3, 4.0, 2.1 Hz, 1H), 4.44 (q, J=6.8 Hz, 1H), 3.93 (s, 3H), 3.62-3.45 (m, 3H), 3.34-3.25 (m, 2H), 3.22-3.06 (m, 1H), 2.94 (s, 2H), 2.50-2.37 (m, 1H), 2.32-1.70 (m, 5H), 1.69 (d, J=6.8 Hz, 3H).

Example 181

(1R/S,3R)—N-[(1R)-1-(4-fluoro-3-methoxy-phenyl)ethyl]-3-[4-(2-morpholinosulfonylethyl)phenyl]cyclopentanamine (mixture of 2 isomers) (Compound 1180)

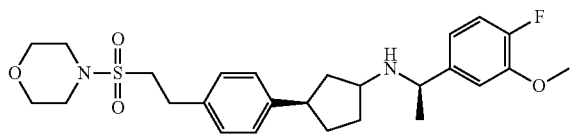 [SMILES: COc1cc([C@@H](C)NC2CC[C@@H](c3ccc(CCS(=O)(=O)N4CCOCC4)cc3)C2)ccc1F]

General procedure B was followed using (3R)-3-{4-[2-(morpholine-4-sulfonyl)-ethyl]-phenyl}-cyclopentanone (preparation 49) as the ketone and (1R)-1-(4-fluoro-3-methoxyphenyl)ethylamine hydrochloride as the amine. $^1$H NMR (300 MHz, DMSO) δ 7.23-7.04 (m, 6H), 6.92-6.83 (m, 1H), 3.82 (s, 3H), 3.80-3.68 (m, 1H), 3.66-3.55 (m, 4H), 3.37-3.26 (m, 2H), 3.22-3.10 (m, 4H), 3.06-2.78 (m, 4H), 2.20-1.13 (m, 6H), 1.23 (d, J=6.6 Hz, 3H).

Example 182

N-[[4-[(1R/S,3R/S)-3-[[(1R)-1-(4-fluoro-3-methoxyphenyl)ethyl]amino]cyclopentyl]-phenyl]methyl]methanesulfonamide (mixture of 4 isomers) (Compound 1181)

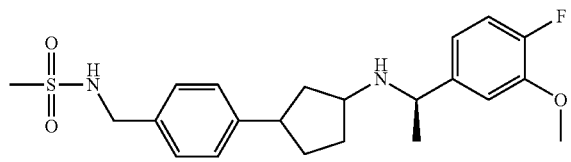

General procedure E was followed using (4-methanesulfonylaminomethyl)-phenylboronic acid as the ketone and (1R)-1-(4-fluoro-3-methoxyphenyl)ethylamine hydrochloride as the amine. LC-MS: RT=5.26, M=420.

Example 183

(1S,3R)—N-[(1R)-1-(4-fluoro-3-methoxy-phenyl)ethyl]-3-[4-(1H-tetrazol-5-yl)phenyl]cyclopentanamine (Compound 1182)

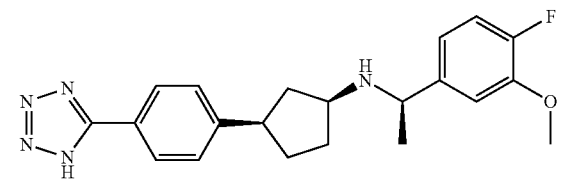 [SMILES: COc1cc([C@@H](C)N[C@H]2CC[C@@H](c3ccc(-c4nnn[nH]4)cc3)C2)ccc1F]

4-[(1R,3S)-3-[[(1R)-1-(4-fluoro-3-methoxy-phenyl)ethyl]amino]cyclopentyl]benzonitrile (5.1 g, 14.4 mmol) in toluene (160 ml) was treated with trimethylsilylazide (9.5 ml, 72 mmol, dropwise addition) followed by SnBu$_2$O (717 mg, 2.88 mmol). The reaction mixture was stirred at 118° C. overnight. The precipitate was filtered off, and the filtrate was evaporated and purified by flash chromatography (gradient of 0-10%, MeOH in DCM containing 2% NEt$_3$). The product thus obtained was precipitated from EtOH, redissolved in DCM and extracted with aqueous HCl (pH 1). The aqueous phase was neutralized to pH 5-6 with NaOH aq. (1M), and the resulting precipitate was filtered off and dried to afford the title compound. $^1$H NMR (300 MHz, DMSO) δ 7.89 (d, J=8.2 Hz, 2H), 7.39 (dd, J=8.3, 1.8 Hz, 1H), 7.33-7.23 (m, 3H), 7.14-7.03 (m, 1H), 4.38 (q, J=6.5 Hz, 1H), 3.86 (s, 3H), 3.45-3.32 (m, 1H), 3.09-2.95 (m, 1H), 2.38-2.25 (m, 1H), 2.10-1.64 (m, 5H), 1.56 (d, J=6.7 Hz, 3H).

Example 184

[4-[(1S,3R/S)-3-[[(1R)-1-(3-ethoxyphenyl)ethyl]amino]cyclopentyl]-phenyl]morpholino-methanone (Compound 1183)

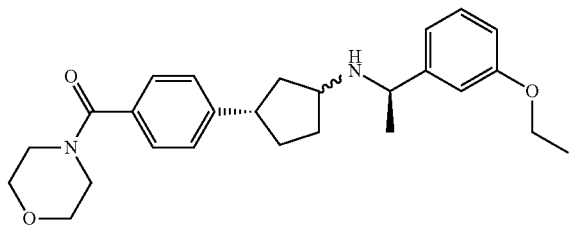 [SMILES: CCOc1cccc([C@@H](C)NC2CC[C@H](c3ccc(C(=O)N4CCOCC4)cc3)C2)c1]

General procedure B was followed using (3S)-3-[4-(Morpholine-4-carbonyl)phenyl]-cyclopentanone (preparation 15) as the ketone and (1R)-1-(3-ethoxyphenyl)-ethanamine hydrochloride as the amine. $^1$H NMR (600 MHz, DMSO) δ 7.33-7.21 (m, 4H), 7.19 (t, J=7.8 Hz, 1H), 6.93-6.86 (m, 2H), 6.74 (dd, J=7.9, 2.3 Hz, 1H), 4.00 (q, J=7.0 Hz, 2H), 3.70 (q, J=6.6 Hz, 1H), 3.57 (br s, 4H), 3.33 (br s, 4H), 3.27-3.20 (m, 1H), 3.03 (t, J=8.3 Hz, 1H), 2.11-2.03 (m, 1H), 1.95-1.88 (m, 1H), 1.78-1.72 (m, 1H), 1.64-1.41 (m, 3H), 1.34-1.28 (m, 3H), 1.23 (d, J=6.6 Hz, 3H).

Example 185

[4-[(1S,3R/S)-3-[[(1R)-1-(3-chlorophenyl)ethyl]amino]cyclopentyl]-phenyl]morpholino-methanone (Compound 1184)

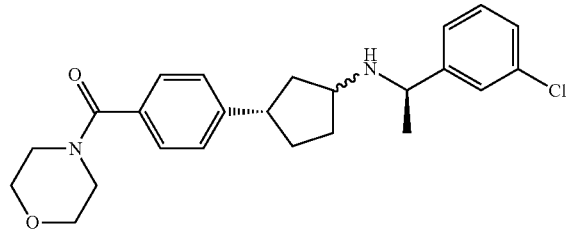 [SMILES: C[C@@H](NC1CC[C@H](c2ccc(C(=O)N3CCOCC3)cc2)C1)c1cccc(Cl)c1]

General procedure B was followed using (3S)-3-[4-(Morpholine-4-carbonyl)phenyl]-cyclopentanone (preparation 15) as the ketone and (R)-1-(3-chlorophenyl)ethanamine as the amine. $^1$H NMR (600 MHz, DMSO) δ 7.44-7.42 (m, 1H), 7.35-7.22 (m, 7H), 3.76 (q, J=6.6 Hz, 1H), 3.57 (br m, 4H), 3.33 (br m, 4H), 3.27-3.19 (m, 1H), 3.02 (m, 1H), 2.07 (m, 1H), 1.93 (m, 1H), 1.77-1.41 (m, 4H), 1.23 (d, J=5.3 Hz, 3H).

Example 186

[4-[(1S,3R/S)-3-[[(1R)-1-(4-fluoro-3-methoxy-phenyl)ethyl]amino]-cyclopentyl]phenyl]-morpholinomethanone (Compound 1185)

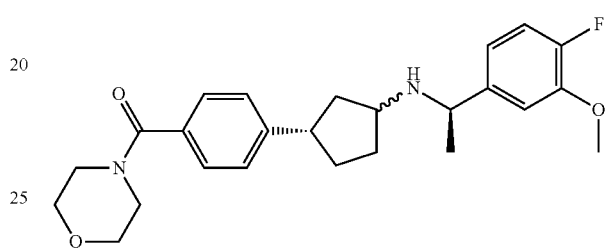

General procedure B was followed using (3S)-3-[4-(Morpholine-4-carbonyl)phenyl]-cyclopentanone (preparation 15) as the ketone and (1R)-1-(4-fluoro-3-methoxyphenyl)ethanamine hydrochloride as the amine. $^1$H NMR (600 MHz, DMSO) δ 7.30-7.27 (m, 2H), 7.23 (d, J=8.2 Hz, 2H), 7.16 (dd, J=8.6, 1.9 Hz, 1H), 7.10 (dd, J=11.5, 8.2 Hz, 1H), 6.89 (ddd, J=8.1, 4.4, 1.9 Hz, 1H), 3.82 (s, 3H), 3.73 (q, J=6.4 Hz, 1H), 3.57 (m, 4H), 3.32 (m, 4H), 3.27-3.19 (m, 1H), 3.06-3.00 (m, 1H), 2.11-1.90 (m, 2H), 1.78-1.72 (m, 1H), 1.65-1.57 (m, 1H), 1.53-1.41 (m, 2H), 1.24 (d, J=6.6 Hz, 3H).

Example 187

N-(3-amino-3-oxo-propyl)-4-[(1S,3R/S)-3-[[(1R)-1-(1,3-benzodioxol-4-yl)ethyl]amino]cyclopentyl]benzamide (Compound 1186)

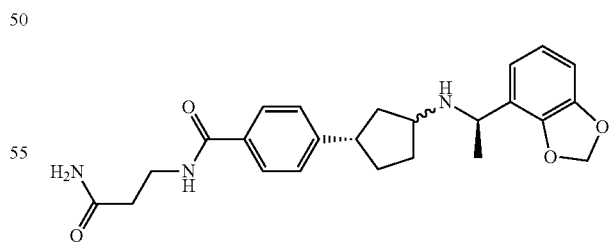

General procedure B was followed using N-(3-amino-3-oxo-propyl)-4-[(1S)-3-oxocyclopentyl]benzamide as the ketone and (1R)-1-(1,3-benzodioxol-4-yl)ethanamine hydrochloride as the amine. $^1$H NMR (600 MHz, DMSO) δ 8.39 (t, 1H), 7.74 (d, J=8.2 Hz, 2H), 7.36-7.31 (m, 3H), 6.92 (d, J=7.8 Hz, 1H), 6.84-6.79 (m, 2H), 6.78-6.75 (m, 1H), 5.97 (s, 2H), 3.91 (q, J=6.7 Hz, 1H), 3.46-3.31 (m, 2H), 3.01-2.93 (m, 2H), 2.33 (t, 2H), 2.24-2.17 (m, 1H), 1.96-1.86 (m, 1H), 1.80-1.59 (m, 2H), 1.54-1.46 (m, 1H), 1.42-1.34 (m, 1H), 1.26 (d, J=6.7 Hz, 3H).

Example 188

4-[(1R,3S)-3-[[(1R)-1-(4-fluoro-3-methoxy-phenyl)ethyl]amino]-cyclopentyl]-N-(2-hydroxyethyl)benzenesulfonamide (Compound 1187)

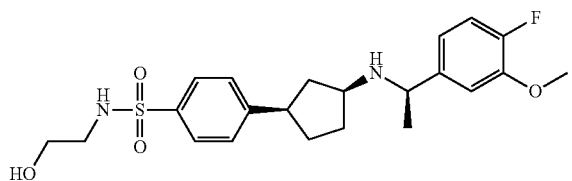 [SMILES: COc1cc([C@@H](C)N[C@H]2CC[C@@H](c3ccc(S(=O)(=O)NCCO)cc3)C2)ccc1F]

([(1S,3R)-3-(4-Bromo-phenyl)-cyclopentyl]-[1-(4-fluoro-3-methoxy-phenyl)-ethyl]-amine (Preparation 50) (117 mg) in THF (3.0 mL) was cooled to −8° C., and isopropylmagnesium chloride (160 mL) were added over 2 min. The mixture was stirred at 0° C. for 15 min, then cooled to −78° C. t-BuLi (370 mL) were added slowly, and stirring was continued at −78° C. for 20 min. Then, $SO_2$ was bubbled into the mixture for 15 s. The cooling bath was removed after 5 min, and the mixture was warmed to r.t. After 60 min, the solvents were removed in vacuo, and the residue was redissolved in DCM (4.0 mL) and treated with N-chlorosuccinimide (46 mg) for 45 min at r.t. Ethanolamine (73 mg) was added, and the mixture was stirred over night. After quenching with sat. $NaHCO_3$, the mixture was extracted with EtOAc. The organics were dried and concentrated in vacuo. The residue was purified by preparative HPLC-MS to afford the title compound. $^1$H NMR (600 MHz, DMSO) δ 7.69 (d, J=8.3 Hz, 2H), 7.59 (s, 1H), 7.44 (d, J=8.3 Hz, 2H), 7.18 (dd, J=8.6, 1.8 Hz, 1H), 7.11 (dd, J=11.5, 8.2 Hz, 1H), 6.89 (ddd, J=8.1, 4.3, 1.9 Hz, 1H), 3.83 (s, 3H), 3.77 (dd, J=13.1, 6.5 Hz, 1H), 3.36 (t, J=6.4 Hz, 2H), 2.95 (m, 2H), 2.75 (s, 2H), 2.14-2.07 (m, 1H), 1.98-1.89 (m, 1H), 1.84-1.58 (m, 3H), 1.41-1.33 (m, 1H), 1.25 (d, J=6.6 Hz, 3H).

Example 189

N-(3-amino-3-oxo-propyl)-4-[(1S,3R/S)-3-[[(1R)-1-(3-ethoxyphenyl)ethyl]-amino]cyclopentyl]benzamide (Compound 1188)

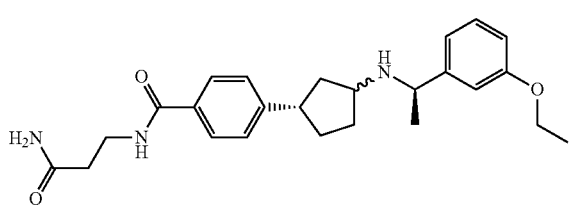 [SMILES: CCOc1cccc([C@@H](C)NC2CC[C@H](c3ccc(C(=O)NCCC(N)=O)cc3)C2)c1]

General procedure B was followed using N-(3-amino-3-oxo-propyl)-4-[(1S)-3-oxocyclopentyl]benzamide as the ketone and (1R)-1-(3-ethoxyphenyl)-ethanamine hydrochloride as the amine. $^1$H NMR (600 MHz, DMSO) δ 8.37 (t, J=5.6 Hz, 1H), 7.70 (d, J=8.3 Hz, 2H), 7.33 (br s, 1H), 7.23 (d, J=8.3 Hz, 2H), 7.19 (t, J=7.8 Hz, 1H), 6.92 (s, 1H), 6.89 (d, J=7.6 Hz, 1H), 6.81 (br s, 1H), 6.74 (d, J=8.0 Hz, 1H), 4.00 (q, J=7.0 Hz, 2H), 3.75-3.66 (m, 1H), 3.28-3.20 (m, 1H), 3.08-3.00 (m, 1H), 2.58-2.52 (m, 2H), 2.32 (t, J=7.3 Hz, 2H), 2.12-1.41 (m, 7H), 1.31 (t, J=7.0 Hz, 3H), 1.23 (d, J=6.6 Hz, 3H).

Example 190

N-(3-amino-3-oxo-propyl)-4-[(1S,3R/S)-3-[[(1R)-1-(4-fluoro-3-methoxy-phenyl)ethyl]amino]cyclopentyl]benzamide (Compound 1189)

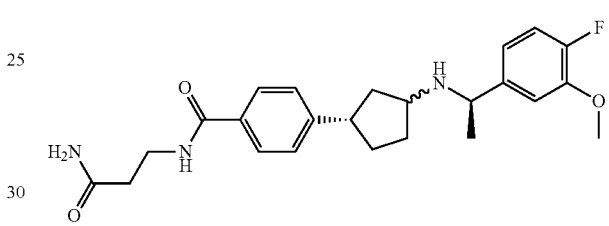

General procedure B was followed using N-(3-amino-3-oxo-propyl)-4-[(1S)-3-oxocyclopentyl]benzamide as the ketone and (1R)-1-(4-fluoro-3-methoxyphenyl)-ethylamine hydrochloride as the amine. $^1$H NMR (600 MHz, DMSO) δ 8.39 (t, J=5.6 Hz, 1H), 7.74 (d, J=8.3 Hz, 2H), 7.37-7.31 (m, 3H), 7.16 (dd, J=8.6, 1.8 Hz, 1H), 7.10 (dd, J=11.5, 8.2 Hz, 1H), 6.91-6.87 (m, 1H), 6.82 (br s, 1H), 3.83 (s, 3H), 3.77-3.71 (m, 1H), 3.46-3.37 (m, 2H), 2.99-2.87 (m, 2H), 2.34 (t, J=7.3 Hz, 2H), 2.26-2.19 (m, 1H), 1.96-1.85 (m, 1H), 1.78-1.58 (m, 2H), 1.53-1.34 (m, 2H), 1.23 (d, J=6.6 Hz, 3H).

Example 191

N-{2-[Bis-(2-hydroxy-ethyl)-amino]-ethyl}-4-{(1R,3S)-3-[(1R)-1-(4-fluoro-3-methoxy-phenyl)-ethylamino]-cyclopentyl}-benzamide (compound 1190)

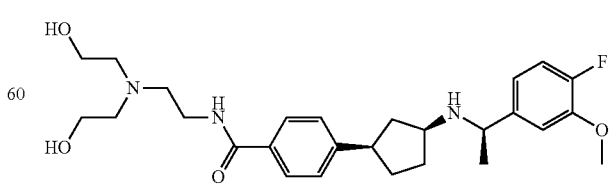

General procedure G is followed using N,N-bis(2-hydroxyethyl)ethylenediamine as the amine.

Example 192

(N)-[(1S,3R)-3-[4-(4-hydroxypiperidine-1-carbonyl)
phenyl]cyclopentyl]-(1R)-1-(4-fluoro-3-methoxyphenyl)ethylamine (compound 1191)

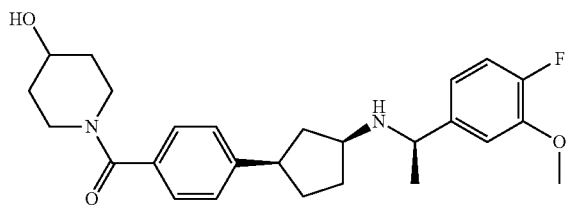 [SMILES: COc1cc([C@@H](C)N[C@H]2CC[C@@H](c3ccc(C(=O)N4CCC(O)CC4)cc3)C2)ccc1F]

General procedure B is followed using (3R)-3-[4-(4-hydroxypiperidine-1-carbonyl)phenyl]-cyclopentanone as the ketone and (1R)-1-(4-fluoro-3-methoxyphenyl)ethylamine hydrochloride as the amine.

Example 193

(N)-[(1S,3R)-3-[4-(4-hydroxypiperidine-1-carbonyl)
phenyl]cyclopentyl]-(1R)-1-(3-ethoxyphenyl)-ethanamine (compound 1192)

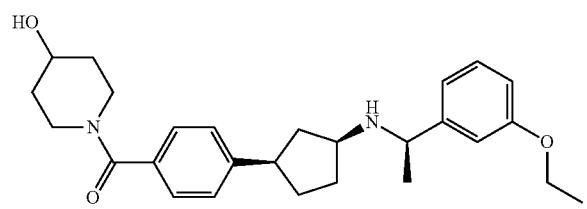 [SMILES: CCOc1cccc([C@@H](C)N[C@H]2CC[C@@H](c3ccc(C(=O)N4CCC(O)CC4)cc3)C2)c1]

General procedure B is followed using (3R)-3-[4-(4-hydroxypiperidine-1-carbonyl)phenyl]-cyclopentanone as the ketone and (1R)-1-(3-ethoxyphenyl)-ethanamine hydrochloride as the amine.

Example 194

(N)-[(1S,3R)-3-[4-(4-hydroxypiperidine-1-carbonyl)
phenyl]cyclopentyl]-(1R)-1-(3-chlorophenyl)ethanamine (compound 1193)

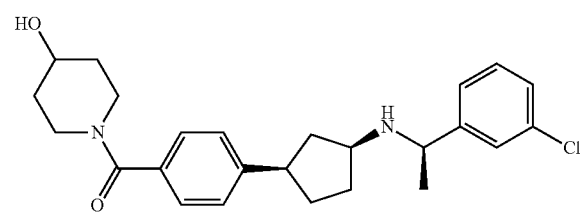 [SMILES: C[C@@H](N[C@H]1CC[C@@H](c2ccc(C(=O)N3CCC(O)CC3)cc2)C1)c1cccc(Cl)c1]

General procedure B is followed using (3R)-3-[4-(4-hydroxypiperidine-1-carbonyl)phenyl]-cyclopentanone as the ketone and (1R)-1-(3-chlorophenyl)ethanamine as the amine.

Example 195

(N)-[(1S,3R)-3-[4-(4-hydroxypiperidine-1-carbonyl)
phenyl]cyclopentyl]-(1R)-1-(1,3-benzodioxol-4-yl)
ethanamine (compound 1194)

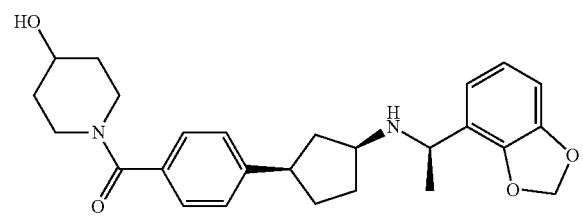 [SMILES: C[C@@H](N[C@H]1CC[C@@H](c2ccc(C(=O)N3CCC(O)CC3)cc2)C1)c1cccc2c1OCO2]

General procedure B is followed using (3R)-3-[4-(4-hydroxypiperidine-1-carbonyl)phenyl]-cyclopentanone as the ketone and (1R)-1-(1,3-benzodioxol-4-yl)ethanamine hydrochloride as the amine.

Example 196

(N)-[(1S,3R)-3-[4-(4-hydroxypiperidine-1-carbonyl)
phenyl]cyclopentyl]-(1R)-1-(3-fluoro-5-methoxyphenyl)-ethanamine (compound 1195)

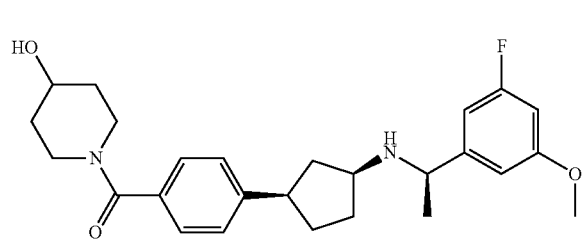 [SMILES: COc1cc(F)cc([C@@H](C)N[C@H]2CC[C@@H](c3ccc(C(=O)N4CCC(O)CC4)cc3)C2)c1]

General procedure B is followed using (3R)-3-[4-(4-hydroxypiperidine-1-carbonyl)phenyl]-cyclopentanone as the ketone and (1R)-1-(3-fluoro-5-methoxy-phenyl)-ethanamine as the amine.

Example 197

(N)-[(1S,3R)-3-[4-(4-hydroxypiperidine-1-carbonyl)
phenyl]cyclopentyl]-(1R)-1-(2,3-Dihydro-benzo[1,4]
dioxin-5-yl)-ethylamine (compound 1196)

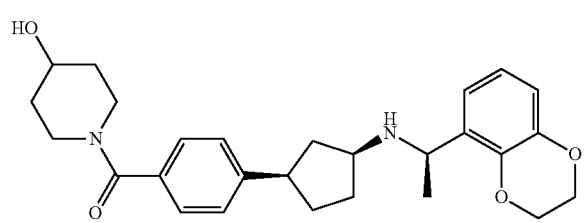 [SMILES: C[C@@H](N[C@H]1CC[C@@H](c2ccc(C(=O)N3CCC(O)CC3)cc2)C1)c1cccc2c1OCCO2]

General procedure B is followed using (3R)-3-[4-(4-hydroxypiperidine-1-carbonyl)phenyl]-cyclopentanone as the ketone and (1R)-1-(2,3-Dihydro-benzo[1,4]dioxin-5-yl)-ethylamine hydrochloride as the amine.

Example 198

(N)-[(1S,3R)-3-[4-[(3S)-3-hydroxypyrrolidin-1-yl-carbonyl]phenyl]-cyclopentyl]-(1R)-1-(4-fluoro-3-methoxyphenyl)ethylamine (compound 1197)

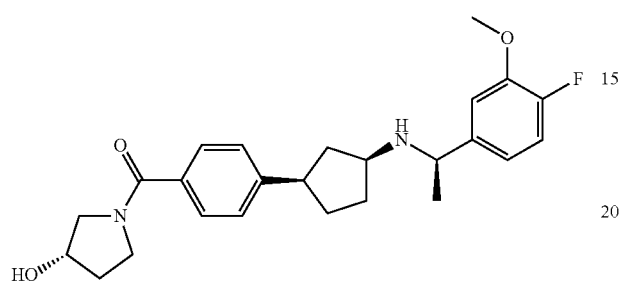

General procedure B is followed using (3R)-3-[4-[(3S)-3-hydroxypyrrolidine-1-carbonyl]phenyl]cyclopentanone as the ketone and (1R)-1-(4-fluoro-3-methoxyphenyl)ethylamine hydrochloride as the amine.

Example 199

(N)-[(1S,3R)-3-[4-[(3S)-3-hydroxypyrrolidin-1-yl-carbonyl]phenyl]-cyclopentyl]-(1R)-1-(3-ethoxyphenyl)-ethanamine (compound 1198)

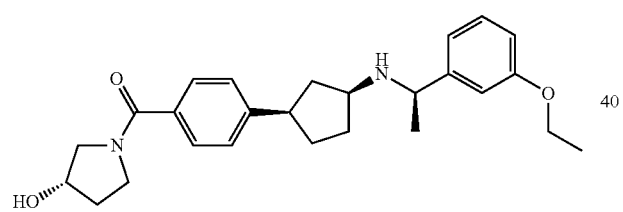

General procedure B is followed using (3R)-3-[4-[(3S)-3-hydroxypyrrolidine-1-carbonyl]phenyl]cyclopentanone as the ketone and (1R)-1-(3-ethoxyphenyl)-ethanamine hydrochloride as the amine.

Example 200

(N)-[(1S,3R)-3-[4-[(3S)-3-hydroxypyrrolidin-1-yl-carbonyl]phenyl]-cyclopentyl]-(1R)-1-(3-chlorophenyl)ethanamine (compound 1199)

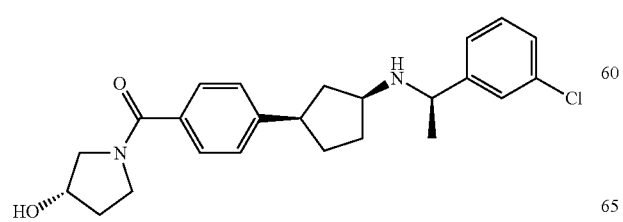

General procedure B is followed using (3R)-3-[4-[(3S)-3-hydroxypyrrolidine-1-carbonyl]phenyl]cyclopentanone as the ketone and (1R)-1-(3-chlorophenyl)ethanamine as the amine.

Example 201

(N)-[(1S,3R)-3-[4-[(3S)-3-hydroxypyrrolidin-1-yl-carbonyl]phenyl]-cyclopentyl]-(1R)-1-(1,3-benzo-dioxol-4-yl)ethanamine (compound 1200)

General procedure B is followed using (3R)-3-[4-[(3S)-3-hydroxypyrrolidine-1-carbonyl]phenyl]cyclopentanone as the ketone and (1R)-1-(1,3-benzodioxol-4-yl)ethanamine hydrochloride as the amine.

Example 202

(N)-[(1S,3R)-3-[4-[(3S)-3-hydroxypyrrolidin-1-yl-carbonyl]phenyl]-cyclopentyl]-(1R)-1-(3-fluoro-5-methoxy-phenyl)-ethanamine (compound 1201)

General procedure B is followed using (3R)-3-[4-[(3S)-3-hydroxypyrrolidine-1-carbonyl]phenyl]cyclopentanone as the ketone and (1R)-1-(3-fluoro-5-methoxy-phenyl)-ethanamine as the amine.

Example 203

(N)-[(1S,3R)-3-[4-[(3S)-3-hydroxypyrrolidin-1-yl-carbonyl]phenyl]-cyclopentyl]-(1R)-1-(2,3-Dihydro-benzo[1,4]dioxin-5-yl)-ethylamine (compound 1202)

General procedure B is followed using (3R)-3-[4-[(3S)-3-hydroxypyrrolidine-1-carbonyl]phenyl]cyclopentanone as

Example 204

(N)-[(1S,3R)-3-[4-(2-(aminosulfonyl)ethylaminocarbonyl)phenyl]-cyclopentyl]-(1R)-1-(4-fluoro-3-methoxyphenyl)ethylamine (compound 1203)

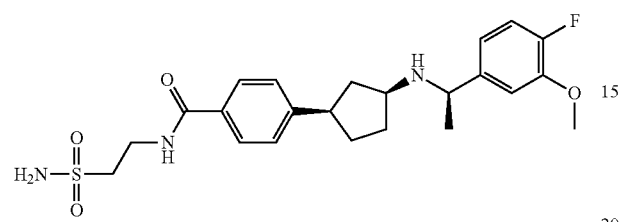

General procedure B is followed using 4-[(1R)-3-oxocyclopentyl]-N-(2-sulfamoylethyl)-benzamide as the ketone and (1R)-1-(4-fluoro-3-methoxyphenyl)ethylamine hydrochloride as the amine.

Example 205

(N)-[(1S,3R)-3-[4-(2-(aminosulfonyl)ethylaminocarbonyl)phenyl]-cyclopentyl]-(1R)-1-(3-ethoxyphenyl)-ethanamine (compound 1204)

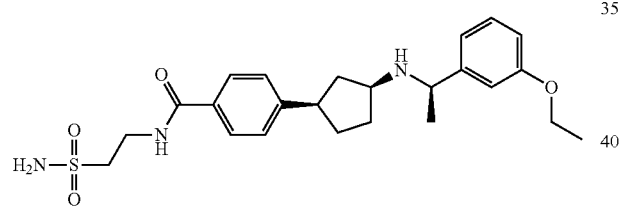

General procedure B is followed using 4-[(1R)-3-oxocyclopentyl]-N-(2-sulfamoylethyl)-benzamide as the ketone and (1R)-1-(3-ethoxyphenyl)-ethanamine hydrochloride as the amine.

Example 206

(N)-[(1S,3R)-3-[4-(2-(aminosulfonyl)ethylaminocarbonyl)phenyl]-cyclopentyl]-(1R)-1-(3-chlorophenyl)ethanamine (compound 1205)

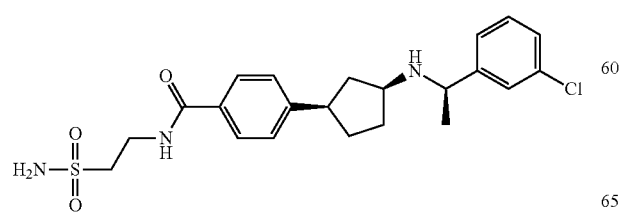

General procedure B is followed using 4-[(1R)-3-oxocyclopentyl]-N-(2-sulfamoylethyl)-benzamide as the ketone and (1R)-1-(3-chlorophenyl)ethanamine as the amine.

Example 207

(N)-[(1S,3R)-3-[4-(2-(aminosulfonyl)ethylaminocarbonyl)phenyl]-cyclopentyl]-(1R)-1-(1,3-benzodioxol-4-yl)ethanamine (compound 1206)

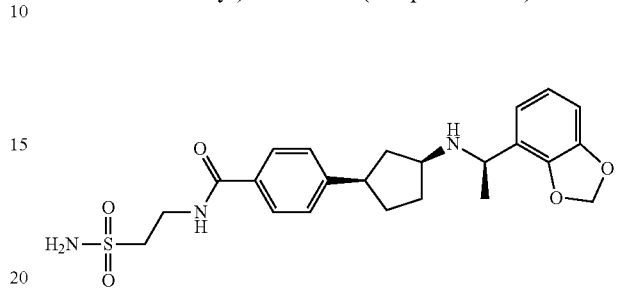

General procedure B is followed using 4-[(1R)-3-oxocyclopentyl]-N-(2-sulfamoylethyl)-benzamide as the ketone and (1R)-1-(1,3-benzodioxol-4-yl)ethanamine hydrochloride as the amine.

Example 208

(N)-[(1S,3R)-3-[4-(2-(aminosulfonyl)ethylaminocarbonyl)phenyl]-cyclopentyl]-(1R)-1-(3-fluoro-5-methoxy-phenyl)-ethanamine (compound 1207)

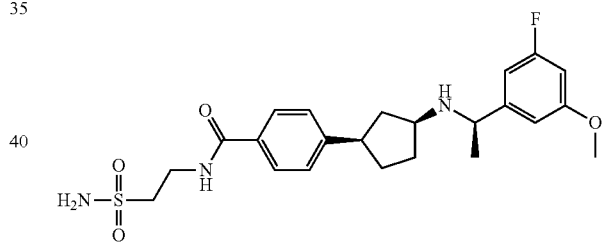

General procedure B is followed using 4-[(1R)-3-oxocyclopentyl]-N-(2-sulfamoylethyl)-benzamide as the ketone and (1R)-1-(3-fluoro-5-methoxy-phenyl)-ethanamine as the amine.

Example 209

(N)-[(1S,3R)-3-[4-(2-(aminosulfonyl)ethylaminocarbonyl)phenyl]-cyclopentyl]-(1R)-1-(2,3-Dihydro-benzo[1,4]dioxin-5-yl)-ethylamine (compound 1208)

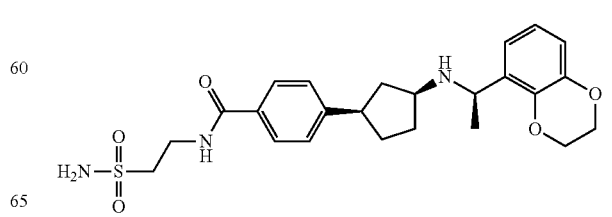

General procedure B is followed using 4-[(1R)-3-oxocyclopentyl]-N-(2-sulfamoylethyl)-benzamide as the ketone and (1R)-1-(2,3-Dihydro-benzo[1,4]dioxin-5-yl)-ethylamine hydrochloride as the amine.

Example 210

(N)-[(1S,3R)-3-[4-(3-oxo-piperazinylcarbonyl)phenyl]cyclopentyl]-(1R)-1-(3-fluoro-5-methoxy-phenyl)-ethanamine (compound 1209)

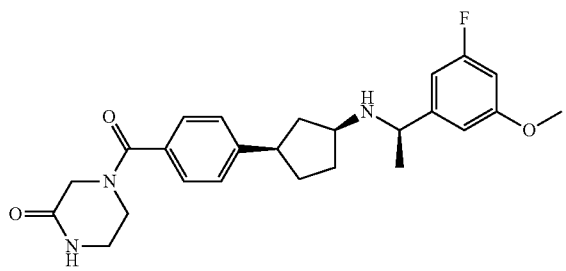 [SMILES: COc1cc(F)cc([C@@H](C)N[C@H]2CC[C@@H](c3ccc(C(=O)N4CCNC(=O)C4)cc3)C2)c1]

General procedure B is followed using 4-[4-[(1R)-3-oxocyclopentyl]benzoyl]piperazin-2-one as the ketone and (1R)-1-(3-fluoro-5-methoxy-phenyl)-ethanamine as the amine.

Example 211

(N)-[(1S,3R)-3-[4-(3-oxo-piperazinylcarbonyl)phenyl]cyclopentyl]-(1R)-1-(3-ethoxyphenyl)-ethanamine (compound 1210)

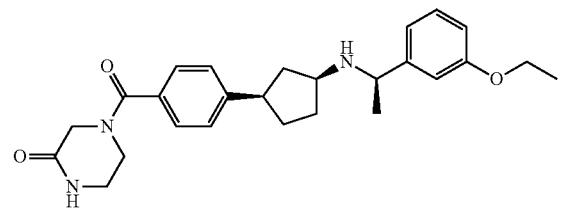 [SMILES: CCOc1cccc([C@@H](C)N[C@H]2CC[C@@H](c3ccc(C(=O)N4CCNC(=O)C4)cc3)C2)c1]

General procedure B is followed using 4-[4-[(1R)-3-oxocyclopentyl]benzoyl]piperazin-2-one as the ketone and (1R)-1-(3-ethoxyphenyl)-ethanamine hydrochloride as the amine.

Example 212

(N)-[(1S,3R)-3-[4-(3-oxo-piperazinylcarbonyl)phenyl]cyclopentyl]-(1R)-1-(3-chlorophenyl)ethanamine (compound 1211)

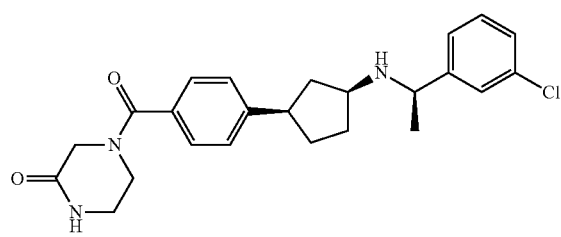 [SMILES: C[C@@H](N[C@H]1CC[C@@H](c2ccc(C(=O)N3CCNC(=O)C3)cc2)C1)c1cccc(Cl)c1]

General procedure B is followed using 4-[4-[(1R)-3-oxocyclopentyl]benzoyl]piperazin-2-one as the ketone and (1R)-1-(3-chlorophenyl)ethanamine as the amine.

Example 213

(N)-[(1S,3R)-3-[4-(3-oxo-piperazinylcarbonyl)phenyl]cyclopentyl]-(1R)-1-(1,3-benzodioxol-4-yl)ethanamine (compound 1212)

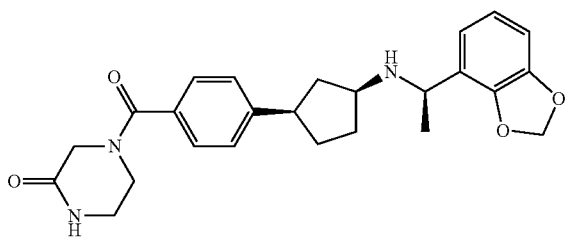 [SMILES: C[C@@H](N[C@H]1CC[C@@H](c2ccc(C(=O)N3CCNC(=O)C3)cc2)C1)c1cccc2c1OCO2]

General procedure B is followed using 4-[4-[(1R)-3-oxocyclopentyl]benzoyl]piperazin-2-one as the ketone and (1R)-1-(1,3-benzodioxol-4-yl)ethanamine hydrochloride as the amine.

Example 214

(N)-[(1S,3R)-3-[4-(3-oxo-piperazinylcarbonyl)phenyl]cyclopentyl]-(1R)-1-(2,3-Dihydro-benzo[1,4]dioxin-5-yl)-ethylamine (compound 1213)

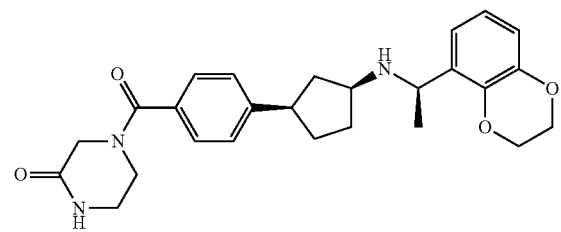 [SMILES: C[C@@H](N[C@H]1CC[C@@H](c2ccc(C(=O)N3CCNC(=O)C3)cc2)C1)c1cccc2c1OCCO2]

General procedure B is followed using 4-[4-[(1R)-3-oxocyclopentyl]benzoyl]piperazin-2-one as the ketone and (1R)-1-(2,3-Dihydro-benzo[1,4]dioxin-5-yl)-ethylamine hydrochloride as the amine.

Example 215

(N)-[(1S,3R)-3-[4-(aminocarbonylmethylaminocarbonyl)phenyl]-cyclopentyl]-(1R)-1-(4-fluoro-3-methoxyphenyl)ethylamine (compound 1214)

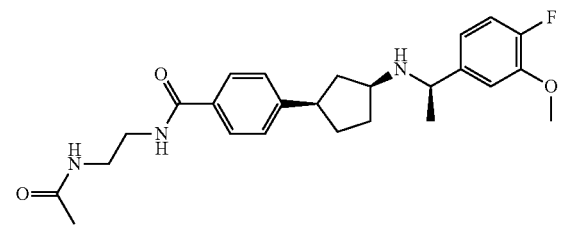 [SMILES: COc1cc([C@@H](C)N[C@H]2CC[C@@H](c3ccc(C(=O)NCCNC(C)=O)cc3)C2)ccc1F]

General procedure B is followed using N-(2-acetamidoethyl)-4-[(1R)-3-oxocyclopentyl]-benzamide as the ketone and (1R)-1-(4-fluoro-3-methoxyphenyl)ethylamine hydrochloride as the amine.

Example 216

(N)-[(1S,3R)-3-[4-(aminocarbonylmethylaminocarbonyl)phenyl]-cyclopentyl]-(1R)-1-(3-ethoxyphenyl)-ethanamine (compound 1215)

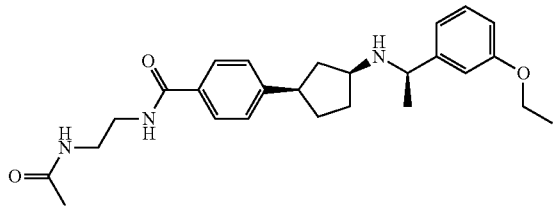 [SMILES: CCOc1cccc([C@@H](C)N[C@H]2CC[C@@H](c3ccc(C(=O)NCCNC(C)=O)cc3)C2)c1]

General procedure B is followed using N-(2-acetamidoethyl)-4-[(1R)-3-oxocyclopentyl]-benzamide as the ketone and (1R)-1-(3-ethoxyphenyl)-ethanamine hydrochloride as the amine.

Example 217

(N)-[(1S,3R)-3-[4-(aminocarbonylmethylaminocarbonyl)phenyl]-cyclopentyl]-(1R)-1-(3-chlorophenyl)ethanamine (compound 1216)

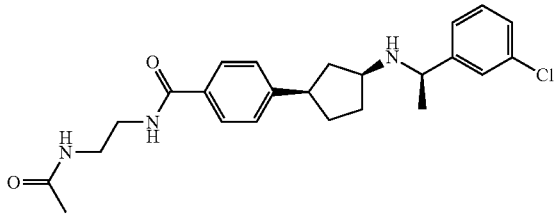 [SMILES: CC(=O)NCCNC(=O)c1ccc([C@@H]2CC[C@H](N[C@H](C)c3cccc(Cl)c3)C2)cc1]

General procedure B is followed using N-(2-acetamidoethyl)-4-[(1R)-3-oxocyclopentyl]-benzamide as the ketone and (1R)-1-(3-chlorophenyl)ethanamine as the amine.

Example 218

(N)-[(1S,3R)-3-[4-(aminocarbonylmethylaminocarbonyl)phenyl]-cyclopentyl]-(1R)-1-(1,3-benzodioxol-4-yl)ethanamine (compound 1217)

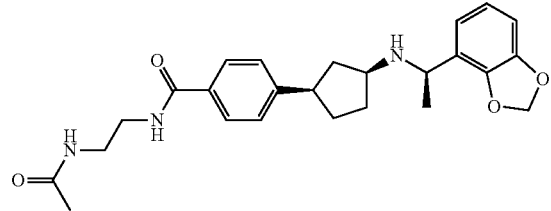 [SMILES: CC(=O)NCCNC(=O)c1ccc([C@@H]2CC[C@H](N[C@H](C)c3cccc4c3OCO4)C2)cc1]

General procedure B is followed using N-(2-acetamidoethyl)-4-[(1R)-3-oxocyclopentyl]-benzamide as the ketone and (1R)-1-(1,3-benzodioxol-4-yl)ethanamine hydrochloride as the amine.

Example 219

(N)-[(1S,3R)-3-[4-(aminocarbonylmethylaminocarbonyl)phenyl]-cyclopentyl]-(1R)-1-(3-fluoro-5-methoxy-phenyl)-ethanamine (compound 1218)

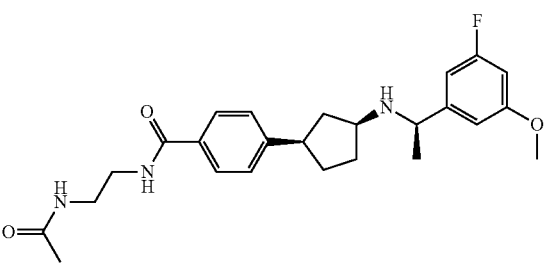 [SMILES: COc1cc(F)cc([C@@H](C)N[C@H]2CC[C@@H](c3ccc(C(=O)NCCNC(C)=O)cc3)C2)c1]

General procedure B is followed using N-(2-acetamidoethyl)-4-[(1R)-3-oxocyclopentyl]-benzamide as the ketone and (1R)-1-(3-fluoro-5-methoxy-phenyl)-ethanamine as the amine.

Example 220

(N)-[(1S,3R)-3-[4-(aminocarbonylmethylaminocarbonyl)phenyl]-cyclopentyl]-(1R)-1-(2,3-Dihydro-benzo[1,4]dioxin-5-yl)-ethylamine (compound 1219)

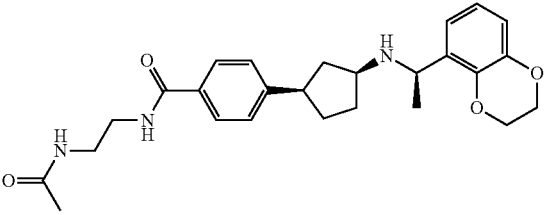 [SMILES: CC(=O)NCCNC(=O)c1ccc([C@@H]2CC[C@H](N[C@H](C)c3cccc4c3OCCO4)C2)cc1]

General procedure B is followed using N-(2-acetamidoethyl)-4-[(1R)-3-oxocyclopentyl]-benzamide as the ketone and (1R)-1-(2,3-Dihydro-benzo[1,4]dioxin-5-yl)-ethylamine hydrochloride as the amine.

Example 221

(N)-[(1S,3R)-3-[4-(2-(methanesulfonylamino)-ethylaminocarbonyl)phenyl]-cyclopentyl]-(1R)-1-(3-ethoxyphenyl)-ethanamine

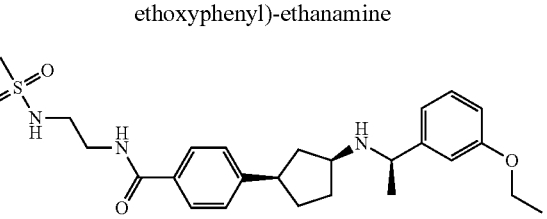

General procedure B is followed using N-[2-(methanesulfonamido)ethyl]-4-[(1R)-3-oxocyclopentyl]benzamide as the ketone and (1R)-1-(3-ethoxyphenyl)-ethanamine hydrochloride as the amine.

Example 222

(N)-[(1S,3R)-3-[4-(2-(methanesulfonylamino)-ethylaminocarbonyl)phenyl]-cyclopentyl]-(1R)-1-(3-chlorophenyl)ethanamine (compound 1221)

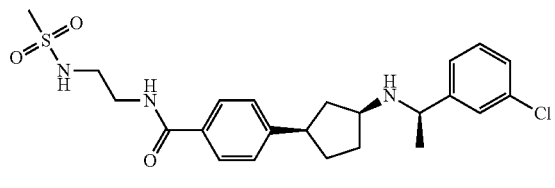 [SMILES: C[C@@H](N[C@H]1CC[C@@H](c2ccc(C(=O)NCCNS(C)(=O)=O)cc2)C1)c1cccc(Cl)c1]

General procedure B is followed using N-[2-(methanesulfonamido)ethyl]-4-[(1R)-3-oxocyclopentyl]benzamide as the ketone and (1R)-1-(3-chlorophenyl)ethanamine as the amine.

Example 223

(N)-[(1S,3R)-3-[4-(2-(methanesulfonylamino)-ethylaminocarbonyl)phenyl]-cyclopentyl]-(1R)-1-(1,3-benzodioxol-4-yl)ethanamine (compound 1222)

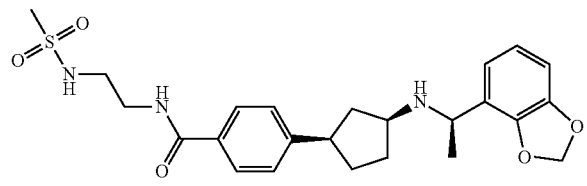 [SMILES: C[C@@H](N[C@H]1CC[C@@H](c2ccc(C(=O)NCCNS(C)(=O)=O)cc2)C1)c1cccc2c1OCO2]

General procedure B is followed using N-[2-(methanesulfonamido)ethyl]-4-[(1R)-3-oxocyclopentyl]benzamide as the ketone and (1R)-1-(1,3-benzodioxol-4-yl)ethanamine hydrochloride as the amine.

Example 224

(N)-[(1S,3R)-3-[4-(2-(methanesulfonylamino)-ethylaminocarbonyl)phenyl]-cyclopentyl]-(1R)-1-(3-fluoro-5-methoxy-phenyl)-ethanamine (compound 1223)

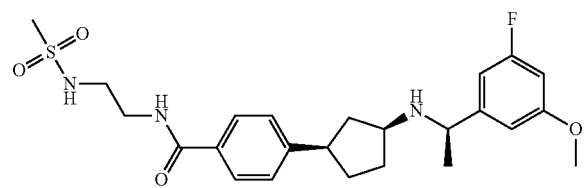 [SMILES: COc1cc(F)cc([C@@H](C)N[C@H]2CC[C@@H](c3ccc(C(=O)NCCNS(C)(=O)=O)cc3)C2)c1]

General procedure B is followed using N-[2-(methanesulfonamido)ethyl]-4-[(1R)-3-oxocyclopentyl]benzamide as the ketone and (1R)-1-(3-fluoro-5-methoxy-phenyl)-ethanamine as the amine.

Example 225

(N)-[(1S,3R)-3-[4-(2-(methanesulfonylamino)-ethylaminocarbonyl)phenyl]-cyclopentyl]-(1R)-1-(2,3-Dihydro-benzo[1,4]dioxin-5-yl)-ethylamine (compound 1224)

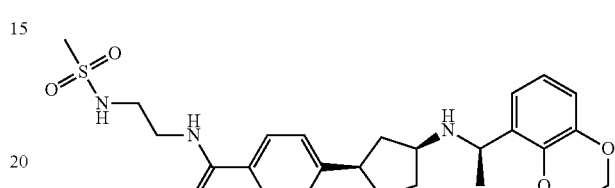

General procedure B is followed using N-[2-(methanesulfonamido)ethyl]-4-[(1R)-3-oxocyclopentyl]benzamide as the ketone and (1R)-1-(2,3-Dihydro-benzo[1,4]dioxin-5-yl)-ethylamine hydrochloride as the amine.

Example 226

(N)-[(1S,3R)-3-[4-[piperidin-4-ylaminocarbonyl]phenyl]cyclopentyl]-(1R)-1-(4-fluoro-3-methoxyphenyl)ethylamine (compound 1225)

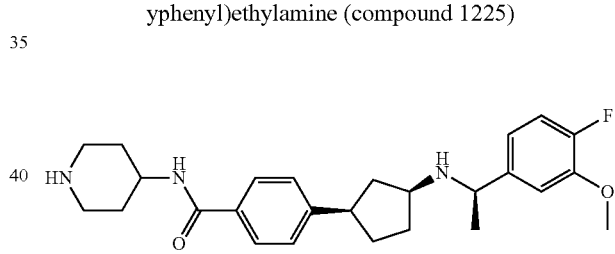

General procedure C is followed using tert-butyl 4-[[4-[(1R)-3-oxocyclopentyl]benzoyl]-amino]piperidine-1-carboxylate as the ketone and (1R)-1-(4-fluoro-3-methoxyphenyl)ethylamine hydrochloride as the amine.

Example 227

(N)-[(1S,3R)-3-[4-[piperidin-4-ylaminocarbonyl]phenyl]cyclopentyl]-(1R)-1-(3-ethoxyphenyl)-ethanamine (compound 1226)

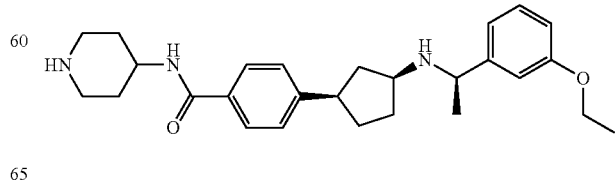

General procedure C is followed using tert-butyl 4-[[4-[(1R)-3-oxocyclopentyl]benzoyl]-amino]piperidine-1-carboxylate as the ketone and (1R)-1-(3-ethoxyphenyl)-ethanamine hydrochloride as the amine.

Example 228

(N)-[(1S,3R)-3-[4-[piperidin-4-ylaminocarbonyl]phenyl]cyclopentyl]-(1R)-1-(3-chlorophenyl)ethanamine (compound 1227)

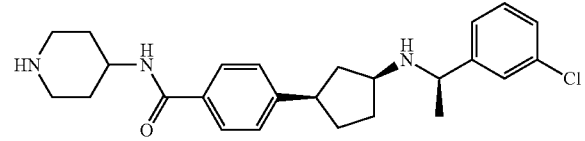 [SMILES: C[C@@H](N[C@H]1CC[C@@H](c2ccc(C(=O)NC3CCNCC3)cc2)C1)c1cccc(Cl)c1]

General procedure C is followed using tert-butyl 4-[[4-[(1R)-3-oxocyclopentyl]benzoyl]-amino]piperidine-1-carboxylate as the ketone and (1R)-1-(3-chlorophenyl)ethanamine as the amine.

Example 229

(N)-[(1S,3R)-3-[4-[piperidin-4-ylaminocarbonyl]phenyl]cyclopentyl]-(1R)-1-(1,3-benzodioxol-4-yl)ethanamine (compound 1228)

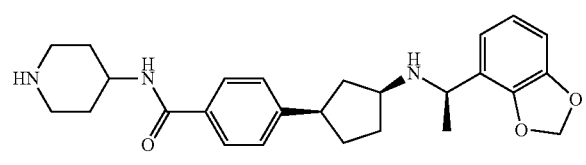 [SMILES: C[C@@H](N[C@H]1CC[C@@H](c2ccc(C(=O)NC3CCNCC3)cc2)C1)c1cccc2c1OCO2]

General procedure C is followed using tert-butyl 4-[[4-[(1R)-3-oxocyclopentyl]benzoyl]-amino]piperidine-1-carboxylate as the ketone and (1R)-1-(1,3-benzodioxol-4-yl)ethanamine hydrochloride as the amine.

Example 230

(N)-[(1S,3R)-3-[4-[piperidin-4-ylaminocarbonyl]phenyl]cyclopentyl]-(1R)-1-(3-fluoro-5-methoxyphenyl)-ethanamine (compound 1229)

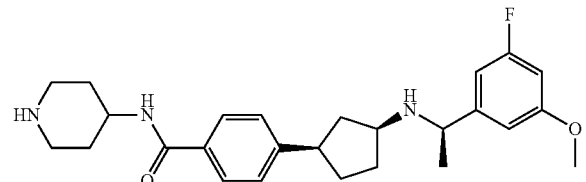

General procedure C is followed using tert-butyl 4-[[4-[(1R)-3-oxocyclopentyl]benzoyl]-amino]piperidine-1-carboxylate as the ketone and (1R)-1-(3-fluoro-5-methoxy-phenyl)-ethanamine as the amine.

Example 231

(N)-[(1S,3R)-3-[4-[piperidin-4-ylaminocarbonyl]phenyl]cyclopentyl]-(1R)-1-(2,3-Dihydro-benzo[1,4]dioxin-5-yl)-ethylamine (compound 1230)

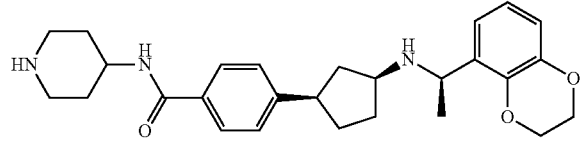 [SMILES: C[C@@H](N[C@H]1CC[C@@H](c2ccc(C(=O)NC3CCNCC3)cc2)C1)c1cccc2c1OCCO2]

General procedure C is followed using tert-butyl 4-[[4-[(1R)-3-oxocyclopentyl]benzoyl]-amino]piperidine-1-carboxylate as the ketone and (1R)-1-(2,3-Dihydro-benzo[1,4]dioxin-5-yl)-ethylamine hydrochloride as the amine.

Example 232

4-{(1R,3S)-3-[(1R)-1-(4-Fluoro-3-methoxy-phenyl)-ethylamino]-cyclopentyl}-N-[2-(2-hydroxy-ethylamino)-ethyl]-benzamide (compound 1231)

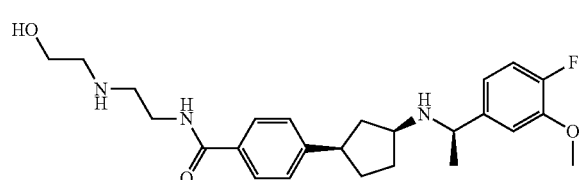

General procedure G is followed using N-(3-hydroxyethyl)ethylenediamine as the amine.

Example 233

(4-{(1R,3S)-3-[(1R)-1-(4-Fluoro-3-methoxy-phenyl)-ethylamino]-cyclopentyl}-phenyl)-[4-(2-hydroxy-ethyl)-piperazin-1-yl]-methanone (compound 1232)

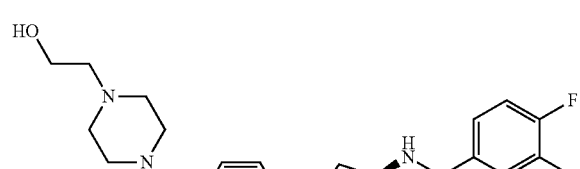

General procedure G is followed using N-hydroxyethylpiperazine as the amine.

Example 234

(4-{(1R,3S)-3-[(1R)-1-(4-Fluoro-3-methoxy-phenyl)-ethylamino]-cyclopentyl}-phenyl)-piperazin-1-yl-methanone (compound 1233)

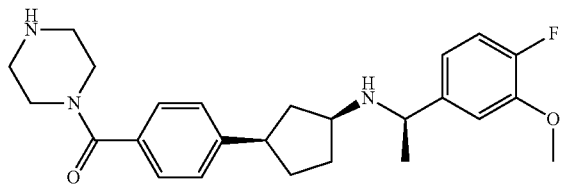 [SMILES: COc1cc([C@@H](C)N[C@H]2CC[C@@H](c3ccc(C(=O)N4CCNCC4)cc3)C2)ccc1F]

General procedure G is followed using piperazine as the amine.

Example 235

(4-{(1R,3S)-3-[(1R)-1-(4-Fluoro-3-methoxy-phenyl)-ethylamino]-cyclopentyl}-phenyl)-(4-methanesulfonyl-piperazin-1-yl)-methanone (compound 1234)

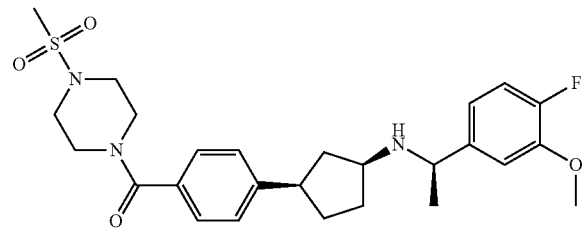 [SMILES: COc1cc([C@@H](C)N[C@H]2CC[C@@H](c3ccc(C(=O)N4CCN(S(C)(=O)=O)CC4)cc3)C2)ccc1F]

General procedure G is followed using 1-(methylsulfonyl) piperazine hydrochloride as the amine.

Example 236

N-(2-Amino-ethyl)-4-{(1R,3S)-3-[1-(4-fluoro-3-methoxy-phenyl)-ethylamino]-cyclopentyl}-benzamide (compound 1235)

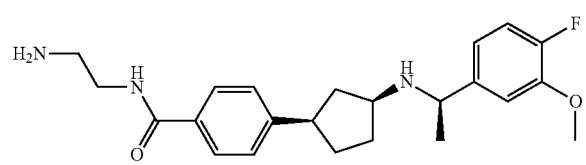 [SMILES: COc1cc([C@@H](C)N[C@H]2CC[C@@H](c3ccc(C(=O)NCCN)cc3)C2)ccc1F]

General procedure G is followed using ethylenediamine as the amine.

Example 237

4-{(1R,3S)-3-[(1R)-1-(4-Fluoro-3-methoxy-phenyl)-ethylamino]-cyclopentyl}-N-[1-(2-hydroxy-ethyl)-piperidin-4-yl]-benzamide (compound 1236)

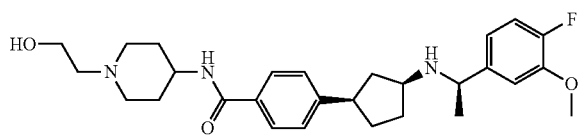 [SMILES: COc1cc([C@@H](C)N[C@H]2CC[C@@H](c3ccc(C(=O)NC4CCN(CCO)CC4)cc3)C2)ccc1F]

General procedure G is followed using 2-(4-amino-1-piperidyl)ethanol as the amine.

The invention claimed is:
1. A compound according to formula I

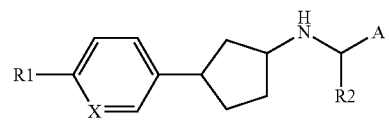

wherein
A represents phenyl, $C_{6-9}$heterocycloalkylphenyl, $C_{1-9}$heteroaryl or $C_{3-7}$cycloalkyl, wherein said phenyl, $C_{6-9}$heterocycloalkylphenyl, $C_{1-9}$heteroaryl or $C_{3-7}$cycloalkyl is optionally further substituted with one or more, same or different substituents represented by halogen, hydroxy, mercapto, trifluoromethyl, cyano, carboxy, —C(O)H, —NH$_2$, —C(O)NH$_2$, nitro, oxo, —S(O)$_2$NH$_2$, $C_{1-6}$alkyl, $C_{2-6}$alkenyl, $C_{2-6}$alkynyl, $C_{1-6}$hydroxyalkyl, $C_{1-6}$haloalkyl, $C_{1-4}$-alkoxy, $C_{1-4}$alkoxycarbonyl, $C_{1-4}$alkylcarbonyloxy, $C_{1-4}$alkoxycarbonyloxy, $C_{1-4}$alkoxysulfonyloxy, $C_{1-4}$alkoxycarbamoyk $C_{1-4}$aminocarbonyl, $C_{1-4}$alkylthio, $C_{3-7}$cycloalkyl, $C_{3-7}$cycloalkenyl, $C_{1-6}$amino, iminomethyl, $C_{1-4}$aminosulfonyl, $C_{1-4}$aminocarbonyloxy, $C_{1-4}$alkylsulfonylamino, hydroxyiminomethyl, $C_{1-4}$alkylcarbonylamino, $C_{1-4}$alkylsulfonyl, $C_{1-6}$heterocycloalkyl, $C_{1-6}$heterocycloalkenyl, $C_{1-5}$heteroaryl or phenyl;

X represents CH or N;

$R_1$ represents halogen, cyano, —NH$_2$, $C_{1-6}$amino, hydroxy, mercapto, —C(O)H, —C(O)NH$_2$, nitro, oxo, hydroxymethyl, $C_{1-6}$alkoxy, $C_{1-6}$alkylcarbonyl, $C_{1-6}$aminocarbonyl, NH$_2$—$C_{1-6}$aminocarbonyl, $C_{1-6}$amino$C_{1-6}$aminocarbonyl, di($C_{1-6}$alkyl)amino $C_{1-6}$alkylaminocarbonyl, hydroxyaminocarbonyl, $C_{1-4}$alkylcarbonylamino$C_{1-6}$alkylaminocarbonyl, $C_{3-6}$cycloalkylaminocarbonyl, $C_{1-6}$heterocycloalkylaminocarbonyl, $C_{1-6}$alkylsulfonylamino$C_{1-6}$aminocarbonyl, $C_{1-4}$amino$C_{1-4}$aminocarbonyl, $C_{1-4}$alkylsulfonylaminocarbonyl$C_{1-4}$alkoxy, aminocarbonyl $C_{1-6}$alkylaminocarbonyl, aminocarbonyl$C_{1-6}$alkoxy, $C_{3-6}$cycloalkylamino, $C_{1-4}$alkyl$C_{1-6}$heterocycloalkylcarbonyl, $C_{1-4}$alkyl$C_{1-6}$heterocycloalkylaminocarbonyl, $C_{1-6}$heterocycloalkylcarbonyl, $C_{1-4}$alkylsulfonyl$C_{1-6}$heterocycloalkylcarbonyl, oxo$C_{1-6}$heterocycloalkylcarbonyl, $C_{6-14}$aryl, $C_{1-9}$heteroaryl, $C_{1-6}$heteroarylaminocarbonyl, —S(O)$_2$NH$_2$, C$_{1-6}$ureido, C$_{1-6}$thioureido, C$_{1-4}$alkylcarbonyloxy, C$_{1-4}$alkoxysulfonyloxy, C$_{1-6}$heterocycloalkyloxy, C$_{1-6}$alkylthio, C$_{1-6}$aminosulfonyl, C$_{1-6}$aminocarbonyloxy, C$_{1-6}$alkylsulfonylamino, C$_{1-6}$alkylsulfonylaminoC$_{1-3}$alkyl, C$_{6-10}$arylamino, C$_{6-10}$arylaminocarbonyl, C$_{6-10}$aryloxycarbonyl, C$_{1-4}$alkoxycarbamoyl, C$_{6-10}$arylcarbonylamino, C$_{6-10}$arylsulfonylamino, C$_{1-6}$alkylcarbonylamino, C$_{1-3}$alkylcarbonylaminomethyl, C$_{1-6}$alkenylcarbonylamino, C$_{3-6}$cycloalkenylcarbonylamino, C$_{3-6}$cycloalkylcarbonylamino, C$_{1-6}$heterocycloalkylcarbonylamino, C$_{1-6}$alkylsulfonyl, C$_{1-6}$heterocycloalkylsulfonyl, C$_{1-6}$ heterocycloalkylsulfonyl C$_{1-4}$alkyl, C$_{1-4}$alkylsulfonylaminocarbonyl, aminosulfonylC$_{1-3}$alkylaminocarbonyl, iminomethyl, hydroxyiminomethyl, amidino, trifluoromethyl, C$_{1-6}$alkyl, C$_{2-4}$alkenyl, C$_{2-6}$alkynyl, C$_{1-6}$hydroxyalkyl, amino C$_{1-6}$alkyl, C$_{1-6}$haloalkyl, C$_{3-6}$cycloalkyl, C$_{3-6}$cycloalkenyl, C$_{1-6}$heterocycloalkyl, or C$_{1-6}$heterocycloalkenyl, wherein said C$_{1-6}$amino, C$_{1-6}$alkoxy, C$_{1-6}$alkylcarbonyl, C$_{1-6}$aminocarbonyl, C$_{1-4}$aminoC$_{1-4}$aminocarbonyl, di(C$_{1-6}$alkyl)aminoC$_{1-6}$alkylaminocarbonyl, C$_{3-6}$cycloalkylaminocarbonyl, C$_{1-6}$heterocycloalkylaminocarbonyl, aminocarbonylC$_{1-6}$alkoxy, C$_{3-6}$cycloalkylamino, C$_{1-6}$heterocycloalkylcarbonyl, C$_{1-4}$alkylC$_{1-6}$heterocycloalkylcarbonyl, C$_{1-4}$ alkylC$_{1-6}$heterocycloalkylaminocarbonyl, C$_{6-14}$aryl, C$_{1-9}$heteroaryl, C$_{1-6}$heteroarylaminocarbonyl, C$_{1-6}$ureido, C$_{1-6}$thioureido, C$_{1-4}$alkylcarbonyloxy, C$_{1-4}$alkoxysulfonyloxy, C$_{1-6}$heterocycloalkyloxy, C$_{1-6}$alkylthio, C$_{1-6}$aminosulfonyl, C$_{1-6}$aminocarbonyloxy, C$_{1-6}$alkylsulfonylamino, C$_{1-6}$alkylsulfonylaminoC$_{1-3}$alkyl, C$_{6-10}$arylamino, C$_{6-10}$arylaminocarbonyl, C$_{6-10}$aryloxycarbonyl, C$_{1-4}$alkoxycarbamoyl, C$_{1-10}$arylcarbonylamino, C$_{6-10}$arylsulfonylamino, C$_{1-6}$alkylcarbonylamino, C$_{1-6}$alkenylcarbonylamino, C$_{3-6}$cycloalkenylcarbonylamino, C$_{3-6}$cycloalkylcarbonylamino, C$_{1-6}$heterocycloalkylcarbonylamino, C$_{1-6}$alkylsulfonyl, C$_{1-6}$heterocycloalkylsulfonyl, C$_{1-6}$ heterocycloalkylsulfonyl C$_{1-4}$alkyl, C$_{1-4}$alkylsulfonylaminocarbonyl, C$_{1-6}$alkyl, C$_{2-6}$alkenyl, C$_{2-6}$alkynyl, C$_{1-6}$hydroxyalkyl, amino C$_{1-6}$alkyl, C$_{1-6}$haloalkyl, C$_{3-6}$cycloalkyl, C$_{3-6}$cycloalkenyl, C$_{1-6}$heterocycloalkyl or C$_{1-6}$heterocycloalkenyl and is optionally substituted with one or more, same or different substituents selected from the group consisting of halogen, trifluoromethyl, hydroxy, cyano, C$_{1-4}$alkyl or —C(O)NH$_2$;

R$_2$ represents C$_{1-6}$alkyl, C$_{2-6}$alkenyl, C$_{2-6}$alkynyl, C$_{1-6}$hydroxyalkyl, C$_{1-6}$haloalkyl, C$_{1-6}$amino, C$_{1-6}$alkoxy or C$_{3-6}$cycloalkyl;

or a pharmaceutically acceptable stereoisomer or salt thereof.

2. A compound according to claim 1, wherein R$_1$ represents halogen, cyano, —NH$_2$, hydroxy, mercapto, —C(O)H, —C(O)NH$_2$, nitro, oxo, iminomethyl, hydroxyiminomethyl, amidino, trifluoromethyl, cyanoC$_{1-4}$aminocarbonyl, C$_{1-4}$hydroxyalkyl, C$_{1-6}$amino, C$_{1-4}$alkoxy, hydroxyC$_{1-4}$aminosulfonyl, aminocarbonylC$_{1-4}$alkoxy, C$_{1-4}$alkylcarbonyl, C$_{1-4}$aminocarbonyl, NH$_2$—C$_{1-4}$aminocarbonyl, C$_{1-4}$amino C$_{1-4}$aminocarbonyl, di(hydroxyC$_{1-4}$alkyl)aminoC$_{1-4}$alkylaminocarbonyl, hydroxyC$_{1-3}$aminoC$_{1-3}$aminocarbonyl, aminosulfonylC$_{1-3}$alkylaminocarbonyl, C$_{1-3}$alkylsulfonylaminocarbonylC$_{1-3}$alkoxy, C$_{1-3}$carbonylaminoC$_{1-3}$alkylaminocarbonyl, aminocarbonylC$_{1-4}$alkylaminocarbonyl, hydroxyC$_{1-4}$aminocarbonyl, C$_{3-6}$cycloalkylaminocarbonyl, C$_{1-5}$heterocycloalkylaminocarbonyl, C$_{1-5}$heterocycloalkyl-N-methyl-aminocarbonyl, C$_{3-6}$cycloalkylamino, C$_{1-5}$heterocycloalkylcarbonyl, hydroxyC$_{1-3}$alkylC$_{1-6}$heterocycloalkylcarbonyl, hydroxyC$_{1-3}$alkyl C$_{1-6}$heterocycloalkylaminocarbonyl, hydroxyC$_{1-5}$heterocycloalkylcarbonyl, C$_{1-3}$alkylsulfonylC$_{1-6}$heterocycloalkylcarbonyl, oxoC$_{1-4}$heterocycloalkylcarbonyl, C$_{6-10}$aryl, C$_{1-5}$heteroaryl, C$_{1-5}$heteroarylaminocarbonyl, C$_{1-4}$alkylsulfonylaminoC$_{1-4}$aminocarbonyl, —S(O)$_2$NH$_2$, C$_{1-4}$ureido, C$_{1-4}$thioureido, C$_{1-4}$alkoxysulfonyloxy, C$_{1-5}$heterocycloalkyloxy, C$_{1-4}$alkylthio, C$_{1-4}$aminosulfonyl, hydroxyC$_{1-4}$aminosulfonyl, C$_{1-4}$aminocarbonyloxy, C$_{1-4}$alkylsulfonylamino, C$_{1-4}$alkylsulfonylaminoC$_{1-3}$alkyl, C$_{6-10}$arylamino, C$_{6-10}$arylaminocarbonyl, C$_{6-10}$aryloxycarbonyl, C$_{1-4}$alkoxycarbamoyl, C$_{6-10}$arylcarbonylamino, C$_{6-10}$arylsulfonylamino, C$_{1-4}$alkylcarbonylamino, C$_{1-4}$alkenylcarbonylamino, C$_{3-6}$cycloalkenylcarbonylamino, C$_{3-6}$cycloalkylcarbonylamino, C$_{1-5}$heterocycloalkylcarbonylamino, C$_{1-4}$alkylsulfonyl, C$_{1-5}$heterocycloalkylsulfonyl, C$_{1-5}$heterocycloalkylsulfonylC$_{1-3}$alkyl or C$_{1-4}$alkylsulfonylaminocarbonyl.

3. A compound according to claim 1, wherein R$_1$ represents oxo, halogen, trifluoromethyl, C(O)NH$_2$, cyano, cyanomethylaminocarbonyl, C$_{1-3}$hydroxyalkyl, C$_{1-3}$alkoxy, C$_{1-3}$alkylcarbonylamino, C$_{1-3}$alkylcarbonylaminomethyl, NH$_2$—C$_{1-3}$aminocarbonyl, C$_{1-3}$aminoC$_{1-3}$aminocarbonyl, di(hydroxyC$_{1-3}$alkyl)aminoC$_{1-3}$alkylaminocarbonyl, hydroxyC$_{1-3}$aminoC$_{1-3}$aminocarbonyl, methylcarbonylaminoC$_{1-3}$aminocarbonyl, C$_{1-3}$alkylsulfonylaminoC$_{1-3}$aminocarbonyl, C$_{3-6}$heterocycloalkylaminocarbonyl, C$_{3-5}$heterocycloalkyl-N-methyl-aminocarbonyl, C$_{3-5}$heterocycloalkylcarbonyl, hydroxyC$_{1-3}$alkylC$_{3-5}$heterocycloalkylcarbonyl, hydroxyC$_{1-3}$alkylC$_{3-5}$heterocycloalkylaminocarbonyl, hydroxyC$_{3-6}$heterocycloalkylcarbonyl, C$_{1-3}$alkylsulfonylC$_{3-5}$heterocycloalkylcarbonyl, oxoC$_{1-4}$heterocycloalkylcarbonyl, aminocarbonylC$_{1-3}$alkoxy, C$_{1-5}$heteroaryl, C$_{1-3}$alkylsulfonyl, hydroxyC$_{1-3}$aminosulfonyl, hydroxyC$_{1-3}$aminocarbonyl, C$_{1-5}$heterocycloalkylsulfonyl, C$_{3-5}$heterocycloalkylsulfonylC$_{1-3}$alkyl, C$_{1-3}$alkylsulfonylamino, aminosulfonylC$_{1-3}$alkylaminocarbonyl, C$_{1-3}$alkylsulfonylaminocarbonylC$_{1-3}$alkoxy, aminocarbonylC$_{1-3}$alkylaminocarbonyl or C$_{1-3}$alkylsulfonylaminomethyl.

4. A compound according to claim 1, wherein R$_1$ represents oxo, hydroxymethyl, piperidylaminocarbonyl, oxetanyl-N-methyl-aminocarbonyl, tetrazolyl, hydroxyethylaminocarbonyl, aminoethylaminocarbonyl, di(hydroxyethyl)aminoethylaminocarbonyl, hydroxyethylaminoethylaminocarbonyl, cyanomethylaminocarbonyl, hydroxyethylaminosulfonyl, hydroxyethylaminocarbonyl, methylsulfonyl, aminocarbonylmethoxy, morpholinosulfonyl, morpholinocarbonyl, azetidinylcarbonyl, isoxazolidinycarbonyl, methylsulfonylpiperazinylcarbonyl, hydroxypiperidinocarbonyl, piperazinylcarbonyl, hydroxyethylpiperazinylcarbonyl, hydroxyethylpiperidinylaminocarbonyl, oxopiperazinylcarbonyl, hydroxypyrrolidinylcarbonyl, aminosulfonylethylaminocarbonyl, methylsulfonylaminoethylaminocarbonyl, methylsulfonylamino, methylsulfonylaminomethyl, methylsulfonylaminocarbonylmethoxy, morpholinosulfonylethyl, methylcarbonylamino, methylcarbonylaminoethylaminocarbonyl, aminocarbonylmethylaminocarbonyl, aminocarbonylethylaminocarbonyl or methylcarbonylaminomethyl.

5. A compound according to claim 1, wherein R$_1$ represents —S(O)$_2$NH$_2$, C$_{1-4}$alkoxysulfonyloxy, C$_{1-6}$aminosulfonyl, C$_{1-6}$alkylsulfonylamino, C$_{1-6}$alkylsulfonylaminoC$_{1-3}$alkyl, C$_{6-10}$arylsulfonyl, C$_{1-6}$alkylsulfonyl, C$_{1-6}$heterocycloalkylsulfonyl or C$_{1-6}$ heterocycloalkylsulfonylC$_{1-4}$alkyl, wherein said C$_{1-4}$alkoxysulfonyloxy, C$_{1-6}$aminosulfonyl, C$_{1-6}$alkylsulfonylamino, C$_{1-6}$alkylsulfonylaminoC$_{1-3}$alkyl, $C_{6-10}$arylsulfonylamino, $C_{1-6}$alkylsulfonyl, $C_{1-6}$heterocycloalkylsulfonyl or $C_{1-6}$ heterocycloalkylsulfonyl$C_{1-4}$alkyl, is optionally substituted with one or more, same or different substituents selected from the group consisting of halogen, trifluoromethyl, hydroxy, cyano, $C_{1-4}$alkyl or –C(O)NH$_2$.

6. A compound according to claim 5, wherein R$_1$ represents —S(O)$_2$NH$_2$, $C_{1-4}$aminosulfonyl, $C_{1-4}$alkylsulfonyl or $C_{1-4}$heterocycloalkylsulfonyl, wherein said $C_{1-4}$aminosulfonyl, $C_{1-4}$alkylsulfonyl or $C_{1-6}$heterocycloalkylsulfonyl is optionally substituted with one or more, same or different substituents selected from the group consisting of halogen, trifluoromethyl, hydroxy, cyano, $C_{1-4}$alkyl or —C(O)NH$_2$.

7. A compound according to claim 1, wherein R$_1$ represents —C(O)H, —C(O)NH$_2$, $C_{1-6}$alkylcarbonyl, $C_{1-6}$aminocarbonyl, hydroxyaminocarbonyl, $C_{1-4}$alkylcarbonylamino $C_{1-6}$alkylaminocarbonyl, $C_{3-6}$cycloalkylaminocarbonyl, $C_{1-6}$heterocycloalkylaminocarbonyl, $C_{1-6}$alkylsulfonylamino$C_{1-6}$minocarbonyl, aminocarbonyl$C_{1-6}$alkylaminocarbonyl, $C_{1-6}$heterocycloalkylcarbonyl, oxo$C_{1-6}$heterocycloalkylcarbonyl, $C_{1-6}$heteroarylaminocarbonyl, $C_{6-10}$arylaminocarbonyl, $C_{1-4}$alkoxycarbamoyl, $C_{1-4}$alkylsulfonylaminocarbonyl, aminosulfonyl$C_{1-3}$alkylaminocarbonyl, wherein said $C_{1-6}$alkylcarbonyl, $C_{1-6}$aminocarbonyl, $C_{3-6}$cycloalkylaminocarbonyl, $C_{1-6}$heterocycloalkylaminocarbonyl, $C_{1-6}$heterocycloalkylcarbonyl, $C_{1-6}$heteroarylaminocarbonyl, $C_{6-10}$arylaminocarbonyl, $C_{6-10}$aryloxycarbonyl, $C_{1-4}$alkoxycarbamoyl, $C_{1-4}$alkylsulfonylaminocarbonyl, is optionally substituted with one or more, same or different substituents selected from the group consisting of halogen, trifluoromethyl, hydroxy, cyano, $C_{1-4}$alkyl or —C(O)NH$_2$.

8. A compound according to claim 1, wherein A represents phenyl, $C_{6-9}$heterocycloalkylphenyl, $C_{2-9}$heteroaryl or $C_{3-7}$cycloalkyl, wherein said phenyl, $C_{6-9}$heterocycloalkylphenyl, $C_{2-9}$heteroaryl or $C_{3-7}$cycloalkyl is optionally further substituted with one or more, same or different substituents represented by halogen, hydroxy, trifluoromethyl, cyano, carboxy, —C(O)H, —NH$_2$, —C(O)NH$_2$, $C_{1-6}$alkyl, $C_{2-6}$alkenyl, $C_{2-6}$alkynyl, $C_{1-6}$hydroxyalkyl, $C_{1-6}$haloalkyl, $C_{1-4}$alkoxy, $C_{3-6}$cycloalkyl or phenyl.

9. A compound according to claim 8, wherein A represents phenyl or phenyl substituted with one or more, same or different substituents represented by halogen, hydroxy, trifluoromethyl, cyano, carboxy, —C(O)H, —NH$_2$, —C(O)NH$_2$, $C_{1-6}$alkyl, $C_{2-6}$alkenyl, $C_{2-6}$alkynyl, $C_{1-6}$hydroxyalkyl, $C_{1-6}$haloalkyl, $C_{1-4}$alkoxy, $C_{3-6}$cycloalkyl or phenyl.

10. A compound according to claim 9, wherein A represents phenyl substituted with one or more, same or different substituents selected from fluoro, chloro, bromo, iodo, methoxy, ethoxy, isopropoxy, n-propoxy, n-butoxy, isobutoxy, sec-butoxy, tert-butoxy, cyano or trifluoromethyl.

11. A compound according to claim 10, wherein A represents 3-chloro-phenyl, 3,4-dichloro-phenyl, 3-fluoro-phenyl, 3,4-difluoro-phenyl, 3-chloro-4-fluoro-phenyl, 3-trifluoromethyl-phenyl, 3-trifluoromethyl-4-fluoro-phenyl, 3-methoxy-phenyl, 3-ethoxy-phenyl, 3,4-dimethoxy-phenyl, 3,5-dimethoxy-phenyl, 2-fluoro-5-methoxy-phenyl, 3-fluoro-5-methoxy-phenyl, 4-fluoro-3-methoxy-phenyl, 2-fluoro-3-methoxy-phenyl, 3-fluoro-4-methoxy-phenyl, 4-fluoro-2-methoxy-phenyl, 2,3-dimethoxy-phenyl, 3-isopropoxy-phenyl, 3-ethoxy-phenyl or 3-cyano-4-fluoro-phenyl.

12. A compound according to claim 1, wherein A represents $C_3$-$C_9$heteroaryl optionally further substituted with one or more, same or different substituents selected from oxo, halogen, hydroxy, trifluoromethyl, cyano, carboxy, —C(O) H, —NH$_2$, —C(O)NH$_2$, $C_{1-6}$alkyl, $C_{2-6}$alkenyl, $C_{2-6}$alkynyl, $C_{1-6}$hydroxyalkyl, $C_{1-6}$haloalkyl, $C_{1-4}$alkoxy, $C_{3-6}$cycloalkyl or phenyl.

13. A compound according to claim 12, wherein A represents $C_3$-$C_9$heteroaryl optionally further substituted with one or more, same or different substituents selected from oxo, fluoro, chloro, bromo, iodo, methyl, methoxy, ethoxy, isopropoxy, n-propoxy, n-butoxy, isobutoxy, sec-butoxy, tert-butoxy, cyano, trifluoromethyl or phenyl.

14. A compound according to claim 13, wherein A represents quinolonyl, imidazo[1,2-a]pyridinyl, 5-fluoro-imidazo[1,2-a]pyridinyl, imidazo[1,5-a]pyridinyl, pyrazolo[1,5-a]pyridinyl, pyrazolyl substituted with phenyl and methyl, thiazolyl substituted with methyl, thiophenyl substituted with chloro or benzo[b]thiophenyl.

15. A compound according to claim 1, wherein A represents $C_3$-$C_9$heterocycloalkylphenyl optionally substituted with one or more, same or different substituents selected from halogen and oxo.

16. A compound according to claim 15, wherein A represents 2,3-dihydro-benzofuranyl, 1,3-benzodioxolyl, 2,2-difluoro-benzodioxolyl, 2,3-dihydro-benzo[1,4]dioxinyl, 3,4-dihydro-2H-1,5-benzodioxepinyl or 3,4-dihydro-3-oxo-[2H]-1,4-benzoxazinyl.

17. A compound according to claim 1, wherein A represents cyclopropyl, cyclobutyl, cyclooentyl, cyclohexyl or cycloheptyl, each of which are optionally further substituted with one or more, same or different substituents selected from halogen, hydroxy, trifluoromethyl, cyano, carboxy, —C(O) H, —NH$_2$, —C(O)NH$_2$, $C_{1-6}$alkyl, $C_{2-6}$alkenyl, $C_{2-6}$alkynyl, $C_{1-6}$hydroxyalkyl, $C_{1-6}$haloalkyl, $C_{1-4}$alkoxy or phenyl.

18. A compound according to claim 1, wherein X represents CH.

19. A compound according to claim 1, wherein X represents N.

20. A compound according to claim 1, wherein X represents N, and R$_1$ represents oxo.

21. A compound according to claim 1, wherein R$_2$ represents methyl.

22. A compound according to claim 1, wherein R$_1$ represents $C_{1-6}$heteroaryl, and A represents $C_{6-9}$heterocycloalkylphenyl, $C_{1-9}$heteroaryl or $C_{3-7}$cycloalkyl, wherein said $C_{6-9}$heterocycloalkylphenyl, $C_{1-9}$heteroaryl or $C_{3-7}$cycloalkyl is optionally further substituted with one or more, same or different substituents represented by halogen, hydroxy, mercapto, trifluoromethyl, cyano, carboxy, —C(O)H, —NH$_2$, —C(O)NH$_2$, nitro, oxo, —S(O)$_2$NH$_2$, $C_{1-6}$alkyl, $C_{2-6}$alkenyl, $C_{2-6}$alkynyl, $C_{1-6}$hydroxyalkyl, $C_{1-6}$haloalkyl.

23. A compound according to claim 1, wherein R$_1$ represents $C_{1-6}$heteroaryl, and A represents phenyl, wherein said phenyl is further substituted with more, same or different substituents represented by halogen, hydroxy, mercapto, trifluoromethyl, cyano, carboxy, —C(O)H, —NH$_2$, —C(O) NH$_2$, nitro, oxo, —S(O)$_2$NH$_2$, $C_{1-6}$alkyl, $C_{2-6}$alkenyl, $C_{2-6}$alkynyl, $C_{1-6}$hydroxyalkyl, $C_{1-6}$haloalkyl.

24. A compound according to claim 22 wherein R$_1$ represents tetrazolyl.

25. A compound according to claim 1 selected from the group consisting of
(1R)—(N)-[(1R/S,3S)-3-(4-methanesulfonylphenyl)cyclopentyl]-1-(1,3-benzodioxol-4-yl)ethanamine (compound 1000),
(1R)—(N)-[(1R/S,3S)-3-(4-methanesulfonylphenyl)cyclopentyl]-1-(1,3-benzodioxol-5-yl)ethanamine (compound 1001), (1R)—(N)-[(1R/S,3S)-3-(4-methanesulfonylphenyl)cyclopentyl]-1-(1-methyl-5-phenyl-pyrazol-3-yl)ethanamine (compound 1002),
(1R)—(N)-[(1R/S,3S)-3-(4-methanesulfonylphenyl)cyclopentyl]-1-(2,2-difluoro-1,3-benzodioxol-4-yl)ethanamine (compound 1003),
(1R)—(N)-[(1R/S,3S)-3-(4-methanesulfonylphenyl)cyclopentyl]-1-(2,3-dihydro-1,4-benzodioxin-5-yl)ethanamine (compound 1004),
(1R)—(N)-[(1R/S,3S)-3-(4-methanesulfonylphenyl)cyclopentyl]-1-(2,3-dihydrobenzofuran-5-yl)ethanamine (compound 1005),
(1R)—(N)-[(1R/S,3S)-3-(4-methanesulfonylphenyl)cyclopentyl]-1-(2,3-dimethoxyphenyl)ethanamine (compound 1006),
(1R)—(N)-[(1R/S,3S)-3-(4-methanesulfonylphenyl)cyclopentyl]-1-(2-fluoro-3-methoxy-phenyl)ethanamine (compound 1007),
(1R)—(N)-[(1R/S,3S)-3-(4-methanesulfonylphenyl)cyclopentyl]-1-(2-fluoro-5-methoxy-phenyl)ethanamine (compound 1008),
(1R)—(N)-[(1R/S,3S)-3-(4-methanesulfonylphenyl)cyclopentyl]-1-(2-methylthiazol-4-yl)ethanamine (compound 1009),
(1R)—(N)-[(1R/S,3R)-3-(4-methanesulfonylphenyl)cyclopentyl]-1-(3-chloro-4-fluoro-phenyl)ethanamine (compound 1010),
(1R)—(N)-[(1R/S,3S)-3-(4-methanesulfonylphenyl)cyclopentyl]-1-(3-ethoxyphenyl)ethanamine (compound 1011),
(1R)—(N)-[(1R/S,3S)-3-(4-methanesulfonylphenyl)cyclopentyl]-1-(3-fluoro-5-methoxyphenyl)ethanamine (compound 1012),
(1R)—(N)-[(1R/S,3S)-3-(4-methanesulfonylphenyl)cyclopentyl]-1-(4-fluoro-2-methoxyphenyl)ethanamine (compound 1013),
(1R)—(N)-[(1R/S,3S)-3-(4-methanesulfonylphenyl)cyclopentyl]-1-(4-fluoro-3-methoxyphenyl)ethanamine (compound 1014),
(1R)—(N)-[(1R/S,3R)-3-(4-methanesulfonylphenyl)cyclopentyl]-1-(4-quinolyl)ethanamine (compound 1015),
(1R)—(N)-[(1R/S,3R)-3-(4-methanesulfonylphenyl)cyclopentyl]-1-(5-chloro-2-thienyl)ethanamine (compound 1016),
(1R)—(N)-[(1R/S,3S)-3-(4-methanesulfonylphenyl)cyclopentyl]-1-(8-quinolyl)ethanamine (compound 1017),
(1R)—(N)-[(1R/S,3S)-3-(4-methanesulfonylphenyl)cyclopentyl]-1-[3-(methylethoxy)phenyl]ethanamine (compound 1018),
(1R)—(N)-[(1R/S,3S)-3-(4-methanesulfonylphenyl)cyclopentyl]-1-[4-fluoro-3-(trifluoromethyl)phenyl]ethanamine (compound 1019),
(1R)—(N)-[(1R/S,3S)-3-(4-methanesulfonylphenyl)cyclopentyl]-1-cyclopropylethanamine (compound 1020),
(1R)—(N)-[(1R/S,3S)-3-(4-methanesulfonylphenyl)cyclopentyl]-1-imidazo[1,2-a]pyridin-3-ylethanamine (compound 1021),
(1R)—(N)-[(1R/S,3S)-3-(4-methanesulfonylphenyl)cyclopentyl]-1-imidazo[1,5-a]pyridin-3-ylethanamine (compound 1022),
(1R)—(N)-[(1R/S,3S)-3-(4-methanesulfonylphenyl)cyclopentyl]-1-pyrazolo[1,5-a]pyridin-3-ylethanamine (compound 1023),
(1R)—(N)-[(1R/S,3S)-3-(4-methanesulfonylphenyl)cyclopentyl]-1-cyclohexylethanamine (compound 1024),
(1R)—(N)-[(1R/S,3S)-3-(4-methanesulfonylphenyl)cyclopentyl]-1-(3-fluoro-4-methoxyphenyl)ethanamine (compound 1025),
(1R)—(N)-[(1R/S,3S)-3-(4-methanesulfonylphenyl)cyclopentyl]-1-(3-fluorophenyl)ethanamine (compound 1026),
(1R)—(N)-[(1R/S,3R/S)-3-(4-methanesulfonylphenyl)cyclopentyl]-1-(3-methoxyphenyl)ethanamine (compound 1027),
(1R)—(N)-[(1R/S,3S)-3-(4-methanesulfonylphenyl)cyclopentyl]-1-[3-(trifluoromethyl)phenyl]ethanamine (compound 1028),
(1R)—(N)-[(1R/S,3S)-3-(4-methanesulfonylphenyl)cyclopentyl]-1-benzo[b]thiophen-3-yl-ethanamine (compound 1029),
(1R)—(N)-[(1R/S,3S)-3-(4-methanesulfonylphenyl)cyclopentyl]-1-(3-cyano-4-fluorophenyl)ethanamine (compound 1030),
(1R/S)—(N)-[(1R/S,3S)-3-(4-methanesulfonylphenyl)cyclopentyl]-1-(3,4-dihydro-3-oxo-[2H]-1,4-benzoxazin-6-yl)ethanamine (compound 1031),
(1R)—(N)-[(1R/S,3S)-3-[4-(1H-tetrazol-5-yl)phenyl]cyclopentyl]-1-(1,3-benzodioxol-4-yl)ethanamine (compound 1032),
(1R)—(N)-[(1R/S,3S)-3-[4-(1H-tetrazol-5-yl)phenyl]cyclopentyl]-1-(2,3-dihydro-1,4-benzodioxin-5-yl)ethanamine (compound 1033),
(1R)—(N)-[(1R/S,3S)-3-[4-(1H-tetrazol-5-yl)phenyl]cyclopentyl]-1-(4-fluoro-2-methoxyphenyl)ethanamine (compound 1034),
(1R)—(N)-[(1R/S,3S)-3-[4-(1H-tetrazol-5-yl)phenyl]cyclopentyl]-1-(4-fluoro-3-methoxyphenyl)ethanamine (compound 1035),
(1R)—(N)-[(1R/S,3S)-3-[4-(1H-tetrazol-5-yl)phenyl]cyclopentyl]-1-(3-chlorophenyl)ethanamine (compound 1036),
(1R)—(N)-[(1R/S,3S)-3-[4-(4-hydroxypiperidine-1-carbonyl)phenyl]cyclopentyl]-1-(1,3-benzodioxol-4-yl)ethanamine (compound 1037),
(1R)—(N)-[(1R/S,3S)-3-[4-(4-hydroxypiperidine-1-carbonyl)phenyl]cyclopentyl]-1-(1-isoquinolyl)ethanamine (compound 1038),
(1R)—(N)-[(1R/S,3S)-3-[4-(4-hydroxypiperidine-1-carbonyl)phenyl]cyclopentyl]-1-(3,4-dichlorophenyl)ethanamine (compound 1039),
(1R)—(N)-[(1R/S,3S)-3-[4-(4-hydroxypiperidine-1-carbonyl)phenyl]cyclopentyl]-1-(3,4-difluorophenyl)ethanamine (compound 1040),
(1R)—(N)-[(1R/S,3S)-3-[4-(4-hydroxypiperidine-1-carbonyl)phenyl]cyclopentyl]-1-(3,4-dihydro-2H-1,5-benzodioxepin-6-yl)ethanamine (compound 1041),
(1R)—(N)-[(1R/S,3S)-3-[4-(4-hydroxypiperidine-1-carbonyl)phenyl]cyclopentyl]-1-(3,4-dimethoxyphenyl)ethanamine (compound 1042),
(1R)—(N)-[(1R/S,3S)-3-[4-(4-hydroxypiperidine-1-carbonyl)phenyl]cyclopentyl]-1-(3,5-dimethoxyphenyl)ethanamine (compound 1043),
(1R)—(N)-[(1R/S,3R)-3-[4-(4-hydroxypiperidine-1-carbonyl)phenyl]cyclopentyl]-1-(3-chloro-4-fluoro-phenyl)ethanamine (compound 1044),
(1R)—(N)-[(1R/S,3S)-3-[4-(4-hydroxypiperidine-1-carbonyl)phenyl]cyclopentyl]-1-(3-fluoro-5-methoxyphenyl)ethanamine (compound 1045), (1R)—(N)-[(1R/S,3S)-3-[4-(4-hydroxypiperidine-1-carbonyl)phenyl]cyclopentyl]-1-(4-fluoro-2-methoxyphenyl)ethanamine (compound 1046), (1R)—(N)-[(1R/S,3S)-3-[4-(4-hydroxypiperidine-1-carbonyl)phenyl]cyclopentyl]-1-(4-fluoro-3-methoxyphenyl)ethanamine (compound 1047), (1R)—(N)-[(1R/S,3S)-3-[4-(4-hydroxypiperidine-1-carbonyl)phenyl]cyclopentyl]-1-pyrazolo[1,5-a]pyridin-3-ylethanamine (compound 1048), (1R)—(N)-[(1R/S,3S)-3-[4-(4-hydroxypiperidine-1-carbonyl)phenyl]cyclopentyl]-1-benzo[b]thiophen-3-yl-ethanamine (compound 1049), (1R)—(N)-[(3S)-(1R/S,3S)-3-[4-[3-hydroxypyrrolidin-1-ylcarbonyl]phenyl]-cyclopentyl]-1-(3-ethoxyphenyl)ethanamine (compound 1050), (1R)—(N)-[(3S)-(1R/S,3S)-3-[4-[3-hydroxypyrrolidin-1-ylcarbonyl]phenyl]-cyclopentyl]-1-(4-fluoro-3-methoxyphenyl)ethanamine (compound 1051), (1R)—(N)-[(3S)-(1R/S,3S)-3-[4-[3-hydroxypyrrolidin-1-ylcarbonyl]phenyl]-cyclopentyl]-1-(3-chlorophenyl)ethanamine (compound 1052), (1R)—(N)-[(3S)-(1R/S,3S)-3-[4-[3-hydroxypyrrolidin-1-ylcarbonyl]phenyl]-cyclopentyl]-1-benzo[b]thiophen-3-yl-ethanamine (compound 1053), (1R)—(N)-[(1R/S,3R/S)-3-[4-acetamidophenyl]cyclopentyl]-1-(3-methoxyphenyl)-ethanamine (compound 1054), (1R)—(N)-[(1R/S,3R/S)-3-[4-methanesulfonylaminophenyl]cyclopentyl]-1-(3-methoxyphenyl)ethanamine (compound 1055), (1R)—(N)-[(1R/S,3R)-3-[4-[aminocarbonylmethoxy]phenyl]cyclopentyl]-1-(1,3-benzodioxol-4-yl)ethanamine (compound 1056), (1R)—(N)-[(1R/S,3R)-3-[4-[aminocarbonylmethoxy]phenyl]cyclopentyl]-1-(3-chloro-4-fluoro-phenyl)ethanamine (compound 1057), (1R)—(N)-[(1R/S,3R)-3-[4-[aminocarbonylmethoxy]phenyl]cyclopentyl]-1-(3-ethoxyphenyl)ethanamine (compound 1058), (1R)—(N)-[(1R/S,3R)-3-[4-(aminocarbonylmethoxy)-phenyl]cyclopentyl]-1-(4-fluoro-2-methoxyphenyl)ethanamine (compound 1059), (1R)—(N)-[(1R/S,3R)-3-[4-(aminocarbonylmethoxy)-phenyl]cyclopentyl]-1-(4-fluoro-3-methoxyphenyl)ethanamine (compound 1060), (1R)—(N)-[(1R/S,3R)-3-[4-[aminocarbonylmethoxy]phenyl]cyclopentyl]-1-(3-chlorophenyl)ethanamine (compound 1061), (1R)—(N)-[(1R/S,3R/S)-3-[3-methylsulfonylaminophenyl]cyclopentyl]-1-(3-methoxyphenyl)ethanamine (compound 1062), (1R)—(N)-[(1R/S,3R/S)-3-[4-morpholinosulfonylphenyl]cyclopentyl]-1-(3-methoxyphenyl)ethanamine (compound 1063), (1R)—(N)-[(1R/S,3R/S)-3-[4-hydroxymethylphenyl]cyclopentyl]-1-(3-methoxyphenyl)ethanamine (compound 1064), (1R)—(N)-[(1R/S,3R/S)-3-[4-methanesulfonylaminophenyl]cyclopentyl]-1-(3-methoxyphenyl)ethanamine (compound 1065), (1R)—(N)-[(1R/S,3S)-3-[4-(2-aminosulfonypethylaminocarbonyl)phenyl]-cyclopentyl]-1-(1,3-benzodioxol-4-yl)ethanamine (compound 1066), (1R)—(N)-[(1R/S,3S)-3-[4-(2-(aminosulfonyl)ethylaminocarbonyl)phenyl]-cyclopentyl]-1-(3-ethoxyphenyl)ethanamine (compound 1067), (1R)—(N)-[(1R/S,3S)-3-[4-(2-(aminosulfonypethylaminocarbonyl)phenyl]-cyclopentyl]-1-(4-fluoro-2-methoxyphenyl)ethanamine (compound 1068), (1R)—(N)-[(1R/S,3S)-3-[4-(2-(aminosulfonypethylaminocarbonyl)phenyl]-cyclopentyl]-1-(4-fluoro-3-methoxyphenyl)ethanamine (compound 1069), (1R)—(N)-[(1R/S,3S)-3-[4-(2-(aminosulfonypethylaminocarbonyl)phenyl]-cyclopentyl]-1-(3-chlorophenyl)ethanamine (compound 1070), (1R)—(N)-[(1R/S,3S)-3-[4-(2-(aminosulfonyl)ethylaminocarbonyl)phenyl]cyclopentyl]-1-benzo[b]thiophen-3-yl-ethanamine (compound 1071), (1R)—(N)-[(1R/S,3S)-3-[4-(3-oxo-piperazinylcarbonyl)phenyl]cyclopentyl]-1-(1,3-benzodioxol-4-yl)ethanamine (compound 1072), (1R)—(N)-[(1R/S, 3S)-3-[4-(3-oxo-piperazinylcarbonyl)phenyl]cyclopentyl]-1-(3-ethoxyphenyl)ethanamine (compound 1073), (1R)—(N)-[(1R/S,3S)-3-[4-(3-oxo-piperazinylcarbonyl)phenyl]cyclopentyl]-1-(4-fluoro-3-methoxyphenyl)ethanamine (compound 1074), (1R)—(N)-[(1R/S,3S)-3-[4-(3-oxo-piperazinylcarbonyl)phenyl]cyclopentyl]-1-(3-chlorophenyl)ethanamine (compound 1075), (1R)—(N)-[(1R/S,3S)-3-[4-(3-oxo-piperazinylcarbonyl)phenyl]cyclopentyl]-1-benzo[b]thiophen-3-yl-ethanamine (compound 1076), (1R)—(N)-[(1R/S,3R/S)-3-[4-(acetamidomethyl)phenyl]cyclopentyl]-1-(3-methoxyphenyl)ethanamine (compound 1077), (1R)—(N)-[(1R/S,3S)-3-[2-hydroxypyridin-5-yl]cyclopentyl]-1-(1,3-benzodioxol-4-yl)ethanamine (compound 1078), (1R)—(N)-[(1R/S,3S)-3-[2-hydroxypyridin-5-yl]cyclopentyl]-1-(1,3-benzodioxol-5-yl)ethanamine (compound 1079), (1R)—(N)-[(1R/S,3S)-3-[2-hydroxypyridin-5-yl]cyclopentyl]-1-(1-methyl-5-phenyl-pyrazol-3-yl)ethanamine (compound 1080), (1R)—(N)-[(1R/S,3S)-3-[2-hydroxypyridin-5-yl]cyclopentyl]-1-(2,3-dihydro-1,4-benzodioxin-5-yl)ethanamine (compound 1081), (1R)—(N)-[(1R/S,3S)-3-[2-hydroxypyridin-5-yl]cyclopentyl]-1-(2,3-dihydrobenzofuran-5-yl)ethanamine (compound 1082), (1R)—(N)-[(1R/S,3S)-3-[2-hydroxypyridin-5-yl]cyclopentyl]-1-(2,3-dimethoxyphenyl)ethanamine (compound 1083), (1R)—(N)-[(1R/S,3S)-3-[2-hydroxypyridin-5-yl]cyclopentyl]-1-(2-fluoro-3-methoxy-phenyl)ethanamine (compound 1084), (1R)—(N)-[(1R/S,3S)-3-[2-hydroxypyridin-5-yl]cyclopentyl]-1-(2-fluoro-5-methoxy-phenyl)ethanamine (compound 1085), (1R)—(N)-[(1R/S,3S)-3-[2-hydroxypyridin-5-yl]cyclopentyl]-1-(2-methylthiazol-4-yl)ethanamine (compound 1086), (1R)—(N)-[(1R/S,3S)-3-[2-hydroxypyridin-5-yl]cyclopentyl]-1-(3-fluoro-5-methoxyphenyl)ethanamine (compound 1087), (1R)—(N)-[(1R/S,3S)-3-[2-hydroxypyridin-5-yl]cyclopentyl]-1-(4-fluoro-2-methoxyphenyl)ethanamine (compound 1088), (1R)—(N)-[(1R/S,3S)-3-[2-hydroxypyridin-5-yl]cyclopentyl]-1-(4-fluoro-3-methoxyphenyl)ethanamine (compound 1089), (1R)—(N)-[(1R/S,3S)-3-[2-hydroxypyridin-5-yl]cyclopentyl]-1-(8-quinolyl)ethanamine (compound 1090), (1R)—(N)-[(1R/S,3S)-3-[2-hydroxypyridin-5-yl]cyclopentyl]-1-cyclopropylethanamine (compound 1091), (1R)—(N)-[(1R/S,3S)-3-[2-hydroxypyridin-5-yl]cyclopentyl]-1-imidazo[1,2-a]pyridin-3-ylethanamine (compound 1092), (1R)—(N)-[(1R/S,3S)-3-[2-hydroxypyridin-5-yl]cyclopentyl]-1-pyrazolo[1,5-a]pyridin-3-ylethanamine (compound 1093), (1R)—(N)-[(1R/S,3S)-3-[2-hydroxypyridin-5-yl]cyclopentyl]-1-cyclohexylethanamine (compound 1094), (1R)—(N)-[(1R/S,3S)-3-[2-hydroxypyridin-5-yl]cyclopentyl]-1-(3-chlorophenyl)ethanamine (compound 1095), (1R)—(N)-[(1R/S,3S)-3-[2-hydroxypyridin-5-yl]cyclopentyl]-1-(3-fluoro-4-methoxyphenyl)ethanamine (compound 1096), (1R)—(N)-[(1R/S,3S)-3-[2-hydroxypyridin-5-yl]cyclopentyl]-1-(3-fluorophenyl)ethanamine (compound 1097), (1R)—(N)-[(1R/S,3S)-3-[2-hydroxypyridin-5-yl]cyclopentyl]-1-[3-(trifluoromethyl)phenyl]ethanamine (compound 1098), (1R)—(N)-[(1R/S,3S)-3-[2-hydroxypyridin-5-yl]cyclopentyl]-1-benzo[b]thiophen-3-yl-ethanamine (compound 1099), (1R/S)—(N)-[(1R/S,3S)-3-[2-hydroxypyridin-5-yl]cyclopentyl]-1-pyrimidin-4-ylethanamine (compound 1100), (1R)—(N)-[(1R/S,3S)-3-[2-hydroxypyridin-5-yl]cyclopentyl]-1-(3-cyano-4-fluorophenyl)ethanamine (compound 1101), (1R)—(N)-[(1R/S,3S)-3-(4-(2-(acetamido)ethylaminocarbonyl)phenyl)-cyclopentyl]-1-(1,3-benzodioxol-4-yl)ethanamine (compound 1102), (1R)—(N)-[(1R/S,3S)-3-(4-(2-(acetamido)ethylaminocarbonyl)phenyl)-cyclopentyl]-1-(3-ethoxyphenyl)ethanamine (compound 1103), (1R)—(N)-[(1R/S,3S)-3-(4-(2-(acetamido)ethylaminocarbonyl)phenyl)-cyclopentyl]-1-(4-fluoro-2-methoxyphenyl)ethanamine (compound 1104), (1R)—(N)-[(1R/S,3S)-3-(4-(2-(acetamido)ethylaminocarbonyl)phenyl)-cyclopentyl]-1-(4-fluoro-3-methoxyphenyl)ethanamine (compound 1105), (1R)—(N)-[(1R/S,3S)-3-(4-(2-(acetamido)ethylaminocarbonyl)phenyl)-cyclopentyl]-1-(3-chlorophenyl)ethanamine (compound 1106), (1R)—(N)-[(1R/S,3S)-3-(4-(2-(acetamido)ethylaminocarbonyl)phenyl)-cyclopentyl]-1-benzo[b]thiophen-3-yl-ethanamine (compound 1107), (1R)—(N)-[(1R/S,3S)-3-[4-(aminocarbonylmethylaminocarbonyl)phenyl]-cyclopentyl]-1-(3-ethoxyphenyl)ethanamine (compound 1108), (1R)—(N)-[(1R/S,3S)-3-[4-(aminocarbonylmethylaminocarbonyl)phenyl]-cyclopentyl]-1-(4-fluoro-2-methoxyphenyl)ethanamine (compound 1109), (1R)—(N)-[(1R/S,3S)-3-[4-(aminocarbonylmethylaminocarbonyl)phenyl]-cyclopentyl]-1-(4-fluoro-3-methoxyphenyl)ethanamine (compound 1110), (1R)—(N)-[(1R/S,3S)-3-[4-(aminocarbonylmethylaminocarbonyl)phenyl]-cyclopentyl]-1-benzo[b]thiophen-3-yl-ethanamine (compound 1111), (1R)—(N)-[(1R/S,3S)-3-[4-(2-hydroxyethylaminosulfonyl)phenyl]cyclopentyl]-1-(3,4-difluorophenyl)ethanamine (compound 1112

(1R)—(N)-[(1R/S,3S)-3-[4-(2-hydroxyethylaminosulfonyl)phenyl]cyclopentyl]-1-(3,4-dihydro-2H-1,5-benzodioxepin-6-yl)ethanamine (compound 1113), (1R)—(N)-[(1R/S,3S)-3-[4-(2-hydroxyethylaminosulfonyl)phenyl]cyclopentyl]-1-(3,4-dimethoxyphenyl)ethanamine (compound 1114), (1R)—(N)-[(1R/S,3S)-3-[4-(2-hydroxyethylaminosulfonyl)phenyl]cyclopentyl]-1-(3-fluoro-5-methoxyphenyl)ethanamine (compound 1115), (1R)—(N)-[(1R/S,3S)-3-[4-(2-hydroxyethylaminosulfonyl)phenyl]cyclopentyl]-1-(4-fluoro-2-methoxyphenyl)ethanamine (compound 1116), (1R)—(N)-[(1R/S,3S)-3-[4-(2-hydroxyethylaminosulfonyl)phenyl]cyclopentyl]-1-(4-fluoro-3-methoxyphenyl)ethanamine (compound 1117), (1R)—(N)-[(1R/S,3S)-3-[4-(2-hydroxyethylaminocarbonyl)phenyl]cyclopentyl]-1-(3-chloro-4-fluoro-phenyl)ethanamine (compound 1118), (1R)—(N)-[(1R/S,3S)-3-[4-(2-hydroxyethylaminocarbonyl)phenyl]cyclopentyl]-1-(3-ethoxyphenyl)ethanamine (compound 1119), (1R)—(N)-[(1R/S,3S)-3-[4-(2-hydroxyethylaminocarbonyl)phenyl]cyclopentyl]-1-(3-fluoro-5-methoxyphenyl)ethanamine (compound 1120), (1R)—(N)-[(1R/S,3S)-3-[4-(2-hydroxyethylaminocarbonyl)phenyl]cyclopentyl]-1-(4-fluoro-3-methoxyphenyl)ethanamine (compound 1121), (1R)—(N)-[(1R/S,3S)-3-[4-(2-hydroxyethylaminocarbonyl)phenyl]cyclopentyl]-1-(3-chlorophenyl)ethanamine (compound 1122), (1R)—(N)-[(1R/S,3S)-3-[4-(2-hydroxyethylaminocarbonyl)phenyl]cyclopentyl]-1-benzo[b]thiophen-3-yl-ethanamine (compound 1123), (1R)—(N)-[(1R/S,3S)-3-[4-(cyanomethylaminocarbonyl)phenyl]cyclopentyl]-1-(3-chloro-4-fluoro-phenyl)ethanamine (compound 1124), (1R)—(N)-[(1R/S,3S)-3-[4-(cyanomethylaminocarbonyl)phenyl]cyclopentyl]-1-(3-ethoxyphenyl)ethanamine (compound 1125), (1R)—(N)-[(1R/S,3S)-3-[4-(cyanomethylaminocarbonyl)phenyl]cyclopentyl]-1-(3-fluoro-5-methoxyphenyl)ethanamine (compound 1126), (1R)—(N)-[(1R/S,3S)-3-[4-(cyanomethylaminocarbonyl)phenyl]cyclopentyl]-1-(4-fluoro-2-methoxyphenyl)ethanamine (compound 1127), (1R)—(N)-[(1R/S,3S)-3-[4-(cyanomethylaminocarbonyl)phenyl]cyclopentyl]-1-(4-fluoro-3-methoxyphenyl)ethanamine (compound 1128), (1R)—(N)-[(1R/S,3S)-3-[4-(cyanomethylaminocarbonyl)phenyl]cyclopentyl]-1-(3-chlorophenyl)ethanamine (compound 1129), (1R)—(N)-[(1R/S,3S)-3-[4-(cyanomethylaminocarbonyl)phenyl]cyclopentyl]-1-benzo[b]thiophen-3-yl-ethanamine (compound 1130), (1R)—(N)-[(1R/S,3S)-3-[4-(2-(methanesulfonylamino)-ethylaminocarbonyl)-phenyl]cyclopentyl]-1-(3-ethoxyphenyl)ethanamine (compound 1131), (1R)—(N)-[(1R/S,3S)-3-[4-(2-(methanesulfonylamino)-ethylaminocarbonye-phenyl]cyclopentyl]-1-(3-fluoro-5-methoxyphenyl)ethanamine (compound 1132), (1R)—(N)-[(1R/S,3S)-3-[4-(2-(methanesulfonylamino)-ethylaminocarbonyl)-phenyl]cyclopentyl]-1-(4-fluoro-2-methoxyphenyl)ethanamine (compound 1133), (1R)—(N)-[(1R/S,3S)-3-[4-(2-(methanesulfonylamino)-ethylaminocarbonyl)-phenyl]cyclopentyl]-1-(4-fluoro-3-methoxyphenyl)ethanamine (compound 1134), (1R)—(N)-[(1R/S,3S)-3-[4-(2-(methanesulfonylamino)-ethylaminocarbonyl)-phenyl]cyclopentyl]-1-(3-chlorophenyl)ethanamine (compound 1135),
(1R)—(N)-[(1R/S,3S)-3-[4-(2-(methanesulfonylamino)-ethylaminocarbonyl)-phenyl]cyclopentyl]-1-benzo[b]thiophen-3-yl-ethanamine (compound 1136),
(1R)—(N)-[(1R/S,3R)-3-[4-[methanesulfonylaminocarbonylmethoxy]phenyl]-cyclopentyl]-1-(1,3-benzodioxol-4-yl)ethanamine (compound 1137),
(1R)—(N)-[(1R/S,3R)-3-[4-[methanesulfonylaminocarbonylmethoxy]phenyl]-cyclopentyl]-1-(3-chloro-4-fluoro-phenyl)ethanamine (compound 1138),
(1R)—(N)-[(1R/S,3R)-3-[4-[methanesulfonylaminocarbonylmethoxy]phenyl]-cyclopentyl]-1-(3-ethoxyphenyl)ethanamine (compound 1139),
(1R)—(N)-[(1R/S,3R)-3-[4-(methanesulfonylaminocarbonylmethoxy)-phenyl]cyclopentyl]-1-(3-fluoro-5-methoxyphenyl)ethanamine (compound 1140),
(1R)—(N)-[(1R/S,3R)-3-[4-(methanesulfonylaminocarbonylmethoxy)-phenyl]cyclopentyl]-1-(4-fluoro-2-methoxyphenyl)ethanamine (compound 1141),
(1R)—(N)-[(1R/S,3R)-3-[4-(methanesulfonylaminocarbonylmethoxy)-phenyl]cyclopentyl]-1-(4-fluoro-3-methoxyphenyl)ethanamine (compound 1142),
(1R)—(N)-[(1R/S,3S)-3-[4-[piperidin-4-ylaminocarbonyl]phenyl]cyclopentyl]-1-(1,3-benzodioxol-4-yl)ethanamine (compound 1143),
(1R)—(N)-[(1R/S,3S)-3-[4-[piperidin-4-ylaminocarbonyl]phenyl]cyclopentyl]-1-(1,3-benzodioxol-5-yl)ethanamine (compound 1144),
(1R)—(N)-[(1R/S,3S)-3-[4-[piperidin-4-ylaminocarbonyl]phenyl]cyclopentyl]-1-(1-methyl-5-phenyl-pyrazol-3-yl)ethanamine (compound 1145),
(1R)—(N)-[(1R/S,3S)-3-[4-[piperidin-4-ylaminocarbonyl]phenyl]cyclopentyl]-1-(2,2-difluoro-1,3-benzodioxol-4-yl)ethanamine (compound 1146),
(1R)—(N)-[(1R/S,3S)-3-[4-[piperidin-4-ylaminocarbonyl]phenyl]cyclopentyl]-1-(2,3-dihydro-1,4-benzodioxin-5-yl)ethanamine (compound 1147),
(1R)—(N)-[(1R/S,3S)-3-[4-[piperidin-4-ylaminocarbonyl]phenyl]cyclopentyl]-1-(2,3-dihydrobenzofuran-5-yl)ethanamine (compound 1148),
(1R)—(N)-[(1R/S,3S)-3-[4-[piperidin-4-ylaminocarbonyl]phenyl]cyclopentyl]-1-(2,3-dimethoxyphenyl)ethanamine (compound 1149),
(1R)—(N)-[(1R/S,3S)-3-[4-[piperidin-4-ylaminocarbonyl]phenyl]cyclopentyl]-1-(2-fluoro-3-methoxy-phenyl)ethanamine (compound 1150),
(1R)—(N)-[(1R/S,3S)-3-[4-[piperidin-4-ylaminocarbonyl]phenyl]cyclopentyl]-1-(2-fluoro-5-methoxy-phenyl)ethanamine (compound 1151),
(1R)—(N)-[(1R/S,3S)-3-[4-[piperidin-4-ylaminocarbonyl]phenyl]cyclopentyl]-1-(2-methylthiazol-4-yl)ethanamine (compound 1152),
(1R)—(N)-[(1R/S,3S)-3-[4-[piperidin-4-ylaminocarbonyl]phenyl]cyclopentyl]-1-(3-chloro-4-fluoro-phenyl)ethanamine (compound 1153),
(1R)—(N)-[(1R/S,3S)-3-[4-[piperidin-4-ylaminocarbonyl]phenyl]cyclopentyl]-1-(3-ethoxyphenyl)ethanamine (compound 1154),
(1R)—(N)-[(1R/S,3S)-3-[4-[piperidin-4-ylaminocarbonyl]phenyl]cyclopentyl]-1-(3-fluoro-5-methoxyphenyl)ethanamine (compound 1155),
(1R)—(N)-[(1R/S,3S)-3-[4-[piperidin-4-ylaminocarbonyl]phenyl]cyclopentyl]-1-(4-fluoro-2-methoxyphenyl)ethanamine (compound 1156),
(1R)—(N)-[(1R/S,3S)-3-[4-[piperidin-4-ylaminocarbonyl]phenyl]cyclopentyl]-1-(4-fluoro-3-methoxyphenyl)ethanamine (compound 1157),
(1R)—(N)-[(1R/S,3S)-3-[4-[piperidin-4-ylaminocarbonyl]phenyl]cyclopentyl]-1-(5-chloro-2-thienyl)ethanamine (compound 1158),
(1R)—(N)-[(1R/S,3S)-3-[4-[piperidin-4-ylaminocarbonyl]phenyl]cyclopentyl]-1-(5-fluoroimidazo[1,2-a]pyridin-2-yl)ethanamine (compound 1159),
(1R)—(N)-[(1R/S,3S)-3-[4-[piperidin-4-ylaminocarbonyl]phenyl]cyclopentyl]-1-(8-quinolyl)ethanamine (compound 1160),
(1R)—(N)-[(1R/S,3S)-3-[4-[piperidin-4-ylaminocarbonyl]phenyl]cyclopentyl]-1-[3-(methylethoxy)phenyl]ethanamine (compound 1161),
(1R)—(N)-[(1R/S,3S)-3-[4-[piperidin-4-ylaminocarbonyl]phenyl]cyclopentyl]-1-[4-fluoro-3-(trifluoromethyl)phenyl]ethanamine (compound 1162),
(1R)—(N)-[(1R/S,3S)-3-[4-[piperidin-4-ylaminocarbonyl]phenyl]cyclopentyl]-1-cyclopropylethanamine (compound 1163),
(1R)—(N)-[(1R/S,3S)-3-[4-[piperidin-4-ylaminocarbonyl]phenyl]cyclopentyl]-1-imidazo[1,5-a]pyridin-3-ylethanamine (compound 1164),
(1R)—(N)-[(1R/S,3S)-3-[4-[piperidin-4-ylaminocarbonyl]phenyl]cyclopentyl]-1-pyrazolo[1,5-a]pyridin-3-ylethanamine (compound 1165),
(1R)—(N)-[(1R/S,3S)-3-[4-[piperidin-4-ylaminocarbonyl]phenyl]cyclopentyl]-1-(3-chlorophenyl)ethanamine (compound 1166),
(1R)—(N)-[(1R/S,3S)-3-[4-[piperidin-4-ylaminocarbonyl]phenyl]cyclopentyl]-1-(3-fluoro-4-methoxyphenyl)ethanamine (compound 1167),
(1R)—(N)-[(1R/S,3S)-3-[4-[piperidin-4-ylaminocarbonyl]phenyl]cyclopentyl]-1-(3-fluorophenyl)ethanamine (compound 1168),
(1R)—(N)-[(1R/S,3S)-3-[4-[piperidin-4-ylaminocarbonyl]phenyl]cyclopentyl]-1-[3-(trifluoromethyl)phenyl]ethanamine (compound 1169),
(1R)—(N)-[(1R/S,3S)-3-[4-[piperidin-4-ylaminocarbonyl]phenyl]cyclopentyl]-1-benzo[b]thiophen-3-yl-ethanamine (compound 1170),
(1R/S)—(N)-[(1R/S,3S)-3-[4-[piperidin-4-ylaminocarbonyl]phenyl]cyclopentyl]-1-pyrimidin-4-ylethanamine (compound 1171), or
(1R)—(N)-[(1R/S,3S)-3-[4-[piperidin-4-ylaminocarbonyl]phenyl]cyclopentyl]-1-(3-cyano-4-fluorophenyl)ethanamine (compound 1172).

26. A compound according to claim 1 selected from the group consisting of
(4-{(1R,3S)-3-[(1R)-1-(4-Fluoro-3-methoxy-phenyl)-ethylamino]-cyclopentyl}-phenyl)-(3-hydroxy-azetidin-1-yl)-methanone (compound 1173),
4-{(1R,3S)-3-[(1R)-1-(4-Fluoro-3-methoxy-phenyl)-ethylamino]-cyclopentyl}-N-methyl-N-oxetan-3-yl-benzamide (compound 1174),
(4-{(1R,3S)-3-[(1R)-1-(4-Fluoro-3-methoxy-phenyl)-ethylamino]-cyclopentyl}-phenyl)-isoxazolidin-2-yl-methanone (compound 1175),
4-{(1R,3S)-3-[(1R)-1-(4-Fluoro-3-methoxy-phenyl)-ethylamino]-cyclopentyl}-N-(2-hydroxy-ethyl)-benzamide (compound 1176),
(4-{(1R,3S)-3-[(1R)-1-(4-Fluoro-3-methoxy-phenyl)-ethylamino]-cyclopentyl}-phenyl)-(3-hydroxy-pyrrolidin-1-yl)-methanone (compound 1177), 4-{(1R,3S)-3-[(1R)-1-(4-Fluoro-3-methoxy-phenyl)-ethylamino]-cyclopentyl}-N-(2-methanesulfonylamino-ethyl)-benzamide hydrochloride (compound 1178), 4-(4-{(1R,3S)-3-[(1R)-1-(4-Fluoro-3-methoxy-phenyl)-ethylamino]-cyclopentyl}-benzoyl)-piperazin-2-one (compound 1179), (1R/S,3R)—N-[(1R)-1-(4-fluoro-3-methoxy-phenyl)ethyl]-3-[4-(2-morpholinosulfonylethyl)-phenyl]cyclopentanamine (mixture of 2 isomers) (compound 1180), N-[[4-[(1R/S,3R/S)-3-[[(1R)-1-(4-fluoro-3-methoxy-phenyl)ethyl]amino]cyclopentyl]phenyl]methyl]methanesulfonamide (mixture of 4 isomers) (compound 1181), (1S,3R)—N-[(1R)-1-(4-fluoro-3-methoxy-phenyl)ethyl]-3-[4-(1H-tetrazol-5-yl)phenyl]cyclopentanamine (compound 1182),

[4-[(1S,3R/S)-3-[[(1R)-1-(3-ethoxyphenyl)ethyl]amino]cyclopentyl]phenyl]-morpholino-methanone (compound 1183),

[4-[(1S,3R/S)-3-[[(1R)-1-(3-chlorophenyl)ethyl]amino]cyclopentyl]phenyl]-morpholino-methanone (compound 1184),

[4-[(1S,3R/S)-3-[[(1R)-1-(4-fluoro-3-methoxy-phenyl)ethyl]amino]cyclopentyl]phenyl]-morpholino-methanone (compound 1185), N-(3-amino-3-oxo-propyl)-4-[(1S,3R/S)-3-[[(1R)-1-(1,3-benzodioxol-4-yl)ethyl]amino]cyclopentyl]benzamide (compound 1186), 4-[(1R,3S)-3-[[(1R)-1-(4-fluoro-3-methoxy-phenyl)ethyl]amino]cyclopentyl]-N-(2-hydroxyethyl)benzenesulfonamide (compound 1187), N-(3-amino-3-oxo-propyl)-4-[(1S,3R/S)-3-[[(1R)-1-(3-ethoxyphenyl)ethyl]amino]-cyclopentyl]benzamide (compound 1188), N-(3-amino-3-oxo-propyl)-4-[(1S,3R/S)-3-[[(1R)-1-(4-fluoro-3-methoxy-phenyl)ethyl]amino]cyclopentyl]benzamide (compound 1189), (N)-[(1S,3R)-3-[4-(4-hydroxypiperidine-1-carbonyl)phenyl]cyclopentyl]-(1R)-1-(4-fluoro-3-methoxyphenyl)ethylamine (Compound 1191), (N)-[(1S,3R)-3-[4-(4-hydroxypiperidine-1-carbonyl)phenyl]cyclopentyl]-(1R)-1-(3-ethoxyphenyl)-ethanamine (Compound 1192), (N)-[(1S,3R)-3-[4-(4-hydroxypiperidine-1-carbonyl)phenyl]cyclopentyl]-(1R)-1-(3-chlorophenyl)ethanamine (Compound 1193), (N)-[(1S,3R)-3-[4-(4-hydroxypiperidine-1-carbonyl)phenyl]cyclopentyl]-(1R)-1-(1,3-benzodioxol-4-yl)ethanamine (Compound 1194), (N)-[(1S,3R)-3-[4-(4-hydroxypiperidine-1-carbonyl)phenyl]cyclopentyl]-(1R)-1-(3-fluoro-5-methoxy-phenyl)-ethanamine (Compound 1195), (N)-[(1S,3R)-3-[4-(4-hydroxypiperidine-1-carbonyl)phenyl]cyclopentyl]-(1R)-1-(2,3-Dihydro-benzo[1,4]dioxin-5-yl)-ethylamine (Compound 1196), (N)-[(1S,3R)-3-[4-[(3S)-3-hydroxypyrrolidin-1-ylcarbonyl]phenyl]cyclopentyl]-(1R)-1-(4-fluoro-3-methoxyphenyl)ethylamine (Compound 1197), (N)-[(1S,3R)-3-[4-[(3S)-3-hydroxypyrrolidin-1-ylcarbonyl]phenyl]cyclopentyl]-(1R)-1-(3-ethoxyphenyl)-ethanamine (Compound 1198), (N)-[(1S,3R)-3-[4-[(3S)-3-hydroxypyrrolidin-1-ylcarbonyl]phenyl]cyclopentyl]-(1R)-1-(3-chlorophenyl)ethanamine (Compound 1199), (N)-[(1S,3R)-3-[4-[(3S)-3-hydroxypyrrolidin-1-ylcarbonyl]phenyl]cyclopentyl]-(1R)-1-(1,3-benzodioxol-4-yl)ethanamine (Compound 1200), (N)-[(1S,3R)-3-[4-[(3S)-3-hydroxypyrrolidin-1-ylcarbonyl]phenyl]cyclopentyl]-(1R)-1-(3-fluoro-5-methoxyphenyl)-ethanamine (Compound 1201), (N)-[(1S,3R)-3-[4-[(3S)-3-hydroxypyrrolidin-1-ylcarbonyl]phenyl]cyclopentyl]-(1R)-1-(2,3-Dihydro-benzo[1,4]dioxin-5-yl)-ethylamine (Compound 1202), (N)-[(1S,3R)-3-[4-(2-(aminosulfonypethylaminocarbonyl)phenyl]cyclopentyl]-(1R)-1-(4-fluoro-3-methoxyphenyl)ethylamine (Compound 1203), (N)-[(1S,3R)-3-[4-(2-(aminosulfonyl)ethylaminocarbonyl)phenyl]cyclopentyl]-(1R)-1-(3-ethoxyphenyl)-ethanamine (Compound 1204), (N)-[(1S,3R)-3-[4-(2-(aminosulfonyl)ethylaminocarbonyl)phenyl]cyclopentyl]-(1R)-1-(3-chlorophenyl)ethanamine (Compound 1205), (N)-[(1S,3R)-3-[4-(2-(aminosulfonypethylaminocarbonyl)phenyl]cyclopentyl]-(1R)-1-(1,3-benzodioxol-4-yl)ethanamine (Compound 1206), (N)-[(1S,3R)-3-[4-(2-(aminosulfonypethylaminocarbonyl)phenyl]cyclopentyl]-(1R)-1-(3-fluoro-5-methoxyphenyl)-ethanamine (Compound 1207), (N)-[(1S,3R)-3-[4-(2-(aminosulfonyl)ethylaminocarbonyl)phenyl]cyclopentyl]-(1R)-1-(2,3-Dihydro-benzo[1,4]dioxin-5-yl)-ethylamine (Compound 1208), (N)-[(1S,3R)-3-[4-(3-oxo-piperazinylcarbonyl)phenyl]cyclopentyl]-(1R)-1-(3-fluoro-5-methoxy-phenyl)-ethanamine (Compound 1209), (N)-[(1S,3R)-3-[4-(3-oxo-piperazinylcarbonyl)phenyl]cyclopentyl]-(1R)-1-(3-ethoxyphenyl)-ethanamine (Compound 1210), (N)-[(1S,3R)-3-[4-(3-oxo-piperazinylcarbonyl)phenyl]cyclopentyl]-(1R)-1-(3-chlorophenyl)ethanamine (Compound 1211), (N)-[(1S,3R)-3-[4-(3-oxo-piperazinylcarbonyl)phenyl]cyclopentyl]-(1R)-1-(1,3-benzodioxol-4-yl)ethanamine (Compound 1212), (N)-[(1S,3R)-3-[4-(3-oxo-piperazinylcarbonyl)phenyl]cyclopentyl]-(1R)-1-(2,3-Dihydro-benzo[1,4]dioxin-5-yl)-ethylamine (Compound 1213), (N)-[(1S,3R)-3-[4-(aminocarbonylmethylaminocarbonyl)phenyl]cyclopentyl]-(1R)-1-(4-fluoro-3-methoxyphenyl)ethylamine (Compound 1214), (N)-[(1S,3R)-3-[4-(aminocarbonylmethylaminocarbonyl)phenyl]cyclopentyl]-(1R)-1-(3-ethoxyphenyl)-ethanamine (Compound 1215), (N)-[(1S,3R)-3-[4-(aminocarbonylmethylaminocarbonyl)phenyl]cyclopentyl]-(1R)-1-(3-chlorophenyl)ethanamine (Compound 1216), (N)-[(1S,3R)-3-[4-(aminocarbonylmethylaminocarbonyl)phenyl]cyclopentyl]-(1R)-1-(1,3-benzodioxol-4-yl)ethanamine (Compound 1217), (N)-[(1S,3R)-3-[4-(aminocarbonylmethylaminocarbonyl)phenyl]cyclopentyl]-(1R)-1-(3-fluoro-5-methoxy-phenyl)-ethanamine (Compound 1218), (N)-[(1S,3R)-3-[4-(aminocarbonylmethylaminocarbonyl)phenyl]cyclopentyl]-(1R)-1-(2,3-Dihydro-benzo[1,4]dioxin-5-yl)-ethylamine (Compound 1219), (N)-[(1S,3R)-3-[4-(2-(methanesulfonylamino)-ethylaminocarbonyl)phenyl]cyclopentyl]-(1R)-1-(3-ethoxyphenyl)-ethanamine (Compound 1220), (N)-[(1S,3R)-3-[4-(2-(methanesulfonylamino)-ethylaminocarbonyl)phenyl]cyclopentyl]-(1R)-1-(3-chlorophenyl)ethanamine (Compound 1221), (N)-[(1S,3R)-3-[4-(2-(methanesulfonylamino)-ethylaminocarbonyl)phenyl]cyclopentyl]-(1R)-1-(1,3-benzodioxol-4-yl)ethanamine (Compound 1222),
(N)-[(1S,3R)-3-[4-(2-(methanesulfonylamino)-ethylaminocarbonyl)phenyl]cyclopentyl]-(1R)-1-(3-fluoro-5-methoxy-phenyl)-ethanamine (Compound 1223),
(N)-[(1S,3R)-3-[4-(2-(methanesulfonylamino)-ethylaminocarbonyl)phenyl]cyclopentyl]-(1R)-1-(2,3-Dihydro-benzo[1,4]dioxin-5-yl)-ethylamine (Compound 1224),
(N)-[(1S,3R)-3-[4-[piperidin-4-ylaminocarbonyl]phenyl]cyclopentyl]-(1R)-1-(4-fluoro-3-methoxyphenyl)ethylamine (Compound 1225),
(N)-[(1S,3R)-3-[4-[piperidin-4-ylaminocarbonyl]phenyl]cyclopentyl]-(1R)-1-(3-ethoxyphenyl)-ethanamine (Compound 1226),
(N)-[(1S,3R)-3-[4-[piperidin-4-ylaminocarbonyl]phenyl]cyclopentyl]-(1R)-1-(3-chlorophenyl)ethanamine (Compound 1227),
(N)-[(1S,3R)-3-[4-[piperidin-4-ylaminocarbonyl]phenyl]cyclopentyl]-(1R)-1-(1,3-benzodioxol-4-yl)ethanamine (Compound 1228),
(N)-[(1S,3R)-3-[4-[piperidin-4-ylaminocarbonyl]phenyl]cyclopentyl]-(1R)-1-(3-fluoro-5-methoxy-phenyl)-ethanamine (Compound 1229), or
(N)-[(1S,3R)-3-[4-[piperidin-4-ylaminocarbonyl]phenyl]cyclopentyl]-(1R)-1-(2,3-Dihydro-benzo[1,4]dioxin-5-yl)-ethylamine (Compound 1230).

27. A compound according to claim 1 selected from the group consisting of
N-{2-[Bis-(2-hydroxy-ethyl)-amino]-ethyl}-4-{(1R,3S)-3-[(1R)-1-(4-fluoro-3-methoxy-phenyl)-ethylamino]-cyclopentyl}-benzamide (Compound 1190),
4-{(1S,3R)-3-[(1R)-1-(4-Fluoro-3-methoxy-phenyl)-ethylamino]-cyclopentyl}-N-[2-(2-hydroxy-ethylamino)-ethyl]-benzamide (Compound 1231),
(4-{(1R,3S)-3-[(1R)-1-(4-Fluoro-3-methoxy-phenyl)-ethylamino]-cyclopentyl}-phenyl)-[4-(2-hydroxy-ethyl)-piperazin-1-yl]-methanone (Compound 1232),
(4-{(1R,3S)-3-[(1R)-1-(4-Fluoro-3-methoxy-phenyl)-ethylamino]-cyclopentyl}-phenyl)-piperazin-1-yl-methanone (Compound 1233),
(4-{(1R,3S)-3-[(1R)-1-(4-Fluoro-3-methoxy-phenyl)-ethylamino]-cyclopentyl}-phenyl)-(4-methanesulfonyl-piperazin-1-yl)-methanone (Compound 1234),
N-(2-Amino-ethyl)-4-{(1R,3S)-3-[(1R)-1-(4-fluoro-3-methoxy-phenyl)-ethylamino]-cyclopentyl}-benzamide (Compound 1235), or
4-{(1R,3S)-3-[(1R)-1-(4-Fluoro-3-methoxy-phenyl)-ethylamino]-cyclopentyl}-N-[1-(2-hydroxy-ethyl)-piperidin-4-yl]-benzamide (Compound 1236).

28. An intermediate for the preparation of compounds according to claim 1 selected from the group consisting of
(3S)-3-(4-methylsulfonylphenyl)cyclopentanone (preparation 1),
tert-butyl 4-[[4-[(1S)-3-oxocyclopentyl]benzoyl]amino]piperidine-1-carboxylate (preparation 2),
(3S)-3-(6-methoxy-3-pyridyl)cyclopentanone (preparation 3),
5-[(1S)-3-oxocyclopentyl]-1H-pyridin-2-one (preparation 4),
(3S)-3-[4-(1H-tetrazol-5-yl)phenyl]cyclopentanone (preparation 5),
N-(2-Hydroxyethyl)-4-[(1S)-3-oxocyclopentyl]benzenesulfonamide (preparation 6),
(3S)-3-[4-(4-hydroxypiperidine-1-carbonyl)phenyl]cyclopentanone (preparation 7),
N-methylsulfonyl-2-[4-[(1R)-3-oxocyclopentyl]phenoxy]acetamide (preparation 8),
2-[4-[(1R)-3-oxocyclopentyl]phenoxy]acetamide (preparation 9),
N-(2-acetamidoethyl)-4-[(1S)-3-oxocyclopentyl]benzamide (preparation 10), 4-[(1S)-3-oxocyclopentyl]-N-(2-sulfamoylethyl)benzamide (preparation 11),
4-[4-[(1S)-3-oxocyclopentyl]benzoyl]piperazin-2-one (preparation 12), (3S)-3-[4-[(3S)-3-hydroxypyrrolidine-1-carbonyl]phenyl]cyclopentanone (preparation 13),
N-(2-amino-2-oxo-ethyl)-4-[(1S)-3-oxocyclopentyl]benzamide (preparation 14),
(3S)-3-[4-(morpholine-4-carbonyl)phenyl]cyclopentanone (preparation 15), N-(2-hydroxyethyl)-4-[(1S)-3-oxocyclopentyl]benzamide (preparation 16),
N-[2-(methanesulfonamido)ethyl]-4-[(1S)-3-oxocyclopentyl]benzamide (preparation 17),
N-(cyanomethyl)-4-[(1S)-3-oxocyclopentyl]benzamide (preparation 18),
(R)-1-Isoquinolin-1-yl-ethylamine dihydrochloride (preparation 21),
(R)-1-(2,3-Dihydro-benzo[1,4]dioxin-5-yl)-ethylamine hydrochloride (preparation 22),
(R)-1-Pyrazolo[1,5-a]pyridin-3-yl-ethylamine hydrochloride (preparation 23),
(R)-1-(2,2-Difluoro-benzo[1,3]dioxol-4-yl)-ethylamine hydrochloride (preparation 24),
(R)-1-(3,4-Dihydro-2H-benzo[b][1,4]dioxepin-6-yl)-ethylamine hydrohchloride (preparation 25),
(R)-1-(1-Methyl-5-phenyl-1H-pyrazol-3-yl)-ethylamine (preparation 26),
(R)-1-Imidazo[1,2-a]pyridin-3-yl-ethylamine hydrochloride (preparation 27),
(R)-1-(5-Fluoro-imidazo[1,2-a]pyridin-2-yl)-ethylamine hydrochloride (preparation 28),
(R)-1-Imidazo[1,5-a]pyridin-3-yl-ethylamine hydrochloride (preparation 29),
[4-(3-Oxo-cyclopentyl)-phenoxy]-acetic acid ethyl ester (Preparation 30),
(R)-[4-(3-Oxo-cyclopentyl)-phenoxy]-acetic acid (Preparation 31),
Methyl 4-[(1R,3S)-3-[[(1R)-1-(4-fluoro-3-methoxy-phenyl)ethyl]amino]cyclopentyl]-benzoate (preparation 33),
4-[(1R,3S)-3-[[(1R)-1-(4-Fluoro-3-methoxy-phenyl)ethyl]amino]-cyclopentyl]benzoic acid (preparation 34),
4-[(1R,3S)-3-[[(1R)-1-(4-Fluoro-3-methoxy-phenyl)ethyl]amino]cyclopentyl]benzonitrile (preparation 36),
N-(3-Amino-3-oxo-propyl)-4-[(1S)-3-oxocyclopentyl]benzamide (preparation 37),
4-[(1R)-3-oxocyclopentyl]benzoic acid (Preparation 39),
4-[4-[(1R)-3-oxocyclopentyl]benzoyl]piperazin-2-one (Preparation 40),
N-(2-acetamidoethyl)-4-[(1R)-3-oxocyclopentyl]benzamide (Preparation 41),
4-[(1R)-3-oxocyclopentyl]-N-(2-sulfamoylethyl)benzamide (Preparation 42),
(3R)-3-[4-(4-hydroxypiperidine-1-carbonyl)phenyl]cyclopentanone (Preparation 43),
N-[2-(methanesulfonamido)ethyl]-4-[(1R)-3-oxocyclopentyl]benzamide (Preparation 44),
(3R)-3-[4-[(3S)-3-hydroxypyrrolidine-1-carbonyl]phenyl]cyclopentanone (Preparation 45),
tert-butyl 4-[[4-[(1R)-3-oxocyclopentyl]benzoyl]amino]piperidine-1-carboxylate (Preparation 46), or ([(1S,3R)-3-(4-Bromo-phenyl)-cyclopentyl]-(1R)-[1-(4-fluoro-3-methoxy-phenyl)-ethyl]-amine (Preparation 50).

29. A compound according to claim 1 for use as a medicament in therapy.

30. A pharmaceutical composition comprising a compound according claim 1 or a pharmaceutically acceptable stereoisomer or salt thereof together with a pharmaceutically acceptable vehicle or excipient.

* * * * *